(12) United States Patent
Abend et al.

(10) Patent No.: US 10,654,914 B2
(45) Date of Patent: *May 19, 2020

(54) POLYOMAVIRUS NEUTRALIZING ANTIBODIES

(71) Applicant: Novartis AG, Basel (CH)

(72) Inventors: Johanna Abend, Emeryville, CA (US); Zorica Dragic, Basel (CH); Adam Lloyd Feire, Hull, MA (US); Mark Knapp, Oakland, CA (US); Steven Kovacs, Randolph, NJ (US); Elisabetta Traggiai, Basel (CH); Lichun Wang, Shanghai (CN); Yongqiang Wang, Shanghai (CN); Danqing Wu, Shanghai (CN); Qilong Wu, Shanghai (CN); Fangmin Xu, Belmont, MA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/183,262

(22) Filed: Nov. 7, 2018

(65) Prior Publication Data

US 2019/0071488 A1    Mar. 7, 2019

Related U.S. Application Data

(60) Continuation of application No. 15/829,115, filed on Dec. 1, 2017, which is a division of application No. 15/258,925, filed on Sep. 7, 2016, now Pat. No. 9,862,760.

(30) Foreign Application Priority Data

Sep. 16, 2015  (WO) ............... PCT/CN2015/089764

(51) Int. Cl.
| | | |
|---|---|---|
| *A61K 9/19* | (2006.01) | |
| *A61K 39/42* | (2006.01) | |
| *C07K 16/08* | (2006.01) | |
| *A61K 45/06* | (2006.01) | |

(52) U.S. Cl.
CPC ............. *C07K 16/084* (2013.01); *A61K 9/19* (2013.01); *A61K 39/42* (2013.01); *A61K 45/06* (2013.01); *C07K 2317/20* (2013.01); *C07K 2317/21* (2013.01); *C07K 2317/24* (2013.01); *C07K 2317/33* (2013.01); *C07K 2317/34* (2013.01); *C07K 2317/41* (2013.01); *C07K 2317/56* (2013.01); *C07K 2317/565* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 8,470,979 B2 | 6/2013 | Bondensgaard | |
| 9,862,760 B2 | 1/2018 | Abend et al. | |
| 10,435,460 B2 | 10/2019 | Abend et al. | |
| 10,450,366 B2 | 10/2019 | Abend et al. | |
| 2010/0215662 A1* | 8/2010 | Bradbury | C07K 16/1018 424/147.1 |
| 2015/0056188 A1 | 2/2015 | Simon | |
| 2017/0088605 A1 | 3/2017 | Abend et al. | |
| 2018/0079799 A1 | 3/2018 | Abend et al. | |
| 2019/0002533 A1 | 1/2019 | Abend et al. | |

FOREIGN PATENT DOCUMENTS

| | | |
|---|---|---|
| WO | 2003/105894 | 12/2003 |
| WO | 2013/142299 | 9/2013 |
| WO | 2014/002035 | 1/2014 |
| WO | 2014/102399 | 7/2014 |
| WO | WO-2017/046676 | 3/2017 |

OTHER PUBLICATIONS

Abend et al., "Inhibitory Effect of Gamma Interferon on BK Virus Gene Expression and Replication" J. Virology 81:272-279, 2007.
Antinori et al., "Clinical epidemiology and survival of progressive multifocal leukoencephalopathy in the era of highly active antiretroviral therapy: Data from the Italian Registry Investigative Neuro AIDS (IRINA)" Journal of NeuroVirology 9(supplemental 1):47-53, Jan. 2003.
Astrom et al., "Progressive Multifocal Leuko-Encephalopathy a Hitherto Unrecognized Complication of Chronic Lymphatic Leukemia and Hodgkin's Disease" Brain 81(1):93-111, 1958.
Bennett et al., "BK polyomavirus: emerging pathogen" Microbes and Infection 14(9):672-683, Aug. 2012.
Binet et al., "Polyomavirus Disease Under New Immunosuppressive Drugs: A Cause of Renal Graft Dysfunction and Graft Loss" Transplantation 67(6):918-922, 1999.
Brennan et al., "Incidence of BK with tacrolimus versus cyclosporine and impact of preemptive immunosuppression reduction" Am. J. Transplant 5(3):582-594, 2005.
Bressollette-Bodin et al., "A Prospective Longitudinal Study of BK Virus Infectionin 104 Renal Transplant Recipients" American Journal of Transplantation 5(8):1926-1933, 2005.
Broekema et al., "A system for the analysis of BKV non-coding control regions: Application to clinical isolates from an HIV/AIDS patient" Virology 407:368-373, 2010.
Chatterjee et al., "Identification of Archetype and Rearranged Forms of BK Virus in Leukocytes From Healthy Individuals" Journal of Medical Virology 60:353-362, 2000.
Chen et al., "Synthetic antibodies and peptides recognizing progressive multifocal leukoencephalopathyspecific point mutations in polyomavirus JC capsid viral protein 1" mABS 7(4):681-692, 2015.
Derienzo et al., "Evaluation of the Half-Life of Intravenous Human Cytomegalovirus Immune Globulin in Patients Receiving Partially Mismatched Related Donor Bone Marrow Transplantation" Pharmacotherapy 20:1175-1178, 2000.

(Continued)

*Primary Examiner* — Nianxiang Zou
(74) *Attorney, Agent, or Firm* — Cooley LLP

(57) ABSTRACT

The present invention relates to anti-VP1 antibodies, antibody fragments, and their uses for the prevention and treatment of polyoma virus infection and associated diseases.

21 Claims, 45 Drawing Sheets

Specification includes a Sequence Listing.

(56) References Cited

OTHER PUBLICATIONS

Garcia-Suarez et al., "Changes in the Natural History of Progressive Multifocal Leukoencephalopathy in HIV-negative Lymphoproliferative Disorders: Impact of Novel Therapies" Am. J Hematol 80(4):271-281, 2005.
Gardner, "New human papovavirus (B.K.) isolated from urine after renal transplantation" Lancet 297(7712):1253-1257, 1971.
Goudsmit et al., "The role of BK virus in acute respiratory tract disease and the presence of BKV DNA in tonsils" Journal of Medical Virology 10:91-99, 1982.
Heritage et al., "The persistence of papovavirus BK DNA sequences in normal human renal tissue" Journal of Medical Virology 8:143-150, 1981.
Hirsch, "Polyomavirus BK nephropathy: a (re-)emerging complication in renal transplantation" Am. J. Transplant 2 (1):25-30, 2002.
Hirsch et al., "Prospective Study of Polyomavirus Type BK Replication and Nephropathy in Renal-Transplant Recipients" New England J. Medicine 347(7):488-496, 2002.
Hirsch et al., "Polyomavirus-Associated Nephropathy in Renal Transplantation: Interdisciplinary Analyses and Recommendations" Transplantation 79(1):1277-1286, 2005.
Jiang et al., "The Role of Polyomaviruses in Human Disease" Virology 384(2):266-273, 2009.
Johne et al., "Taxonomical Developments in the Family Polyomaviridae" Arch. Virol. 156(9):1627-1634, 2011.
Knowles, "Discovery and Epidemiology of the Human Polyomaviruses BK Virus (BKV) and JC Virus (JCV)" Adv. Exp. Med. Biol. 577:19-45, 2006.
Neu et al., Plos Pathogens 9(10):e1003714 and e1003688, Oct. 2013.
Nickeleit et al., "Polymavirus Infection of Renal Allograft Recipients: From Latent Infection to Manifest Disease" J. Am. Sco. Neprol. 10(5):1080-1089, 1999.
O'Hara et al., "Gallic acid-based small-molecule inhibitors of JC and BK polyomaviral infection" Virus Research 189:280-285, 2014.
Padgett et al., "Cultivation of Papova-Like Virus from Human Brain with Progressive Multifocal Leucoencephalopathy" Lancet 297(7712):1257-1260, 1971.
Padgett et al., "Prevalence of Antibodies in Human Sera against JC Virus, an Isolate from a Case of Progressive Multifocal Leukoencephalopathy" Journal of Infectious Diseases 127(4):467-470, Apr. 1973.
Purighalla et al., BK Virus Infection in a Kidney Allograft Diagnosed by Needle Biopsy American Journal of Kidney Diseases 26(4):671-673, Oct. 1995.
Randhawa et al., "Human Polyoma Virus-Associated Interstital Nephritis in the Allograft Kidney" Transplantation 67:103-109, 1999.
Randhawa and Brennan, "BK Virus Infection in Transplant Recipients: An Overview and Update" American Journal of Transplantation 6(9):2000-2005, Sep. 2006.
Reid et al., "Sequencing and Analysis of JC Virus DNA From Natalizumab-Treated PML Patients" J Infect Dis. 204:237-244, 2011.
Reploeg et al., "BK Virus: A Clinical Review" Clin Infect. Dis. 33(2):191-202, Jul. 15, 2001.
Richardson, "Progressive Multifocal Leukoencephalopathy" New England Journal of Medicine 265(17):815-823, 1961.
Sabath et al., "Traffic of JC Virus from Sites of Initial Infection to the Brain: The Path to Progressive Multifocal Leukoencephalopathy" Journal Infectious Diseases 186:S180-S186, 2002.
Shinohara et al., "BK Virus Infection of the Human Urinary Tract" Journal of Medical Virology 41(4):301-305, 1993.
Qian and Tsai, "Lipids and Proteins Act in Opposing Manners To Regulate Polyomavirus Infection" Journal of Virology 84(19):9840-9852, Oct. 1, 2010.
Wiseman et al., "Polyomavirus Nephropathy: A Current Perspective and Clinical Considerations" Am.J. Kidney Dis 54 (1):131-142, 2009.
Lipshutz et al., "BK Nephropathy in Kidney Transplant Recipients Treated with a Calcineurin Inhibitor-Free Immunosuppression Regimen" American Journal of Transplantation 2004; 4: 2132-2134, 2004.
Gorelik et al., "Progressive Multifocal Leukoencephalopathy (PML) Development is Associated with Mutations in JC Virus Capsid Protein VP1 that Change its Receptor Specificity" Journal of Infectious Diseases 204:237-244, 2011.
Pastrana et al., "Neutralization Serotyping of BK Polyomavirus Infection in Kidney Transplant Recipients" PLoS Pathogens vol. 8(4)e1002650, 2012.
Randhawa et al., "Identification of Species-Specific and Cross-Reactive Epitopes in Human Polyomavirus Capsids Using Monoclonal Antibodies" Journal of General Virology 90:634-639, 2009.
Randhawa et al., "Commercially Available Immunoglobulins Contain Virus Neutralizing Antibodies Against all Major Genotypes of Polyomavirus" BK. Am J Transplant. 15(4):1014-20, 2015.
Carter et al., "Lack of Serologic Evidence for Prevalent Simian Virus 40 Infection in Humans" J. Natl. Cancer Inst. 95:1522-1530, 2003.
Mengelle et al., JC Virus DNA in the Peripheral Blood of Renal Transplant Patients: a 1-Year Prospective Follow-up in France J. Med. Virol. 83(1):132-136, 2011.
Liu., "Antibody Glycosylation and its Impact on the Pharmacokinetics and Pharmacodynamics of Monoclonal Antibodies and Fc-fusion Proteins" J. Pharm. Sci. 104(6):1866-1884, 2015.
Rudikoff et al., "Single Amino Acid Substitution Altering Antigen-Binding Specificity" Proc. Natl. Acad. Sci. U.S.A. 79:1979-1983, 1982.
Johne et al. (2004). "Nuclear Localization of Avian Polyomavirus Structural Protein VP1 Is a Prerequisite for the Formation of Virus-Like Particles." Journal of Virology. 78(2): 930-937.

\* cited by examiner

SET BKV VP1-serotype I Affinity Assay

SET BKV VP1-serotype II Affinity Assay

SET BKV VP1-serotype III Affinity Assay

SET BKV VP1-serotype IV Affinity Assay

FIGURE 2

SET affinity assay on BKV VP1 from all four serotypes

Solution Equilibrium Titration (SET) assay, K$_D$ (pM)

| Antigen (VP1) | P165E2 | NEG447 | NEG447A | P7G11 | P7G11A | P8D11 | P8D11A | P8D11B | P8D11C | P8D11D | P8D11E |
|---|---|---|---|---|---|---|---|---|---|---|---|
| serotype I | 1.5 ± 0.1 | 1.0 ± 0.2 | 0.9 ± 0.3 | 4.2 ± 0.2 | 3.0 ± 0.8 | 4.3 ± 1.4 | 4.4 ± 1.2 | 3.8 ± 0.2 | 4.5 ± 1.2 | 5.0 ± 2.0 | 4.3 ± 1.4 |
| serotype II | 154 ± 8 | 29 ± 24.6 | 9.6 ± 2.4 | 1877 ± 118 | 12 ± 2.4 | 2.1 ± 0.4 | 2.5 ± 0.7 | 1.8 ± 0.6 | 2.7 ± 0.9 | 2.0 ± 0.5 | 1.7 ± 0.4 |
| serotype III | >10000 | >10000 | >10000 | >10000 | >10000 | 6.0 ± 3.0 | 3.7 ± 0.5 | 2.5 ± 0.06 | 4.8 ± 1.3 | 5.0 ± 2.0 | 6.0 ± 4.0 |
| serotype IV | 1769 ± 112 | 1049 ± 166 | 185 ± 11 | 2117 ± 140 | 153 ± 17 | 3.0 ± 1.0 | 2.9 ± 1.7 | 2.9 ± 0.4 | 2.7 ± 0.7 | 3.2 ± 0.3 | 2.7 ± 1.2 |

FIGURE 3A

Binding to BKV serotype I VP1 pentamers by SPR

Binding to BKV serotype I VLPs by SPR

Binding to BKV serotype II VP1 pentamers by SPR

Binding to BKV serotype III VLPs by SPR

Binding to BKV serotype IV VP1 pentamers by SPR

Binding to BKV serotype I VLPs by ELISA

Binding to BKV serotype IV VLPs by ELISA

Binding to BKV serotype IV VP1 pentamers by ELISA

FIGURE 7

Binding to BKV serotype I VLPs or serotype IV VLPs or pentamers by ELISA

| Antibody | Serotype I VLP IC50 (nM) | Serotype IV VLP IC50 (nM) | Serotype IV pentamer IC50 (nM) |
|---|---|---|---|
| EBB-C1975-A3 | 14.53 | 0.045 | 0.064 |
| EBB-C1975-A7 | 85.7 | 0.081 | 0.078 |
| EBB-C1975-E7 | 4.32 | 0.044 | 0.026 |
| EBB-C1975-B5 | 55.07 | 0.10 | 0.078 |

Binding to BKV serotype I VLPs by ELISA

FIGURE 9

Binding to BKV serotype I VLPs by ELISA

| Antibody | BKV serotype I VLP IC50 (nM) |
|---|---|
| 2081-20-8 | 0.053 |
| 2075-16-1 | 0.104 |
| 2075-456-4 | 0.052 |
| 2081-36-8 | 0.267 |
| 2081-66-5 | 0.067 |
| 2081-38-5 | 0.046 |
| 2081-25-6 |

Binding to JCV VLPs by ELISA

FIGURE 11

| Antibody | JCV VLP IC50 (nM) |
|---|---|
| 2077-4-1 | 0.034 |
| 2077-7-5 | 0.651 |
| 2077-10-1 | 0.100 |
| 2077-26-1 | 0.067 |
| 2077-28-2 | 0.088 |

Binding to JCV VLPs by ELISA

FIGURE 12A-B

Anti-VP1 antibodies bind to a conformational epitope

Anti-VP1 antibodies bind to a conformational epitope: Reference BKV serotype I VP1

Anti-VP1 antibodies bind to a conformational epitope: BKV VP1 F66A

Anti-VP1 antibodies bind to a conformational epitope: BKV VP1 L68A

Anti-VP1 antibodies bind to a conformational epitope: BVK VP1 K69A

Anti-VP1 antibodies bind to a conformational epitope: BKV VP1 E82A

Anti-VP1 antibodies bind to a conformational epitope: BKV VP1 I145A

FIGURE 14

Anti-VP1 antibodies bind to a conformational epitope

| Antibody | Residues identified |
|---|---|
| P165E2 | F66, K69, E82, I145 |
| NEG447 | F66, K69, E82, I145 |
| P7G11A | F66, K69, E82, I145 |
| P8D11 | F66, I145 |

| Name | Location | P165E2 | NEG447 | P7G11A | P8D11 |
|---|---|---|---|---|---|
| E61A | BC loop | + | + | + | + |
| N62A | BC loop | + | + | + | + |
| F66A | BC loop | - | - | - | - |
| L68A | BC loop | + | + | + | + |
| K69A | BC loop | - | - | - | + |
| H69K (III) | BC loop | + | + | + | + |
| S71A | BC loop | + | + | + | + |
| N74A | BC loop | + | + | + | + |
| D75A | BC loop | + | + | + | + |
| S77A | BC loop | + | + | + | + |
| E82A | BC loop | - | - | - | + |
| R83A | BC loop | + | + | + | + |
| I145A | DE loop | - | - | - | - |
| E175A | EF loop | + | + |

Neutralization of BKV serotype I infection by anti-VP1 antibodies

Neutralization of BKV serotype II infection by anti-VP1 antibodies

Neutralization of BKV serotype III infection by anti-VP1 antibodies

Neutralization of BKV serotype IV infection by anti-VP1 antibodies

FIGURE 19

Summary of neutralization of BKV and JCV infection by anti-VP1 antibodies

| | Neutralization (μg/ml) | | | | | | | | | |
|---|---|---|---|---|---|---|---|---|---|---|
| | Serotype I | | Serotype II | | Serotype III | | Serotype IV | | JCV | |
| Antibody | EC50 | EC90 | EC50 | EC90 | EC50 | EC90 | EC50 | EC90 | EC50 | EC90 |
| P165E2 | 0.009 | 0.37 | 0.081 | 7.98 | >100 | >100 | 0.012 | 0.46 | >100 | >100 |
| NEG447 | 0.004 | 0.27 | 0.024 | 6.72 | >100 | >100 | 0.012 | 0.34 | >100 | >100 |
| NEG447A | 0.0001 | 0.094 | 0.110 | 0.84 | >100 | >100 | 0.011 | 0.26 | ND | ND |
| P7G11 | 0.007 | 0.37 | 0.187 | 1.79 | >100 | >100 | 0.011 | 0.48 | >100 | >100 |
| P7G11A | 0.0008 | 0.34 | 0.074 | 2.89 | >100 | >100 | 0.015 | 0.53 | >100 | >100 |
| P8D11 | 0.015 | 0.24 | 0.089 | 6.34 | 0.092 | 0.53 | 0.023 | 0.39 | 0.090 | 2.76 |
| P8D11A | 0.005 | 0.19 | 0.029 | 8.68 | 0.010 | 0.59 | 0.015 | 0.064 | ND | ND |
| P8D11B | 0.003 | 0.30 | 0.088 | 1.93 | 0.014 | 0.50 | 0.005 | 0.54 | ND | ND |
| P8D11C | 0.0003 | 0.34 | 0.180 | 0.50 | 0.049 | 0.51 | 0.005 | 0.54 | ND | ND |
| P8D11D | 0.034 | 0.15 | 0.161 | 1.64 | 0.185 | 0.87 | 0.003 | 0.063 | ND | ND |
| P8D11E | 0.032 | 0.11 | 0.144 | 2.52 | 0.236 | 0.90 | 0.002 | 0.087 | ND | ND |
| P46F4 | 0.004 | 0.29 | >100 | >100 | >100 | >100 | >100 | >100 | ND | ND |

FIGURE 21

Neutralization of BKV infection by anti-VP1 antibodies

| Antibody | Serotype I | | Serotype II | | Serotype III | | Serotype IV | |
|---|---|---|---|---|---|---|---|---|
| | EC50 | EC90 | EC50 | EC90 | EC50 | EC90 | EC50 | EC90 |
| EBB-C1975-A3 | 0.045 | 4.84 | 0.12 | 25.18 | >100 | >100 | 0.13 | 8.18 |
| EBB-C1975-A7 | 0.024 | 5.15 | 0.11 | 14.19 | >100 | >100 | 0.28 | 7.79 |
| EBB-C1975-E7 | 0.010 | 2.62 | 0.33 | 9.61 | >100 | >100 | 0.35 | 8.61 |
| EBB-C1975-B5 | 0.033 | 5.53 | 0.42 | 24.17 | 0.76 | >100 | 0.15 | 7.83 |

Neutralization (μg/ml)

Neutralization of BKV serotype I infection by anti-VP1 antibodies

FIGURE 23

Neutralization of BKV serotype I infection by anti-VP1 antibodies

| Antibody | Neutralization (μg/ml) | |
|---|---|---|
| | EC50 | EC90 |
| 2081-20-8 | 0.062 | 0.556 |
| 2075-16-1 | 0.065 | 1.253 |
| 2075-456-4 | 0.092 | 0.503 |
| 2081-36-8 | 0.147 | 0.909 |
| 2081-66-5 | 0.041 | 0.601 |
| 2081-38-5 | 0.053 | 1.799 |
| 2081-25-6 | 0.213 | 0.723 |

Neutralization of JCV infection by anti-VP1 antibodies

Neutralization of JCV infection by anti-VP1 antibodies

FIGURE 26

Neutralization of JCV infection by anti-VP1 antibodies

| Antibody | Neutralization (µg/ml) | |
|---|---|---|
| | EC50 | EC90 |
| 2077-4-1 | 0.138 | 3.06 |
| 2077-7-5 | 0.097 | 1.10 |
| 2077-10-1 | 1.492 | >10 |
| 2077-26-1 | 0.702 | 3.20 |
| 2077-28-2 | 0.347 | 6.82 |

FIGURE 27

SET Affinity Assay of P8D11 on JCV VLPs

| Antigen (VLPs) | Solution Equilibrium Tit

FIGURE 29A

Anti-VP1 antibodies bind to a conformational epitope in BKV VP1 EF loop

| Mutation | P8D11 binding | P7G11A binding |
|---|---|---|
| Y169A | - | - |
| R170A | - | - |
| K172A | - | + |
| E175A | + | + |
| K181A | + | + |
| N182A | + | + |
| T184A | + | + |
| Q186A | + | + |

| Antibody | Contact residues identified |
|---|---|
| P8D11 | Y169, R170, K172 |
| P7G11A | Y169, R170 |

FIGURE 29B

Anti-VP1 antibodies bind to a conformational epitope in BKV VP1 EF loop

Anti-VP1 antibodies bind to a conformational epitope in BKV VP1 EF loop

Representation of the scFv chains from P8D11 (black) bound to the BKV capsid protein (VP1) pentamer (gray), each VP1 monomer has a binding site for the scFv.

FIGURE 31A-B

Figure 31A is a representation of the P8D11 scFv (black) bound to the BKV capsid protein (VP1) pentamer (gray), as a single unit removed from the resolution of the larger 5-unit in Figure 30. Figure 31B is a magnification of the contacts between the P8D11 scFv and the VP1 pentamer

POLYOMAVIRUS NEUTRALIZING ANTIBODIES

CROSS-REFERENCE TO RELATED APPLICATIONS

This application is a continuation of U.S. Ser. No. 15/829,115, filed 1 Dec. 2017, which is a divisional of U.S. Ser. No. 15/258,925, filed 7 Sep. 2016, which issued as U.S. Pat. No. 9,862,760, which claims priority to International Application Serial No. PCT/CN2015/089764, filed 16 Sep. 2015, the contents of which are incorporated herein by reference in their entirety.

FIELD OF THE INVENTION

The present disclosure is directed to anti-VP1 antibodies, antibody fragments, and their uses for the reducing the likelihood or treatment of polyoma virus infection.

BACKGROUND OF THE INVENTION

Of the human polyomaviruses, BK virus (BKV) and JC virus (JCV) were the first two identified. These two polyomavirus were isolated from immunosuppressed patients and published in the same issue of Lancet in 1971 (Gardner et al., Lancet 1971 1:1253-1527, and Padgett et al., Lancet 1971 1:1257-1260). Polyomaviruses are icosahedral, non-enveloped, double-stranded DNA viruses. They measure 40-45 nm in diameter and are comprised of 88% protein and 12% DNA.

The BKV genome is a circular double-stranded DNA of approximately 5 Kb in length and contains three major divisions: the early coding region, the late coding region, and a non-coding control region. The early coding region encodes for the three regulatory proteins (large tumor antigen [TAg], small tumor antigen [tAg], and truncated tumor antigen [truncTAg]), which are the first viral proteins expressed in a newly infected cell and are responsible for facilitating viral DNA replication and establishing a favorable cellular environment. The late coding region encodes the three structural proteins (VP1, VP2, and VP3) that make up the viral capsid, as well as the agnoprotein, the role of which during viral replication is less well-defined. The non-coding control region contains the origin of replication as well as the early and late promoters that drive expression of the viral gene products.

BKV has been detected in many different cell types including epithelial cells of the kidney, bladder, and ureter (typical sites of persistence), tonsillar tissue, and lymphocytes (proposed sites of primary infection and dissemination) (Chatterjee et al., J. Med. Virol. 2000; 60:353-362, Goudsmit et al., J. Med. Virol. 1982; 10:91-99, Heritage et al., J. Med. Virol. 1981; 8:143-150, Shinohara et al., J. Med. Virol. 1993; 41(4):301-305). The primary cell surface receptors for BKV are the gangliosides GT1b, GD1b, and GD3, all of which have a terminal α2,8-linked sialic acid and are fairly ubiquitous, allowing infection of various cell types (Neu et al., PLos Patholog. 2013; 9(10):e1003714 and e1003688, see also, O'Hara et al., Virus Res. 2014; 189: 208-285). The non-enveloped icosahedral virion of BKV is composed of three different viral proteins: 360 copies of the major viral capsid protein VP1 arranged in 72 pentamers and 72 copies combined of the minor viral capsid proteins VP2 and VP3, with one VP2 or VP3 molecule associated with each VP1 pentamer. Only VP1 is exposed on the virion surface at entry and each pentamer has five low affinity binding sites for the ganglioside receptor. Binding of VP1 pentamers to ganglioside receptors on the cell surface initiates internalization through a caveolae-mediated endocytic pathway, followed by trafficking of the virus to the endoplasmic reticulum and finally to the nucleus (Tsai and Qian, J. Virol 2010; 84(19):9840-9852).

Infection with the human polyomavirus BK (BKV) is essentially ubiquitous, with estimates ranging between 80 and 90% of the population globally infected (Knowles W. A., Adv. Exp. Med. Biol. 2006; 577:19-45). Primary infection most often occurs during childhood (i.e., before age 10) and results in either a mild, non-specific, self-limited illness or no symptoms at all. Persistent infection is established in the epithelial cells of the renal tubules, ureters, and bladder, and is effectively controlled by the immune system. Transient asymptomatic viral shedding in the urine of immunocompetent adults occurs sporadically but results in no disease or sequelae. However, compromised immune function, particularly with immunosuppression following renal or hematopoietic stem cell transplantation, can lead to uncontrolled BKV replication and ultimately to BKV-associated nephropathy (BKVAN) or hemorrhagic cystitis (HC), a painful disease of the bladder. There are no effective antiviral therapies against BKV and the current standard of care is reduction of immunosuppression, which increases the risk of acute rejection. Even with the current, more aggressive approaches to monitoring and prevention, up to 10% of renal transplant recipients will develop BKVAN and 15-30% of those patients will suffer graft loss due to BKVAN. Among those undergoing reduction in immunosuppressive regimen upon detection of BKV viremia, up to 30% will experience an acute rejection episode as a result.

Although BKV was first described in 1971 (supra), it was not until the 1990s that BK associated nephropathy (BKVAN) was reported in the literature as a cause of kidney transplant injury (Purighalla et al., Am. J. Kidney Dis. 1995; 26:671-673 and Randhawa et al., Transplantation 1999; 67:103-109). In early management of BKVAN, testing positive for BK had severe consequences, with more than 50% of the patients having graft dysfunction and graft loss (Hirsch et al., New Engl. J. Med. 2002; 347:488-496). BK viral reactivation may begin after transplantation, and is seen in about 30%-50% of the patients by 3 months post-transplantation (Bressollette-Bodin et al., Am J. Transplant. 2005; 5(8):1926-1933 and Brennan et al., Am. J. Transplant. 2004; 4(12):2132-2134). BK viral reactivation can be first seen by virus and viral DNA in the urine, then in the plasma and finally in the kidney. (Brennan et al., Am. J. Transplant. 2005; 5(3):582-594 and Hirsch et al., N Eng. J. Med. 2002; 347(7):488-496). About 80% of kidney transplant patients have BK virus in the urine (BK viruria) and 5-10% of these patients progress to BKVAN (Binet et al., Transplantation 1999; 67(6):918-922 and Bressollette-Bodin et al., Am J. Transplant. 2005; 5(8):1926-1933). BKV effects the renal tubular epithelial cells causing necrosis and lytic destruction with denudation of the basement membrane, which allows tubular fluid to accumulate in the interstitum, which results in interstitial fibrosis and tubular atrophy (Nickeleit et al., J. Am. Soc. Neprol. 1999; 10(5):1080-1089) all of which can affect the condition of the transplant. Patients may present with deterioration of renal function, tubule-interstitial nephritis and ureteric stenosis (Garner et al., Lancet 1971; 1(7712):1253-1257 and Hirsch Am. J. Transplant 2002; 2(1)25-30).

BKV can also cause pneumonitis, retinitis and meningoencephalitis in immunocompromised hosts (Reploeg et al., Clin. Infect. Dis. 2001; 33(2):191-202). BKV disease in hematopoietic stem cell transplant (HSCT) recipients typically manifests as hemorrhagic cystitis (HC), which can vary in severity. Viruria (but not viremia) and painful hematuria are associated with the clinical presentation of HC. The current standard of care is supportive in nature, involving primarily forced hydration/diuresis and pain management measures. The most severe cases require blood transfusions, clot evacuation, and can lead to death in some instances. HC of any cause (e.g. drug, radiation, viral) is relatively common among HSCT recipients but BKV-associated HC occurs in approximately 10-12% of patients usually within 6 months after transplantation. There are other viral etiologies of HC, with adenovirus being a more common cause of HC among pediatric HSCT recipients compared with adult HSCT recipients. BK virus has also been observed in other immunocompromised conditions such as systemic lupus erythromatosis, other solid organ transplants and in HIV/AIDS patients (Jiang et al., Virol. 2009; 384:266-273).

At this point, the treatment of BK nephropathy associated with organ transplantation is the reduction of immunosuppression in an attempt to prevent graft dysfunction and graft loss (Wiseman et al., Am. J. Kidney Dis. 2009; 54(1): 131-142 and Hirsch et al., Transplantation 2005; 79(1): 1277-1286). There are no fixed clinical regimes for the reduction, as reduction of the immunosuppression may help to prevent progression from viremia to the extensive damage associated with clinical nephropathy, but this also increases the risk of acute organ rejection (Brennan et al., Am. J. Transplant 2005; 5(3):582-594). Clinicians have reported the use of therapeutics such as cidofovir, leflunomide or quinolones in combination with the reduction of immunosuppressants, however the reports find this approach ineffective, with the added burden of managing additional side effects (Randhawa and Brennan Am. J. Transplant 2006; 6(9):2000-2005). As such, there is an unmet and useful need in the field for therapies that neutralize polyoma viruses such as BK and that can be used in an immunocompromised host.

JC virus is also a polyoma virus which is also highly prevalent in the population (80%), although JC virus is generally acquired later than BK virus (Padgett et al., J. Infect. Dis. 1973; 127(4):467-470 and Sabath et al., J. Infect. Dis. 2002; 186 Suppl. 2:5180-5186). After initial infection, JC virus establishes latency in the lymphoid organs and kidneys and when reactivated, invades the central nervous system via infected B-lymphocytes. Once in the CNS, the JC virus causes progressive multifocal leukoencephalopathy (PML), which is a progressive demyelinating central nervous system disorder. PML most often presents as an opportunistic infection in HIV/AIDS patients and has also been reported in immunosuppressed patients (Angstrom et al., Brain 1958; 81(1):93-111 and Garcia-Suarez et al., Am. J. Hematol. 2005; 80(4):271-281). PML patients present with confusion, mental status changes, gait ataxia, focal neurological defects such as hemi paresis, limb paresis and visual changes (Richardson E. P., N. Eng. J. Med. 1961; 265:815-823). The prognosis of patients with PML is poor and is especially poor in patients with HIV/AIDS (Antinori et al., J. Neurovirol. 2003; 9 suppl. 1:47-53). This further highlights the unmet and useful need in the field for therapies that neutralize polyoma viruses such as JC.

SUMMARY OF THE INVENTION

The present disclosure is directed to neutralizing antibodies to human polyomaviruses and/or fragments thereof, antibodies that recognize BK virus and/or JC virus and their respective VP1 pentamers and fragments thereof.

An antibody, wherein said antibody or antigen binding fragment thereof specifically binds VP1.

The antibody wherein said antibody or antigen binding fragment thereof specifically binds BK virus serotype I-serotype IV VP1. In one embodiment, the antibody or antigen binding fragment thereof binds to BKV serotype I VP1 with a binding affinity of 5.0 pM or less, binds to BKV serotype II VP1 with a binding affinity of 29.0 pM or less, binds to BKV serotype III VP1 with a binding affinity of 6.0 pM or less and/or binds to BKV serotype IV VP1 with a binding affinity of 185.0 pM or less. In another embodiment, the antibody or antigen binding fragment thereof further binds to JCV VP1 and specific JCV VP1 mutants with a binding affinity in the high nanomolar range.

The antibody wherein said antibody or antigen binding fragment specifically binds to a VP1 of Table 1. In one embodiment, the antibody or antigen binding fragment thereof binds to two or more of the VP1s of Table 1. In one embodiment, the antibody or antigen binding fragment thereof binds to BKV VP1 serotype I and BKV VP1 serotype II. In another embodiment, the antibody or antigen binding fragment thereof binds to BKV VP1 serotype I and BKV VP1 serotype III. In another embodiment, the antibody or antigen binding fragment thereof binds to BKV VP1 serotype I and BKV VP1 serotype IV. In another embodiment, the antibody or antigen binding fragment thereof binds to BKV VP1 serotype II and BKV VP1 serotype III. In another embodiment, the antibody or antigen binding fragment thereof binds to BKV VP1 serotype II and BKV VP1 serotype IV. In another embodiment, the antibody or antigen binding fragment thereof binds to BKV VP1 serotype I and JCV VP1. In a preferred embodiment, the antibody or antigen binding fragment thereof binds to BKV VP1 serotypes I, II, III and IV. Furthermore, the antibody or antigen binding fragment thereof binds to BKV VP1 serotypes I, II, III and IV and JCV VP1.

The antibody wherein said antibody or antigen binding fragment specifically binds to one or more amino acids residues of a VP1 epitope (SEQ ID NO:500 or SEQ ID NO:501). In one embodiment, the antibody or antigen binding fragment specifically binds to one or more of amino acids Y169, R170 and K172, e.g., binds to Y169 and R170, e.g., as determined by scanning alanine mutagenesis, as described herein.

The antibody wherein said antibody or antigen binding fragment comprises the sequence GFTFXNYWMT (SEQ ID NO. 507), wherein X can be any amino acid (Xaa). In another embodiment, X can be N (Asn), S (Ser), K (Lys) or Q (Gln).

An antibody, wherein said antibody or antigen binding fragment thereof comprises: (i) a heavy chain variable region that comprises (a) a HCDR1 (CDR-Complementarity Determining Region) of SEQ ID NO: 6, (b) a HCDR2 of SEQ ID NO:7, (c) a HCDR3 of SEQ ID NO:8 and a light chain variable region that comprises: (d) a LCDR1 of SEQ ID NO:16, (e) a LCDR2 of SEQ ID NO:17, and (f) a LCDR3 of SEQ ID NO:18;

(ii) a heavy chain variable region that comprises (a) a HCDR1 of SEQ ID NO:26, (b) a HCDR2 of SEQ ID NO:27, (c) a HCDR3 of SEQ ID NO:28; and a light chain variable region that comprises: (d) a LCDR1 of SEQ ID NO:36, (e) a LCDR2 of SEQ ID NO:37, and (f) a LCDR3 of SEQ ID NO:38;

(iii) a heavy chain variable region that comprises (a) a HCDR1 of SEQ ID NO:46, (b) a HCDR2 of SEQ ID NO:47, (c) a HCDR3 of SEQ ID NO:48; and a light chain variable region that comprises: (d) a LCDR1 of SEQ ID NO:56, (e) a LCDR2 of SEQ ID NO:57, and (f) a LCDR3 of SEQ ID NO:58;

(iv) a heavy chain variable region that comprises: (a) a HCDR1 of SEQ ID NO:66, (b) a HCDR2 of SEQ ID NO:67, (c) a HCDR3 of SEQ ID NO:68; and a light chain variable region that comprises: (d) a LCDR1 of SEQ ID NO:76, (e) a LCDR2 of SEQ ID NO:77, and (f) a LCDR3 of SEQ ID NO:78;

(v) a heavy chain variable region that comprises: (a) a HCDR1 of SEQ ID NO:86, (b) a HCDR2 of SEQ ID NO:87, (c) a HCDR3 of SEQ ID NO:88; and a light chain variable region that comprises: (d) a LCDR1 of SEQ ID NO:96, (e) a LCDR2 of SEQ ID NO:97, and (f) a LCDR3 of SEQ ID NO:98;

(vi) a heavy chain variable region that comprises: (a) a HCDR1 of SEQ ID NO:106, (b) a HCDR2 of SEQ ID NO: 107, (c) a HCDR3 of SEQ ID NO:108; and a light chain variable region that comprises: (d) a LCDR1 of SEQ ID NO:116, (e) a LCDR2 of SEQ ID NO:117, and (f) a LCDR3 of SEQ ID NO:118;

(vii) a heavy chain variable region that comprises: (a) a HCDR1 of SEQ ID NO:126, (b) a HCDR2 of SEQ ID NO: 127, (c) a HCDR3 of SEQ ID NO:128; and a light chain variable region that comprises: (d) a LCDR1 of SEQ ID NO:136, (e) a LCDR2 of SEQ ID NO:137, and (f) a LCDR3 of SEQ ID NO:138;

(viii) a heavy chain variable region that comprises: (a) a HCDR1 of SEQ ID NO:146, (b) a HCDR2 of SEQ ID NO:147, (c) a HCDR3 of SEQ ID NO:148; and a light chain variable region that comprises: (d) a LCDR1 of SEQ ID NO:156, (e) a LCDR2 of SEQ ID NO:157, and (f) a LCDR3 of SEQ ID NO:158;

(ix) a heavy chain variable region that comprises: (a) a HCDR1 of SEQ ID NO:166, (b) a HCDR2 of SEQ ID NO: 167, (c) a HCDR3 of SEQ ID NO:168; and a light chain variable region that comprises: (d) a LCDR1 of SEQ ID NO:176, (e) a LCDR2 of SEQ ID NO:177, and (f) a LCDR3 of SEQ ID NO: 178;

(x) a heavy chain variable region that comprises: (a) a HCDR1 of SEQ ID NO:186, (b) a HCDR2 of SEQ ID NO:187, (c) a HCDR3 of SEQ ID NO:188; and a light chain variable region that comprises: (d) a LCDR1 of SEQ ID NO:196, (e) a LCDR2 of SEQ ID NO:197, and (f) a LCDR3 of SEQ ID NO:198;

(xi) a heavy chain variable region that comprises: (a) a HCDR1 of SEQ ID NO:206, (b) a HCDR2 of SEQ ID NO:207, (c) a HCDR3 of SEQ ID NO:208; and a light chain variable region that comprises: (d) a LCDR1 of SEQ ID NO:216, (e) a LCDR2 of SEQ ID NO:217, and (f) a LCDR3 of SEQ ID NO:218;

(xii) a heavy chain variable region that comprises: (a) a HCDR1 of SEQ ID NO:226, (b) a HCDR2 of SEQ ID NO:227, (c) a HCDR3 of SEQ ID NO:228; and a light chain variable region that comprises: (d) a LCDR1 of SEQ ID NO:236, (e) a LCDR2 of SEQ ID NO:237, and (f) a LCDR3 of SEQ ID NO:238;

(xiii) a heavy chain variable region that comprises: (a) a HCDR1 of SEQ ID NO:246, (b) a HCDR2 of SEQ ID NO:247, (c) a HCDR3 of SEQ ID NO:248; and a light chain variable region that comprises: (d) a LCDR1 of SEQ ID NO:256, (e) a LCDR2 of SEQ ID NO:257, and (f) a LCDR3 of SEQ ID NO:258;

(xiv) a heavy chain variable region that comprises: (a) a HCDR1 of SEQ ID NO:266, (b) a HCDR2 of SEQ ID NO:267, (c) a HCDR3 of SEQ ID NO:268; and a light chain variable region that comprises: (d) a LCDR1 of SEQ ID NO: 276, (e) a LCDR2 of SEQ ID NO:277, and (f) a LCDR3 of SEQ ID NO:278;

(xv) a heavy chain variable region that comprises: (a) a HCDR1 of SEQ ID NO:286, (b) a HCDR2 of SEQ ID NO:287, (c) a HCDR3 of SEQ ID NO:288; and a light chain variable region that comprises: (d) a LCDR1 of SEQ ID NO:296, (e) a LCDR2 of SEQ ID NO:297, and (f) a LCDR3 of SEQ ID NO:298;

(xvi) a heavy chain variable region that comprises: (a) a HCDR1 of SEQ ID NO:306, (b) a HCDR2 of SEQ ID NO:307, (c) a HCDR3 of SEQ ID NO:308; and a light chain variable region that comprises: (d) a LCDR1 of SEQ ID NO:314, (e) a LCDR2 of SEQ ID NO:315, and (f) a LCDR3 of SEQ ID NO:316;

(xvii) a heavy chain variable region that comprises: (a) a HCDR1 of SEQ ID NO:322, (b) a HCDR2 of SEQ ID NO:323, (c) a HCDR3 of SEQ ID NO:324; and a light chain variable region that comprises: (d) a LCDR1 of SEQ ID NO:332, (e) a LCDR2 of SEQ ID NO:333, and (f) a LCDR3 of SEQ ID NO:334;

(xviii) a heavy chain variable region that comprises: (a) a HCDR1 of SEQ ID NO:342, (b) a HCDR2 of SEQ ID NO:343, (c) a HCDR3 of SEQ ID NO:344; and a light chain variable region that comprises: (d) a LCDR1 of SEQ ID NO:349, (e) a LCDR2 of SEQ ID NO:350, and (f) a LCDR3 of SEQ ID NO:351;

(xix) a heavy chain variable region that comprises: (a) a HCDR1 of SEQ ID NO:356, (b) a HCDR2 of SEQ ID NO:357, (c) a HCDR3 of SEQ ID NO:358; and a light chain variable region that comprises: (d) a LCDR1 of SEQ ID NO:363, (e) a LCDR2 of SEQ ID NO:364, and (f) a LCDR3 of SEQ ID NO:365;

(xx) a heavy chain variable region that comprises: (a) a HCDR1 of SEQ ID NO:370, (b) a HCDR2 of SEQ ID NO:371, (c) a HCDR3 of SEQ ID NO:372; and a light chain variable region that comprises: (d) a LCDR1 of SEQ ID NO:377, (e) a LCDR2 of SEQ ID NO:378, and (f) a LCDR3 of SEQ ID NO:379;

(xxi) a heavy chain variable region that comprises: (a) a HCDR1 of SEQ ID NO:384, (b) a HCDR2 of SEQ ID NO:385, (c) a HCDR3 of SEQ ID NO:386; and a light chain variable region that comprises: (d) a LCDR1 of SEQ ID NO:391, (e) a LCDR2 of SEQ ID NO:392, and (f) a LCDR3 of SEQ ID NO:393;

(xxii) a heavy chain variable region that comprises: (a) a HCDR1 of SEQ ID NO:398, (b) a HCDR2 of SEQ ID NO:399, (c) a HCDR3 of SEQ ID NO:400; and a light chain variable region that comprises: (d) a LCDR1 of SEQ ID NO:405, (e) a LCDR2 of SEQ ID NO:406, and (f) a LCDR3 of SEQ ID NO:407;

(xxiii) a heavy chain variable region that comprises: (a) a HCDR1 of SEQ ID NO:412, (b) a HCDR2 of SEQ ID NO:413, (c) a HCDR3 of SEQ ID NO:414; and a light chain variable region that comprises: (d) a LCDR1 of SEQ ID NO:419, (e) a LCDR2 of SEQ ID NO:420, and (f) a LCDR3 of SEQ ID NO:421;

(xxiv) a heavy chain variable region that comprises: (a) a HCDR1 of SEQ ID NO:426, (b) a HCDR2 of SEQ ID NO:427, (c) a HCDR3 of SEQ ID NO:428; and a light chain variable region that comprises: (d) a LCDR1 of SEQ ID NO:433, (e) a LCDR2 of SEQ ID NO:434, and (f) a LCDR3 of SEQ ID NO:435;

(xxv) a heavy chain variable region that comprises: (a) a HCDR1 of SEQ ID NO:440, (b) a HCDR2 of SEQ ID NO:441, (c) a HCDR3 of SEQ ID NO:442; and a light chain variable region that comprises: (d) a LCDR1 of SEQ ID NO:447, (e) a LCDR2 of SEQ ID NO:448, and (f) a LCDR3 of SEQ ID NO:449;

(xxvi) a heavy chain variable region that comprises: (a) a HCDR1 of SEQ ID NO:454, (b) a HCDR2 of SEQ ID NO:455, (c) a HCDR3 of SEQ ID NO:456; and a light chain variable region that comprises: (d) a LCDR1 of SEQ ID NO:461, (e) a LCDR2 of SEQ ID NO:462, and (f) a LCDR3 of SEQ ID NO:463;

(xxvii) a heavy chain variable region that comprises: (a) a HCDR1 of SEQ ID NO:468, (b) a HCDR2 of SEQ ID NO:469, (c) a HCDR3 of SEQ ID NO:470; and a light chain variable region that comprises: (d) a LCDR1 of SEQ ID NO:475, (e) a LCDR2 of SEQ ID NO:476, and (f) a LCDR3 of SEQ ID NO:477;

(xxviii) a heavy chain variable region that comprises: (a) a HCDR1 of SEQ ID NO:482, (b) a HCDR2 of SEQ ID NO:483, (c) a HCDR3 of SEQ ID NO:484; and a light chain variable region that comprises: (d) a LCDR1 of SEQ ID NO:489, (e) a LCDR2 of SEQ ID NO:490, and (f) a LCDR3 of SEQ ID NO:491.

An antibody, wherein said antibody or antigen binding fragment thereof comprises: (i) a heavy chain variable region that comprises (a) a HCDR1 (CDR-Complementarity Determining Region) of SEQ ID NO: 508, (b) a HCDR2 of SEQ ID NO:509, (c) a HCDR3 of SEQ ID NO:510 and a light chain variable region that comprises: (d) a LCDR1 of SEQ ID NO:511, (e) a LCDR2 of SEQ ID NO:512, and (f) a LCDR3 of SEQ ID NO:513;

(ii) a heavy chain variable region that comprises (a) a HCDR1 of SEQ ID NO:514, (b) a HCDR2 of SEQ ID NO:515, (c) a HCDR3 of SEQ ID NO:516; and a light chain variable region that comprises: (d) a LCDR1 of SEQ ID NO:517, (e) a LCDR2 of SEQ ID NO:518, and (f) a LCDR3 of SEQ ID NO:519;

(iii) a heavy chain variable region that comprises (a) a HCDR1 of SEQ ID NO:520, (b) a HCDR2 of SEQ ID NO:521, (c) a HCDR3 of SEQ ID NO:522; and a light chain variable region that comprises: (d) a LCDR1 of SEQ ID NO:523, (e) a LCDR2 of SEQ ID NO:524, and (f) a LCDR3 of SEQ ID NO:525;

(iv) a heavy chain variable region that comprises: (a) a HCDR1 of SEQ ID NO:526, (b) a HCDR2 of SEQ ID NO:527, (c) a HCDR3 of SEQ ID NO:528; and a light chain variable region that comprises: (d) a LCDR1 of SEQ ID NO:529, (e) a LCDR2 of SEQ ID NO:530, and (f) a LCDR3 of SEQ ID NO:531;

(v) a heavy chain variable region that comprises: (a) a HCDR1 of SEQ ID NO:532, (b) a HCDR2 of SEQ ID NO:533, (c) a HCDR3 of SEQ ID NO:534; and a light chain variable region that comprises: (d) a LCDR1 of SEQ ID NO:535, (e) a LCDR2 of SEQ ID NO:536, and (f) a LCDR3 of SEQ ID NO:537;

(vi) a heavy chain variable region that comprises: (a) a HCDR1 of SEQ ID NO:538, (b) a HCDR2 of SEQ ID NO:539, (c) a HCDR3 of SEQ ID NO:540; and a light chain variable region that comprises: (d) a LCDR1 of SEQ ID NO:541, (e) a LCDR2 of SEQ ID NO:542, and (f) a LCDR3 of SEQ ID NO:543.

The antibody wherein at least one amino acid within a CDR is substituted by a corresponding residue of a corresponding CDR of another anti-VP1 antibody of Table 2.

The antibody wherein one or two amino acids within a CDR have been modified, deleted or substituted.

The antibody that retains at least 90, 91, 92, 93, 94, 95, 96, 97, 98 or 99% identity over either the variable heavy chain region or the variable light chain region.

The antibody that comprises the modifications in Table 3.

The antibody wherein the antibody is a monoclonal antibody, a chimeric antibody, a humanized antibody, a human engineered antibody, a human antibody, a single chain antibody (scFv) or an antibody fragment.

The antibody wherein said antibody or antigen binding fragment thereof comprises:

(i) a heavy chain variable region (vH) that comprises SEQ ID NO:12, and a light chain variable region (vL) that comprises SEQ ID NO: 22;

(ii) a heavy chain variable region (vH) that comprises SEQ ID NO: 32, and a light chain variable region (vL) that comprises SEQ ID NO: 42;

(iii) a heavy chain variable region (vH) that comprises SEQ ID NO: 52, and a light chain variable region (vL) that comprises SEQ ID NO: 62;

(iv) a heavy chain variable region (vH) that comprises SEQ ID NO: 72, and a light chain variable region (vL) that comprises SEQ ID NO: 82;

(v) a heavy chain variable region (vH) that comprises SEQ ID NO:92, and a light chain variable region (vL) that comprises SEQ ID NO:102;

(vi) a heavy chain variable region (vH) that comprises SEQ ID NO:112, and a light chain variable region (vL) that comprises SEQ ID NO:122;

(vii) a heavy chain variable region (vH) that comprises SEQ ID NO: 132, and a light chain variable region (vL) that comprises SEQ ID NO:142;

(viii) a heavy chain variable region (vH) that comprises SEQ ID NO: 152, and a light chain variable region (vL) that comprises SEQ ID NO:162;

(ix) a heavy chain variable region (vH) that comprises SEQ ID NO:172, and a light chain variable region (vL) that comprises SEQ ID NO:182;

(x) a heavy chain variable region (vH) that comprises SEQ ID NO: 192, and a light chain variable region (vL) that comprises SEQ ID NO:202;

(xi) a heavy chain variable region (vH) that comprises SEQ ID NO:212, and a light chain variable region (vL) that comprises SEQ ID NO:222;

(xii) a heavy chain variable region (vH) that comprises SEQ ID NO:232, and a light chain variable region (vL) that comprises SEQ ID NO:242;

(xiii) a heavy chain variable region (vH) that comprises SEQ ID NO:252, and a light chain variable region (vL) that comprises SEQ ID NO:262;

(xiv) a heavy chain variable region (vH) that comprises SEQ ID NO:272, and a light chain variable region (vL) that comprises SEQ ID NO:282;

(xv) a heavy chain variable region (vH) that comprises SEQ ID NO:292, and a light chain variable region (vL) that comprises SEQ ID NO:302;

(xvi) a heavy chain variable region (vH) that comprises SEQ ID NO:312, and a light chain variable region (vL) that comprises SEQ ID NO:320;

(xvii) a heavy chain variable region (vH) that comprises SEQ ID NO:328, and a light chain variable region (vL) that comprises SEQ ID NO:338;

(xviii) a heavy chain variable region (vH) that comprises SEQ ID NO:348, and a light chain variable region (vL) that comprises SEQ ID NO:355;

(xix) a heavy chain variable region (vH) that comprises SEQ ID NO:362, and a light chain variable region (vL) that comprises SEQ ID NO:369;

(xx) a heavy chain variable region (vH) that comprises SEQ ID NO:376, and a light chain variable region (vL) that comprises SEQ ID NO:383;

(xxi) a heavy chain variable region (vH) that comprises SEQ ID NO:390, and a light chain variable region (vL) that comprises SEQ ID NO:397;

(xxii) a heavy chain variable region (vH) that comprises SEQ ID NO:404, and a light chain variable region (vL) that comprises SEQ ID NO:411;

(xxiii) a heavy chain variable region (vH) that comprises SEQ ID NO:418, and a light chain variable region (vL) that comprises SEQ ID NO:425;

(xxiv) a heavy chain variable region (vH) that comprises SEQ ID NO:432, and a light chain variable region (vL) that comprises SEQ ID NO:439;

(xxv) a heavy chain variable region (vH) that comprises SEQ ID NO: 446, and a light chain variable region (vL) that comprises SEQ ID NO:453;

(xxvi) a heavy chain variable region (vH) that comprises SEQ ID NO:460, and a light chain variable region (vL) that comprises SEQ ID NO:467;

(xxvii) a heavy chain variable region (vH) that comprises SEQ ID NO:474, and a light chain variable region (vL) that comprises SEQ ID NO:481; or (xxviii) a heavy chain variable region (vH) that comprises SEQ ID NO:488, and a light chain variable region (vL) that comprises SEQ ID NO:495.

The antibody that retains at least 90, 91, 92, 93, 94, 95, 96, 97, 98 or 99% identity over either the variable light or variable heavy region.

The antibody wherein one, two, three, four or five, but less than 10 amino acids within the variable light or variable heavy region have been modified, deleted or substituted.

The antibody wherein the antibody is a monoclonal antibody, a chimeric antibody, a humanized antibody, a human engineered antibody, a human antibody, a single chain antibody (scFv) or an antibody fragment.

The antibody of any of the preceding embodiments wherein the antibody or fragment thereof has reduced glycosylation or no glycosylation or is hypofucosylated.

A composition comprising a plurality of an antibody or antigen binding fragment of any of the preceding embodiments, wherein at least 0.05%, 0.1%, 0.5%, 1%, 2%, 3%, 5% or more of the antibodies in the composition have an α2,3-linked sialic acid residue, and wherein said antibody or antigen binding fragment thereof comprises: (i) a heavy chain variable region that comprises (a) a HCDR1 (CDR-Complementarity Determining Region) of SEQ ID NO: 6, (b) a HCDR2 of SEQ ID NO:7, (c) a HCDR3 of SEQ ID NO:8 and a light chain variable region that comprises: (d) a LCDR1 of SEQ ID NO:16, (e) a LCDR2 of SEQ ID NO:17, and (f) a LCDR3 of SEQ ID NO:18;

(ii) a heavy chain variable region that comprises (a) a HCDR1 of SEQ ID NO:26, (b) a HCDR2 of SEQ ID NO:27, (c) a HCDR3 of SEQ ID NO:28; and a light chain variable region that comprises: (d) a LCDR1 of SEQ ID NO:36, (e) a LCDR2 of SEQ ID NO:37, and (f) a LCDR3 of SEQ ID NO:38;

(iii) a heavy chain variable region that comprises (a) a HCDR1 of SEQ ID NO:46, (b) a HCDR2 of SEQ ID NO:47, (c) a HCDR3 of SEQ ID NO:48; and a light chain variable region that comprises: (d) a LCDR1 of SEQ ID NO:56, (e) a LCDR2 of SEQ ID NO:57, and (f) a LCDR3 of SEQ ID NO:58;

(iv) a heavy chain variable region that comprises: (a) a HCDR1 of SEQ ID NO:66, (b) a HCDR2 of SEQ ID NO:67, (c) a HCDR3 of SEQ ID NO:68; and a light chain variable region that comprises: (d) a LCDR1 of SEQ ID NO:76, (e) a LCDR2 of SEQ ID NO:77, and (f) a LCDR3 of SEQ ID NO:78;

(v) a heavy chain variable region that comprises: (a) a HCDR1 of SEQ ID NO:86, (b) a HCDR2 of SEQ ID NO:87, (c) a HCDR3 of SEQ ID NO:88; and a light chain variable region that comprises: (d) a LCDR1 of SEQ ID NO:96, (e) a LCDR2 of SEQ ID NO:97, and (f) a LCDR3 of SEQ ID NO:98;

(vi) a heavy chain variable region that comprises: (a) a HCDR1 of SEQ ID NO:106, (b) a HCDR2 of SEQ ID NO: 107, (c) a HCDR3 of SEQ ID NO:108; and a light chain variable region that comprises: (d) a LCDR1 of SEQ ID NO:116, (e) a LCDR2 of SEQ ID NO:117, and (f) a LCDR3 of SEQ ID NO:118;

(vii) a heavy chain variable region that comprises: (a) a HCDR1 of SEQ ID NO:126, (b) a HCDR2 of SEQ ID NO: 127, (c) a HCDR3 of SEQ ID NO:128; and a light chain variable region that comprises: (d) a LCDR1 of SEQ ID NO:136, (e) a LCDR2 of SEQ ID NO:137, and (f) a LCDR3 of SEQ ID NO:138;

(viii) a heavy chain variable region that comprises: (a) a HCDR1 of SEQ ID NO:146, (b) a HCDR2 of SEQ ID NO:147, (c) a HCDR3 of SEQ ID NO:148; and a light chain variable region that comprises: (d) a LCDR1 of SEQ ID NO:156, (e) a LCDR2 of SEQ ID NO:157, and (f) a LCDR3 of SEQ ID NO:158;

(ix) a heavy chain variable region that comprises: (a) a HCDR1 of SEQ ID NO:166, (b) a HCDR2 of SEQ ID NO: 167, (c) a HCDR3 of SEQ ID NO:168; and a light chain variable region that comprises: (d) a LCDR1 of SEQ ID NO:176, (e) a LCDR2 of SEQ ID NO:177, and (f) a LCDR3 of SEQ ID NO:178;

(x) a heavy chain variable region that comprises: (a) a HCDR1 of SEQ ID NO:186, (b) a HCDR2 of SEQ ID NO:187, (c) a HCDR3 of SEQ ID NO:188; and a light chain variable region that comprises: (d) a LCDR1 of SEQ ID NO:196, (e) a LCDR2 of SEQ ID NO:197, and (f) a LCDR3 of SEQ ID NO:198;

(xi) a heavy chain variable region that comprises: (a) a HCDR1 of SEQ ID NO:206, (b) a HCDR2 of SEQ ID NO:207, (c) a HCDR3 of SEQ ID NO:208; and a light chain variable region that comprises: (d) a LCDR1 of SEQ ID NO:216, (e) a LCDR2 of SEQ ID NO:217, and (f) a LCDR3 of SEQ ID NO:218;

(xii) a heavy chain variable region that comprises: (a) a HCDR1 of SEQ ID NO:226, (b) a HCDR2 of SEQ ID NO:227, (c) a HCDR3 of SEQ ID NO:228; and a light chain variable region that comprises: (d) a LCDR1 of SEQ ID NO:236, (e) a LCDR2 of SEQ ID NO:237, and (f) a LCDR3 of SEQ ID NO:238;

(xiii) a heavy chain variable region that comprises: (a) a HCDR1 of SEQ ID NO:246, (b) a HCDR2 of SEQ ID NO:247, (c) a HCDR3 of SEQ ID NO:248; and a light chain variable region that comprises: (d) a LCDR1 of SEQ ID NO:256, (e) a LCDR2 of SEQ ID NO:257, and (f) a LCDR3 of SEQ ID NO:258;

(xiv) a heavy chain variable region that comprises: (a) a HCDR1 of SEQ ID NO:266, (b) a HCDR2 of SEQ ID NO:267, (c) a HCDR3 of SEQ ID NO:268; and a light chain variable region that comprises: (d) a LCDR1 of SEQ ID NO: 276, (e) a LCDR2 of SEQ ID NO:277, and (f) a LCDR3 of SEQ ID NO:278;

(xv) a heavy chain variable region that comprises: (a) a HCDR1 of SEQ ID NO:286, (b) a HCDR2 of SEQ ID NO:287, (c) a HCDR3 of SEQ ID NO:288; and a light chain variable region that comprises: (d) a LCDR1 of SEQ ID NO:296, (e) a LCDR2 of SEQ ID NO:297, and (f) a LCDR3 of SEQ ID NO:298;

(xvi) a heavy chain variable region that comprises: (a) a HCDR1 of SEQ ID NO:306, (b) a HCDR2 of SEQ ID NO:307, (c) a HCDR3 of SEQ ID NO:308; and a light chain variable region that comprises: (d) a LCDR1 of SEQ ID NO:314, (e) a LCDR2 of SEQ ID NO:315, and (f) a LCDR3 of SEQ ID NO:316;

(xvii) a heavy chain variable region that comprises: (a) a HCDR1 of SEQ ID NO:322, (b) a HCDR2 of SEQ ID NO:323, (c) a HCDR3 of SEQ ID NO:324; and a light chain variable region that comprises: (d) a LCDR1 of SEQ ID NO:332, (e) a LCDR2 of SEQ ID NO:333, and (f) a LCDR3 of SEQ ID NO:334;

(xviii) a heavy chain variable region that comprises: (a) a HCDR1 of SEQ ID NO:342, (b) a HCDR2 of SEQ ID NO:343, (c) a HCDR3 of SEQ ID NO:344; and a light chain variable region that comprises: (d) a LCDR1 of SEQ ID NO:349, (e) a LCDR2 of SEQ ID NO:350, and (f) a LCDR3 of SEQ ID NO:351;

(xix) a heavy chain variable region that comprises: (a) a HCDR1 of SEQ ID NO:356, (b) a HCDR2 of SEQ ID NO:357, (c) a HCDR3 of SEQ ID NO:358; and a light chain variable region that comprises: (d) a LCDR1 of SEQ ID NO:363, (e) a LCDR2 of SEQ ID NO:364, and (f) a LCDR3 of SEQ ID NO:365;

(xx) a heavy chain variable region that comprises: (a) a HCDR1 of SEQ ID NO:370, (b) a HCDR2 of SEQ ID NO:371, (c) a HCDR3 of SEQ ID NO:372; and a light chain variable region that comprises: (d) a LCDR1 of SEQ ID NO:377, (e) a LCDR2 of SEQ ID NO:378, and (f) a LCDR3 of SEQ ID NO:379;

(xxi) a heavy chain variable region that comprises: (a) a HCDR1 of SEQ ID NO:384, (b) a HCDR2 of SEQ ID NO:385, (c) a HCDR3 of SEQ ID NO:386; and a light chain variable region that comprises: (d) a LCDR1 of SEQ ID NO:391, (e) a LCDR2 of SEQ ID NO:392, and (f) a LCDR3 of SEQ ID NO:393;

(xxii) a heavy chain variable region that comprises: (a) a HCDR1 of SEQ ID NO:398, (b) a HCDR2 of SEQ ID NO:399, (c) a HCDR3 of SEQ ID NO:400; and a light chain variable region that comprises: (d) a LCDR1 of SEQ ID NO:405, (e) a LCDR2 of SEQ ID NO:406, and (f) a LCDR3 of SEQ ID NO:407;

(xxiii) a heavy chain variable region that comprises: (a) a HCDR1 of SEQ ID NO:412, (b) a HCDR2 of SEQ ID NO:413, (c) a HCDR3 of SEQ ID NO:414; and a light chain variable region that comprises: (d) a LCDR1 of SEQ ID NO:419, (e) a LCDR2 of SEQ ID NO:420, and (f) a LCDR3 of SEQ ID NO:421;

(xxiv) a heavy chain variable region that comprises: (a) a HCDR1 of SEQ ID NO:426, (b) a HCDR2 of SEQ ID NO:427, (c) a HCDR3 of SEQ ID NO:428; and a light chain variable region that comprises: (d) a LCDR1 of SEQ ID NO:433, (e) a LCDR2 of SEQ ID NO:434, and (f) a LCDR3 of SEQ ID NO:435;

(xxv) a heavy chain variable region that comprises: (a) a HCDR1 of SEQ ID NO:440, (b) a HCDR2 of SEQ ID NO:441, (c) a HCDR3 of SEQ ID NO:442; and a light chain variable region that comprises: (d) a LCDR1 of SEQ ID NO:447, (e) a LCDR2 of SEQ ID NO:448, and (f) a LCDR3 of SEQ ID NO:449;

(xxvi) a heavy chain variable region that comprises: (a) a HCDR1 of SEQ ID NO:454, (b) a HCDR2 of SEQ ID NO:455, (c) a HCDR3 of SEQ ID NO:456; and a light chain variable region that comprises: (d) a LCDR1 of SEQ ID NO:461, (e) a LCDR2 of SEQ ID NO:462, and (f) a LCDR3 of SEQ ID NO:463;

(xxvii) a heavy chain variable region that comprises: (a) a HCDR1 of SEQ ID NO:468, (b) a HCDR2 of SEQ ID NO:469, (c) a HCDR3 of SEQ ID NO:470; and a light chain variable region that comprises: (d) a LCDR1 of SEQ ID NO:475, (e) a LCDR2 of SEQ ID NO:476, and (f) a LCDR3 of SEQ ID NO:477;

(xxviii) a heavy chain variable region that comprises: (a) a HCDR1 of SEQ ID NO:482, (b) a HCDR2 of SEQ ID NO:483, (c) a HCDR3 of SEQ ID NO:484; and a light chain variable region that comprises: (d) a LCDR1 of SEQ ID NO:489, (e) a LCDR2 of SEQ ID NO:490, and (f) a LCDR3 of SEQ ID NO:491.

A composition comprising a plurality of an antibody or antigen binding fragment of any of the preceding embodiments, wherein none of the antibodies comprise a bisecting GlcNAc.

A pharmaceutical composition comprising the antibody or fragment thereof, of any of the preceding embodiments wherein the composition is prepared as a lyophilisate.

A pharmaceutical composition comprising the antibody or fragment thereof of any of the preceeding embodiments and a pharmaceutically acceptable carrier. In one embodiment, the carrier is a histidine buffer. In one embodiment, the pharmaceutical composition comprises a sugar (e.g., sucrose).

A method of neutralizing a BK virus or JC virus infection comprising administering via injection or infusion to a patient in need an effective amount of the antibody or the pharmaceutical composition. The method wherein the antibody or antigen binding fragment thereof neutralizes BKV serotype I and BKV serotype II. In another embodiment, the antibody or antigen binding fragment thereof neutralizes BKV serotype I and BKV serotype III. In another embodiment, the antibody or antigen binding fragment thereof neutralizes BKV serotype I and BKV serotype IV. In another embodiment, the antibody or antigen binding fragment thereof neutralizes BKV serotype II and BKV serotype III. In another embodiment, the antibody or antigen binding fragment thereof neutralizes BKV serotype II and BKV serotype IV. In another embodiment, the antibody or antigen binding fragment thereof neutralizes BKV serotype I and JCV. In a specific embodiment, the antibody or antigen binding fragment thereof neutralizes BKV serotypes I, II, III and IV. Furthermore, the antibody or antigen binding fragment thereof neutralizes BKV serotypes I, II, III and IV and JCV. In a preferred embodiment, anti-VP1 antibodies neutralized infection by all four serotypes of BKV (I-IV), these anti-VP1 antibodies specifically include P8D11, the modifications of P8D11, and EBB-C1975-B5.

A method of treating or reducing the likelihood of a BK virus or JC virus associated disorder, comprising administering via injection or infusion to a patient in need an effective amount of the antibody or the pharmaceutical composition, and wherein the disorder is: nephropathy, BKVAN, hemorrhagic cystitis (HC), Progressive Multifocal Leukoencephalopathy (PML), granule cell neuronopathy (GCN), interstitial kidney disease, ureteral stenosis, vasculitis, colitis, retinitis, meningitis, and immune reconstitution inflammatory syndrome (IRIS).

The method wherein the antibody or composition is reconstituted prior to injection or infusion.

The method wherein the antibody or the pharmaceutical composition is administered in combination with another therapeutic agent.

The method wherein the therapeutic agent is an immunosuppressive agent.

The method wherein the immunosuppressive agent is a monophosphate dehydrogenase inhibitor, a purine synthesis inhibitor, a calcineurin inhibitor or an mTOR inhibitor.

The method wherein the immunosuppressive agent is mycophenolate mofetil (MMF), mycophenolate sodium, azathioprine, tacrolimus, sirolimus or cyclosporine.

The method wherein the therapeutic agent is an additional anti-VP1 antibody.

The antibody or fragment thereof of any of the preceding embodiments for use as a medicament.

The antibody or fragment thereof or the pharmaceutical composition, for use in the neutralization of a BK virus or JC virus infection.

The antibody or fragment thereof, or the pharmaceutical composition, for use in the treatment or reducing the likelihood of: nephropathy, BKVAN, hemorrhagic cystitis (HC), Progressive Multifocal Leukoencephalopathy (PML), granule cell neuronopathy (GCN), interstitial kidney disease, ureteral stenosis, vasculitis, colitis, retinitis, meningitis, and immune reconstitution inflammatory syndrome (IRIS).

The use of the antibody or fragment thereof, administered in combination with another therapeutic agent.

The use of the antibody or fragment thereof wherein the therapeutic agent is an immunosuppressive agent.

The use of the antibody or fragment thereof wherein the immunosuppressive agent is a monophosphate dehydrogenase inhibitor, a purine synthesis inhibitor, a calcineurin inhibitor or an mTOR inhibitor.

The use of the antibody or fragment thereof, wherein the immunosuppressive agent is: mycophenolate mofetil (MMF), mycophenolate sodium, azathioprine, tacrolimus, sirolimus or cyclosporine.

A nucleic acid that encodes the antibody or antigen binding fragment of any of the preceding embodiments.

A vector comprising the nucleic acid.

A host cell comprising the vector.

A process for producing an antibody or antigen binding fragment comprising cultivating the host cell and recovering the antibody from the culture.

A diagnostic reagent comprising the antibody or antigen binding fragment thereof which is labeled.

The diagnostic reagent wherein the label is selected from the group consisting of a radiolabel, a fluorophore, a chromophore, an imaging agent, and a metal ion.

Definitions

Unless stated otherwise, the following terms and phrases as used herein are intended to have the following meanings:

The term "antibody" as used herein refers to a polypeptide of the immunoglobulin family that is capable of binding a corresponding antigen non-covalently, reversibly, and in a specific manner. For example, a naturally occurring IgG antibody is a tetramer comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antibody" includes, but is not limited to, monoclonal antibodies, human antibodies, humanized antibodies, camelid antibodies, chimeric antibodies, and anti-idiotypic (anti-Id) antibodies (including, e.g., anti-Id antibodies to antibodies of the present disclosure). The antibodies can be of any isotype/class (e.g., IgG, IgE, IgM, IgD, IgA and IgY), or subclass (e.g., IgG1, IgG2, IgG3, IgG4, IgA1 and IgA2).

"Complementarity-determining domains" or "complementary-determining regions" ("CDRs") interchangeably refer to the hypervariable regions of VL and VH. The CDRs are the target protein-binding site of the antibody chains that harbors specificity for such target protein. There are three CDRs (CDR1-3, numbered sequentially from the N-terminus) in each human VL or VH, constituting about 15-20% of the variable domains. CDRs can be referred to by their region and order. For example, "VHCDR1" or "HCDR1" both refer to the first CDR of the heavy chain variable region. The CDRs are structurally complementary to the epitope of the target protein and are thus directly responsible for the binding specificity. The remaining stretches of the VL or VH, the so-called framework regions, exhibit less variation in amino acid sequence (Kuby, Immunology, 4th ed., Chapter 4. W.H. Freeman & Co., New York, 2000).

The positions of the CDRs and framework regions can be determined using various well known definitions in the art, e.g., Kabat, Chothia, and AbM (see, e.g., Johnson et al., Nucleic Acids Res., 29:205-206 (2001); Chothia and Lesk, J. Mol. Biol., 196:901-917 (1987); Chothia et al., Nature, 342:877-883 (1989); Chothia et al., J. Mol. Biol., 227:799-817 (1992); Al-Lazikani et al., J. Mol. Biol., 273:927-748 (1997)). Definitions of antigen combining sites are also described in the following: Ruiz et al., Nucleic Acids Res., 28:219-221 (2000); and Lefranc, M. P., Nucleic Acids Res., 29:207-209 (2001); MacCallum et al., J. Mol. Biol., 262: 732-745 (1996); and Martin et al., Proc. Natl. Acad. Sci. USA, 86:9268-9272 (1989); Martin et al., Methods Enzymol., 203:121-153 (1991); and Rees et al., In Sternberg M. J. E. (ed.), Protein Structure Prediction, Oxford University Press, Oxford, 141-172 (1996).). In a combined Kabat and Chothia numbering scheme, in some embodiments, the CDRs correspond to the amino acid residues that are part of a Kabat CDR, a Chothia CDR, or both. For instance, in some embodiments, the CDRs correspond to amino acid residues 26-35 (HC CDR1), 50-65 (HC CDR2), and 95-102 (HC CDR3) in a VH, e.g., a mammalian VH, e.g., a human VH; and amino acid residues 24-34 (LC CDR1), 50-56 (LC CDR2), and 89-97 (LC CDR3) in a VL, e.g., a mammalian VL, e.g., a human VL.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention, the numbering of the constant region domains increases as they become more distal from the antigen binding site or amino-terminus of the antibody. The N-terminus is a variable region and at the C-terminus is a constant region; the CH3 and CL domains actually comprise the carboxy-terminal domains of the heavy and light chain, respectively.

The term "antigen binding fragment," as used herein, refers to one or more portions of an antibody that retain the ability to specifically interact with (e.g., by binding, steric hindrance, stabilizing/destabilizing, spatial distribution) an epitope of an antigen. Examples of binding fragments include, but are not limited to, single-chain Fvs (scFv), disulfide-linked Fvs (sdFv), Fab fragments, F(ab') fragments, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., Nature 341:544-546, 1989), which consists of a VH domain; and an isolated complementarity determining region (CDR), or other epitope-binding fragments of an antibody.

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv ("scFv"); see, e.g., Bird et al., Science 242:423-426, 1988; and Huston et al., Proc. Natl. Acad. Sci. 85:5879-5883, 1988). Such single chain antibodies are also intended to be encompassed within the term "antigen binding fragment." These antigen binding fragments are obtained using conventional techniques known to those of skill in the art, and the fragments are screened for utility in the same manner as are intact antibodies.

Antigen binding fragments can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can be grafted into scaffolds based on polypeptides such as fibronectin type III (Fn3) (see U.S. Pat. No. 6,703,199, which describes fibronectin polypeptide monobodies).

Antigen binding fragments can be incorporated into single chain molecules comprising a pair of tandem Fv segments (VH-CH1-VH-CH1) which, together with complementary light chain polypeptides, form a pair of antigen binding regions (Zapata et al., Protein Eng. 8:1057-1062, 1995; and U.S. Pat. No. 5,641,870).

The term "monoclonal antibody" or "monoclonal antibody composition" as used herein refers to polypeptides, including antibodies and antigen binding fragments that have substantially identical amino acid sequence or are derived from the same genetic source. This term also includes preparations of antibody molecules of single molecular composition. A monoclonal antibody composition displays a single binding specificity and affinity for a particular epitope.

The term "human antibody," as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., J. Mol. Biol. 296:57-86, 2000).

The human antibodies of the present disclosure can include amino acid residues not encoded by human sequences (e.g., mutations introduced by random or site-specific mutagenesis in vitro or by somatic mutation in vivo, or a conservative substitution to promote stability or manufacturing).

The term "recognize" as used herein refers to an antibody or antigen binding fragment thereof that finds and interacts (e.g., binds) with its epitope, whether that epitope is linear or conformational. The term "epitope" refers to a site on an antigen to which an antibody or antigen binding fragment of the disclosure specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art, for example, x-ray crystallography and 2-dimensional nuclear magnetic resonance (see, e.g., Epitope Mapping Protocols in Methods in Molecular Biology, Vol. 66, G. E. Morris, Ed. (1996)). A "paratope" is the part of the antibody which recognizes the epitope of the antigen.

The phrase "specifically binds" or "selectively binds," when used in the context of describing the interaction between an antigen (e.g., a protein) and an antibody, antibody fragment, or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under certain designated immunoassay conditions, the antibodies or binding agents with a particular binding specificity bind to a particular antigen at least two times the background and do not substantially bind in a significant amount to other antigens present in the sample. In one aspect, under designated immunoassay conditions, the antibody or binding agent with a particular binding specificity binds to a particular antigen at least ten (10) times the background and does not substantially bind in a significant amount to other antigens present in the sample. Specific binding to an antibody or binding agent under such conditions may require the antibody or agent to have been selected for its specificity for a particular protein. As desired or appropriate, this selection may be achieved by subtracting out antibodies that cross-react with molecules from other species (e.g., mouse or rat) or other subtypes. Alternatively, in some aspects, antibodies or antibody fragments are selected that cross-react with certain desired molecules.

The term "affinity" as used herein refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "isolated antibody" refers to an antibody that is substantially free of other antibodies having different antigenic specificities. An isolated antibody that specifically binds to one antigen may, however, have cross-reactivity to other antigens. Moreover, an isolated antibody may be substantially free of other cellular material and/or chemicals.

The term "corresponding human germline sequence" refers to the nucleic acid sequence encoding a human variable region amino acid sequence or subsequence that shares the highest determined amino acid sequence identity with a reference variable region amino acid sequence or subsequence in comparison to all other all other known variable region amino acid sequences encoded by human germline immunoglobulin variable region sequences. The corresponding human germline sequence can also refer to the human variable region amino acid sequence or subsequence with the highest amino acid sequence identity with a reference variable region amino acid sequence or subsequence in comparison to all other evaluated variable region amino acid sequences. The corresponding human germline sequence can be framework regions only, complementarity determining regions only, framework and complementary determining regions, a variable segment (as defined above), or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 91% 92%, 93%, 94%, 95%, 96%, 97%, 98%, 99%, or 100% sequence identity with the reference variable region nucleic acid or amino acid sequence.

A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least 10 to 100 times over the background.

The term "equilibrium dissociation constant (KD, M)" refers to the dissociation rate constant (kd, time-1) divided by the association rate constant (ka, time-1, M-1). Equilibrium dissociation constants can be measured using any known method in the art. The antibodies of the present disclosure generally will have an equilibrium dissociation constant of less than about $10^{-7}$ or $10^{-8}$ M, for example, less than about $10^{-9}$ M or $10^{-10}$ M, in some aspects, less than about $10^{-11}$ M, $10^{-12}$ M or $10^{-13}$ M.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

As used herein, the phrase "consisting essentially of" refers to the genera or species of active pharmaceutical agents included in a method or composition, as well as any excipients inactive for the intended purpose of the methods or compositions. In some aspects, the phrase "consisting essentially of" expressly excludes the inclusion of one or more additional active agents other than an anti-VP1 antibody of the present disclosure. In some aspects, the phrase "consisting essentially of" expressly excludes the inclusion of one or more additional active agents other than an anti-VP1 antibody of the present disclosure and a second co-administered agent.

The term "amino acid" refers to naturally occurring, synthetic, and unnatural amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some aspects, the term "conservative sequence modifications" are used to refer to amino acid modifications that do not significantly affect or alter the binding characteristics of the antibody containing the amino acid sequence.

The term "optimized" as used herein refers to a nucleotide sequence that has been altered to encode an amino acid sequence using codons that are preferred in the production cell or organism, generally a eukaryotic cell, for example, a yeast cell, a *Pichia* cell, a fungal cell, a *Trichoderma* cell, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence.

The terms "percent identical" or "percent identity," in the context of two or more nucleic acids or polypeptide sequences, refers to the extent to which two or more sequences or subsequences that are the same. Two sequences are "identical" if they have the same sequence of amino acids or nucleotides over the region being compared. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 30 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, Adv. Appl. Math. 2:482c (1970), by the homology alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, 2003).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=-4 and a comparison of both strands. For amino acid sequences, the BLASTP program uses as defaults a word length of 3, and expectation (E) of 10, and the BLOSUM62 scoring matrix (see Henikoff and Henikoff, (1989) Proc. Natl. Acad. Sci. USA 89:10915) alignments (B) of 50, expectation (E) of 10, M=5, N=-4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller, (Comput. Appl. Biosci. 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch, (J. Mol. Biol. 48:444-453, 1970), algorithm which has been incorporated into the GAP program in the GCG software package (available from University of South Florida), using either a BLOSUM 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

Yet another indication that two nucleic acid sequences are substantially identical is that the same primers can be used to amplify the sequence.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., (1991) Nucleic Acid Res. 19:5081; Ohtsuka et al., (1985) J. Biol. Chem. 260: 2605-2608; and Rossolini et al., (1994) Mol. Cell. Probes 8:91-98).

The term "operably linked" in the context of nucleic acids refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The terms "BKV" or "BK virus" refer to a member of the family Polyomaviridae, genus Orthopolyomavirus. Polyomaviruses are icosahedral, non-enveloped, double-stranded DNA viruses with a genome of approximately 5,000 base pairs. They measure approximately 40-45 nM in diameter (Bennett et al., Microbes and Infection. 2012:14(9):672-683).

"JCV" or "JC virus" refers to a member of the family Polyomaviridae, genus Orthopolyomavirus. JCV is related to BKV, and is also an icosahedral, non-enveloped, double-stranded DNA virus with a genome of approximately 5,000 base pairs. They measure approximately 40-45 nM in diameter (Johne et al., Arch. Virol. 2011; 156(9):1627-1634).

The terms "BKV nephropathy" or "BKV-associated nephropathy" or "BKVAN" refer to the inflammatory interstitial nephropathy resulting from the lytic infection with BKV, characterized by viral cytopathogenic changes and viral gene expression, primarily in the renal tubular epithelium.

The term "VP1" refers to the major polyoma virus capsid subunit protein. "VP1 pentamers" are composed of five monomers of VP1.

TABLE 1

VP1 sequences

| Name | Sequence | SEQ ID NO |
|---|---|---|
| VP1 BKV serotype I | MAPTKRKGECPGAAPKKPKEPVQVPKLLIKGGVEVLEV KTGVDAITEVECFLNPEMGDPDENLRGFSLKLSAENDFS SDSPERKMLPCYSTARIPLPNLNEDLTCGNLLMWEAVTV QTEVIGITSMLNLHAGSQKVHEHGGGKPIQGSNFHFFAV GGDPLEMQGVLMNYRTKYPEGTITPKNPTAQSQVMN TDHKAYLDKNNAYPVECWIPDPSRNENTRYFGTFTGGE NVPPVLHVTNTATTVLLDEQGVGPLCKADSLYVSAADIC GLFTNSSGTQQWRGLARYFKIRLRKRSVKNPYPISFLLSD LINRRTQRVDGQPMYGMESQVEEVRVFDGTERLPGDPD MIRYIDKQGQLQTKML | (SEQ ID NO: 1) |
| VP1 BKV serotype II | MAPTKRKGECPGAAPKKPKEPVQVPKLLIKGGVEVLEV KTGVDAITEVECFLNPEMGDPDDNLRGYSLKLTAENAFD SDSPDKKMLPCYSTARIPLPNLNEDLTCGNLLMWEAVTV KTEVIGITSMLNLHAGSQKVHENGGGKPVQGSNFHFFAV GGDPLEMQGVLMNYRTKYPQGTITPKNPTAQSQVMN TDHKAYLDKNNAYPVECWIPDPSRNENTRYFGTYTGGE NVPPVLHVTNTATTVLLDEQGVGPLCKADSLYVSAADIC GLFTNSSGTQQWRGLARYFKIRLRKRSVKNPYPISFLLSD LINRRTQKVDGQPMYGMESQVEEVRVFDGTEQLPGDPD MIRYIDRQGQLQTKMV | (SEQ ID NO: 2) |

TABLE 1-continued

VP1 sequences

| Name | Sequence | SEQ ID NO |
|---|---|---|
| VP1 BKV serotype III | MAPTKRKGECPGAAPKKPKEPVQVPKLLIKGGVEVLEV KTGVDAITEVECFLNPEMGDPDDHLRGYSQHLSAENAF DSDSPDKKMLPCYSTARIPLPNLNEDLTCGNLLMWEAVT VKTEVIGITSMLNLHAGSQKVHENGGGKPVQGSNFHFFA VGGDPLEMQGVLMNYRTKYPQGTITPKNPTAQSQVM NTDHKAYLDKNNAYPVECWIPDPSKNENTRYFGTYTGG ENVPPVLHVTNTATTVLLDEQGVGPLCKADSLYVSAADI CGLFTNSSGTQQWRGLARYFKIRLRKRSVKNPYPISFLLS DLINRRTQKVDGQPMYGMESQVEEVRVFDGTEQLPGDP DMIRYIDRQGQLQTKMV | (SEQ ID NO: 3) |
| VP1 BKV serotype IV | MAPTKRKGECPGAAPKKPKEPVQVPKLLIKGGVEVLEV KTGVDAITEVECFLNPEMGDPDNDLRGYSLRLTAETAFD SDSPDRKMLPCYSTARIPLPNLNEDLTCGNLLMWEAVTV KTEVIGITSMLNLHAGSQKVHENGGGKPIQGSNFHFFAV GGDPLEMQGVLMNYRTKYPEGTVTPKNPTAQSQVMN TDHKAYLDKNNAYPVECWIPDPSRNENTRYFGTYTGGE NVPPVLHVTNTATTVLLDEQGVGPLCKADSLYVSAADIC GLFTNSSGTQQWRGLPRYFKIRLRKRSVKNPYPISFLLSD LINRRTQRVDGQPMYGMESQVEEVRVFDGTEQLPGDPD MIRYIDRQGQLQTKMV | (SEQ ID NO: 4) |
| JCV VP1 | MAPTKRKGERKDPVQVPKLLIRGGVEVLEVKTGVDSITE VECFLTPEMGDPDEHLRGFSKSISISDTFESDSPNKDMLP CYSVARIPLPNLNEDLTCGNILMWEAVTLKTEVIGVTTL MNVHSNGQATHDNGAGKPVQGTSFHFFSVGGEALELQG VVFNYRTKYPDGTIFPKNATVQSQVMNTEHKAYLDKN KAYPVECWVPDPTRNENTRYFGTLTGGENVPPVLHITNT ATTVLLDEFGVGPLCKGDNLYLSAVDVCGMFTNRSGSQ QWRGLSRYFKVQLRKRRVKNPYPISFLLTDLINRRTPRV DGQPMYGMDAQVEEVRVFEGTEELPGDPDMMRYVDRY GQLQTKML | (SEQ ID NO: 5) |

"Virus-like particles" or "VLP" are an assembly of VP1 pentamers into viral capsids. VLPs are composed of 72 VP1 pentamers. VLPs are structurally very similar to actual virus but lack the minor capsid proteins (VP2 and VP3) as well as the viral DNA genome, and therefore are non-infectious. VLPs are useful as viral epitopes are presented in a similar conformation to the actual virus.

"IC50" (half-maximal inhibitory concentration) refers to the concentration of a particular antibody which induces a signal halfway (50%) between the baseline control and the maximum possible signal. For example, the IC50 is the concentration of antibody at which 50% of the available binding sites on the VP1 antigen are occupied.

"EC50" (half-maximal effective concentration) refers to the concentration of a particular antibody which induces a response halfway (50%) between the baseline control and the maximum possible effect after a specific exposure or treatment time. For example, the EC50 is the concentration of antibody at which virus infection is neutralized by 50%.

"EC90" refers to the concentration of a particular antibody which induces a response corresponding to 90% of the maximum possible effect after a specific exposure or treatment time. For example, the EC90 is the concentration of antibody at which virus infection is neutralized by 90%.

"Neutralization" refers to the inhibition of viral infection of a host cell, as demonstrated by the absence of viral gene expression. Without being held to any one theory, mechanisms of neutralization by a particular antibody could include blocking the interaction of viral capsid proteins with cell surface receptors or disruption of any stage of the entry and trafficking process prior to delivery of the viral genome to the nucleus of the host cell.

As used herein, the terms "treat," "treating," or "treatment" of any disease or disorder refer in one aspect, to ameliorating the disease or disorder (i.e., slowing or arresting or reducing the development of the disease or at least one of the clinical symptoms thereof). In another aspect, "treat," "treating," or "treatment" refers to alleviating or ameliorating at least one physical parameter including those which may not be discernible by the patient. In yet another aspect, "treat," "treating," or "treatment" refers to modulating the disease or disorder, either physically, (e.g., stabilization of a discernible symptom), physiologically, (e.g., stabilization of a physical parameter), or both.

The phrase "reducing the likelihood" refers to delaying the onset or development or progression of the disease, infection or disorder.

The term "therapeutically acceptable amount" or "therapeutically effective dose" interchangeably refers to an amount sufficient to effect the desired result (i.e., a reduction in tumor size, inhibition of tumor growth, prevention of metastasis, inhibition or prevention of viral, bacterial, fungal or parasitic infection). In some aspects, a therapeutically acceptable amount does not induce or cause undesirable side effects. A therapeutically acceptable amount can be determined by first administering a low dose, and then incrementally increasing that dose until the desired effect is achieved. A "prophylactically effective dosage," and a "therapeutically effective dosage," of the molecules of the present disclosure can prevent the onset of, or result in a decrease in severity of, respectively, disease symptoms, including symptoms associated polyoma viral infection.

The term "co-administer" refers to the simultaneous presence of two active agents in the blood of an individual. Active agents that are co-administered can be concurrently or sequentially delivered.

BRIEF DESCRIPTION OF THE DRAWINGS

FIG. 2 is a table of SET affinity values ($K_D$) for anti-VP1 antibodies on VP1 pentamers for BKV serotypes I-IV.

FIG. 3A-3E graphically represents affinity measurements for anti-VP1 antibodies on VP1 pentamers or VLPs for BKV serotypes I-IV by Biacore.

FIG. 7 is a table of IC50 values generated by ELISA for anti-VP1 antibodies binding to VLPs or VP1 pentamers for BKV serotypes I and IV.

FIG. 9 is a table of IC50 values generated by ELISA for anti-VP1 antibodies binding to BKV serotype I VLPs.

FIG. 11 is a table of IC50 values generated by ELISA for anti-VP1 antibodies binding to JCV VLPs.

FIG. 12A-B shows two blots. The upper panel (FIG. 12A) is a Western blot demonstrating no binding of anti-VP1 antibodies to denatured BKV VP1. The lower panel (FIG. 12B) is a dot-blot of non-denatured BKV VP1 pentamers, demonstrating binding of anti-VP1 antibodies to non-denatured VP1 pentamers.

FIG. 14 is a table summarizing the key residues for binding identified in the epitopes of anti-VP1 antibodies.

FIG. 19 is a table summarizing the neutralizing activity (EC50 and EC90) of anti-VP1 antibodies on BKV serotypes I-IV and JC virus.

FIG. 21 is a table summarizing the neutralizing activity (EC50 and EC90) of anti-VP1 antibodies on BKV serotypes I-IV.

FIG. 23 is a table summarizing the neutralizing activity (EC50 and EC90) of anti-VP1 antibodies on BKV serotype I.

FIG. 26 is table summarizing the neutralizing activity (EC50 and EC90) of anti-VP1 antibodies on JCV infection.

FIG. 27 is table of antibody P8D11 affinity on JC virus VLPs and VLPs containing point mutations.

FIG. 29A is a table that shows anti-BKV antibody contact residues in the EF loop when certain mutations are introduced by alanine scanning. FIG. 29B-29C shows the SPR graphs of anti-BKV antibody binding to wild type and mutated residues in VP1.

DETAILED DESCRIPTION

Figure 1A:
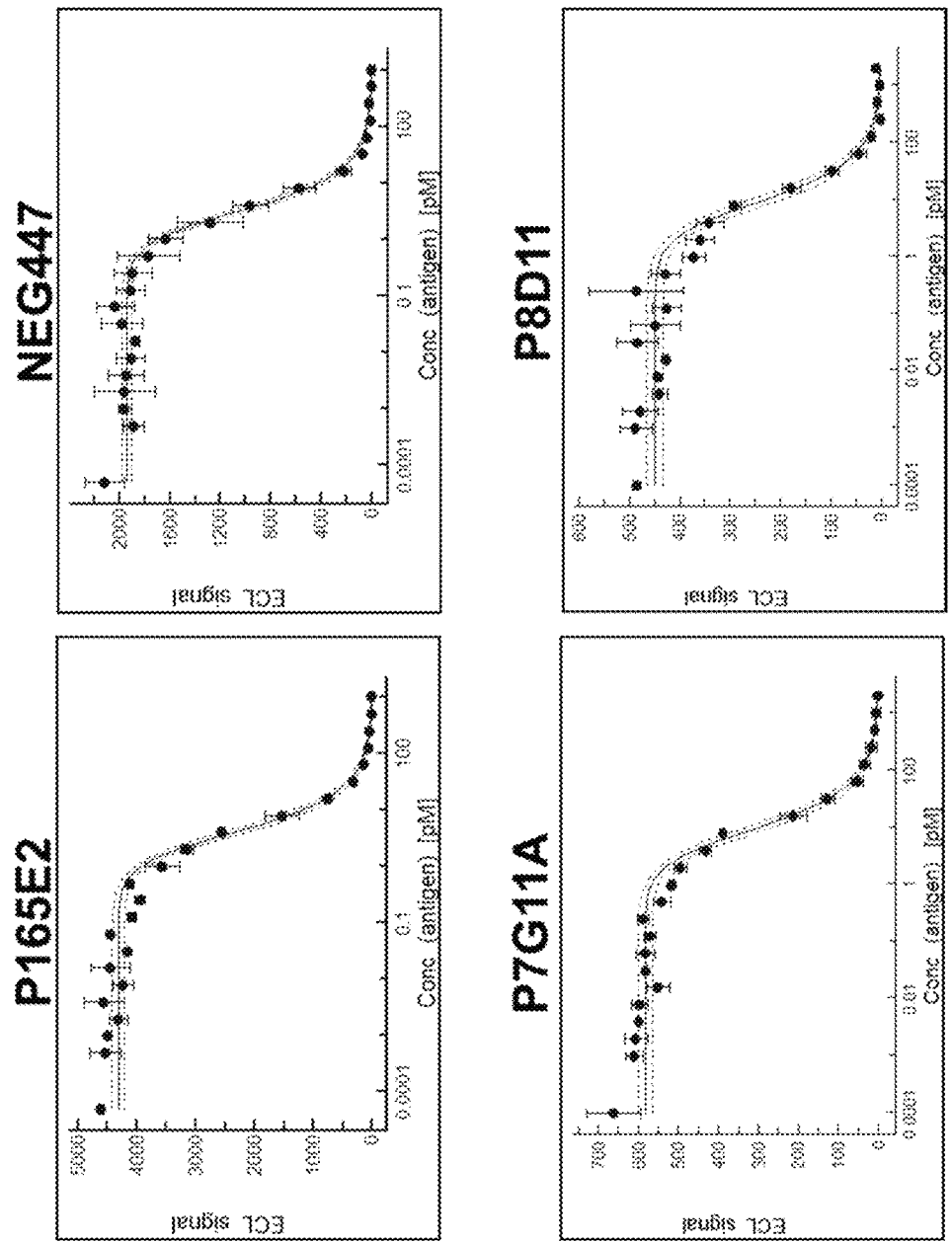
FIG. 1A-1D graphically represents affinity measurements for anti-VP1 antibodies on VP1 pentamers for BKV serotypes I-IV by SET assay.
Figure 1B:
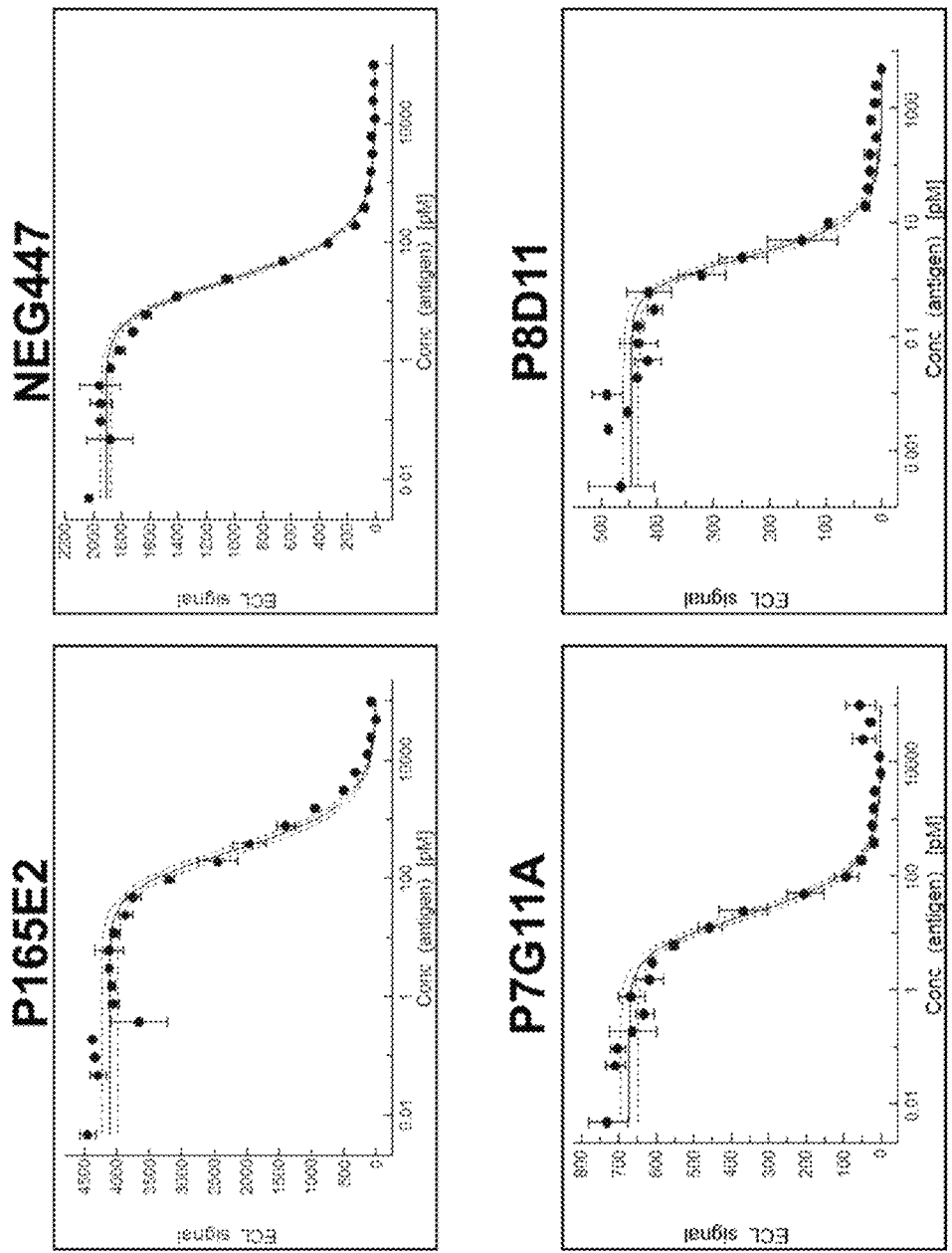
Figure 1C:
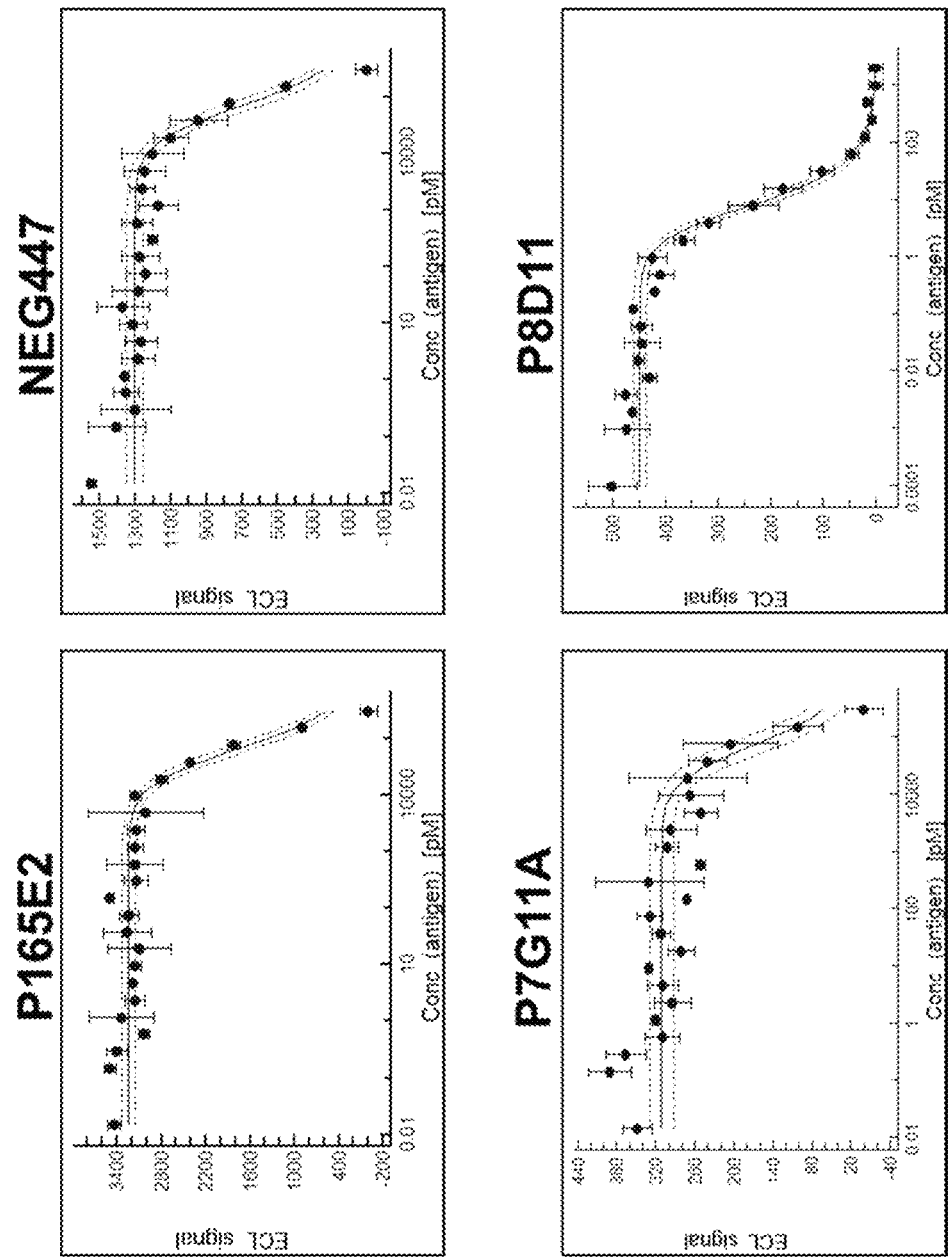
Figure 1D:
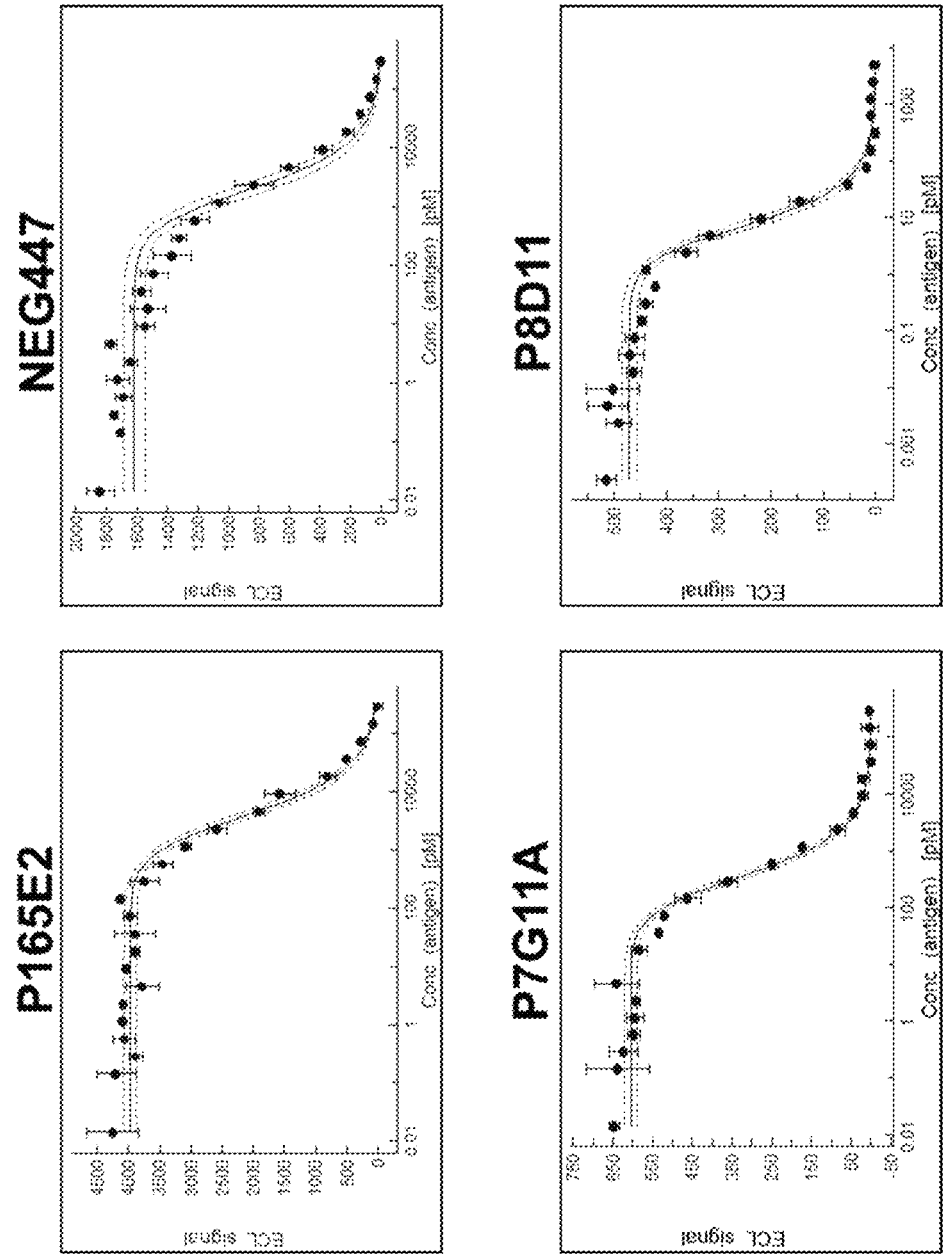

The present disclosure provides for antibodies, antibody fragments (e.g., antigen binding fragments), that bind and neutralize BKV. In particular, the present disclosure is directed to antibodies and antibody fragments (e.g., antigen binding fragments) that bind to VP1 proteins, and neutralize viral infection upon such binding. Furthermore, the present disclosure provides antibodies that have desirable pharmacokinetic characteristics and other desirable attributes, and thus can be used for reducing the likelihood of or treating BK virus-associated nephropathy (e.g. BKVAN). The present disclosure further provides pharmaceutical compositions comprising the antibodies and methods of making and using such pharmaceutical compositions for the prevention and treatment of polyoma virus infection and associated disorders.

Anti-VP1 Antibodies

The present disclosure provides for antibodies or antibody fragments (e.g., antigen binding fragments) that specifically bind to VP1. Antibodies or antibody fragments (e.g., antigen binding fragments) of the present disclosure include, but are not limited to, the human monoclonal antibodies or fragments thereof, isolated as described, in the Examples below.

The present disclosure in certain aspects provides antibodies or antibody fragments (e.g., antigen binding fragments) that specifically bind to VP1, said antibodies or antibody fragments (e.g., antigen binding fragments) comprise a VH domain having an amino acid sequence of SEQ ID NO:12, 32, 52, 72, 92, 112, 132, 152, 172, 192, 212, 232, 252, 272, 292, 312, 328, 348, 362, 376, 390, 404, 418, 432, 446, 460, 474, and 488 (Table 2). The present disclosure also provides antibodies or antibody fragments (e.g., antigen binding fragments) that specifically bind to VP1, said antibodies or antibody fragments (e.g., antigen binding fragments) comprise a VH CDR having an amino acid sequence of any one of the VH CDRs listed in Table 2. In particular aspects, the present disclosure provides antibodies or antibody fragments (e.g., antigen binding fragments) that specifically bind to VP1, said antibodies comprising (or alternatively, consist of) one, two, three, or more VH CDRs having an amino acid sequence of any of the VH CDRs listed in Table 2.

The present disclosure provides antibodies or antibody fragments (e.g., antigen binding fragments) that specifically bind to VP1, said antibodies or antibody fragments (e.g., antigen binding fragments) comprise a VL domain having an amino acid sequence of SEQ ID NO: 22, 42, 62, 82, 102, 122, 142, 162, 182, 202, 222, 242, 262, 282, 302, 320, 338, 355, 369, 383, 397, 411, 425, 439, 453, 467, 481, and 495 (Table 2). The present disclosure also provides antibodies or antibody fragments (e.g., antigen binding fragments) that specifically bind to VP1, said antibodies or antibody fragments (e.g., antigen binding fragments) comprise a VL CDR having an amino acid sequence of any one of the VL CDRs listed in Table 2. In particular, the disclosure provides antibodies or antibody fragments (e.g., antigen binding fragments) that specifically bind to VP1, said antibodies or antibody fragments (e.g., antigen binding fragments) comprise (or alternatively, consist of) one, two, three or more VL CDRs having an amino acid sequence of any of the VL CDRs listed in Table 2.

Other antibodies or antibody fragments (e.g., antigen binding fragments) of the present disclosure include amino acids that have been mutated, yet have at least 60, 70, 80, 90 or 95 percent identity in the CDR regions with the CDR regions depicted in the sequences described in Table 2. In some aspects, it includes mutant amino acid sequences wherein no more than 1, 2, 3, 4 or 5 amino acids have been mutated in the CDR regions when compared with the CDR regions depicted in the sequence described in Table 2.

The present disclosure also provides nucleic acid sequences that encode VH, VL, the full length heavy chain, and the full length light chain of the antibodies that specifically bind to VP1. Such nucleic acid sequences can be optimized for expression in mammalian cells.

TABLE 2 anti-VP1 Antibodies

P8D11

| SEQ ID NO: 6 (Kabat) | HCDR1 | NYWMT |
|---|---|---|
| SEQ ID NO: 7 (Kabat) | HCDR2 | NIKKDGSEKYYVDSVRG |
| SEQ ID NO: 8 (Kabat) | HCDR3 | VRSGRYFALDD |
| SEQ ID NO: 9 (Chothia) | HCDR1 | GFTFNNY |
| SEQ ID NO: 10 (Chothia) | HCDR2 | KKDGSE |
| SEQ ID NO: 11 (Chothia) | HCDR3 | VRSGRYFALDD |
| SEQ ID NO: 12 | VH | QVQLVESGGTLVQPGGSLRLSCAASGFTFNNYWM TWVRQAPGKGLEWVANIKKDGSEKYYVDSVRGR FTISRDNAKNSLFLQMNSLRPEDTAVYFCATVRSG RYFALDDWGQGTLVTVSS |
| SEQ ID NO: 13 | DNA VH | CAGGTGCAGCTGGTGGAATCAGGCGGCACACTG GTGCAGCCTGGCGGTAGCCTGAGACTGAGCTGCG CTGCTAGTGGCTTCACCTTTAACAACTACTGGAT GACCTGGGTTAGGCAGGCCCCTGGTAAAGGCCTC GAGTGGGTGGCAAATATCAAGAAGGACGGTAGC GAGAAGTACTACGTGGACTCAGTCAGAGGCCGG TTCACTATCTCTAGGGATAACGCTAAGAATAGCC TGTTCCTGCAGATGAACTCACTGAGGCCCGAGGA TACCGCCGTCTACTTCTGTGCTACCGTCAGATCA GGCCGCTACTTCGCCCTGGACGACTGGGGTCAAG GCACACTGGTCACCGTGTCTAGC |
| SEQ ID NO: 14 | Heavy Chain | QVQLVESGGTLVQPGGSLRLSCAASGFTFNNYWM TWVRQAPGKGLEWVANIKKDGSEKYYVDSVRGRF TISRDNAKNSLFLQMNSLRPEDTAVYFCATVRSGR YFALDDWGQGTLVTVSSASTKGPSVFPLAPSSKSTS GGTAALGCLVKDYFPEPVTVSWNSGALTSGVHTFP AVLQSSGLYSLSSVVTVPSSSLGTQTYICNVNHKPS NTKVDKRVEPKSCDKTHTCPPCPAPELLGGPSVFLF PPKPKDTLMISRTPEVTCVVVDVSHEDPEVKFNWY VDGVEVHNAKTKPREEQYNSTYRVVSVLTVLHQD WLNGKEYKCKVSNKALPAPIEKTISKAKGQPREPQ VYTLPPSREEMTKNQVSLTCLVKGFYPSDIAVEWE SNGQPENNYKTTPPVLDSDGSFFLYSKLTVDKSRW QQGNVFSCSVMHEALHNHYTQKSLSLSPGK |
| SEQ ID NO: 15 | DNA Heavy Chain | CAGGTGCAGCTGGTGGAATCAGGCGGCACACTG GTGCAGCCTGGCGGTAGCCTGAGACTGAGCTGC GCTGCTAGTGGCTTCACCTTTAACAACTACTGGA TGACCTGGGTTAGGCAGGCCCCTGGTAAAGGCCT CGAGTGGGTGGCAAATATCAAGAAGGACGGTAG CGAGAAGTACTACGTGGACTCAGTCAGAGGCCG GTTCACTATCTCTAGGGATAACGCTAAGAATAGC CTGTTCCTGCAGATGAACTCACTGAGGCCCGAGG ATACCGCCGTCTACTTCTGTGCTACCGTCAGATC AGGCCGCTACTTCGCCCTGGACGACTGGGGTCAA GGCACACTGGTCACCGTGTCTAGCGCTAGCACTA |

TABLE 2-continued anti-VP1 Antibodies

|  |  |  |
|---|---|---|
|  |  | AGGGCCCAAGTGTGTTTCCCCTGGCCCCCAGCAG<br>CAAGTCTACTTCCGGCGGAACTGCTGCCCTGGGT<br>TGCCTGGTGAAGGACTACTTCCCCGAGCCCGTGA<br>CAGTGTCCTGGAACTCTGGGGCTCTGACTTCCGG<br>CGTGCACACCTTCCCCGCCGTGCTGCAGAGCAGC<br>GGCCTGTACAGCCTGAGCAGCGTGGTGACAGTG<br>CCCTCCAGCTCTCTGGGAACCCAGACCTATATCT<br>GCAACGTGAACCACAAGCCCAGCAACACCAAGG<br>TGGACAAGAGAGTGGAGCCCAAGAGCTGCGACA<br>AGACCCACACCTGCCCCCCCTGCCCAGCTCCAGA<br>ACTGCTGGGAGGGCCTTCCGTGTTCCTGTTCCCC<br>CCCAAGCCCAAGGACACCCTGATGATCAGCAGG<br>ACCCCCGAGGTGACCTGCGTGGTGGTGGACGTGT<br>CCCACGAGGACCCAGAGGTGAAGTTCAACTGGT<br>ACGTGGACGGCGTGGAGGTGCACAACGCCAAGA<br>CCAAGCCCAGAGAGGAGCAGTACAACAGCACCT<br>ACAGGGTGGTGTCCGTGCTGACCGTGCTGCACCA<br>GGACTGGCTGAACGGCAAAGAATACAAGTGCAA<br>AGTCTCCAACAAGGCCCTGCCAGCCCCAATCGA<br>AAAGACAATCAGCAAGGCCAAGGGCCAGCCACG<br>GGAGCCCCAGGTGTACACCCTGCCCCCCAGCCG<br>GGAGGAGATGACCAAGAACCAGGTGTCCCTGAC<br>CTGTCTGGTGAAGGGCTTCTACCCCAGCGATATC<br>GCCGTGGAGTGGGAGAGCAACGGCCAGCCCGAG<br>AACAACTACAAGACCACCCCCCCAGTGCTGGAC<br>AGCGACGGCAGCTTCTTCCTGTACAGCAAGCTGA<br>CCGTGGACAAGTCCAGGTGGCAGCAGGGCAACG<br>TGTTCAGCTGCAGCGTGATGCACGAGGCCCTGCA<br>CAACCACTACACCCAGAAGTCCCTGAGCCTGAG<br>CCCCGGCAAG |
| SEQ ID NO: 16<br>(Kabat) | LCDR1 | GGDNIGSRPVH |
| SEQ ID NO: 17<br>(Kabat) | LCDR2 | DDSNRPS |
| SEQ ID NO: 18<br>(Kabat) | LCDR3 | QVWSSSTDHP |
| SEQ ID NO: 19<br>(Chothia) | LCDR1 | DNIGSRP |
| SEQ ID NO: 20<br>(Chothia) | LCDR2 | DDS |
| SEQ ID NO: 21<br>(Chothia) | LCDR3 | WSSSTDH |
| SEQ ID NO: 22 | VL | QSVLTQPPSVSVAPGKTARITCGGDNIGSRPVHWY<br>QQKPGQAPILVVYDDSNRPSGIPERFSGSNSGNTAT<br>LTISRVEAGDEADYYCQVWSSSTDHPFGGGTKVTVL |
| SEQ ID NO: 23 | DNA VL | CAGTCAGTCCTGACTCAGCCCCCTAGCGTCAGCG<br>TGGCCCCTGGTAAAACCGCTAGAATCACCTGTGG<br>CGGCGATAATATCGGCTCTAGGCCCGTGCACTGG<br>TATCAGCAGAAGCCCGGTCAAGCCCCTATCCTGG<br>TGGTCTACGACGACTCTAATAGACCTAGCGGAAT<br>CCCCGAGCGGTTTAGCGGCTCTAATTCTGGTAAT<br>ACCGCTACCCTGACTATCTCTAGGGTGGAAGCCG<br>GCGACGAGGCCGACTACTACTGTCAAGTCTGGTC<br>TAGCTCTACCGATCACCCCTTCGGCGGAGGCACT<br>AAGGTTACAGTGCTG |
| SEQ ID NO: 24 | Light<br>Chain | QSVLTQPPSVSVAPGKTARITCGGDNIGSRPVHWY<br>QQKPGQAPILVVYDDSNRPSGIPERFSGSNSGNTAT<br>LTISRVEAGDEADYYCQVWSSSTDHPFGGGTKVTV<br>LGQPKAAPSVTLFPPSSEELQANKATLVCLISDFYP<br>GAVTVAWKADSSPVKAGVETTTPSKQSNNKYAAS<br>SYLSLTPEQWKSHRSYSCQVTHEGSTVEKTVAPTE<br>CS |
| SEQ ID NO: 25 | DNA<br>Light<br>Chain | CAGTCAGTCCTGACTCAGCCCCCTAGCGTCAGCG<br>TGGCCCCTGGTAAAACCGCTAGAATCACCTGTGG<br>CGGCGATAATATCGGCTCTAGGCCCGTGCACTGG<br>TATCAGCAGAAGCCCGGTCAAGCCCCTATCCTGG<br>TGGTCTACGACGACTCTAATAGACCTAGCGGAAT<br>CCCCGAGCGGTTTAGCGGCTCTAATTCTGGTAAT |

TABLE 2-continued anti-VP1 Antibodies

```
ACCGCTACCCTGACTATCTCTAGGGTGGAAGCCG
GCGACGAGGCCGACTACTACTGTCAAGTCTGGTC
TAGCTCTACCGATCACCCCTTCGGCGGAGGCACT
AAGGTTACAGTGCTGGGTCAACCTAAGGCTGCCC
CCAGCGTGACCCTGTTCCCCCCCAGCAGCGAGGA
GCTGCAGGCCAACAAGGCCACCCTGGTGTGCCT
GATCAGCGACTTCTACCCAGGCGCCGTGACCGTG
GCCTGGAAGGCCGACAGCAGCCCCGTGAAGGCC
GGCGTGGAGACCACCACCCCCAGCAAGCAGAGC
AACAACAAGTACGCCGCCAGCAGCTACCTGAGC
CTGACCCCCGAGCAGTGGAAGAGCCACAGGTCC
TACAGCTGCCAGGTGACCCACGAGGGCAGCACC
GTGGAAAAGACCGTGGCCCCAACCGAGTGCAGC
```

P8D11A

SEQ ID NO: 26  HCDR1     NYWMT
(Kabat)

SEQ ID NO: 27  HCDR2     NIKKDGSEKYYVDSVRG
(Kabat)

SEQ ID NO: 28  HCDR3     VRSGRYFALDD
(Kabat)

SEQ ID NO: 29  HCDR1     GFTFSNY
(Chothia)

SEQ ID NO: 30  HCDR2     KKDGSE
(Chothia)

SEQ ID NO: 31  HCDR3     VRSGRYFALDD
(Chothia)

SEQ ID NO: 32  VH        QVQLVESGGTLVQPGGSLRLSCAASGFTFSNYWM
                         TWVRQAPGKGLEWVANIKKDGSEKYYVDSVRGR
                         FTISRDNAKNSLFLQMNSLRPEDTAVYFCATVRSG
                         RYFALDDWGQGTLVTVSS

SEQ ID NO: 33  DNA VH    CAGGTGCAGCTGGTGGAATCAGGCGGCACACTG
                         GTGCAGCCTGGCGGTAGCCTGAGACTGAGCTGC
                         GCTGCTAGTGGCTTCACCTTCTCTAACTACTGGA
                         TGACCTGGGTCAGGCAGGCCCCTGGTAAAGGCC
                         TCGAGTGGGTGGCAAATATCAAGAAGGACGGTA
                         GCGAGAAGTACTACGTGGACTCAGTCAGAGGCC
                         GGTTCACTATCTCTAGGGATAACGCTAAGAATAG
                         CCTGTTCCTGCAGATGAACTCACTGAGGCCCGAG
                         GATACCGCCGTCTACTTCTGTGCTACCGTCAGAT
                         CAGGCCGCTACTTCGCCCTGGACGACTGGGGTCA
                         AGGCACACTGGTCACCGTGTCTAGC

SEQ ID NO: 34  Heavy     QVQLVESGGTLVQPGGSLRLSCAASGFTFSNYWM
               Chain     TWVRQAPGKGLEWVANIKKDGSEKYYVDSVRGR
                         FTISRDNAKNSLFLQMNSLRPEDTAVYFCATVRSG
                         RYFALDDWGQGTLVTVSSASTKGPSVFPLAPSSKS
                         TSGGTAALGCLVKDYFPEPVTVSWNSGALTSGVHT
                         FPAVLQSSGLYSLSSVVTVPSSSLGTQTYICNVNHK
                         PSNTKVDKRVEPKSCDKTHTCPPCPAPELLGGPSVF
                         LFPPKPKDTLMISRTPEVTCVVVDVSHEDPEVKFN
                         WYVDGVEVHNAKTKPREEQYNSTYRVVSVLTVLH
                         QDWLNGKEYKCKVSNKALPAPIEKTISKAKGQPRE
                         PQVYTLPPSREEMTKNQVSLTCLVKGFYPSDIAVE
                         WESNGQPENNYKTTPPVLDSDGSFFLYSKLTVDKS
                         RWQQGNVFSCSVMHEALHNHYTQKSLSLSPGK SEQ ID NO: 35  DNA       CAGGTGCAGCTGGTGGAATCAGGCGGCACACTG
               Heavy     GTGCAGCCTGGCGGTAGCCTGAGACTGAGCTGC
               Chain     GCTGCTAGTGGCTTCACCTTCTCTAACTACTGGA
                         TGACCTGGGTCAGGCAGGCCCCTGGTAAAGGCC
                         TCGAGTGGGTGGCAAATATCAAGAAGGACGGTA
                         GCGAGAAGTACTACGTGGACTCAGTCAGAGGCC
                         GGTTCACTATCTCTAGGGATAACGCTAAGAATAG
                         CCTGTTCCTGCAGATGAACTCACTGAGGCCCGAG
                         GATACCGCCGTCTACTTCTGTGCTACCGTCAGAT
                         CAGGCCGCTACTTCGCCCTGGACGACTGGGGTCA
                         AGGCACACTGGTCACCGTGTCTAGCGCTAGCACT
                         AAGGGCCCAAGTGTGTTTCCCCTGGCCCCCAGCA
                         GCAAGTCTACTTCCGGCGGAACTGCTGCCCTGGG
```

TABLE 2-continued anti-VP1 Antibodies

```
TTGCCTGGTGAAGGACTACTTCCCCGAGCCCGTG
ACAGTGTCCTGGAACTCTGGGGCTCTGACTTCCG
GCGTGCACACCTTCCCCGCCGTGCTGCAGAGCAG
CGGCCTGTACAGCCTGAGCAGCGTGGTGACAGT
GCCCTCCAGCTCTCTGGGAACCCAGACCTATATC
TGCAACGTGAACCACAAGCCCAGCAACACCAAG
GTGGACAAGAGAGTGGAGCCCAAGAGCTGCGAC
AAGACCCACACCTGCCCCCCCTGCCCAGCTCCAG
AACTGCTGGGAGGCCTTCCGTGTTCCTGTTCCC
CCCCAAGCCCAAGGACACCCTGATGATCAGCAG
GACCCCCGAGGTGACCTGCGTGGTGGTGGACGT
GTCCCACGAGGACCCAGAGGTGAAGTTCAACTG
GTACGTGGACGGCGTGGAGGTGCACAACGCCAA
GACCAAGCCCAGAGAGGAGCAGTACAACAGCAC
CTACAGGGTGGTGTCCGTGCTGACCGTGCTGCAC
CAGGACTGGCTGAACGGCAAAGAATACAAGTGC
AAAGTCTCCAACAAGGCCCTGCCAGCCCCAATC
GAAAAGACAATCAGCAAGGCCAAGGGCCAGCCA
CGGGAGCCCCAGGTGTACACCCTGCCCCCCAGCC
GGGAGGAGATGACCAAGAACCAGGTGTCCCTGA
CCTGTCTGGTGAAGGGCTTCTACCCCAGCGATAT
CGCCGTGGAGTGGGAGAGCAACGGCCAGCCCGA
GAACAACTACAAGACCACCCCCCCAGTGCTGGA
CAGCGACGGCAGCTTCTTCCTGTACAGCAAGCTG
ACCGTGGACAAGTCCAGGTGGCAGCAGGGCAAC
GTGTTCAGCTGCAGCGTGATGCACGAGGCCCTGC
ACAACCACTACACCCAGAAGTCCCTGAGCCTGA
GCCCCGGCAAG
```

| SEQ ID NO: 36 | LCDR1 (Kabat) | GGDNIGSRPVH |
|---|---|---|
| SEQ ID NO: 37 | LCDR2 (Kabat) | DDSNRPS |
| SEQ ID NO: 38 | LCDR3 (Kabat) | QVWSSSTDHP |
| SEQ ID NO: 39 | LCDR1 (Chothia) | DNIGSRP |
| SEQ ID NO: 40 | LCDR2 (Chothia) | DDS |
| SEQ ID NO: 41 | LCDR3 (Chothia) | WSSSTDH |
| SEQ ID NO: 42 | VL | QSVLTQPPSVSVAPGKTARITCGGDNIGSRPVHWY QQKPGQAPILVVYDDSNRPSGIPERFSGSNSGNTAT LTISRVEAGDEADYYCQVWSSSTDHPFGGGTKVTVL |
| SEQ ID NO: 43 | DNA VL | CAGTCAGTCCTGACTCAGCCCCCTAGCGTCAGCG TGGCCCCTGGTAAAACCGCTAGAATCACCTGTGG CGGCGATAATATCGGCTCTAGGCCCGTGCACTGG TATCAGCAGAAGCCCGGTCAAGCCCCTATCCTGG TGGTCTACGACGACTCTAATAGACCTAGCGGAAT CCCCGAGCGGTTTAGCGGCTCTAATTCTGGTAAT ACCGCTACCCTGACTATCTCTAGGGTGGAAGCCG GCGACGAGGCCGACTACTACTGTCAAGTCTGGTC TAGCTCTACCGATCACCCCTTCGGCGGAGGCACT AAGGTTACAGTGCTG |
| SEQ ID NO: 44 | Light Chain | QSVLTQPPSVSVAPGKTARITCGGDNIGSRPVHWY QQKPGQAPILVVYDDSNRPSGIPERFSGSNSGNTAT LTISRVEAGDEADYYCQVWSSSTDHPFGGGTKVTV LGQPKAAPSVTLFPPSSEELQANKATLVCLISDFYP GAVTVAWKADSSPVKAGVETTTPSKQSNNKYAAS SYLSLTPEQWKSHRSYSCQVTHEGSTVEKTVAPTE CS |
| SEQ ID NO: 45 | DNA Light Chain | CAGTCAGTCCTGACTCAGCCCCCTAGCGTCAGCG TGGCCCCTGGTAAAACCGCTAGAATCACCTGTGG CGGCGATAATATCGGCTCTAGGCCCGTGCACTGG TATCAGCAGAAGCCCGGTCAAGCCCCTATCCTGG TGGTCTACGACGACTCTAATAGACCTAGCGGAAT CCCCGAGCGGTTTAGCGGCTCTAATTCTGGTAAT ACCGCTACCCTGACTATCTCTAGGGTGGAAGCCG GCGACGAGGCCGACTACTACTGTCAAGTCTGGTC |

TABLE 2-continued anti-VP1 Antibodies

```
TAGCTCTACCGATCACCCCTTCGGCGGAGGCACT
AAGGTTACAGTGCTGGGTCAACCTAAGGCTGCCC
CCAGCGTGACCCTGTTCCCCCCCAGCAGCGAGGA
GCTGCAGGCCAACAAGGCCACCCTGGTGTGCCT
GATCAGCGACTTCTACCCAGGCGCCGTGACCGTG
GCCTGGAAGGCCGACAGCAGCCCCGTGAAGGCC
GGCGTGGAGACCACCACCCCCAGCAAGCAGAGC
AACAACAAGTACGCCGCCAGCAGCTACCTGAGC
CTGACCCCCGAGCAGTGGAAGAGCCACAGGTCC
TACAGCTGCCAGGTGACCCACGAGGGCAGCACC
GTGGAAAAGACCGTGGCCCCAACCGAGTGCAGC
```

P8D11B

| | | |
|---|---|---|
| SEQ ID NO: 46 (Kabat) | HCDR1 | NYWMT |
| SEQ ID NO: 47 (Kabat) | HCDR2 | NIKKDGSEKYYVDSVRG |
| SEQ ID NO: 48 (Kabat) | HCDR3 | VRSGRYFALDD |
| SEQ ID NO: 49 (Chothia) | HCDR1 | GFTFKNY |
| SEQ ID NO: 50 (Chothia) | HCDR2 | KKDGSE |
| SEQ ID NO: 51 (Chothia) | HCDR3 | VRSGRYFALDD |
| SEQ ID NO: 52 | VH | QVQLVESGGTLVQPGGSLRLSCAASGFTFKNYWM TWVRQAPGKGLEWVANIKKDGSEKYYVDSVRGR FTISRDNAKNSLFLQMNSLRPEDTAVYFCATVRSG RYFALDDWGQGTLVTVSS |
| SEQ ID NO: 53 | DNA VH | CAGGTGCAGCTGGTGGAATCAGGCGGCACACTG GTGCAGCCTGGCGGTAGCCTGAGACTGAGCTGC GCTGCTAGTGGCTTCACCTTTAAGAACTACTGGA TGACCTGGGTCAGGCAGGCCCCTGGTAAAGGCC TCGAGTGGGTGGCAAATATCAAGAAGGACGGTA GCGAGAAGTACTACGTGGACTCAGTCAGAGGCC GGTTCACTATCTCTAGGGATAACGCTAAGAATAG CCTGTTCCTGCAGATGAACTCACTGAGGCCCGAG GATACCGCCGTCTACTTCTGTGCTACCGTCAGAT CAGGCCGCTACTTCGCCCTGGACGACTGGGGTCA AGGCACACTGGTCACCGTGTCTAGC |
| SEQ ID NO: 54 | Heavy Chain | QVQLVESGGTLVQPGGSLRLSCAASGFTFKNYWM TWVRQAPGKGLEWVANIKKDGSEKYYVDSVRGR FTISRDNAKNSLFLQMNSLRPEDTAVYFCATVRSG RYFALDDWGQGTLVTVSSASTKGPSVFPLAPSSKS TSGGTAALGCLVKDYFPEPVTVSWNSGALTSGVHT FPAVLQSSGLYSLSSVVTVPSSSLGTQTYICNVNHK PSNTKVDKRVEPKSCDKTHTCPPCPAPELLGGPSVF LFPPKPKDTLMISRTPEVTCVVVDVSHEDPEVKFN WYVDGVEVHNAKTKPREEQYNSTYRVVSVLTVLH QDWLNGKEYKCKVSNKALPAPIEKTISKAKGQPRE PQVYTLPPSREEMTKNQVSLTCLVKGFYPSDIAVE WESNGQPENNYKTTPPVLDSDGSFFLYSKLTVDKS RWQQGNVFSCSVMHEALHNHYTQKSLSLSPGK |
| SEQ ID NO: 55 | DNA Heavy Chain | CAGGTGCAGCTGGTGGAATCAGGCGGCACACTG GTGCAGCCTGGCGGTAGCCTGAGACTGAGCTGC GCTGCTAGTGGCTTCACCTTTAAGAACTACTGGA TGACCTGGGTCAGGCAGGCCCCTGGTAAAGGCC TCGAGTGGGTGGCAAATATCAAGAAGGACGGTA GCGAGAAGTACTACGTGGACTCAGTCAGAGGCC GGTTCACTATCTCTAGGGATAACGCTAAGAATAG CCTGTTCCTGCAGATGAACTCACTGAGGCCCGAG GATACCGCCGTCTACTTCTGTGCTACCGTCAGAT CAGGCCGCTACTTCGCCCTGGACGACTGGGGTCA AGGCACACTGGTCACCGTGTCTAGCGCTAGCACT AAGGGCCCAAGTGTGTTTCCCCTGGCCCCCAGCA GCAAGTCTACTTCCGGCGGAACTGCTGCCCTGGG TTGCCTGGTGAAGGACTACTTCCCCGAGCCCGTG ACAGTGTCCTGGAACTCTGGGGCTCTGACTTCCG |

TABLE 2-continued anti-VP1 Antibodies

|  |  |  |
|---|---|---|
|  |  | GCGTGCACACCTTCCCCGCCGTGCTGCAGAGCAG<br>CGGCCTGTACAGCCTGAGCAGCGTGGTGACAGT<br>GCCCTCCAGCTCTCTGGGAACCCAGACCTATATC<br>TGCAACGTGAACCACAAGCCCAGCAACACCAAG<br>GTGGACAAGAGAGTGGAGCCCAAGAGCTGCGAC<br>AAGACCCACACCTGCCCCCCCTGCCCAGCTCCAG<br>AACTGCTGGGAGGGCCTTCCGTGTTCCTGTTCCC<br>CCCCAAGCCCAAGGACACCCTGATGATCAGCAG<br>GACCCCCGAGGTGACCTGCGTGGTGGTGGACGT<br>GTCCCACGAGGACCCAGAGGTGAAGTTCAACTG<br>GTACGTGGACGGCGTGGAGGTGCACAACGCCAA<br>GACCAAGCCCAGAGAGGAGCAGTACAACAGCAC<br>CTACAGGGTGGTGTCCGTGCTGACCGTGCTGCAC<br>CAGGACTGGCTGAACGGCAAAGAATACAAGTGC<br>AAAGTCTCCAACAAGGCCCTGCCAGCCCCAATC<br>GAAAAGACAATCAGCAAGGCCAAGGGCCAGCCA<br>CGGGAGCCCCAGGTGTACACCCTGCCCCCCAGCC<br>GGGAGGAGATGACCAAGAACCAGGTGTCCCTGA<br>CCTGTCTGGTGAAGGGCTTCTACCCCAGCGATAT<br>CGCCGTGGAGTGGGAGAGCAACGGCCAGCCCGA<br>GAACAACTACAAGACCACCCCCCCAGTGCTGGA<br>CAGCGACGGCAGCTTCTTCCTGTACAGCAAGCTG<br>ACCGTGGACAAGTCCAGGTGGCAGCAGGGCAAC<br>GTGTTCAGCTGCAGCGTGATGCACGAGGCCCTGC<br>ACAACCACTACACCCAGAAGTCCCTGAGCCTGA<br>GCCCCGGCAAG |
| SEQ ID NO: 56<br>(Kabat) | LCDR1 | GGDNIGSRPVH |
| SEQ ID NO: 57<br>(Kabat) | LCDR2 | DDSNRPS |
| SEQ ID NO: 58<br>(Kabat) | LCDR3 | QVWSSSTDHP |
| SEQ ID NO: 59<br>(Chothia) | LCDR1 | DNIGSRP |
| SEQ ID NO: 60<br>(Chothia) | LCDR2 | DDS |
| SEQ ID NO: 61<br>(Chothia) | LCDR3 | WSSSTDH |
| SEQ ID NO: 62 | VL | QSVLTQPPSVSVAPGKTARITCGGDNIGSRPVHWY<br>QQKPGQAPILVVYDDSNRPSGIPERFSGSNSGNTAT<br>LTISRVEAGDEADYYCQVWSSSTDHPFGGGTKVTVL |
| SEQ ID NO: 63 | DNA VL | CAGTCAGTCCTGACTCAGCCCCCTAGCGTCAGCG<br>TGGCCCCTGGTAAAACCGCTAGAATCACCTGTGG<br>CGGCGATAATATCGGCTCTAGGCCCGTGCACTGG<br>TATCAGCAGAAGCCCGGTCAAGCCCCTATCCTGG<br>TGGTCTACGACGACTCTAATAGACCTAGCGGAAT<br>CCCCGAGCGGTTTAGCGGCTCTAATTCTGGTAAT<br>ACCGCTACCCTGACTATCTCTAGGGTGGAAGCCG<br>GCGACGAGGCCGACTACTACTGTCAAGTCTGGTC<br>TAGCTCTACCGATCACCCCTTCGGCGGAGGCACT<br>AAGGTTACAGTGCTG |
| SEQ ID NO: 64 | Light<br>Chain | QSVLTQPPSVSVAPGKTARITCGGDNIGSRPVHWY<br>QQKPGQAPILVVYDDSNRPSGIPERFSGSNSGNTAT<br>LTISRVEAGDEADYYCQVWSSSTDHPFGGGTKVTV<br>LGQPKAAPSVTLFPPSSEELQANKATLVCLISDFYP<br>GAVTVAWKADSSPVKAGVETTTPSKQSNNKYAAS<br>SYLSLTPEQWKSHRSYSCQVTHEGSTVEKTVAPTE<br>CS |
| SEQ ID NO: 65 | DNA<br>Light<br>Chain | CAGTCAGTCCTGACTCAGCCCCCTAGCGTCAGCG<br>TGGCCCCTGGTAAAACCGCTAGAATCACCTGTGG<br>CGGCGATAATATCGGCTCTAGGCCCGTGCACTGG<br>TATCAGCAGAAGCCCGGTCAAGCCCCTATCCTGG<br>TGGTCTACGACGACTCTAATAGACCTAGCGGAAT<br>CCCCGAGCGGTTTAGCGGCTCTAATTCTGGTAAT<br>ACCGCTACCCTGACTATCTCTAGGGTGGAAGCCG<br>GCGACGAGGCCGACTACTACTGTCAAGTCTGGTC<br>TAGCTCTACCGATCACCCCTTCGGCGGAGGCACT<br>AAGGTTACAGTGCTGGGTCAACCTAAGGCTGCCC |

TABLE 2-continued anti-VP1 Antibodies

```
CCAGCGTGACCCTGTTCCCCCCCAGCAGCGAGGA
GCTGCAGGCCAACAAGGCCACCCTGGTGTGCCT
GATCAGCGACTTCTACCCAGGCGCCGTGACCGTG
GCCTGGAAGGCCGACAGCAGCCCCGTGAAGGCC
GGCGTGGAGACCACCACCCCCAGCAAGCAGAGC
AACAACAAGTACGCCGCCAGCAGCTACCTGAGC
CTGACCCCCGAGCAGTGGAAGAGCCACAGGTCC
TACAGCTGCCAGGTGACCCACGAGGGCAGCACC
GTGGAAAAGACCGTGGCCCCAACCGAGTGCAGC
```

P8D11C

| SEQ ID NO: 66 (Kabat) | HCDR1 | NYWMT |
|---|---|---|
| SEQ ID NO: 67 (Kabat) | HCDR2 | NIKKDGSEKYYVDSVRG |
| SEQ ID NO: 68 (Kabat) | HCDR3 | VRSGRYFALDD |
| SEQ ID NO: 69 (Chothia) | HCDR1 | GFTFQNY |
| SEQ ID NO: 70 (Chothia) | HCDR2 | KKDGSE |
| SEQ ID NO: 71 (Chothia) | HCDR3 | VRSGRYFALDD |

SEQ ID NO: 72  VH
```
QVQLVESGGTLVQPGGSLRLSCAASGFTFQNYWM
TWVRQAPGKGLEWVANIKKDGSEKYYVDSVRGR
FTISRDNAKNSLFLQMNSLRPEDTAVYFCATVRSG
RYFALDDWGQGTLVTVSS
```

SEQ ID NO: 73  DNA VH
```
CAGGTGCAGCTGGTGGAATCAGGCGGCACACTG
GTGCAGCCTGGCGGTAGCCTGAGACTGAGCTGC
GCCGCTAGTGGATTCACCTTTCAGAACTACTGGA
TGACCTGGGTCAGACAGGCCCCTGGTAAAGGCC
TCGAGTGGGTGGCAAATATCAAGAAGGACGGTA
GCGAGAAGTACTACGTGGACTCAGTCAGAGGCC
GGTTCACTATCTCTAGGGATAACGCTAAGAATAG
CCTGTTCCTGCAGATGAACTCACTGAGGCCCGAG
GATACCGCCGTCTACTTCTGTGCTACCGTCAGAT
CAGGCCGCTACTTCGCCCTGGACGACTGGGGTCA
AGGCACACTGGTCACCGTGTCTAGC
```

SEQ ID NO: 74  Heavy Chain
```
QVQLVESGGTLVQPGGSLRLSCAASGFTFQNYWM
TWVRQAPGKGLEWVANIKKDGSEKYYVDSVRGR
FTISRDNAKNSLFLQMNSLRPEDTAVYFCATVRSG
RYFALDDWGQGTLVTVSSASTKGPSVFPLAPSSKS
TSGGTAALGCLVKDYFPEPVTVSWNSGALTSGVHT
FPAVLQSSGLYSLSSVVTVPSSSLGTQTYICNVNHK
PSNTKVDKRVEPKSCDKTHTCPPCPAPELLGGPSVF
LFPPKPKDTLMISRTPEVTCVVVDVSHEDPEVKFN
WYVDGVEVHNAKTKPREEQYNSTYRVVSVLTVLH
QDWLNGKEYKCKVSNKALPAPIEKTISKAKGQPRE
PQVYTLPPSREEMTKNQVSLTCLVKGFYPSDIAVE
WESNGQPENNYKTTPPVLDSDGSFFLYSKLTVDKS
RWQQGNVFSCSVMHEALHNHYTQKSLSLSPGK
```

SEQ ID NO: 75  DNA Heavy Chain
```
CAGGTGCAGCTGGTGGAATCAGGCGGCACACTG
GTGCAGCCTGGCGGTAGCCTGAGACTGAGCTGC
GCCGCTAGTGGATTCACCTTTCAGAACTACTGGA
TGACCTGGGTCAGACAGGCCCCTGGTAAAGGCC
TCGAGTGGGTGGCAAATATCAAGAAGGACGGTA
GCGAGAAGTACTACGTGGACTCAGTCAGAGGCC
GGTTCACTATCTCTAGGGATAACGCTAAGAATAG
CCTGTTCCTGCAGATGAACTCACTGAGGCCCGAG
GATACCGCCGTCTACTTCTGTGCTACCGTCAGAT
CAGGCCGCTACTTCGCCCTGGACGACTGGGGTCA
AGGCACACTGGTCACCGTGTCTAGCGCTAGCACT
AAGGGCCCAAGTGTGTTTCCCCTGGCCCCCAGCA
GCAAGTCTACTTCCGGCGGAACTGCTGCCCTGGG
TTGCCTGGTGAAGGACTACTTCCCCGAGCCCGTG
ACAGTGTCCTGGAACTCTGGGGCTCTGACTTCCG
GCGTGCACACCTTCCCGCCGTGCTGCAGAGCAG
CGGCCTGTACAGCCTGAGCAGCGTGGTGACAGT
```

TABLE 2-continued anti-VP1 Antibodies

```
GCCCTCCAGCTCTCTGGGAACCCAGACCTATATC
TGCAACGTGAACCACAAGCCCAGCAACACCAAG
GTGGACAAGAGAGTGGAGCCCAAGAGCTGCGAC
AAGACCCACACCTGCCCCCCCTGCCCAGCTCCAG
AACTGCTGGGAGGCCTTCCGTGTTCCTGTTCCC
CCCCAAGCCCAAGGACACCCTGATGATCAGCAG
GACCCCCGAGGTGACCTGCGTGGTGGTGGACGT
GTCCCACGAGGACCCAGAGGTGAAGTTCAACTG
GTACGTGGACGGCGTGGAGGTGCACAACGCCAA
GACCAAGCCCAGAGAGGAGCAGTACAACAGCAC
CTACAGGGTGGTGTCCGTGCTGACCGTGCTGCAC
CAGGACTGGCTGAACGGCAAGAATACAAGTGC
AAAGTCTCCAACAAGGCCCTGCCAGCCCCAATC
GAAAAGACAATCAGCAAGGCCAAGGGCCAGCCA
CGGGAGCCCCAGGTGTACACCCTGCCCCCCAGCC
GGGAGGAGATGACCAAGAACCAGGTGTCCCTGA
CCTGTCTGGTGAAGGGCTTCTACCCCAGCGATAT
CGCCGTGGAGTGGGAGAGCAACGGCCAGCCCGA
GAACAACTACAAGACCACCCCCCCAGTGCTGGA
CAGCGACGGCAGCTTCTTCCTGTACAGCAAGCTG
ACCGTGGACAAGTCCAGGTGGCAGCAGGGCAAC
GTGTTCAGCTGCAGCGTGATGCACGAGGCCCTGC
ACAACCACTACACCCAGAAGTCCCTGAGCCTGA
GCCCCGGCAAG
```

SEQ ID NO: 76 LCDR1 GGDNIGSRPVH
(Kabat)

SEQ ID NO: 77 LCDR2 DDSNRPS
(Kabat)

SEQ ID NO: 78 LCDR3 QVWSSSTDHP
(Kabat)

SEQ ID NO: 79 LCDR1 DNIGSRP
(Chothia)

SEQ ID NO: 80 LCDR2 DDS
(Chothia)

SEQ ID NO: 81 LCDR3 WSSSTDH
(Chothia)

SEQ ID NO: 82 VL QSVLTQPPSVSVAPGKTARITCGGDNIGSRPVHWY
QQKPGQAPILVVYDDSNRPSGIPERFSGSNSGNTAT
LTISRVEAGDEADYYCQVWSSSTDHPFGGGTKVTVL

SEQ ID NO: 83 DNA VL CAGTCAGTCCTGACTCAGCCCCCTAGCGTCAGCG
TGGCCCCTGGTAAAACCGCTAGAATCACCTGTGG
CGGCGATAATATCGGCTCTAGGCCCGTGCACTGG
TATCAGCAGAAGCCCGGTCAAGCCCCTATCCTGG
TGGTCTACGACGACTCTAATAGACCTAGCGGAAT
CCCCGAGCGGTTTAGCGGCTCTAATTCTGGTAAT
ACCGCTACCCTGACTATCTCTAGGGTGGAAGCCG
GCGACGAGGCCGACTACTACTGTCAAGTCTGGTC
TAGCTCTACCGATCACCCCTTCGGCGGAGGCACT
AAGGTTACAGTGCTG

SEQ ID NO: 84 Light QSVLTQPPSVSVAPGKTARITCGGDNIGSRPVHWY
Chain QQKPGQAPILVVYDDSNRPSGIPERFSGSNSGNTAT
LTISRVEAGDEADYYCQVWSSSTDHPFGGGTKVTV
LGQPKAAPSVTLFPPSSEELQANKATLVCLISDFYP
GAVTVAWKADSSPVKAGVETTTPSKQSNNKYAAS
SYLSLTPEQWKSHRSYSCQVTHEGSTVEKTVAPTE
CS SEQ ID NO: 85 DNA CAGTCAGTCCTGACTCAGCCCCCTAGCGTCAGCG
Light TGGCCCCTGGTAAAACCGCTAGAATCACCTGTGG
Chain CGGCGATAATATCGGCTCTAGGCCCGTGCACTGG
TATCAGCAGAAGCCCGGTCAAGCCCCTATCCTGG
TGGTCTACGACGACTCTAATAGACCTAGCGGAAT
CCCCGAGCGGTTTAGCGGCTCTAATTCTGGTAAT
ACCGCTACCCTGACTATCTCTAGGGTGGAAGCCG
GCGACGAGGCCGACTACTACTGTCAAGTCTGGTC
TAGCTCTACCGATCACCCCTTCGGCGGAGGCACT
AAGGTTACAGTGCTGGGTCAACCTAAGGCTGCCC
CCAGCGTGACCCTGTTCCCCCCCAGCAGCGAGGA
GCTGCAGGCCAACAAGGCCACCCTGGTGTGCCT
```

TABLE 2-continued

| anti-VP1 Antibodies |
|---|

```
GATCAGCGACTTCTACCCAGGCGCCGTGACCGTG
GCCTGGAAGGCCGACAGCAGCCCCGTGAAGGCC
GGCGTGGAGACCACCACCCCCAGCAAGCAGAGC
AACAACAAGTACGCCGCCAGCAGCTACCTGAGC
CTGACCCCCGAGCAGTGGAAGAGCCACAGGTCC
TACAGCTGCCAGGTGACCCACGAGGGCAGCACC
GTGGAAAAGACCGTGGCCCCAACCGAGTGCAGC
```

P8D11D

SEQ ID NO: 86 HCDR1 NYWMT
(Kabat)

SEQ ID NO: 87 HCDR2 NIKKDGSEKYYVDSVRG
(Kabat)

SEQ ID NO: 88 HCDR3 VRSGRYFALDD
(Kabat)

SEQ ID NO: 89 HCDR1 GFTFNNY
(Chothia)

SEQ ID NO: 90 HCDR2 KKDGSE
(Chothia)

SEQ ID NO: 91 HCDR3 VRSGRYFALDD
(Chothia)

SEQ ID NO: 92 VH QVQLQESGPGLVQPGGSLRLSCAASGFTFNNYWM
TWVRQAPGKGLEWVANIKKDGSEKYYVDSVRGR
FTISRDNAKNSLFLQMNSLRPEDTAVYFCATVRSG
RYFALDDWGQGTLVTVSS

SEQ ID NO: 93 DNA VH CAGGTGCAGCTGCAGGAATCAGGCCCAGGACTG
GTGCAGCCTGGCGGTAGCCTGAGACTGAGCTGC
GCTGCTAGTGGCTTCACCTTTAACAACTACTGGA
TGACCTGGGTCCGCCAGGCCCCTGGCAAAGGCCT
GGAGTGGGTGGCAAATATCAAGAAGGACGGTAG
CGAGAAGTACTACGTGGACTCAGTCAGAGGCCG
GTTCACTATCTCTAGGGATAACGCTAAGAATAGC
CTGTTCCTGCAGATGAACTCACTGAGGCCCGAGG
ATACCGCCGTCTACTTCTGTGCTACCGTCAGATC
AGGCCGCTACTTCGCCCTGGACGACTGGGGCCA
GGGCACCCTGGTCACCGTGTCTTCC

SEQ ID NO: 94 Heavy QVQLQESGPGLVQPGGSLRLSCAASGFTFNNYWM
              Chain TWVRQAPGKGLEWVANIKKDGSEKYYVDSVRGR
                    FTISRDNAKNSLFLQMNSLRPEDTAVYFCATVRSG
                    RYFALDDWGQGTLVTVSSASTKGPSVFPLAPSSKS
                    TSGGTAALGCLVKDYFPEPVTVSWNSGALTSGVHT
                    FPAVLQSSGLYSLSSVVTVPSSSLGTQTYICNVNHK
                    PSNTKVDKRVEPKSCDKTHTCPPCPAPELLGGPSVF
                    LFPPKPKDTLMISRTPEVTCVVVDVSHEDPEVKFN
                    WYVDGVEVHNAKTKPREEQYNSTYRVVSVLTVLH
                    QDWLNGKEYKCKVSNKALPAPIEKTISKAKGQPRE
                    PQVYTLPPSREEMTKNQVSLTCLVKGFYPSDIAVE
                    WESNGQPENNYKTTPPVLDSDGSFFLYSKLTVDKS
                    RWQQGNVFSCSVMHEALHNHYTQKSLSLSPGK SEQ ID NO: 95 DNA    CAGGTGCAGCTGCAGGAATCAGGCCCAGGACTG
              Heavy  GTGCAGCCTGGCGGTAGCCTGAGACTGAGCTGC
              Chain  GCTGCTAGTGGCTTCACCTTTAACAACTACTGGA
                     TGACCTGGGTCCGCCAGGCCCCTGGCAAAGGCCT
                     GGAGTGGGTGGCAAATATCAAGAAGGACGGTAG
                     CGAGAAGTACTACGTGGACTCAGTCAGAGGCCG
                     GTTCACTATCTCTAGGGATAACGCTAAGAATAGC
                     CTGTTCCTGCAGATGAACTCACTGAGGCCCGAGG
                     ATACCGCCGTCTACTTCTGTGCTACCGTCAGATC
                     AGGCCGCTACTTCGCCCTGGACGACTGGGGCCA
                     GGGCACCCTGGTCACCGTGTCTTCCGCTAGCACT
                     AAGGGCCCAAGTGTGTTTCCCCTGGCCCCCAGCA
                     GCAAGTCTACTTCCGGCGGAACTGCTGCCCTGGG
                     TTGCCTGGTGAAGGACTACTTCCCCGAGCCCGTG
                     ACAGTGTCCTGGAACTCTGGGGCTCTGACTTCCG
                     GCGTGCACACCTTCCCCGCCGTGCTGCAGAGCAG
                     CGGCCTGTACAGCCTGAGCAGCGTGGTGACAGT
                     GCCCTCCAGCTCTCTGGGAACCCAGACCTATATC
                     TGCAACGTGAACCACAAGCCCAGCAACACCAAG
```

TABLE 2-continued

| anti-VP1 Antibodies |
|---|

|  |  |  |
|---|---|---|
|  |  | GTGGACAAGAGAGTGGAGCCCAAGAGCTGCGAC<br>AAGACCCACACCTGCCCCCCCTGCCCAGCTCCAG<br>AACTGCTGGGAGGGCCTTCCGTGTTCCTGTTCCC<br>CCCCAAGCCCAAGGACACCCTGATGATCAGCAG<br>GACCCCCGAGGTGACCTGCGTGGTGGTGGACGT<br>GTCCCACGAGGACCCAGAGGTGAAGTTCAACTG<br>GTACGTGGACGGCGTGGAGGTGCACAACGCCAA<br>GACCAAGCCCAGAGAGGAGCAGTACAACAGCAC<br>CTACAGGGTGGTGTCCGTGCTGACCGTGCTGCAC<br>CAGGACTGGCTGAACGGCAAAGAATACAAGTGC<br>AAAGTCTCCAACAAGGCCCTGCCAGCCCCAATC<br>GAAAAGACAATCAGCAAGGCCAAGGGCCAGCCA<br>CGGGAGCCCCAGGTGTACACCCTGCCCCCCAGCC<br>GGGAGGAGATGACCAAGAACCAGGTGTCCCTGA<br>CCTGTCTGGTGAAGGGCTTCTACCCCAGCGATAT<br>CGCCGTGGAGTGGGAGAGCAACGGCCAGCCCGA<br>GAACAACTACAAGACCACCCCCCCAGTGCTGGA<br>CAGCGACGGCAGCTTCTTCCTGTACAGCAAGCTG<br>ACCGTGGACAAGTCCAGGTGGCAGCAGGGCAAC<br>GTGTTCAGCTGCAGCGTGATGCACGAGGCCCTGC<br>ACAACCACTACACCCAGAAGTCCCTGAGCCTGA<br>GCCCCGGCAAG |
| SEQ ID NO: 96<br>(Kabat) | LCDR1 | GGDNIGSRPVH |
| SEQ ID NO: 97<br>(Kabat) | LCDR2 | DDSNRPS |
| SEQ ID NO: 98<br>(Kabat) | LCDR3 | QVWSSSTDHP |
| SEQ ID NO: 99<br>(Chothia) | LCDR1 | DNIGSRP |
| SEQ ID NO: 100<br>(Chothia) | LCDR2 | DDS |
| SEQ ID NO: 101<br>(Chothia) | LCDR3 | WSSSTDH |
| SEQ ID NO: 102 | VL | QSVLTQPPSVSVAPGKTARITCGGDNIGSRPVHWY<br>QQKPGQAPILVVYDDSNRPSGIPERFSGSNSGNTAT<br>LTISRVEAGDEADYYCQVWSSSTDHPFGGGTKVTVL |
| SEQ ID NO: 103 | DNA VL | CAGTCAGTCCTGACTCAGCCCCCTAGCGTCAGCG<br>TGGCCCCTGGTAAAACCGCTAGAATCACCTGTGG<br>CGGCGATAATATCGGCTCTAGGCCCGTGCACTGG<br>TATCAGCAGAAGCCCGGTCAAGCCCCTATCCTGG<br>TGGTCTACGACGACTCTAATAGACCTAGCGGAAT<br>CCCCGAGCGGTTTAGCGGCTCTAATTCTGGTAAT<br>ACCGCTACCCTGACTATCTCTAGGGTGGAAGCCG<br>GCGACGAGGCCGACTACTACTGTCAAGTCTGGTC<br>TAGCTCTACCGATCACCCCTTCGGCGGAGGCACT<br>AAGGTTACAGTGCTG |
| SEQ ID NO: 104 | Light<br>Chain | QSVLTQPPSVSVAPGKTARITCGGDNIGSRPVHWY<br>QQKPGQAPILVVYDDSNRPSGIPERFSGSNSGNTAT<br>LTISRVEAGDEADYYCQVWSSSTDHPFGGGTKVTV<br>LGQPKAAPSVTLFPPSSEELQANKATLVCLISDFYP<br>GAVTVAWKADSSPVKAGVETTTPSKQSNNKYAAS<br>SYLSLTPEQWKSHRSYSCQVTHEGSTVEKTVAPTE<br>CS |
| SEQ ID NO: 105 | DNA<br>Light<br>Chain | CAGTCAGTCCTGACTCAGCCCCCTAGCGTCAGCG<br>TGGCCCCTGGTAAAACCGCTAGAATCACCTGTGG<br>CGGCGATAATATCGGCTCTAGGCCCGTGCACTGG<br>TATCAGCAGAAGCCCGGTCAAGCCCCTATCCTGG<br>TGGTCTACGACGACTCTAATAGACCTAGCGGAAT<br>CCCCGAGCGGTTTAGCGGCTCTAATTCTGGTAAT<br>ACCGCTACCCTGACTATCTCTAGGGTGGAAGCCG<br>GCGACGAGGCCGACTACTACTGTCAAGTCTGGTC<br>TAGCTCTACCGATCACCCCTTCGGCGGAGGCACT<br>AAGGTTACAGTGCTGGGTCAACCTAAGGCTGCCC<br>CCAGCGTGACCCTGTTCCCCCCCAGCAGCGAGGA<br>GCTGCAGGCCAACAAGGCCACCCTGGTGTGCCT<br>GATCAGCGACTTCTACCCAGGCGCCGTGACCGTG<br>GCCTGGAAGGCCGACAGCAGCCCCGTGAAGGCC |

TABLE 2-continued anti-VP1 Antibodies

```
GGCGTGGAGACCACCACCCCCAGCAAGCAGAGC
AACAACAAGTACGCCGCCAGCAGCTACCTGAGC
CTGACCCCCGAGCAGTGGAAGAGCCACAGGTCC
TACAGCTGCCAGGTGACCCACGAGGGCAGCACC
GTGGAAAAGACCGTGGCCCCAACCGAGTGCAGC
```

P8D11E

SEQ ID NO: 106 HCDR1 NYWMT
(Kabat)

SEQ ID NO: 107 HCDR2 NIKKDGSEKYYVDSVRG
(Kabat)

SEQ ID NO: 108 HCDR3 VRSGRYFALDD
(Kabat)

SEQ ID NO: 109 HCDR1 GFTFNNY
(Chothia)

SEQ ID NO: 110 HCDR2 KKDGSE
(Chothia)

SEQ ID NO: 111 HCDR3 VRSGRYFALDD
(Chothia)

SEQ ID NO: 112 VH QVQLVESGGGLVQPGGSLRLSCAASGFTFNNYWM
TWVRQAPGKGLEWVANIKKDGSEKYYVDSVRGR
FTISRDNAKNSLFLQMNSLRPEDTAVYFCATVRSG
RYFALDDWGQGTLVTVSS

SEQ ID NO: 113 DNA VH CAGGTGCAGCTGGTGGAATCAGGCGGCGGACTG
GTGCAGCCTGGCGGTAGCCTGAGACTGAGCTGC
GCTGCTAGTGGCTTCACCTTTAACAACTACTGGA
TGACCTGGGTTAGGCAGGCCCCTGGTAAAGGCCT
CGAGTGGGTGGCAAATATCAAGAAGGACGGTAG
CGAGAAGTACTACGTGGACTCAGTCAGAGGCCG
GTTCACTATCTCTAGGGATAACGCTAAGAATAGC
CTGTTCCTGCAGATGAACTCACTGAGGCCCGAGG
ATACCGCCGTCTACTTCTGTGCTACCGTCAGATC
AGGCCGCTACTTCGCCCTGGACGACTGGGGTCAA
GGCACACTGGTCACCGTGTCTAGC

SEQ ID NO: 114 Heavy QVQLVESGGGLVQPGGSLRLSCAASGFTFNNYWM
Chain TWVRQAPGKGLEWVANIKKDGSEKYYVDSVRGR
FTISRDNAKNSLFLQMNSLRPEDTAVYFCATVRSG
RYFALDDWGQGTLVTVSSASTKGPSVFPLAPSSKS
TSGGTAALGCLVKDYFPEPVTVSWNSGALTSGVHT
FPAVLQSSGLYSLSSVVTVPSSSLGTQTYICNVNHK
PSNTKVDKRVEPKSCDKTHTCPPCPAPELLGGPSVF
LFPPKPKDTLMISRTPEVTCVVVDVSHEDPEVKFN
WYVDGVEVHNAKTKPREEQYNSTYRVVSVLTVLH
QDWLNGKEYKCKVSNKALPAPIEKTISKAKGQPRE
PQVYTLPPSREEMTKNQVSLTCLVKGFYPSDIAVE
WESNGQPENNYKTTPPVLDSDGSFFLYSKLTVDKS
RWQQGNVFSCSVMHEALHNHYTQKSLSLSPGK SEQ ID NO: 115 DNA CAGGTGCAGCTGGTGGAATCAGGCGGCGGACTG
Heavy GTGCAGCCTGGCGGTAGCCTGAGACTGAGCTGC
Chain GCTGCTAGTGGCTTCACCTTTAACAACTACTGGA
TGACCTGGGTTAGGCAGGCCCCTGGTAAAGGCCT
CGAGTGGGTGGCAAATATCAAGAAGGACGGTAG
CGAGAAGTACTACGTGGACTCAGTCAGAGGCCG
GTTCACTATCTCTAGGGATAACGCTAAGAATAGC
CTGTTCCTGCAGATGAACTCACTGAGGCCCGAGG
ATACCGCCGTCTACTTCTGTGCTACCGTCAGATC
AGGCCGCTACTTCGCCCTGGACGACTGGGGTCAA
GGCACACTGGTCACCGTGTCTAGCGCTAGCACTA
AGGGCCCAAGTGTGTTTCCCCTGGCCCCCAGCAG
CAAGTCTACTTCCGGCGGAACTGCTGCCCTGGGT
TGCCTGGTGAAGGACTACTTCCCCGAGCCCGTGA
CAGTGTCCTGGAACTCTGGGGCTCTGACTTCCGG
CGTGCACACCTTCCCCGCCGTGCTGCAGAGCAGC
GGCCTGTACAGCCTGAGCAGCGTGGTGACAGTG
CCCTCCAGCTCTCTGGGAACCCAGACCTATATCT
GCAACGTGAACCACAAGCCCAGCAACACCAAGG
TGGACAAGAGAGTGGAGCCCAAGAGCTGCGACA
AGACCCACACCTGCCCCCCCTGCCCAGCTCCAGA
```

TABLE 2-continued anti-VP1 Antibodies

```
ACTGCTGGGAGGGCCTTCCGTGTTCCTGTTCCCC
CCCAAGCCCAAGGACACCCTGATGATCAGCAGG
ACCCCCGAGGTGACCTGCGTGGTGGTGGACGTGT
CCCACGAGGACCCAGAGGTGAAGTTCAACTGGT
ACGTGGACGGCGTGGAGGTGCACAACGCCAAGA
CCAAGCCCAGAGAGGAGCAGTACAACAGCACCT
ACAGGGTGGTGTCCGTGCTGACCGTGCTGCACCA
GGACTGGCTGAACGGCAAAGAATACAAGTGCAA
AGTCTCCAACAAGGCCCTGCCAGCCCCAATCGA
AAAGACAATCAGCAAGGCCAAGGGCCAGCCACG
GGAGCCCCAGGTGTACACCCTGCCCCCCCAGCCG
GGAGGAGATGACCAAGAACCAGGTGTCCCTGAC
CTGTCTGGTGAAGGGCTTCTACCCCAGCGATATC
GCCGTGGAGTGGGAGAGCAACGGCCAGCCCGAG
AACAACTACAAGACCACCCCCCCAGTGCTGGAC
AGCGACGGCAGCTTCTTCCTGTACAGCAAGCTGA
CCGTGGACAAGTCCAGGTGGCAGCAGGGCAACG
TGTTCAGCTGCAGCGTGATGCACGAGGCCCTGCA
CAACCACTACACCCAGAAGTCCCTGAGCCTGAG
CCCCGGCAAG
```

SEQ ID NO: 116 LCDR1 GGDNIGSRPVH
(Kabat)

SEQ ID NO: 117 LCDR2 DDSNRPS
(Kabat)

SEQ ID NO: 118 LCDR3 QVWSSSTDHP
(Kabat)

SEQ ID NO: 119 LCDR1 DNIGSRP
(Chothia)

SEQ ID NO: 120 LCDR2 DDS
(Chothia)

SEQ ID NO: 121 LCDR3 WSSSTDH
(Chothia)

SEQ ID NO: 122 VL    QSVLTQPPSVSVAPGKTARITCGGDNIGSRPVHWY
               QQKPGQAPILVVYDDSNRPSGIPERFSGSNSGNTAT
               LTISRVEAGDEADYYCQVWSSSTDHPFGGGTKVTVL

SEQ ID NO: 123 DNA VL CAGTCAGTCCTGACTCAGCCCCCTAGCGTCAGCG
               TGGCCCCTGGTAAAACCGCTAGAATCACCTGTGG
               CGGCGATAATATCGGCTCTAGGCCCGTGCACTGG
               TATCAGCAGAAGCCCGGTCAAGCCCCTATCCTGG
               TGGTCTACGACGACTCTAATAGACCTAGCGGAAT
               CCCCGAGCGGTTTAGCGGCTCTAATTCTGGTAAT
               ACCGCTACCCTGACTATCTCTAGGGTGGAAGCCG
               GCGACGAGGCCGACTACTACTGTCAAGTCTGGTC
               TAGCTCTACCGATCACCCCTTCGGCGGAGGCACT
               AAGGTTACAGTGCTG

SEQ ID NO: 124 Light  QSVLTQPPSVSVAPGKTARITCGGDNIGSRPVHWY
               Chain  QQKPGQAPILVVYDDSNRPSGIPERFSGSNSGNTAT
                      LTISRVEAGDEADYYCQVWSSSTDHPFGGGTKVTV
                      LGQPKAAPSVTLFPPSSEELQANKATLVCLISDFYP
                      GAVTVAWKADSSPVKAGVETTTPSKQSNNKYAAS
                      SYLSLTPEQWKSHRSYSCQVTHEGSTVEKTVAPTE
                      CS SEQ ID NO: 125 DNA    CAGTCAGTCCTGACTCAGCCCCCTAGCGTCAGCG
               Light  TGGCCCCTGGTAAAACCGCTAGAATCACCTGTGG
               Chain  CGGCGATAATATCGGCTCTAGGCCCGTGCACTGG
                      TATCAGCAGAAGCCCGGTCAAGCCCCTATCCTGG
                      TGGTCTACGACGACTCTAATAGACCTAGCGGAAT
                      CCCCGAGCGGTTTAGCGGCTCTAATTCTGGTAAT
                      ACCGCTACCCTGACTATCTCTAGGGTGGAAGCCG
                      GCGACGAGGCCGACTACTACTGTCAAGTCTGGTC
                      TAGCTCTACCGATCACCCCTTCGGCGGAGGCACT
                      AAGGTTACAGTGCTGGGTCAACCTAAGGCTGCCC
                      CCAGCGTGACCCTGTTCCCCCCCAGCAGCGAGGA
                      GCTGCAGGCCAACAAGGCCACCCTGGTGTGCCT
                      GATCAGCGACTTCTACCAGGCGCCGTGACCGTG
                      GCCTGGAAGGCCGACAGCAGCCCCGTGAAGGCC
                      GGCGTGGAGACCACCACCCCCAGCAAGCAGAGC
                      AACAACAAGTACGCCGCCAGCAGCTACCTGAGC
```

TABLE 2-continued

| anti-VP1 Antibodies | | |
|---|---|---|
| | | CTGACCCCCGAGCAGTGGAAGAGCCACAGGTCC<br>TACAGCTGCCAGGTGACCCACGAGGGCAGCACC<br>GTGGAAAAGACCGTGGCCCCAACCGAGTGCAGC |
| P165E2<br>SEQ ID NO: 126<br>(Kabat) | HCDR1 | RDYWT |
| SEQ ID NO: 127<br>(Kabat) | HCDR2 | NIYYSGSTNYNPSLKS |
| SEQ ID NO: 128<br>(Kabat) | HCDR3 | VPGCSSTSCIDGWFDP |
| SEQ ID NO: 129<br>(Chothia) | HCDR1 | GGSISRD |
| SEQ ID NO: 130<br>(Chothia) | HCDR2 | YYSGS |
| SEQ ID NO: 131<br>(Chothia) | HCDR3 | VPGCSSTSCIDGWFDP |
| SEQ ID NO: 132 | VH | QVQLQESGPGLVKPSETLSLTCTVSGGSISRDYWT<br>WVRQPPGEGLEWIGNIYYSGSTNYNPSLKSRVTISV<br>AASKKQFSLKLTSVTAADTAVYYCARVPGCSSTSC<br>IDGWFDPWGQGILVTVSS |
| SEQ ID NO: 133 | DNA VH | CAGGTGCAGCTGCAAGAATCAGGCCCTGGCCTG<br>GTCAAGCCTAGCGAGACACTGAGCCTGACCTGC<br>ACCGTCAGCGGCGGCTCTATCTCTAGGGACTACT<br>GGACCTGGGTCCGACAGCCTCCTGGCGAGGGCC<br>TCGAGTGGATCGGTAATATCTACTATAGCGGCTC<br>TACTAACTATAACCCTAGCCTGAAGTCTAGGGTC<br>ACAATTAGCGTGGCCGCCTCTAAGAAGCAGTTTA<br>GCCTGAAGCTGACTAGCGTGACCGCCGCTGACA<br>CCGCCGTCTACTACTGCGCTAGAGTGCCCGGCTG<br>CTCTAGCACTAGCTGTATCGACGGCTGGTTTGAC<br>CCTTGGGGTCAAGGGATCCTGGTCACCGTGTCTA<br>GC |
| SEQ ID NO: 134 | Heavy<br>Chain | QVQLQESGPGLVKPSETLSLTCTVSGGSISRDYWT<br>WVRQPPGEGLEWIGNIYYSGSTNYNPSLKSRVTISV<br>AASKKQFSLKLTSVTAADTAVYYCARVPGCSSTSC<br>IDGWFDPWGQGILVTVSSASTKGPSVFPLAPSSKST<br>SGGTAALGCLVKDYFPEPVTVSWNSGALTSGVHTF<br>PAVLQSSGLYSLSSVVTVPSSSLGTQTYICNVNHKP<br>SNTKVDKRVEPKSCDKTHTCPPCPAPELLGGPSVFL<br>FPPKPKDTLMISRTPEVTCVVVDVSHEDPEVKFNW<br>YVDGVEVHNAKTKPREEQYNSTYRVVSVLTVLHQ<br>DWLNGKEYKCKVSNKALPAPIEKTISKAKGQPREP<br>QVYTLPPSREEMTKNQVSLTCLVKGFYPSDIAVEW<br>ESNGQPENNYKTTPPVLDSDGSFFLYSKLTVDKSR<br>WQQGNVFSCSVMHEALHNHYTQKSLSLSPGK |
| SEQ ID NO: 135 | DNA<br>Heavy<br>Chain | CAGGTGCAGCTGCAAGAATCAGGCCCTGGCCTG<br>GTCAAGCCTAGCGAGACACTGAGCCTGACCTGC<br>ACCGTCAGCGGCGGCTCTATCTCTAGGGACTACT<br>GGACCTGGGTCCGACAGCCTCCTGGCGAGGGCC<br>TCGAGTGGATCGGTAATATCTACTATAGCGGCTC<br>TACTAACTATAACCCTAGCCTGAAGTCTAGGGTC<br>ACAATTAGCGTGGCCGCCTCTAAGAAGCAGTTTA<br>GCCTGAAGCTGACTAGCGTGACCGCCGCTGACA<br>CCGCCGTCTACTACTGCGCTAGAGTGCCCGGCTG<br>CTCTAGCACTAGCTGTATCGACGGCTGGTTTGAC<br>CCTTGGGGTCAAGGGATCCTGGTCACCGTGTCTA<br>GCGCTAGCACTAAGGGCCCAAGTGTGTTTCCCCT<br>GGCCCCCAGCAGCAAGTCTACTTCCGGCGGAACT<br>GCTGCCCTGGGTTGCCTGGTGAAGGACTACTTCC<br>CCGAGCCCGTGACAGTGTCCTGGAACTCTGGGGC<br>TCTGACTTCCGGCGTGCACACCTTCCCCGCCGTG<br>CTGCAGAGCAGCGGCCTGTACAGCCTGAGCAGC<br>GTGGTGACAGTGCCCTCCAGCTCTCTGGGAACCC<br>AGACCTATATCTGCAACGTGAACCACAAGCCCA<br>GCAACACCAAGGTGGACAAGAGAGTGGAGCCCA<br>AGAGCTGCGACAAGACCCACACCTGCCCCCCCT<br>GCCCAGCTCCAGAACTGCTGGGAGGGCCTTCCGT<br>GTTCCTGTTCCCCCCCAAGCCCAAGGACACCCTG |

TABLE 2-continued anti-VP1 Antibodies

ATGATCAGCAGGACCCCCGAGGTGACCTGCGTG
GTGGTGGACGTGTCCCACGAGGACCCAGAGGTG
AAGTTCAACTGGTACGTGGACGGCGTGGAGGTG
CACAACGCCAAGACCAAGCCCAGAGAGGAGCAG
TACAACAGCACCTACAGGGTGGTGTCCGTGCTGA
CCGTGCTGCACCAGGACTGGCTGAACGGCAAAG
AATACAAGTGCAAAGTCTCCAACAAGGCCCTGC
CAGCCCCAATCGAAAAGACAATCAGCAAGGCCA
AGGGCCAGCCACGGGAGCCCCAGGTGTACACCC
TGCCCCCCAGCCGGGAGGAGATGACCAAGAACC
AGGTGTCCCTGACCTGTCTGGTGAAGGGCTTCTA
CCCCAGCGATATCGCCGTGGAGTGGGAGAGCAA
CGGCCAGCCCGAGAACAACTACAAGACCACCCC
CCCAGTGCTGGACAGCGACGGCAGCTTCTTCCTG
TACAGCAAGCTGACCGTGGACAAGTCCAGGTGG
CAGCAGGGCAACGTGTTCAGCTGCAGCGTGATG
CACGAGGCCCTGCACAACCACTACACCCAGAAG
TCCCTGAGCCTGAGCCCCGGCAAG

SEQ ID NO: 136 LCDR1 SGSSSNIGNTYVS
(Kabat)

SEQ ID NO: 137 LCDR2 DNNKRPS
(Kabat)

SEQ ID NO: 138 LCDR3 GTWDSSLSAWV
(Kabat)

SEQ ID NO: 139 LCDR1 SSSNIGNTY
(Chothia)

SEQ ID NO: 140 LCDR2 DNN
(Chothia)

SEQ ID NO: 141 LCDR3 WDSSLSAW
(Chothia)

SEQ ID NO: 142 VL QSVLTQPPSLSAAPGQRVTISCSGSSSNIGNTYVSW
YQQLPGTAPKLLIYDNNKRPSGIPGRFSGSKSGTSA
TLGITGLQTGDEAAYYCGTWDSSLSAWVFGGGTR
LTVL

SEQ ID NO: 143 DNA VL CAGTCAGTCCTGACTCAGCCCCCTAGCCTGAGCG
CCGCTCCCGGTCAAAGAGTGACTATTAGCTGTAG
CGGCTCTAGCTCTAATATCGGTAATACCTACGTC
AGCTGGTATCAGCAGCTGCCCGGCACCGCCCCTA
AGCTGCTGATCTACGATAACAACAAGCGGCCTA
GCGGAATCCCTGGTCGCTTTAGCGGATCTAAATC
AGGCACTAGCGCTACCCTGGGAATCACCGGCCT
GCAGACCGGCGACGAAGCCGCCTACTACTGCGG
CACCTGGGACTCTAGTCTGAGCGCCTGGGTGTTC
GGCGGAGGCACTAGACTGACCGTGCTG

SEQ ID NO: 144 Light QSVLTQPPSLSAAPGQRVTISCSGSSSNIGNTYVSW
Chain YQQLPGTAPKLLIYDNNKRPSGIPGRFSGSKSGTSA
TLGITGLQTGDEAAYYCGTWDSSLSAWVFGGGTR
LTVLGQPKAAPSVTLFPPSSEELQANKATLVCLISD
FYPGAVTVAWKADSSPVKAGVETTTPSKQSNNKY
AASSYLSLTPEQWKSHRSYSCQVTHEGSTVEKTVA
PTECS SEQ ID NO: 145 DNA CAGTCAGTCCTGACTCAGCCCCCTAGCCTGAGCG
Light CCGCTCCCGGTCAAAGAGTGACTATTAGCTGTAG
Chain CGGCTCTAGCTCTAATATCGGTAATACCTACGTC
AGCTGGTATCAGCAGCTGCCCGGCACCGCCCCTA
AGCTGCTGATCTACGATAACAACAAGCGGCCTA
GCGGAATCCCTGGTCGCTTTAGCGGATCTAAATC
AGGCACTAGCGCTACCCTGGGAATCACCGGCCT
GCAGACCGGCGACGAAGCCGCCTACTACTGCGG
CACCTGGGACTCTAGTCTGAGCGCCTGGGTGTTC
GGCGGAGGCACTAGACTGACCGTGCTGGGTCAA
CCTAAGGCTGCCCCAGCGTGACCCTGTTCCCCC
CCAGCAGCGAGGAGCTGCAGGCCAACAAGGCCA
CCCTGGTGTGCCTGATCAGCGACTTCTACCCAGG
CGCCGTGACCGTGGCCTGGAAGGCCGACAGCAG
CCCCGTGAAGGCCGGCGTGGAGACCACCACCCC
CAGCAAGCAGAGCAACAACAAGTACGCCGCCAG
CAGCTACCTGAGCCTGACCCCCGAGCAGTGGAA TABLE 2-continued

| anti-VP1 Antibodies | | |
|---|---|---|
| | | GAGCCACAGGTCCTACAGCTGCCAGGTGACCCA CGAGGGCAGCACCGTGGAAAAGACCGTGGCCCC AACCGAGTGCAGC |
| NEG447 SEQ ID NO: 146 (Kabat) | HCDR1 | RDYWS |
| SEQ ID NO: 147 (Kabat) | HCDR2 | NIYYSGSTNYNPSLKS |
| SEQ ID NO: 148 (Kabat) | HCDR3 | VPGCSSTSCIDGWFDP |
| SEQ ID NO: 149 (Chothia) | HCDR1 | GGSISRD |
| SEQ ID NO: 150 (Chothia) | HCDR2 | YYSGS |
| SEQ ID NO: 151 (Chothia) | HCDR3 | VPGCSSTSCIDGWFDP |
| SEQ ID NO: 152 | VH | QVQLQESGPGLVKPSETLSLTCTVSGGSISRDYWS WVRQPPGAGLEWIGNIYYSGSTNYNPSLKSRVTISV ATNKKQFSLKLTSVTAADTAVYYCARVPGCSSTSC IDGWFDPWGQGILVTVSS |
| SEQ ID NO: 153 | DNA VH | CAGGTGCAGCTGCAAGAATCAGGCCCTGGCCTG GTCAAGCCTAGCGAGACACTGAGCCTGACCTGC ACCGTCAGCGGCGGCTCTATCTCTAGGGACTACT GGTCCTGGGTCCGACAACCTCCTGGCGCTGGCCT CGAGTGGATCGGTAATATCTACTATAGCGGCTCT ACTAACTATAACCCTAGCCTGAAGTCTAGGGTCA CAATTAGTGTGGCTACTAACAAGAAGCAGTTTAG CCTGAAGCTGACTAGCGTGACCGCCGCTGACACC GCCGTCTACTACTGCGCTAGAGTGCCCGGCTGCT CTAGCACTAGCTGTATCGACGGTTGGTTTGACCC TTGGGGTCAAGGGATCCTGGTCACCGTGTCTAGC |
| SEQ ID NO: 154 | Heavy Chain | QVQLQESGPGLVKPSETLSLTCTVSGGSISRDYWS WVRQPPGAGLEWIGNIYYSGSTNYNPSLKSRVTISV ATNKKQFSLKLTSVTAADTAVYYCARVPGCSSTSC IDGWFDPWGQGILVTVSSASTKGPSVFPLAPSSKST SGGTAALGCLVKDYFPEPVTVSWNSGALTSGVHTF PAVLQSSGLYSLSSVVTVPSSSLGTQTYICNVNHKP SNTKVDKRVEPKSCDKTHTCPPCPAPELLGGPSVFL FPPKPKDTLMISRTPEVTCVVVDVSHEDPEVKFNW YVDGVEVHNAKTKPREEQYNSTYRVVSVLTVLHQ DWLNGKEYKCKVSNKALPAPIEKTISKAKGQPREP QVYTLPPSREEMTKNQVSLTCLVKGFYPSDIAVEW ESNGQPENNYKTTPPVLDSDGSFFLYSKLTVDKSR WQQGNVFSCSVMHEALHNHYTQKSLSLSPGK |
| SEQ ID NO: 155 | DNA Heavy Chain | CAGGTGCAGCTGCAAGAATCAGGCCCTGGCCTG GTCAAGCCTAGCGAGACACTGAGCCTGACCTGC ACCGTCAGCGGCGGCTCTATCTCTAGGGACTACT GGTCCTGGGTCCGACAACCTCCTGGCGCTGGCCT CGAGTGGATCGGTAATATCTACTATAGCGGCTCT ACTAACTATAACCCTAGCCTGAAGTCTAGGGTCA CAATTAGTGTGGCTACTAACAAGAAGCAGTTTAG CCTGAAGCTGACTAGCGTGACCGCCGCTGACACC GCCGTCTACTACTGCGCTAGAGTGCCCGGCTGCT CTAGCACTAGCTGTATCGACGGTTGGTTTGACCC TTGGGGTCAAGGGATCCTGGTCACCGTGTCTAGC GCTAGCACTAAGGGCCCAAGTGTGTTTCCCCTGG CCCCCAGCAGCAAGTCTACTTCCGGCGGAACTGC TGCCCTGGGTTGCCTGGTGAAGGACTACTTCCCC GAGCCCGTGACAGTGTCCTGGAACTCTGGGGCTC TGACTTCCGGCGTGCACACCTTCCCCGCCGTGCT GCAGAGCAGCGGCCTGTACAGCCTGAGCAGCGT GGTGACAGTGCCCTCCAGCTCTCTGGGAACCCAG ACCTATATCTGCAACGTGAACCACAAGCCCAGC AACACCAAGGTGGACAAGAGAGTGGAGCCCAAG AGCTGCGACAAGACCCACACCTGCCCCCCCTGCC CAGCTCCAGAACTGCTGGGAGGGCCTTCCGTGTT CCTGTTCCCCCCCAAGCCCAAGGACACCCTGATG ATCAGCAGGACCCCCGAGGTGACCTGCGTGGTG |

TABLE 2-continued

| anti-VP1 Antibodies | |
|---|---|
| | GTGGACGTGTCCCACGAGGACCCAGAGGTGAAG<br>TTCAACTGGTACGTGGACGGCGTGGAGGTGCAC<br>AACGCCAAGACCAAGCCCAGAGAGGAGCAGTAC<br>AACAGCACCTACAGGGTGGTGTCCGTGCTGACC<br>GTGCTGCACCAGGACTGGCTGAACGGCAAAGAA<br>TACAAGTGCAAAGTCTCCAACAAGGCCCTGCCA<br>GCCCCAATCGAAAAGACAATCAGCAAGGCCAAG<br>GGCCAGCCACGGGAGCCCCAGGTGTACACCCTG<br>CCCCCCAGCCGGGAGGAGATGACCAAGAACCAG<br>GTGTCCCTGACCTGTCTGGTGAAGGGCTTCTACC<br>CCAGCGATATCGCCGTGGAGTGGGAGAGCAACG<br>GCCAGCCCGAGAACAACTACAAGACCACCCCCC<br>CAGTGCTGGACAGCGACGGCAGCTTCTTCCTGTA<br>CAGCAAGCTGACCGTGGACAAGTCCAGGTGGCA<br>GCAGGGCAACGTGTTCAGCTGCAGCGTGATGCA<br>CGAGGCCCTGCACAACCACTACACCCAGAAGTC<br>CCTGAGCCTGAGCCCCGGCAAG |
| SEQ ID NO: 156 LCDR1 (Kabat) | SGSSSNIGNTYVS |
| SEQ ID NO: 157 LCDR2 (Kabat) | DNNKRPS |
| SEQ ID NO: 158 LCDR3 (Kabat) | GTWDSSLSAWV |
| SEQ ID NO: 159 LCDR1 (Chothia) | SSSNIGNTY |
| SEQ ID NO: 160 LCDR2 (Chothia) | DNN |
| SEQ ID NO: 161 LCDR3 (Chothia) | WDSSLSAW |
| SEQ ID NO: 162 VL | QSVLTQPPSLSAAPGQKVTISCSGSSSNIGNTYVSW<br>YQQLPGTAPKLLIYDNNKRPSGIPDRFSGSKSGTSA<br>TLGITGLQTGDEAVYYCGTWDSSLSAWVFGGGTR<br>LTVL |
| SEQ ID NO: 163 DNA VL | CAGTCAGTCCTGACTCAGCCCCCTAGCCTGAGCG<br>CCGCTCCCGGTCAAAAAGTGACTATTAGCTGTAG<br>CGGCTCTAGCTCTAATATCGGTAATACCTACGTC<br>AGCTGGTATCAGCAGCTGCCCGGCACCGCCCCTA<br>AGCTGCTGATCTACGATAACAACAAGCGGCCTA<br>GCGGAATCCCCGATAGGTTTAGCGGATCTAAGTC<br>AGGCACTAGCGCTACCCTGGGAATCACCGGCCT<br>GCAGACCGGCGACGAGGCCGTCTACTACTGCGG<br>CACCTGGGACTCTAGTCTGAGCGCCTGGGTGTTC<br>GGCGGAGGCACTAGACTGACCGTGCTG |
| SEQ ID NO: 164 Light Chain | QSVLTQPPSLSAAPGQKVTISCSGSSSNIGNTYVSW<br>YQQLPGTAPKLLIYDNNKRPSGIPDRFSGSKSGTSA<br>TLGITGLQTGDEAVYYCGTWDSSLSAWVFGGGTR<br>LTVLGQPKAAPSVTLFPPSSEELQANKATLVCLISD<br>FYPGAVTVAWKADSSPVKAGVETTTPSKQSNNKY<br>AASSYLSLTPEQWKSHRSYSCQVTHEGSTVEKTVA<br>PTECS |
| SEQ ID NO: 165 DNA Light Chain | CAGTCAGTCCTGACTCAGCCCCCTAGCCTGAGCG<br>CCGCTCCCGGTCAAAAAGTGACTATTAGCTGTAG<br>CGGCTCTAGCTCTAATATCGGTAATACCTACGTC<br>AGCTGGTATCAGCAGCTGCCCGGCACCGCCCCTA<br>AGCTGCTGATCTACGATAACAACAAGCGGCCTA<br>GCGGAATCCCCGATAGGTTTAGCGGATCTAAGTC<br>AGGCACTAGCGCTACCCTGGGAATCACCGGCCT<br>GCAGACCGGCGACGAGGCCGTCTACTACTGCGG<br>CACCTGGGACTCTAGTCTGAGCGCCTGGGTGTTC<br>GGCGGAGGCACTAGACTGACCGTGCTGGGTCAA<br>CCTAAGGCTGCCCCCAGCGTGACCCTGTTCCCCC<br>CCAGCAGCGAGGAGCTGCAGGCCAACAAGGCCA<br>CCCTGGTGTGCCTGATCAGCGACTTCTACCCAGG<br>CGCCGTGACCGTGGCCTGGAAGGCCGACAGCAG<br>CCCCGTGAAGGCCGGCGTGGAGACCACCACCCC<br>CAGCAAGCAGAGCAACAACAAGTACGCCGCCAG<br>CAGCTACCTGAGCCTGACCCCCGAGCAGTGGAA<br>GAGCCACAGGTCCTACAGCTGCCAGGTGACCCA |

TABLE 2-continued anti-VP1 Antibodies

CGAGGGCAGCACCGTGGAAAAGACCGTGGCCCC
AACCGAGTGCAGC

NEG447A

SEQ ID NO: 166 HCDR1  RDYWS
(Kabat)

SEQ ID NO: 167 HCDR2  NIYYSGSTNYNPSLKS
(Kabat)

SEQ ID NO: 168 HCDR3  VPGCSSTSCIDGWFDP
(Kabat)

SEQ ID NO: 169 HCDR1  GGSISRD
(Chothia)

SEQ ID NO: 170 HCDR2  YYSGS
(Chothia)

SEQ ID NO: 171 HCDR3  VPGCSSTSCIDGWFDP
(Chothia)

SEQ ID NO: 172 VH     QVQLQESGPGLVKPSETLSLTCTVSGGSISRDYWS
                      WVRQPPGAGLEWIGNIYYSGSTNYNPSLKSRVTISV
                      ATNKKQFSLKLTSVTAADTAVYYCARVPGCSSTSC
                      IDGWFDPWGQGILVTVSS

SEQ ID NO: 173 DNA VH CAGGTGCAATTGCAGGAAAGCGGCCCTGGCCTC
                      GTGAAGCCCAGCGAGACACTGAGCCTGACCTGT
                      ACCGTGTCCGGCGGCAGCATCAGCAGAGACTAC
                      TGGAGCTGGGTTCGCCAGCCTCCAGGCGCAGGA
                      CTGGAATGGATCGGCAACATCTACTACAGCGGC
                      AGCACCAACTACAACCCCAGCCTGAAGTCCAGA
                      GTGACCATCAGCGTGGCCACAAACAAGAAACAG
                      TTCTCCCTGAAGCTGACCAGCGTGACAGCCGCCG
                      ATACCGCCGTGTACTACTGCGCCAGAGTGCCTGG
                      CTGTAGCAGCACCAGCTGCATCGACGGATGGTTC
                      GACCCTTGGGGCCAGGGCATTCTCGTGACCGTCA
                      GCTCA

SEQ ID NO: 174 Heavy  QVQLQESGPGLVKPSETLSLTCTVSGGSISRDYWS
               Chain  WVRQPPGAGLEWIGNIYYSGSTNYNPSLKSRVTISV
                      ATNKKQFSLKLTSVTAADTAVYYCARVPGCSSTSC
                      IDGWFDPWGQGILVTVSSASTKGPSVFPLAPSSKST
                      SGGTAALGCLVKDYFPEPVTVSWNSGALTSGVHTF
                      PAVLQSSGLYSLSSVVTVPSSSLGTQTYICNVNHKP
                      SNTKVDKRVEPKSCDKTHTCPPCPAPELLGGPSVFL
                      FPPKPKDTLMISRTPEVTCVVVDVSHEDPEVKFNW
                      YVDGVEVHNAKTKPREEQYNSTYRVVSVLTVLHQ
                      DWLNGKEYKCKVSNKALPAPIEKTISKAKGQPREP
                      QVYTLPPSREEMTKNQVSLTCLVKGFYPSDIAVEW
                      ESNGQPENNYKTTPPVLDSDGSFFLYSKLTVDKSR
                      WQQGNVFSCSVMHEALHNHYTQKSLSLSPGK SEQ ID NO: 175 DNA    CAGGTGCAATTGCAGGAAAGCGGCCCTGGCCTC
               Heavy  GTGAAGCCCAGCGAGACACTGAGCCTGACCTGT
               Chain  ACCGTGTCCGGCGGCAGCATCAGCAGAGACTAC
                      TGGAGCTGGGTTCGCCAGCCTCCAGGCGCAGGA
                      CTGGAATGGATCGGCAACATCTACTACAGCGGC
                      AGCACCAACTACAACCCCAGCCTGAAGTCCAGA
                      GTGACCATCAGCGTGGCCACAAACAAGAAACAG
                      TTCTCCCTGAAGCTGACCAGCGTGACAGCCGCCG
                      ATACCGCCGTGTACTACTGCGCCAGAGTGCCTGG
                      CTGTAGCAGCACCAGCTGCATCGACGGATGGTTC
                      GACCCTTGGGGCCAGGGCATTCTCGTGACCGTCA
                      GCTCAGCTAGCACCAAGGGCCCCAGCGTGTTCCC
                      CCTGGCCCCCAGCAGCAAGAGCACCAGCGGCGG
                      CACAGCCGCCCTGGGCTGCCTGGTGAAGGACTA
                      CTTCCCCGAGCCCGTGACCGTGTCCTGGAACAGC
                      GGAGCCCTGACCTCCGGCGTGCACACCTTCCCCG
                      CCGTGCTGCAGAGCAGCGGCCTGTACAGCCTGTC
                      CAGCGTGGTGACAGTGCCCAGCAGCAGCCTGGG
                      CACCCAGACCTACATCTGCAACGTGAACCACAA
                      GCCCAGCAACACCAAGGTGGACAAGAGAGTGGA
                      GCCCAAGAGCTGCGACAAGACCCACACCTGCCC
                      CCCCTGCCCAGCCCCAGAGCTGCTGGGCGGACCC
                      TCCGTGTTCCTGTTCCCCCCCAAGCCCAAGGACA TABLE 2-continued

| anti-VP1 Antibodies | |
|---|---|
| | CCCTGATGATCAGCAGGACCCCCGAGGTGACCT<br>GCGTGGTGGTGGACGTGAGCCACGAGGACCCAG<br>AGGTGAAGTTCAACTGGTACGTGGACGGCGTGG<br>AGGTGCACAACGCCAAGACCAAGCCCAGAGAGG<br>AGCAGTACAACAGCACCTACAGGGTGGTGTCCG<br>TGCTGACCGTGCTGCACCAGGACTGGCTGAACG<br>GCAAGGAATACAAGTGCAAGGTCTCCAACAAGG<br>CCCTGCCAGCCCCCATCGAAAAGACCATCAGCA<br>AGGCCAAGGGCCAGCCACGGGAGCCCCAGGTGT<br>ACACCCTGCCCCCCTCCCGGGAGGAGATGACCA<br>AGAACCAGGTGTCCCTGACCTGTCTGGTGAAGG<br>GCTTCTACCCCAGCGACATCGCCGTGGAGTGGGA<br>GAGCAACGGCCAGCCCGAGAACAACTACAAGAC<br>CACCCCCCCAGTGCTGGACAGCGACGGCAGCTTC<br>TTCCTGTACAGCAAGCTGACCGTGGACAAGTCCA<br>GGTGGCAGCAGGGCAACGTGTTCAGCTGCAGCG<br>TGATGCACGAGGCCCTGCACAACCACTACACCC<br>AGAAGAGCCTGAGCCTGTCCCCCGGCAAG |
| SEQ ID NO: 176 LCDR1 (Kabat) | SGSSSNIGNTYVS |
| SEQ ID NO: 177 LCDR2 (Kabat) | DNNKRPS |
| SEQ ID NO: 178 LCDR3 (Kabat) | GTWDSSLSAWV |
| SEQ ID NO: 179 LCDR1 (Chothia) | SSSNIGNTY |
| SEQ ID NO: 180 LCDR2 (Chothia) | DNN |
| SEQ ID NO: 181 LCDR3 (Chothia) | WDSSLSAW |
| SEQ ID NO: 182 VL | QSVLTQPPSVSAAPGQKVTISCSGSSSNIGNTYVSW<br>YQQLPGTAPKLLIYDNNKRPSGIPDRFSGSKSGTSA<br>TLGITGLQTGDEADYYCGTWDSSLSAWVFGGGTR<br>LTVL |
| SEQ ID NO: 183 DNA VL | CAAAGCGTGCTGACCCAGCCTCCTAGCGTGTCTG<br>CTGCCCCTGGCCAGAAGGTGACCATCAGCTGTAG<br>CGGCAGCAGCTCCAACATCGGCAACACCTACGT<br>GTCCTGGTATCAGCAGCTGCCCGGCACCGCCCCC<br>AAACTGCTGATCTACGACAACAACAAGCGGCCC<br>AGCGGCATCCCCGATAGATTTTCTGGCAGCAAGA<br>GCGGCACCAGCGCCACCCTGGGAATCACAGGAC<br>TGCAGACAGGGGACGAGGCCGATTACTACTGTG<br>GCACCTGGGATTCTAGCCTGAGCGCCTGGGTGTT<br>CGGCGGAGGCACAAGACTGACAGTGCTG |
| SEQ ID NO: 184 Light Chain | QSVLTQPPSVSAAPGQKVTISCSGSSSNIGNTYVSW<br>YQQLPGTAPKLLIYDNNKRPSGIPDRFSGSKSGTSA<br>TLGITGLQTGDEADYYCGTWDSSLSAWVFGGGTR<br>LTVLGQPKAAPSVTLFPPSSEELQANKATLVCLISD<br>FYPGAVTVAWKADSSPVKAGVETTTPSKQSNNKY<br>AASSYLSLTPEQWKSHRSYSCQVTHEGSTVEKTVA<br>PTECS |
| SEQ ID NO: 185 DNA Light Chain | CAAAGCGTGCTGACCCAGCCTCCTAGCGTGTCTG<br>CTGCCCCTGGCCAGAAGGTGACCATCAGCTGTAG<br>CGGCAGCAGCTCCAACATCGGCAACACCTACGT<br>GTCCTGGTATCAGCAGCTGCCCGGCACCGCCCCC<br>AAACTGCTGATCTACGACAACAACAAGCGGCCC<br>AGCGGCATCCCCGATAGATTTTCTGGCAGCAAGA<br>GCGGCACCAGCGCCACCCTGGGAATCACAGGAC<br>TGCAGACAGGGGACGAGGCCGATTACTACTGTG<br>GCACCTGGGATTCTAGCCTGAGCGCCTGGGTGTT<br>CGGCGGAGGCACAAGACTGACAGTGCTGGGTCA<br>GCCTAAGGCCGCTCCCTCCGTGACCCTGTTCCCC<br>CCCAGCTCCGAGGAACTGCAGGCCAACAAGGCC<br>ACCCTGGTGTGCCTGATCAGCGACTTCTACCCTG<br>GCGCCGTGACCGTGGCCTGGAAGGCCGACAGCA<br>GCCCCGTGAAGGCCGGCGTGGAGACAACCACCC<br>CCAGCAAGCAGAGCAACAACAAGTACGCCGCCA<br>GCAGCTACCTGAGCCTGACCCCCGAGCAGTGGA |

TABLE 2-continued

| anti-VP1 Antibodies |

AGAGCCACAGAAGCTACAGCTGCCAGGTCACCC
ACGAGGGCAGCACCGTGGAGAAAACCGTGGCCC
CCACCGAGTGCAGC

P7G11

SEQ ID NO: 186 HCDR1 (Kabat)  SGGYSWS

SEQ ID NO: 187 HCDR2 (Kabat)  YIYYRGTTYYNPSLKS

SEQ ID NO: 188 HCDR3 (Kabat)  ALTHLVGVGWFDP

SEQ ID NO: 189 HCDR1 (Chothia)  GGSISSGGY

SEQ ID NO: 190 HCDR2 (Chothia)  YYRGT

SEQ ID NO: 191 HCDR3 (Chothia)  ALTHLVGVGWFDP

SEQ ID NO: 192 VH
QVQLQESGPGLAKPSQTLSLTCSVSGGSISSGGYSW
SWIRQPPGKGLEYIGYIYYRGTTYYNPSLKSRITMS
VDTSNNQISLKLTSVTAADTAVYYCARALTHLVGV
GWFDPWGQGTMVTVSS

SEQ ID NO: 193 DNA VH
CAGGTGCAGCTGCAAGAATCAGGCCCTGGCCTG
GCTAAGCCTAGTCAGACCCTGAGCCTGACCTGTA
GCGTCAGCGGAGGCTCTATCTCTAGCGGCGGCTA
TAGCTGGTCCTGGATTAGACAGCCCCCAGGTAAA
GGCCTCGAGTATATCGGCTATATCTACTATAGGG
GCACTACCTACTATAACCCTAGCCTGAAGTCTAG
GATCACTATGAGCGTGGACACCTCTAACAATCAG
ATTAGCCTGAAGCTGACTAGCGTGACCGCCGCTG
ACACCGCCGTCTACTACTGCGCTAGAGCCCTGAC
TCACCTCGTTGGAGTGGGCTGGTTTGACCCTTGG
GGTCAAGGCACTATGGTCACCGTGTCTAGC

SEQ ID NO: 194 Heavy Chain
QVQLQESGPGLAKPSQTLSLTCSVSGGSISSGGYSW
SWIRQPPGKGLEYIGYIYYRGTTYYNPSLKSRITMS
VDTSNNQISLKLTSVTAADTAVYYCARALTHLVGV
GWFDPWGQGTMVTVSSASTKGPSVFPLAPSSKSTS
GGTAALGCLVKDYFPEPVTVSWNSGALTSGVHTFP
AVLQSSGLYSLSSVVTVPSSSLGTQTYICNVNHKPS
NTKVDKRVEPKSCDKTHTCPPCPAPELLGGPSVFLF
PPKPKDTLMISRTPEVTCVVVDVSHEDPEVKFNWY
VDGVEVHNAKTKPREEQYNSTYRVVSVLTVLHQD
WLNGKEYKCKVSNKALPAPIEKTISKAKGQPREPQ
VYTLPPSREEMTKNQVSLTCLVKGFYPSDIAVEWE
SNGQPENNYKTTPPVLDSDGSFFLYSKLTVDKSRW
QQGNVFSCSVMHEALHNHYTQKSLSLSPGK SEQ ID NO: 195 DNA Heavy Chain
CAGGTGCAGCTGCAAGAATCAGGCCCTGGCCTG
GCTAAGCCTAGTCAGACCCTGAGCCTGACCTGTA
GCGTCAGCGGAGGCTCTATCTCTAGCGGCGGCTA
TAGCTGGTCCTGGATTAGACAGCCCCCAGGTAAA
GGCCTCGAGTATATCGGCTATATCTACTATAGGG
GCACTACCTACTATAACCCTAGCCTGAAGTCTAG
GATCACTATGAGCGTGGACACCTCTAACAATCAG
ATTAGCCTGAAGCTGACTAGCGTGACCGCCGCTG
ACACCGCCGTCTACTACTGCGCTAGAGCCCTGAC
TCACCTCGTTGGAGTGGGCTGGTTTGACCCTTGG
GGTCAAGGCACTATGGTCACCGTGTCTAGCGCTA
GCACTAAGGGCCCAAGTGTGTTTCCCCTGGCCCC
CAGCAGCAAGTCTACTTCCGGCGGAACTGCTGCC
CTGGGTTGCCTGGTGAAGGACTACTTCCCCGAGC
CCGTGACAGTGTCCTGGAACTCTGGGGCTCTGAC
TTCCGGCGTGCACACCTTCCCCGCCGTGCTGCAG
AGCAGCGGCCTGTACAGCCTGAGCAGCGTGGTG
ACAGTGCCCTCCAGCTCTCTGGGAACCCAGACCT
ATATCTGCAACGTGAACCACAAGCCCAGCAACA
CCAAGGTGGACAAGAGAGTGGAGCCCAAGAGCT
GCGACAAGACCCACACCTGCCCCCCCTGCCCAGC
TCCAGAACTGCTGGGAGGCCTTCCGTGTTCCTG
TTCCCCCCCAAGCCCAAGGACACCCTGATGATCA TABLE 2-continued anti-VP1 Antibodies

```
GCAGGACCCCCGAGGTGACCTGCGTGGTGGTGG
ACGTGTCCCACGAGGACCCAGAGGTGAAGTTCA
ACTGGTACGTGGACGGCGTGGAGGTGCACAACG
CCAAGACCAAGCCCAGAGAGGAGCAGTACAACA
GCACCTACAGGGTGGTGTCCGTGCTGACCGTGCT
GCACCAGGACTGGCTGAACGGCAAAGAATACAA
GTGCAAAGTCTCCAACAAGGCCCTGCCAGCCCC
AATCGAAAAGACAATCAGCAAGGCCAAGGGCCA
GCCACGGGAGCCCCAGGTGTACACCCTGCCCCCC
AGCCGGGAGGAGATGACCAAGAACCAGGTGTCC
CTGACCTGTCTGGTGAAGGGCTTCTACCCCAGCG
ATATCGCCGTGGAGTGGGAGAGCAACGGCCAGC
CCGAGAACAACTACAAGACCACCCCCCCAGTGC
TGGACAGCGACGGCAGCTTCTTCCTGTACAGCAA
GCTGACCGTGGACAAGTCCAGGTGGCAGCAGGG
CAACGTGTTCAGCTGCAGCGTGATGCACGAGGC
CCTGCACAACCACTACACCCAGAAGTCCCTGAGC
CTGAGCCCCGGCAAG
```

| SEQ ID NO: 196 LCDR1 (Kabat) | SGGSSNLGSNYVS |
|---|---|

| SEQ ID NO: 197 LCDR2 (Kabat) | DNNKRPS |
|---|---|

| SEQ ID NO: 198 LCDR3 (Kabat) | GTWDGSLSAWV |
|---|---|

| SEQ ID NO: 199 LCDR1 (Chothia) | GSSNLGSNY |
|---|---|

| SEQ ID NO: 200 LCDR2 (Chothia) | DNN |
|---|---|

| SEQ ID NO: 201 LCDR3 (Chothia) | WDGSLSAW |
|---|---|

| SEQ ID NO: 202 VL | QSVLTQPPSVSAAPGQKVTISCSGGSSNLGSNYVS WYQQLPGTAPKLLIYDNNKRPSGIPDRFSGSKSGTS ATLGITGLQTGDEADYYCGTWDGSLSAWVFGGGT KVTVL |
|---|---|

| SEQ ID NO: 203 DNA VL | CAGTCAGTCCTGACTCAGCCCCCTAGCGTCAGCG CCGCTCCCGGTCAAAAAGTGACTATTAGCTGTAG CGGCGGCTCCTCTAACCTGGGCTCTAACTACGTC AGCTGGTATCAGCAGCTGCCCGGCACCGCCCCTA AGCTGCTGATCTACGATAACAACAAGCGGCCTA GCGGAATCCCCGATAGGTTTAGCGGCTCTAAGTC AGGCACTAGCGCTACCCTGGGAATCACCGGCCT GCAGACCGGCGACGAGGCCGACTACTACTGTGG CACCTGGGACGGTAGCCTGAGCGCCTGGGTGTTC GGCGGAGGCACTAAAGTCACAGTGCTG |
|---|---|

| SEQ ID NO: 204 Light Chain | QSVLTQPPSVSAAPGQKVTISCSGGSSNLGSNYVS WYQQLPGTAPKLLIYDNNKRPSGIPDRFSGSKSGTS ATLGITGLQTGDEADYYCGTWDGSLSAWVFGGGT KVTVLGQPKAAPSVTLFPPSSEELQANKATLVCLIS DFYPGAVTVAWKADSSPVKAGVETTTPSKQSNNK YAASSYLSLTPEQWKSHRSYSCQVTHEGSTVEKTV APTECS |
|---|---|

| SEQ ID NO: 205 DNA Light Chain | CAGTCAGTCCTGACTCAGCCCCCTAGCGTCAGCG CCGCTCCCGGTCAAAAAGTGACTATTAGCTGTAG CGGCGGCTCCTCTAACCTGGGCTCTAACTACGTC AGCTGGTATCAGCAGCTGCCCGGCACCGCCCCTA AGCTGCTGATCTACGATAACAACAAGCGGCCTA GCGGAATCCCCGATAGGTTTAGCGGCTCTAAGTC AGGCACTAGCGCTACCCTGGGAATCACCGGCCT GCAGACCGGCGACGAGGCCGACTACTACTGTGG CACCTGGGACGGTAGCCTGAGCGCCTGGGTGTTC GGCGGAGGCACTAAAGTCACAGTGCTGGGTCAA CCTAAGGCTGCCCCCAGCGTGACCCTGTTCCCCC CCAGCAGCGAGGAGCTGCAGGCCAACAAGGCCA CCCTGGTGTGCCTGATCAGCGACTTCTACCCAGG CGCCGTGACCGTGGCCTGGAAGGCCGACAGCAG CCCCGTGAAGGCCGGCGTGGAGACCACCACCCC CAGCAAGCAGAGCAACAACAAGTACGCCGCCAG CAGCTACCTGAGCCTGACCCCCGAGCAGTGGAA |
|---|---|

TABLE 2-continued anti-VP1 Antibodies

GAGCCACAGGTCCTACAGCTGCCAGGTGACCCA
CGAGGGCAGCACCGTGGAAAAGACCGTGGCCCC
AACCGAGTGCAGC

P7G11A

SEQ ID NO: 206 HCDR1 SGGYSWS
(Kabat)

SEQ ID NO: 207 HCDR2 YIYYRGTTYYNPSLKS
(Kabat)

SEQ ID NO: 208 HCDR3 ALTHLVGVGWFDP
(Kabat)

SEQ ID NO: 209 HCDR1 GGSISSGGY
(Chothia)

SEQ ID NO: 210 HCDR2 YYRGT
(Chothia)

SEQ ID NO: 211 HCDR3 ALTHLVGVGWFDP
(Chothia)

SEQ ID NO: 212 VH          QVQLQESGPGLVKPSQTLSLTCTVSGGSISSGGYSW
                            SWIRQPPGKGLEYIGYIYYRGTTYYNPSLKSRVTIS
                            VDTSNNQISLKLSSVTAADTAVYYCARALTHLVGV
                            GWFDPWGQGTMVTVSS

SEQ ID NO: 213 DNA VH       CAGGTGCAGCTGCAAGAATCAGGCCCTGGCCTG
                            GTCAAGCCTAGTCAGACCCTGAGCCTGACCTGCA
                            CCGTCAGCGGAGGCTCTATCTCTAGCGGCGGCTA
                            TAGCTGGTCCTGGATTAGACAGCCCCCAGGTAAA
                            GGCCTCGAGTATATCGGCTATATCTACTATAGGG
                            GCACTACCTACTATAACCCTAGCCTGAAGTCTAG
                            GGTCACAATTAGCGTGGACACCTCTAACAATCAG
                            ATTAGCCTGAAGCTGTCTAGCGTGACCGCCGCTG
                            ACACCGCCGTCTACTACTGCGCTAGAGCCCTGAC
                            TCACCTCGTCGGAGTGGGCTGGTTTGACCCTTGG
                            GGTCAAGGCACTATGGTCACCGTGTCTAGC

SEQ ID NO: 214 Heavy        QVQLQESGPGLVKPSQTLSLTCTVSGGSISSGGYSW
               Chain        SWIRQPPGKGLEYIGYIYYRGTTYYNPSLKSRVTIS
                            VDTSNNQISLKLSSVTAADTAVYYCARALTHLVGV
                            GWFDPWGQGTMVTVSSASTKGPSVFPLAPSSKSTS
                            GGTAALGCLVKDYFPEPVTVSWNSGALTSGVHTFP
                            AVLQSSGLYSLSSVVTVPSSSLGTQTYICNVNHKPS
                            NTKVDKRVEPKSCDKTHTCPPCPAPELLGGPSVFLF
                            PPKPKDTLMISRTPEVTCVVVDVSHEDPEVKFNWY
                            VDGVEVHNAKTKPREEQYNSTYRVVSVLTVLHQD
                            WLNGKEYKCKVSNKALPAPIEKTISKAKGQPREPQ
                            VYTLPPSREEMTKNQVSLTCLVKGFYPSDIAVEWE
                            SNGQPENNYKTTPPVLDSDGSFFLYSKLTVDKSRW
                            QQGNVFSCSVMHEALHNHYTQKSLSLSPGK SEQ ID NO: 215 DNA          CAGGTGCAGCTGCAAGAATCAGGCCCTGGCCTG
               Heavy        GTCAAGCCTAGTCAGACCCTGAGCCTGACCTGCA
               Chain        CCGTCAGCGGAGGCTCTATCTCTAGCGGCGGCTA
                            TAGCTGGTCCTGGATTAGACAGCCCCCAGGTAAA
                            GGCCTCGAGTATATCGGCTATATCTACTATAGGG
                            GCACTACCTACTATAACCCTAGCCTGAAGTCTAG
                            GGTCACAATTAGCGTGGACACCTCTAACAATCAG
                            ATTAGCCTGAAGCTGTCTAGCGTGACCGCCGCTG
                            ACACCGCCGTCTACTACTGCGCTAGAGCCCTGAC
                            TCACCTCGTCGGAGTGGGCTGGTTTGACCCTTGG
                            GGTCAAGGCACTATGGTCACCGTGTCTAGCGCTA
                            GCACTAAGGGCCCAAGTGTGTTCCCCTGGCCCC
                            CAGCAGCAAGTCTACTTCCGGCGGAACTGCTGCC
                            CTGGGTTGCCTGGTGAAGGACTACTTCCCCGAGC
                            CCGTGACAGTGTCCTGGAACTCTGGGGCTCTGAC
                            TTCCGGCGTGCACACCTTCCCCGCCGTGCTGCAG
                            AGCAGCGGCCTGTACAGCCTGAGCAGCGTGGTG
                            ACAGTGCCCTCCAGCTCTCTGGGAACCCAGACCT
                            ATATCTGCAACGTGAACCACAAGCCCAGCAACA
                            CCAAGGTGGACAAGAGAGTGGAGCCCAAGAGCT
                            GCGACAAGACCCACACCTGCCCCCCCTGCCCAGC
                            TCCAGAACTGCTGGGAGGCCTTCCGTGTTCCTG
                            TTCCCCCCCAAGCCCAAGGACACCCTGATGATCA TABLE 2-continued anti-VP1 Antibodies

```
GCAGGACCCCCGAGGTGACCTGCGTGGTGGTGG
ACGTGTCCCACGAGGACCCAGAGGTGAAGTTCA
ACTGGTACGTGGACGGCGTGGAGGTGCACAACG
CCAAGACCAAGCCCAGAGAGGAGCAGTACAACA
GCACCTACAGGGTGGTGTCCGTGCTGACCGTGCT
GCACCAGGACTGGCTGAACGGCAAAGAATACAA
GTGCAAAGTCTCCAACAAGGCCCTGCCAGCCCC
AATCGAAAAGACAATCAGCAAGGCCAAGGGCCA
GCCACGGGAGCCCCAGGTGTACACCCTGCCCCCC
AGCCGGGAGGAGATGACCAAGAACCAGGTGTCC
CTGACCTGTCTGGTGAAGGGCTTCTACCCCAGCG
ATATCGCCGTGGAGTGGGAGAGCAACGGCCAGC
CCGAGAACAACTACAAGACCACCCCCCCCAGTGC
TGGACAGCGACGGCAGCTTCTTCCTGTACAGCAA
GCTGACCGTGGACAAGTCCAGGTGGCAGCAGGG
CAACGTGTTCAGCTGCAGCGTGATGCACGAGGC
CCTGCACAACCACTACACCCAGAAGTCCCTGAGC
CTGAGCCCCGGCAAG
```

| SEQ ID NO: 216 LCDR1 (Kabat) | SGGSSNLGSNYVS |
|---|---|
| SEQ ID NO: 217 LCDR2 (Kabat) | DNNKRPS |
| SEQ ID NO: 218 LCDR3 (Kabat) | GTWDGSLSAWV |
| SEQ ID NO: 219 LCDR1 (Chothia) | GSSNLGSNY |
| SEQ ID NO: 220 LCDR2 (Chothia) | DNN |
| SEQ ID NO: 221 LCDR3 (Chothia) | WDGSLSAW |
| SEQ ID NO: 222 VL | QSVLTQPPSVSAAPGQKVTISCSGGSSNLGSNYVS WYQQLPGTAPKLLIYDNNKRPSGIPDRFSGSKSGTS ATLGITGLQTGDEADYYCGTWDGSLSAWVFGGGT KVTVL |
| SEQ ID NO: 223 DNA VL | CAGTCAGTCCTGACTCAGCCCCCTAGCGTCAGCG CCGCTCCCGGTCAAAAAGTGACTATTAGCTGTAG CGGCGGCTCCTCTAACCTGGGCTCTAACTACGTC AGCTGGTATCAGCAGCTGCCCGGCACCGCCCCTA AGCTGCTGATCTACGATAACAACAAGCGGCCTA GCGGAATCCCCGATAGGTTTAGCGGCTCTAAGTC AGGCACTAGCGCTACCCTGGGAATCACCGGCCT GCAGACCGGCGACGAGGCCGACTACTACTGTGG CACCTGGGACGGTAGCCTGAGCGCCTGGGTGTTC GGCGGAGGCACTAAAGTCACAGTGCTG |
| SEQ ID NO: 224 Light Chain | QSVLTQPPSVSAAPGQKVTISCSGGSSNLGSNYVS WYQQLPGTAPKLLIYDNNKRPSGIPDRFSGSKSGTS ATLGITGLQTGDEADYYCGTWDGSLSAWVFGGGT KVTVLGQPKAAPSVTLFPPSSEELQANKATLVCLIS DFYPGAVTVAWKADSSPVKAGVETTTPSKQSNNK YAASSYLSLTPEQWKSHRSYSCQVTHEGSTVEKTV APTECS |
| SEQ ID NO: 225 DNA Light Chain | CAGTCAGTCCTGACTCAGCCCCCTAGCGTCAGCG CCGCTCCCGGTCAAAAAGTGACTATTAGCTGTAG CGGCGGCTCCTCTAACCTGGGCTCTAACTACGTC AGCTGGTATCAGCAGCTGCCCGGCACCGCCCCTA AGCTGCTGATCTACGATAACAACAAGCGGCCTA GCGGAATCCCCGATAGGTTTAGCGGCTCTAAGTC AGGCACTAGCGCTACCCTGGGAATCACCGGCCT GCAGACCGGCGACGAGGCCGACTACTACTGTGG CACCTGGGACGGTAGCCTGAGCGCCTGGGTGTTC GGCGGAGGCACTAAAGTCACAGTGCTGGGTCAA CCTAAGGCTGCCCCAGCGTGACCCTGTTCCCCC CCAGCAGCGAGGAGCTGCAGGCCAACAAGGCCA CCCTGGTGTGCCTGATCAGCGACTTCTACCCAGG CGCCGTGACCGTGGCCTGGAAGGCCGACAGCAG CCCCGTGAAGGCCGGCGTGGAGACCACCACCCC CAGCAAGCAGAGCAACAACAAGTACGCCGCCAG CAGCTACCTGAGCCTGACCCCCGAGCAGTGGAA |

TABLE 2-continued anti-VP1 Antibodies

```
GAGCCACAGGTCCTACAGCTGCCAGGTGACCCA
CGAGGGCAGCACCGTGGAAAAGACCGTGGCCCC
AACCGAGTGCAGC
```

EBB-C1975-B5-

SEQ ID NO: 226 HCDR1  AYYWT
(Kabat)

SEQ ID NO: 227 HCDR2  YISHSGSTNYNPSLKS
(Kabat)

SEQ ID NO: 228 HCDR3  LGDTASLSRFYYYIDV
(Kabat)

SEQ ID NO: 229 HCDR1  GGSTSAY
(Chothia)

SEQ ID NO: 230 HCDR2  SHSGS
(Chothia)

SEQ ID NO: 231 HCDR3  LGDTASLSRFYYYIDV
(Chothia)

SEQ ID NO: 232 VH      QVQLVQSGPGLVKPSETLSLTCTVSGGSTSAYYWT
                       WIRQPPGKGLEWIGYISHSGSTNYNPSLKSRVTISA
                       DTSKNQLSLKVNSVTAADTAVYYCARLGDTASLS
                       RFYYYIDVWGKGTTVTVSS

SEQ ID NO: 233 DNA VH  CAGGTGCAGCTGGTGCAGTCTGGCCCAGGACTG
                       GTGAAGCCTTCGGAGACCCTGTCCCTCACCTGCA
                       CTGTCTCTGGTGGCTCCACCAGTGCTTACTACTG
                       GACCTGGATTCGGCAGCCCCCAGGGAAGGGACT
                       GGAGTGGATTGGGTATATCTCTCACAGTGGGAGC
                       ACCAACTACAACCCCTCCCTCAAGAGTCGAGTCA
                       CCATATCAGCAGACACGTCCAAGAACCAGCTCTC
                       CCTGAAGGTGAACTCTGTGACCGCCGCAGACAC
                       GGCCGTGTATTACTGTGCGAGACTTGGGGATACA
                       GCTTCACTTAGCCGCTTCTACTACTACATTGACG
                       TCTGGGGCAAAGGGACCACGGTCACCGTCTCCTCA

SEQ ID NO: 234 Heavy   QVQLVQSGPGLVKPSETLSLTCTVSGGSTSAYYWT
               Chain   WIRQPPGKGLEWIGYISHSGSTNYNPSLKSRVTISA
                       DTSKNQLSLKVNSVTAADTAVYYCARLGDTASLS
                       RFYYYIDVWGKGTTVTVSSASTKGPSVFPLAPSSKS
                       TSGGTAALGCLVKDYFPEPVTVSWNSGALTSGVHT
                       FPAVLQSSGLYSLSSVVTVPSSSLGTQTYICNVNHK
                       PSNTKVDKRVEPKSCDKTHTCPPCPAPELLGGPSVF
                       LFPPKPKDTLMISRTPEVTCVVVDVSHEDPEVKFN
                       WYVDGVEVHNAKTKPREEQYNSTYRVVSVLTVLH
                       QDWLNGKEYKCKVSNKALPAPIEKTISKAKGQPRE
                       PQVYTLPPSREEMTKNQVSLTCLVKGFYPSDIAVE
                       WESNGQPENNYKTTPPVLDSDGSFFLYSKLTVDKS
                       RWQQGNVFSCSVMHEALHNHYTQKSLSLSPGK SEQ ID NO: 235 DNA     CAGGTGCAGCTGGTGCAGTCTGGCCCAGGACTG
               Heavy   GTGAAGCCTTCGGAGACCCTGTCCCTCACCTGCA
               Chain   CTGTCTCTGGTGGCTCCACCAGTGCTTACTACTG
                       GACCTGGATTCGGCAGCCCCCAGGGAAGGGACT
                       GGAGTGGATTGGGTATATCTCTCACAGTGGGAGC
                       ACCAACTACAACCCCTCCCTCAAGAGTCGAGTCA
                       CCATATCAGCAGACACGTCCAAGAACCAGCTCTC
                       CCTGAAGGTGAACTCTGTGACCGCCGCAGACAC
                       GGCCGTGTATTACTGTGCGAGACTTGGGGATACA
                       GCTTCACTTAGCCGCTTCTACTACTACATTGACG
                       TCTGGGGCAAAGGGACCACGGTCACCGTCTCCTC
                       AGCTAGCACCAAGGGCCCATCGGTCTTCCCCCTG
                       GCACCCTCCTCCAAGAGCACCTCTGGGGGCACA
                       GCGGCCCTGGGCTGCCTGGTCAAGGACTACTTCC
                       CCGAACCGGTGACGGTGTCGTGGAACTCAGGCG
                       CCCTGACCAGCGGCGTGCACACCTTCCCGGCTGT
                       CCTACAGTCCTCAGGACTCTACTCCCTCAGCAGC
                       GTGGTGACCGTGCCCTCCAGCAGCTTGGGCACCC
                       AGACCTACATCTGCAACGTGAATCACAAGCCCA
                       GCAACACCAAGGTGGACAAGAGAGTTGAGCCCA
                       AATCTTGTGACAAAACTCACACATGCCCACCGTG
                       CCCAGCACCTGAACTCCTGGGGGGACCGTCAGTC
                       TTCCTCTTCCCCCCAAAACCCAAGGACACCCTCA
```

TABLE 2-continued anti-VP1 Antibodies

|  |  |  |
|---|---|---|
|  |  | TGATCTCCCGGACCCCTGAGGTCACATGCGTGGT<br>GGTGGACGTGAGCCACGAAGACCCTGAGGTCAA<br>GTTCAACTGGTACGTGGACGGCGTGGAGGTGCA<br>TAATGCCAAGACAAAGCCGCGGGAGGAGCAGTA<br>CAACAGCACGTACCGTGTGGTCAGCGTCCTCACC<br>GTCCTGCACCAGGACTGGCTGAATGGCAAGGAG<br>TACAAGTGCAAGGTCTCCAACAAAGCCCTCCCA<br>GCCCCCATCGAGAAAACCATCTCCAAAGCCAAA<br>GGGCAGCCCCGAGAACCACAGGTGTACACCCTG<br>CCCCCATCCCGGGAGGAGATGACCAAGAACCAG<br>GTCAGCCTGACCTGCCTGGTCAAAGGCTTCTATC<br>CCAGCGACATCGCCGTGGAGTGGGAGAGCAATG<br>GGCAGCCGGAGAACAACTACAAGACCACGCCTC<br>CCGTGCTGGACTCCGACGGCTCCTTCTTCCTCTA<br>CAGCAAGCTCACCGTGGACAAGAGCAGGTGGCA<br>GCAGGGGAACGTCTTCTCATGCTCCGTGATGCAT<br>GAGGCTCTGCACAACCACTACACGCAGAAGAGC<br>CTCTCCCTGTCTCCGGGTAAA |
| SEQ ID NO: 236 | LCDR1<br>(Kabat) | RASQSVSSNYLA |
| SEQ ID NO: 237 | LCDR2<br>(Kabat) | GASSRAT |
| SEQ ID NO: 238 | LCDR3<br>(Kabat) | QQYGSSPPYT |
| SEQ ID NO: 239 | LCDR1<br>(Chothia) | SQSVSSNY |
| SEQ ID NO: 240 | LCDR2<br>(Chothia) | GAS |
| SEQ ID NO: 241 | LCDR3<br>(Chothia) | YGSSPPY |
| SEQ ID NO: 242 | VL | EIVMTQSPDTLSLSPGERATLSCRASQSVSSNYLAW<br>YQQKPGEAPRLLIYGASSRATGIPDRFSGSGSGTDF<br>TLTISRLEPEDFAVYYCQQYGSSPPYTFGQGTRLEIK |
| SEQ ID NO: 243 | DNA VL | GAAATTGTAATGACGCAGTCTCCAGACACCCTGT<br>CTTTGTCTCCAGGGGAAAGAGCCACCCTCTCCTG<br>CAGGGCCAGTCAGAGTGTTAGCAGCAACTACTT<br>AGCCTGGTACCAGCAGAAACCTGGCGAGGCTCC<br>CAGGCTCCTCATCTATGGTGCATCCAGCAGGGCC<br>ACTGGCATCCCAGACAGGTTCAGTGGCAGTGGG<br>TCTGGGACAGACTTCACTCTCACCATCAGCAGAC<br>TGGAGCCTGAAGATTTTGCAGTGTATTACTGTCA<br>GCAGTATGGTAGCTCACCTCCGTACACTTTTGGC<br>CAGGGGACACGACTGGAGATTAAAC |
| SEQ ID NO: 244 | Light<br>Chain | EIVMTQSPDTLSLSPGERATLSCRASQSVSSNYLAW<br>YQQKPGEAPRLLIYGASSRATGIPDRFSGSGSGTDF<br>TLTISRLEPEDFAVYYCQQYGSSPPYTFGQGTRLEI<br>KRTVAAPSVFIFPPSDEQLKSGTASVVCLLNNFYPR<br>EAKVQWKVDNALQSGNSQESVTEQDSKDSTYSLS<br>STLTLSKADYEKHKVYACEVTHQGLSSPVTKSFNR<br>GEC |
| SEQ ID NO: 245 | DNA<br>Light<br>Chain | GAAATTGTAATGACGCAGTCTCCAGACACCCTGT<br>CTTTGTCTCCAGGGGAAAGAGCCACCCTCTCCTG<br>CAGGGCCAGTCAGAGTGTTAGCAGCAACTACTT<br>AGCCTGGTACCAGCAGAAACCTGGCGAGGCTCC<br>CAGGCTCCTCATCTATGGTGCATCCAGCAGGGCC<br>ACTGGCATCCCAGACAGGTTCAGTGGCAGTGGG<br>TCTGGGACAGACTTCACTCTCACCATCAGCAGAC<br>TGGAGCCTGAAGATTTTGCAGTGTATTACTGTCA<br>GCAGTATGGTAGCTCACCTCCGTACACTTTTGGC<br>CAGGGGACACGACTGGAGATTAAACGTACGGTG<br>GCTGCACCATCTGTCTTCATCTTCCCGCCATCTGA<br>TGAGCAGTTGAAATCTGGAACTGCCTCTGTTGTG<br>TGCCTGCTGAATAACTTCTATCCCCGCGAGGCCA<br>AAGTACAGTGGAAGGTGGATAACGCCCTCCAAT<br>CGGGTAACTCCCAGGAGAGTGTCACAGAGCAGG<br>ACAGCAAGGACAGCACCTACAGCCTCAGCAGCA<br>CCCTGACGCTGAGCAAAGCAGACTACGAGAAAC<br>ACAAAGTCTACGCCTGCGAAGTCACCCATCAGG |

TABLE 2-continued anti-VP1 Antibodies

GCCTGAGCTCGCCCGTCACAAAGAGCTTCAACCG
CGGAGAGTGT

EBB-C1975-A3

SEQ ID NO: 246 HCDR1    RNYMS
(Kabat)

SEQ ID NO: 247 HCDR2    GIYSGGSTYYADSVKG
(Kabat)

SEQ ID NO: 248 HCDR3    EDEFWSGYSAGVD
(Kabat)

SEQ ID NO: 249 HCDR1    GFTVRRN
(Chothia)

SEQ ID NO: 250 HCDR2    YSGGS
(Chothia)

SEQ ID NO: 251 HCDR3    EDEFWSGYSAGVD
(Chothia)

SEQ ID NO: 252 VH       EVQLVETGGGLVQPGGSLRLSCAASGFTVRRNYM
                        SWVRQAPGKGLEWVSGIYSGGSTYYADSVKGRFTI
                        SRDYSKNTLSLQMNTLRVEDTAVYFCAREDEFWS
                        GYSAGVDWGQGTLVTVSS

SEQ ID NO: 253 DNA VH   GAGGTGCAGCTGGTGGAGACTGGAGGAGGCTTG
                        GTCCAGCCGGGGGGGTCCCTGAGACTCTCATGTG
                        CAGCCTCTGGATTCACCGTCAGACGCAATTACAT
                        GAGTTGGGTCCGCCAGGCTCCGGGGAAGGGACT
                        GGAGTGGGTCTCAGGGATCTACAGTGGTGGTAG
                        CACATACTACGCAGACTCCGTGAAGGGCCGATTC
                        ACCATCTCCAGAGACTATTCCAAGAACACACTGT
                        CTCTTCAAATGAACACCCTGAGAGTCGAGGACA
                        CGGCCGTGTATTTCTGTGCGAGAGAAGACGAATT
                        TTGGAGCGGGTATTCCGCTGGGGTCGACTGGGGC
                        CAGGGAACCCTGGTCACCGTCTCCTCAG

SEQ ID NO: 254 Heavy    EVQLVETGGGLVQPGGSLRLSCAASGFTVRRNYM
               Chain    SWVRQAPGKGLEWVSGIYSGGSTYYADSVKGRFTI
                        SRDYSKNTLSLQMNTLRVEDTAVYFCAREDEFWS
                        GYSAGVDWGQGTLVTVSSASTKGPSVFPLAPSSKS
                        TSGGTAALGCLVKDYFPEPVTVSWNSGALTSGVHT
                        FPAVLQSSGLYSLSSVVTVPSSSLGTQTYICNVNHK
                        PSNTKVDKRVEPKSCDKTHTCPPCPAPELLGGPSVF
                        LFPPKPKDTLMISRTPEVTCVVVDVSHEDPEVKFN
                        WYVDGVEVHNAKTKPREEQYNSTYRVVSVLTVLH
                        QDWLNGKEYKCKVSNKALPAPIEKTISKAKGQPRE
                        PQVYTLPPSREEMTKNQVSLTCLVKGFYPSDIAVE
                        WESNGQPENNYKTTPPVLDSDGSFFLYSKLTVDKS
                        RWQQGNVFSCSVMHEALHNHYTQKSLSLSPGK SEQ ID NO: 255 DNA      GAGGTGCAGCTGGTGGAGACTGGAGGAGGCTTG
               Heavy    GTCCAGCCGGGGGGGTCCCTGAGACTCTCATGTG
               Chain    CAGCCTCTGGATTCACCGTCAGACGCAATTACAT
                        GAGTTGGGTCCGCCAGGCTCCGGGGAAGGGACT
                        GGAGTGGGTCTCAGGGATCTACAGTGGTGGTAG
                        CACATACTACGCAGACTCCGTGAAGGGCCGATTC
                        ACCATCTCCAGAGACTATTCCAAGAACACACTGT
                        CTCTTCAAATGAACACCCTGAGAGTCGAGGACA
                        CGGCCGTGTATTTCTGTGCGAGAGAAGACGAATT
                        TTGGAGCGGGTATTCCGCTGGGGTCGACTGGGGC
                        CAGGGAACCCTGGTCACCGTCTCCTCAGCTAGCA
                        CCAAGGGCCCATCGGTCTTCCCCCTGGCACCCTC
                        CTCCAAGAGCACCTCTGGGGGCACAGCGGCCCT
                        GGGCTGCCTGGTCAAGGACTACTTCCCCGAACCG
                        GTGACGGTGTCGTGGAACTCAGGCGCCCTGACC
                        AGCGGCGTGCACACCTTCCCGGCTGTCCTACAGT
                        CCTCAGGACTCTACTCCCTCAGCAGCGTGGTGAC
                        CGTGCCCTCCAGCAGCTTGGGCACCCAGACCTAC
                        ATCTGCAACGTGAATCACAAGCCCAGCAACACC
                        AAGGTGGACAAGAGAGTTGAGCCCAAATCTTGT
                        GACAAAACTCACACATGCCCACCGTGCCCAGCA
                        CCTGAACTCCTGGGGGGACCGTCAGTCTTCCTCT
                        TCCCCCCAAAACCCAAGGACACCCTCATGATCTC
                        CCGGACCCCTGAGGTCACATGCGTGGTGGTGGA TABLE 2-continued anti-VP1 Antibodies

```
CGTGAGCCACGAAGACCCTGAGGTCAAGTTCAA
CTGGTACGTGGACGGCGTGGAGGTGCATAATGC
CAAGACAAAGCCGCGGGAGGAGCAGTACAACAG
CACGTACCGTGTGGTCAGCGTCCTCACCGTCCTG
CACCAGGACTGGCTGAATGGCAAGGAGTACAAG
TGCAAGGTCTCCAACAAAGCCCTCCCAGCCCCCA
TCGAGAAAACCATCTCCAAAGCCAAAGGGCAGC
CCCGAGAACCACAGGTGTACACCCTGCCCCCATC
CCGGGAGGAGATGACCAAGAACCAGGTCAGCCT
GACCTGCCTGGTCAAAGGCTTCTATCCCAGCGAC
ATCGCCGTGGAGTGGGAGAGCAATGGGCAGCCG
GAGAACAACTACAAGACCACGCCTCCCGTGCTG
GACTCCGACGGCTCCTTCTTCCTCTACAGCAAGC
TCACCGTGGACAAGAGCAGGTGGCAGCAGGGGA
ACGTCTTCTCATGCTCCGTGATGCATGAGGCTCT
GCACAACCACTACACGCAGAAGAGCCTCTCCCT
GTCTCCGGGTAAA
```

SEQ ID NO: 256 LCDR1 RASQSISSYLN
(Kabat)

SEQ ID NO: 257 LCDR2 AASSLQS
(Kabat)

SEQ ID NO: 258 LCDR3 QQSYNTPRT
(Kabat)

SEQ ID NO: 259 LCDR1 SQSISSY
(Chothia)

SEQ ID NO: 260 LCDR2 AAS
(Chothia)

SEQ ID NO: 261 LCDR3 SYNTPR
(Chothia)

SEQ ID NO: 262 VL        DIRLTQSPSSLSASVGDRVTITCRASQSISSYLNWYQ
                         QKPGKAPKLLIYAASSLQSGVPSRFSGSGSGTDFTL
                         TISSLQPEDFATYYCQQSYNTPRTFGQGTKVEIK

SEQ ID NO: 263 DNA VL    GACATCCGGTTGACCCAGTCTCCATCCTCCCTGT
                         CTGCATCTGTAGGAGACAGAGTCACCATCACTTG
                         CCGGGCAAGTCAGAGCATTAGCAGCTATTTGAAT
                         TGGTATCAGCAGAAACCAGGGAAAGCCCCTAAG
                         CTCCTGATCTATGCTGCATCCAGTTTGCAAAGTG
                         GGGTCCCATCAAGGTTCAGTGGCAGTGGATCTGG
                         GACAGATTTCACTCTCACCATCAGCAGTCTGCAA
                         CCTGAAGATTTTGCAACTTACTACTGTCAACAGA
                         GTTACAATACCCCTCGAACGTTCGGCCAAGGGAC
                         CAAGGTGGAGATCAAACG

SEQ ID NO: 264 Light     DIRLTQSPSSLSASVGDRVTITCRASQSISSYLNWYQ
               Chain     QKPGKAPKLLIYAASSLQSGVPSRFSGSGSGTDFTL
                         TISSLQPEDFATYYCQQSYNTPRTFGQGTKVEIKRT
                         VAAPSVFIFPPSDEQLKSGTASVVCLLNNFYPREAK
                         VQWKVDNALQSGNSQESVTEQDSKDSTYSLSSTLT
                         LSKADYEKHKVYACEVTHQGLSSPVTKSFNRGEC SEQ ID NO: 265 DNA       GACATCCGGTTGACCCAGTCTCCATCCTCCCTGT
               Light     CTGCATCTGTAGGAGACAGAGTCACCATCACTTG
               Chain     CCGGGCAAGTCAGAGCATTAGCAGCTATTTGAAT
                         TGGTATCAGCAGAAACCAGGGAAAGCCCCTAAG
                         CTCCTGATCTATGCTGCATCCAGTTTGCAAAGTG
                         GGGTCCCATCAAGGTTCAGTGGCAGTGGATCTGG
                         GACAGATTTCACTCTCACCATCAGCAGTCTGCAA
                         CCTGAAGATTTTGCAACTTACTACTGTCAACAGA
                         GTTACAATACCCCTCGAACGTTCGGCCAAGGGAC
                         CAAGGTGGAGATCAAACGTACGGTGGCTGCACC
                         ATCTGTCTTCATCTTCCCGCCATCTGATGAGCAG
                         TTGAAATCTGGAACTGCCTCTGTTGTGTGCCTGC
                         TGAATAACTTCTATCCCGCGAGGCCAAAGTACA
                         GTGGAAGGTGGATAACGCCCTCCAATCGGGTAA
                         CTCCCAGGAGAGTGTCACAGAGCAGGACAGCAA
                         GGACAGCACCTACAGCCTCAGCAGCACCCTGAC
                         GCTGAGCAAAGCAGACTACGAGAAACACAAAGT
                         CTACGCCTGCGAAGTCACCCATCAGGGCCTGAGC
                         TCGCCCGTCACAAAGAGCTTCAACCGCGGAGAG
                         TGT
```

TABLE 2-continued

| anti-VP1 Antibodies |
|---|

EBB-C1975-A7

SEQ ID NO: 266 HCDR1 (Kabat)     RNYMS

SEQ ID NO: 267 HCDR2 (Kabat)     GIYSGGSTYYADSVKG

SEQ ID NO: 268 HCDR3 (Kabat)     EDEFWSGYSAGVD

SEQ ID NO: 269 HCDR1 (Chothia)   GFTVSRN

SEQ ID NO: 270 HCDR2 (Chothia)   YSGGS

SEQ ID NO: 271 HCDR3 (Chothia)   EDEFWSGYSAGVD

SEQ ID NO: 272 VH
QVQLVESGGGLVQPGGSLRLSCAASGFTVSRNYMS
WVRQAPGKGLEWVSGIYSGGSTYYADSVKGRFTIS
RDYSKNTLSLQMNTLRVEDTAVYFCAREDEFWSG
YSAGVDWGQGTLVTVSS

SEQ ID NO: 273 DNA VH
CAGGTGCAGCTGGTGGAATCTGGAGGAGGCTTG
GTCCAGCCTGGGGGGTCCCTGAGACTCTCATGTG
CAGCCTCTGGATTCACCGTCAGTCGCAATTACAT
GAGTTGGGTCCGCCAGGCTCCGGGGAAGGGACT
GGAGTGGGTCTCAGGGATTTACAGTGGTGGTAG
CACATACTACGCAGACTCCGTGAAGGGCCGATTC
ACCATCTCCAGAGACTATTCCAAGAACACACTGT
CTCTTCAAATGAACACCCTGAGAGTCGAGGACA
CGGCCGTGTATTTCTGTGCGAGAGAAGACGAATT
TTGGAGTGGGTATTCCGCTGGGGTCGACTGGGGC
CAGGGAACCCTGGTCACCGTCTCCTCAGC

SEQ ID NO: 274 Heavy Chain
QVQLVESGGGLVQPGGSLRLSCAASGFTVSRNYMS
WVRQAPGKGLEWVSGIYSGGSTYYADSVKGRFTIS
RDYSKNTLSLQMNTLRVEDTAVYFCAREDEFWSG
YSAGVDWGQGTLVTVSSASTKGPSVFPLAPSSKST
SGGTAALGCLVKDYFPEPVTVSWNSGALTSGVHTF
PAVLQSSGLYSLSSVVTVPSSSLGTQTYICNVNHKP
SNTKVDKRVEPKSCDKTHTCPPCPAPELLGGPSVFL
FPPKPKDTLMISRTPEVTCVVVDVSHEDPEVKFNW
YVDGVEVHNAKTKPREEQYNSTYRVVSVLTVLHQ
DWLNGKEYKCKVSNKALPAPIEKTISKAKGQPREP
QVYTLPPSREEMTKNQVSLTCLVKGFYPSDIAVEW
ESNGQPENNYKTTPPVLDSDGSFFLYSKLTVDKSR
WQQGNVFSCSVMHEALHNHYTQKSLSLSPGK SEQ ID NO: 275 DNA Heavy Chain
CAGGTGCAGCTGGTGGAATCTGGAGGAGGCTTG
GTCCAGCCTGGGGGGTCCCTGAGACTCTCATGTG
CAGCCTCTGGATTCACCGTCAGTCGCAATTACAT
GAGTTGGGTCCGCCAGGCTCCGGGGAAGGGACT
GGAGTGGGTCTCAGGGATTTACAGTGGTGGTAG
CACATACTACGCAGACTCCGTGAAGGGCCGATTC
ACCATCTCCAGAGACTATTCCAAGAACACACTGT
CTCTTCAAATGAACACCCTGAGAGTCGAGGACA
CGGCCGTGTATTTCTGTGCGAGAGAAGACGAATT
TTGGAGTGGGTATTCCGCTGGGGTCGACTGGGGC
CAGGGAACCCTGGTCACCGTCTCCTCAGCTAGCA
CCAAGGGCCCATCGGTCTTCCCCCTGGCACCCTC
CTCCAAGAGCACCTCTGGGGGCACAGCGGCCCT
GGGCTGCCTGGTCAAGGACTACTTCCCCGAACCG
GTGACGGTGTCGTGGAACTCAGGCGCCCTGACC
AGCGGCGTGCACACCTTCCCGGCTGTCCTACAGT
CCTCAGGACTCTACTCCCTCAGCAGCGTGGTGAC
CGTGCCCTCCAGCAGCTTGGGCACCCAGACCTAC
ATCTGCAACGTGAATCACAAGCCCAGCAACACC
AAGGTGGACAAGAGAGTTGAGCCCAAATCTTGT
GACAAAACTCACACATGCCCACCGTGCCCAGCA
CCTGAACTCCTGGGGGGACCGTCAGTCTTCCTCT
TCCCCCCAAAACCCAAGGACACCCTCATGATCTC
CCGGACCCCTGAGGTCACATGCGTGGTGGTGGA
CGTGAGCCACGAAGACCCTGAGGTCAAGTTCAA
CTGGTACGTGGACGGCGTGGAGGTGCATAATGC
CAAGACAAAGCCGCGGGAGGAGCAGTACAACAG TABLE 2-continued anti-VP1 Antibodies

```
CACGTACCGTGTGGTCAGCGTCCTCACCGTCCTG
CACCAGGACTGGCTGAATGGCAAGGAGTACAAG
TGCAAGGTCTCCAACAAAGCCCTCCCAGCCCCCA
TCGAGAAAACCATCTCCAAAGCCAAAGGGCAGC
CCCGAGAACCACAGGTGTACACCCTGCCCCCATC
CCGGGAGGAGATGACCAAGAACCAGGTCAGCCT
GACCTGCCTGGTCAAAGGCTTCTATCCCAGCGAC
ATCGCCGTGGAGTGGGAGAGCAATGGGCAGCCG
GAGAACAACTACAAGACCACGCCTCCCGTGCTG
GACTCCGACGGCTCCTTCTTCCTCTACAGCAAGC
TCACCGTGGACAAGAGCAGGTGGCAGCAGGGGA
ACGTCTTCTCATGCTCCGTGATGCATGAGGCTCT
GCACAACCACTACACGCAGAAGAGCCTCTCCCT
GTCTCCGGGTAAA
```

SEQ ID NO: 276 LCDR1 RASQSISSYLN
(Kabat)

SEQ ID NO: 277 LCDR2 AASSLQS
(Kabat)

SEQ ID NO: 278 LCDR3 QQSYSTPRT
(Kabat)

SEQ ID NO: 279 LCDR1 SQSISSY
(Chothia)

SEQ ID NO: 280 LCDR2 AAS
(Chothia)

SEQ ID NO: 281 LCDR3 SYSTPR
(Chothia)

SEQ ID NO: 282 VL DIRMTQSPSSLSASVGDRVTITCRASQSISSYLNWY
QQKPGKAPTLLIYAASSLQSGVPSRFSGSGSGTDFT
LTISSLQPEDFATYYCQQSYSTPRTFGQGTKVEIK

SEQ ID NO: 283 DNA VL GACATCCGGATGACCCAGTCTCCATCCTCCCTGT
CTGCATCTGTAGGAGACAGAGTCACCATCACTTG
CCGGGCAAGTCAGAGCATTAGCAGCTATTTAAAT
TGGTATCAGCAGAAACCAGGGAAAGCCCCTACG
CTCCTGATCTATGCTGCATCCAGTTTGCAAAGTG
GGGTCCCATCAAGGTTCAGTGGCAGTGGATCTGG
GACAGATTTCACTCTCACCATCAGCAGTCTGCAA
CCTGAAGATTTTGCAACTTACTACTGTCAACAGA
GTTACAGTACCCCTCGGACGTTCGGCCAAGGGAC
CAAGGTGGAGATCAAAC

SEQ ID NO: 284 Light DIRMTQSPSSLSASVGDRVTITCRASQSISSYLNWY
Chain QQKPGKAPTLLIYAASSLQSGVPSRFSGSGSGTDFT
LTISSLQPEDFATYYCQQSYSTPRTFGQGTKVEIKR
TVAAPSVFIFPPSDEQLKSGTASVVCLLNNFYPREA
KVQWKVDNALQSGNSQESVTEQDSKDSTYSLSSTL
TLSKADYEKHKVYACEVTHQGLSSPVTKSFNRGEC SEQ ID NO: 285 DNA GACATCCGGATGACCCAGTCTCCATCCTCCCTGT
Light CTGCATCTGTAGGAGACAGAGTCACCATCACTTG
Chain CCGGGCAAGTCAGAGCATTAGCAGCTATTTAAAT
TGGTATCAGCAGAAACCAGGGAAAGCCCCTACG
CTCCTGATCTATGCTGCATCCAGTTTGCAAAGTG
GGGTCCCATCAAGGTTCAGTGGCAGTGGATCTGG
GACAGATTTCACTCTCACCATCAGCAGTCTGCAA
CCTGAAGATTTTGCAACTTACTACTGTCAACAGA
GTTACAGTACCCCTCGGACGTTCGGCCAAGGGAC
CAAGGTGGAGATCAAACGTACGGTGGCTGCACC
ATCTGTCTTCATCTTCCCGCCATCTGATGAGCAG
TTGAAATCTGGAACTGCCTCTGTTGTGTGCCTGC
TGAATAACTTCTATCCCGCGAGGCCAAAGTACA
GTGGAAGGTGGATAACGCCCTCCAATCGGGTAA
CTCCCAGGAGAGTGTCACAGAGCAGGACAGCAA
GGACAGCACCTACAGCCTCAGCAGCACCCTGAC
GCTGAGCAAAGCAGACTACGAGAAACACAAAGT
CTACGCCTGCGAAGTCACCCATCAGGGCCTGAGC
TCGCCCGTCACAAAGAGCTTCAACCGCGGAGAG
TGT
```

TABLE 2-continued

| anti-VP1 Antibodies |

EBB-C1975-E7

SEQ ID NO: 286 HCDR1 (Kabat) RNYMS

SEQ ID NO: 287 HCDR2 (Kabat) GIYGGGRTYYAESVKG

SEQ ID NO: 288 HCDR3 (Kabat) EDEFWSGYSAGVD

SEQ ID NO: 289 HCDR1 (Chothia) GFTVSRN

SEQ ID NO: 290 HCDR2 (Chothia) YGGGR

SEQ ID NO: 291 HCDR3 (Chothia) EDEFWSGYSAGVD

SEQ ID NO: 292 VH
EVQLLESGGGLVRPGGSLRVSCAASGFTVSRNYMS
WVRQAPGKGLEWVSGIYGGGRTYYAESVKGRFTI
SRDYSKNTLFLQMNTLRVEDTALYFCAREDEFWS
GYSAGVDWGQGTLVTVSS

SEQ ID NO: 293 DNA VH
GAGGTGCAGCTGTTGGAGTCCGGGGGAGGCTTG
GTCCGGCCTGGGGGGTCCCTGAGAGTCTCATGTG
CAGCCTCTGGATTCACCGTCAGTCGCAATTACAT
GAGTTGGGTCCGCCAGGCTCCGGGGAAGGGACT
GGAGTGGGTCTCAGGGATTTACGGTGGTGGTAG
GACTTACTACGCAGAGTCCGTGAAGGGCCGATTC
ACCATCTCCAGAGACTATTCCAAGAACACACTGT
TTCTTCAAATGAACACCCTGAGAGTCGAGGACAC
GGCCCTGTATTTCTGTGCGAGAGAAGACGAATTT
TGGAGTGGGTATTCTGCTGGGGTCGACTGGGGCC
AGGGAACCCTGGTCACTGTCTCCTCA

SEQ ID NO: 294 Heavy Chain
EVQLLESGGGLVRPGGSLRVSCAASGFTVSRNYMS
WVRQAPGKGLEWVSGIYGGGRTYYAESVKGRFTI
SRDYSKNTLFLQMNTLRVEDTALYFCAREDEFWS
GYSAGVDWGQGTLVTVSSASTKGPSVFPLAPSSKS
TSGGTAALGCLVKDYFPEPVTVSWNSGALTSGVHT
FPAVLQSSGLYSLSSVVTVPSSSLGTQTYICNVNHK
PSNTKVDKRVEPKSCDKTHTCPPCPAPELLGGPSVF
LFPPKPKDTLMISRTPEVTCVVVDVSHEDPEVKFN
WYVDGVEVHNAKTKPREEQYNSTYRVVSVLTVLH
QDWLNGKEYKCKVSNKALPAPIEKTISKAKGQPRE
PQVYTLPPSREEMTKNQVSLTCLVKGFYPSDIAVE
WESNGQPENNYKTTPPVLDSDGSFFLYSKLTVDKS
RWQQGNVFSCSVMHEALHNHYTQKSLSLSPGK SEQ ID NO: 295 DNA Heavy Chain
GAGGTGCAGCTGTTGGAGTCCGGGGGAGGCTTG
GTCCGGCCTGGGGGGTCCCTGAGAGTCTCATGTG
CAGCCTCTGGATTCACCGTCAGTCGCAATTACAT
GAGTTGGGTCCGCCAGGCTCCGGGGAAGGGACT
GGAGTGGGTCTCAGGGATTTACGGTGGTGGTAG
GACTTACTACGCAGAGTCCGTGAAGGGCCGATTC
ACCATCTCCAGAGACTATTCCAAGAACACACTGT
TTCTTCAAATGAACACCCTGAGAGTCGAGGACAC
GGCCCTGTATTTCTGTGCGAGAGAAGACGAATTT
TGGAGTGGGTATTCTGCTGGGGTCGACTGGGGCC
AGGGAACCCTGGTCACTGTCTCCTCAGCTAGCAC
CAAGGGCCCATCGGTCTTCCCCCTGGCACCCTCC
TCCAAGAGCACCTCTGGGGGCACAGCGGCCCTG
GGCTGCCTGGTCAAGGACTACTTCCCCGAACCGG
TGACGGTGTCGTGGAACTCAGGCGCCCTGACCA
GCGGCGTGCACACCTTCCCGGCTGTCCTACAGTC
CTCAGGACTCTACTCCCTCAGCAGCGTGGTGACC
GTGCCCTCCAGCAGCTTGGGCACCCAGACCTACA
TCTGCAACGTGAATCACAAGCCCAGCAACACCA
AGGTGGACAAGAGAGTTGAGCCCAAATCTTGTG
ACAAAACTCACACATGCCCACCGTGCCCAGCAC
CTGAACTCCTGGGGGGACCGTCAGTCTTCCTCTT
CCCCCCAAAACCCAAGGACACCCTCATGATCTCC
CGGACCCCTGAGGTCACATGCGTGGTGGTGGAC
GTGAGCCACGAAGACCCTGAGGTCAAGTTCAAC
TGGTACGTGGACGGCGTGGAGGTGCATAATGCC
AAGACAAAGCCGCGGGAGGAGCAGTACAACAGC TABLE 2-continued anti-VP1 Antibodies

```
ACGTACCGTGTGGTCAGCGTCCTCACCGTCCTGC
ACCAGGACTGGCTGAATGGCAAGGAGTACAAGT
GCAAGGTCTCCAACAAAGCCCTCCCAGCCCCCAT
CGAGAAAACCATCTCCAAAGCCAAAGGGCAGCC
CCGAGAACCACAGGTGTACACCCTGCCCCCATCC
CGGGAGGAGATGACCAAGAACCAGGTCAGCCTG
ACCTGCCTGGTCAAAGGCTTCTATCCCAGCGACA
TCGCCGTGGAGTGGGAGAGCAATGGGCAGCCGG
AGAACAACTACAAGACCACGCCTCCCGTGCTGG
ACTCCGACGGCTCCTTCTTCCTCTACAGCAAGCT
CACCGTGGACAAGAGCAGGTGGCAGCAGGGGAA
CGTCTTCTCATGCTCCGTGATGCATGAGGCTCTG
CACAACCACTACACGCAGAAGAGCCTCTCCCTGT
CTCCGGGTAAA
```

SEQ ID NO: 296 LCDR1 RASQSISSYLN
(Kabat)

SEQ ID NO: 297 LCDR2 AASTLQT
(Kabat)

SEQ ID NO: 298 LCDR3 QQSYNTPRT
(Kabat)

SEQ ID NO: 299 LCDR1 SQSISSY
(Chothia)

SEQ ID NO: 300 LCDR2 AAS
(Chothia)

SEQ ID NO: 301 LCDR3 SYNTPR
(Chothia)

SEQ ID NO: 302 VL   DIQVTQSPSSLSASVGDRVTITCRASQSISSYLNWY
                   QQEPGKAPKLLIYAASTLQTGVPSRFSGSGSGTDFT
                   LTISSLQPEDFATYYCQQSYNTPRTFGQGTKVEIK

SEQ ID NO: 303 DNA VL GACATCCAGGTGACCCAGTCTCCATCCTCCCTGT
                     CTGCATCTGTAGGAGACAGAGTCACCATCACTTG
                     CCGGGCAAGTCAGAGCATTAGCAGCTATTTAAAT
                     TGGTATCAGCAGGAACCAGGGAAAGCCCCTAAA
                     CTCCTGATCTACGCTGCATCCACTTTGCAAACTG
                     GGGTCCCATCACGGTTCAGTGGTAGTGGATCTGG
                     GACAGATTTCACTCTCACCATCAGCAGTCTGCAA
                     CCTGAAGATTTTGCAACTTATTACTGTCAACAGA
                     GTTACAATACCCCTCGAACCTTCGGCCAAGGGAC
                     CAAGGTGGAAATCAAACG

SEQ ID NO: 304 Light DIQVTQSPSSLSASVGDRVTITCRASQSISSYLNWY
               Chain QQEPGKAPKLLIYAASTLQTGVPSRFSGSGSGTDFT
                     LTISSLQPEDFATYYCQQSYNTPRTFGQGTKVEIKR
                     TVAAPSVFIFPPSDEQLKSGTASVVCLLNNFYPREA
                     KVQWKVDNALQSGNSQESVTEQDSKDSTYSLSSTL
                     TLSKADYEKHKVYACEVTHQGLSSPVTKSFNRGEC SEQ ID NO: 305 DNA   GACATCCAGGTGACCCAGTCTCCATCCTCCCTGT
               Light CTGCATCTGTAGGAGACAGAGTCACCATCACTTG
               Chain CCGGGCAAGTCAGAGCATTAGCAGCTATTTAAAT
                     TGGTATCAGCAGGAACCAGGGAAAGCCCCTAAA
                     CTCCTGATCTACGCTGCATCCACTTTGCAAACTG
                     GGGTCCCATCACGGTTCAGTGGTAGTGGATCTGG
                     GACAGATTTCACTCTCACCATCAGCAGTCTGCAA
                     CCTGAAGATTTTGCAACTTATTACTGTCAACAGA
                     GTTACAATACCCCTCGAACCTTCGGCCAAGGGAC
                     CAAGGTGGAAATCAAACGTACGGTGGCTGCACC
                     ATCTGTCTTCATCTTCCCGCCATCTGATGAGCAG
                     TTGAAATCTGGAACTGCCTCTGTTGTGTGCCTGC
                     TGAATAACTTCTATCCCGCGAGGCCAAAGTACA
                     GTGGAAGGTGGATAACGCCCTCCAATCGGGTAA
                     CTCCCAGGAGAGTGTCACAGAGCAGGACAGCAA
                     GGACAGCACCTACAGCCTCAGCAGCACCCTGAC
                     GCTGAGCAAAGCAGACTACGAGAAACACAAAGT
                     CTACGCCTGCGAAGTCACCCATCAGGGCCTGAGC
                     TCGCCCGTCACAAAGAGCTTCAACCGCGGAGAG
                     TGT
```

TABLE 2-continued anti-VP1 Antibodies

P46F4

| SEQ ID NO: 306 | HCDR1 (Kabat) | NGGYYWS |
| SEQ ID NO: 307 | HCDR2 (Kabat) | CIHYSGGTYYNPSLKS |
| SEQ ID NO: 308 | HCDR3 (Kabat) | ALIAAPGISDWFDP |
| SEQ ID NO: 309 | HCDR1 (Chothia) | GGSISNGGY |
| SEQ ID NO: 310 | HCDR2 (Chothia) | HYSGG |
| SEQ ID NO: 311 | HCDR3 (Chothia) | ALIAAPGISDWFDP |
| SEQ ID NO: 312 | VH | QVQLQESGPGLVKPSQTLSLTCTVSGGSISNGGYYWSWIRLHPGKGLEWIGCIHYSGGTYYNPSLKSRVTVSLDTSKNQFSLNLISVTAADTAIYFCARALIAAPGISDWFDPWGQGTLVTVSS |
| SEQ ID NO: 313 | Heavy Chain | QVQLQESGPGLVKPSQTLSLTCTVSGGSISNGGYYWSWIRLHPGKGLEWIGCIHYSGGTYYNPSLKSRVTVSLDTSKNQFSLNLISVTAADTAIYFCARALIAAPGISDWFDPWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| SEQ ID NO: 314 | LCDR1 (Kabat) | SGSNSNVGHNYVS |
| SEQ ID NO: 315 | LCDR2 (Kabat) | DNNKRPS |
| SEQ ID NO: 316 | LCDR3 (Kabat) | GTWDSSLSAGV |
| SEQ ID NO: 317 | LCDR1 (Chothia) | SNSNVGHNY |
| SEQ ID NO: 318 | LCDR2 (Chothia) | DNN |
| SEQ ID NO: 319 | LCDR3 (Chothia) | WDSSLSAG |
| SEQ ID NO: 320 | VL | QSVLTQPPSVSAAPGQKVTISCSGSNSNVGHNYVSWYQQLPGTAPKLLIYDNNKRPSGIPDRFSGSKSGTSATLGITGLQTGDEADYYCGTWDSSLSAGVFGGGTKVTVL |
| SEQ ID NO: 321 | Light Chain | QSVLTQPPSVSAAPGQKVTISCSGSNSNVGHNYVSWYQQLPGTAPKLLIYDNNKRPSGIPDRFSGSKSGTSATLGITGLQTGDEADYYCGTWDSSLSAGVFGGGTKVTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |

2081-20-8 hz53

| SEQ ID NO: 322 | HCDR1 (Kabat) | SSWMN |
| SEQ ID NO: 323 | HCDR2 (Kabat) | RIYPGDADTYYSGKFKG |

TABLE 2-continued

| anti-VP1 Antibodies | | |
|---|---|---|
| SEQ ID NO: 324 | HCDR3 (Kabat) | HSSGFTY |
| SEQ ID NO: 325 | HCDR1 (Chothia) | GYTFSSS |
| SEQ ID NO: 326 | HCDR2 (Chothia) | YPGDAD |
| SEQ ID NO: 327 | HCDR3 (Chothia) | HSSGFTY |
| SEQ ID NO: 328 | VH | QVQLVQSGAEVKKPGASVKVSCKASGYTFSSSWM NWVRQAPGQRLEWMGRIYPGDADTYYSGKFKGR VTITADSSARTAYMELSSLRSEDTAVYYCAIHSSGF TYWGQGTLVTVSS |
| SEQ ID NO: 329 | DNA VH | CAGGTCCAGCTTGTGCAGTCTGGGGCTGAGGTGA AGAAGCCTGGGGCCTCAGTGAAGGTTTCCTGCA AGGCTTCTGGCTATACATTCAGCAGCTCTTGGAT GAACTGGGTGCGCCAGGCCCCCGGACAAAGGCT TGAGTGGATGGGACGGATCTATCCAGGAGACGC CGATACTTACTACAGTGGGAAATTCAAGGGCAG AGTCACCATTACCGCCGACAGCTCCGCGAGAAC AGCCTACATGGAGCTGAGCAGCCTGAGATCTGA AGACACGGCTGTGTATTACTGTGCGATCCACAGC TCGGGCTTTACTTACTGGGGCCAGGGCACCCTGG TCACCGTCTCCTCAGC |
| SEQ ID NO: 330 | Heavy Chain | QVQLVQSGAEVKKPGASVKVSCKASGYTFSSSWM NWVRQAPGQRLEWMGRIYPGDADTYYSGKFKGR VTITADSSARTAYMELSSLRSEDTAVYYCAIHSSGF TYWGQGTLVTVSSASTKGPSVFPLAPSSKSTSGGT AALGCLVKDYFPEPVTVSWNSGALTSGVHTFPAVL QSSGLYSLSSVVTVPSSSLGTQTYICNVNHKPSNTK VDKRVEPKSCDKTHTCPPCPAPELLGGPSVFLFPPK PKDTLMISRTPEVTCVVVDVSHEDPEVKFNWYVD GVEVHNAKTKPREEQYNSTYRVVSVLTVLHQDWL NGKEYKCKVSNKALPAPIEKTISKAKGQPREPQVY TLPPSREEMTKNQVSLTCLVKGFYPSDIAVEWESN GQPENNYKTTPPVLDSDGSFFLYSKLTVDKSRWQQ GNVFSCSVMHEALHNHYTQKSLSLSPGK |
| SEQ ID NO: 331 | DNA Heavy Chain | CAGGTCCAGCTTGTGCAGTCTGGGGCTGAGGTGA AGAAGCCTGGGGCCTCAGTGAAGGTTTCCTGCA AGGCTTCTGGCTATACATTCAGCAGCTCTTGGAT GAACTGGGTGCGCCAGGCCCCCGGACAAAGGCT TGAGTGGATGGGACGGATCTATCCAGGAGACGC CGATACTTACTACAGTGGGAAATTCAAGGGCAG AGTCACCATTACCGCCGACAGCTCCGCGAGAAC AGCCTACATGGAGCTGAGCAGCCTGAGATCTGA AGACACGGCTGTGTATTACTGTGCGATCCACAGC TCGGGCTTTACTTACTGGGGCCAGGGCACCCTGG TCACCGTCTCCTCAGCTAGCACCAAGGGCCCATC GGTCTTCCCCCTGGCACCCTCCTCCAAGAGCACC TCTGGGGGCACAGCGGCCCTGGGCTGCCTGGTCA AGGACTACTTCCCCGAACCGGTGACGGTGTCGTG GAACTCAGGCGCCCTGACCAGCGGCGTGCACAC CTTCCCGGCTGTCCTACAGTCCTCAGGACTCTAC TCCCTCAGCAGCGTGGTGACCGTGCCCTCCAGCA GCTTGGGCACCCAGACCTACATCTGCAACGTGAA TCACAAGCCCAGCAACACCAAGGTGGACAAGAG AGTTGAGCCCAAATCTTGTGACAAAACTCACACA TGCCCACCGTGCCCAGCACCTGAACTCCTGGGGG GACCGTCAGTCTTCCTCTTCCCCCCAAAACCCAA GGACACCCTCATGATCTCCCGGACCCCTGAGGTC ACATGCGTGGTGGTGGACGTGAGCCACGAAGAC CCTGAGGTCAAGTTCAACTGGTACGTGGACGGC GTGGAGGTGCATAATGCCAAGACAAAGCCGCGG GAGGAGCAGTACAACAGCACGTACCGTGTGGTC AGCGTCCTCACCGTCCTGCACCAGGACTGGCTGA ATGGCAAGGAGTACAAGTGCAAGGTCTCCAACA AAGCCCTCCCAGCCCCCATCGAGAAAACCATCTC CAAAGCCAAAGGGCAGCCCCGAGAACCACAGGT GTACACCCTGCCCCCATCCCGGGAGGAGATGAC CAAGAACCAGGTCAGCCTGACCTGCCTGGTCAA AGGCTTCTATCCCAGCGACATCGCCGTGGAGTGG GAGAGCAATGGGCAGCCGGAGAACAACTACAAG |

TABLE 2-continued anti-VP1 Antibodies

```
ACCACGCCTCCCGTGCTGGACTCCGACGGCTCCT
TCTTCCTCTACAGCAAGCTCACCGTGGACAAGAG
CAGGTGGCAGCAGGGGAACGTCTTCTCATGCTCC
GTGATGCATGAGGCTCTGCACAACCACTACACGC
AGAAGAGCCTCTCCCTGTCTCCGGGTAAA
```

SEQ ID NO: 332 LCDR1 RASQDISDYLN
(Kabat)

SEQ ID NO: 333 LCDR2 YTSRLHS
(Kabat)

SEQ ID NO: 334 LCDR3 QQTHTLPFT
(Kabat)

SEQ ID NO: 335 LCDR1 SQDISDY
(Chothia)

SEQ ID NO: 336 LCDR2 YTS
(Chothia)

SEQ ID NO: 337 LCDR3 THTLPF
(Chothia)

SEQ ID NO: 338 VL DIQMTQSPSSLSASVGDRVTITCRASQDISDYLNWY
QQKPGKAPKLLIYYTSRLHSGVPSRFSGSGSGTDYT
LTISSLQPEDFATYFCQQTHTLPFTFGGGTKVEIK

SEQ ID NO: 339 DNA VL GACATCCAGATGACCCAGTCTCCATCCTCCCTGT
CTGCATCTGTAGGAGACAGAGTCACCATCACTTG
CAGGGCAAGTCAGGACATTAGCGATTATTTAAA
CTGGTATCAGCAGAAACCAGGGAAAGCCCCTAA
GCTCCTGATCTATTATACATCAAGATTACACTCA
GGGGTCCCATCAAGGTTCAGTGGCAGTGGATCTG
GGACAGATTACACTCTCACCATCAGCAGTCTGCA
ACCTGAAGATTTTGCAACTTACTTCTGTCAACAG
ACTCATACGCTTCCTTTCACGTTCGGCGGAGGGA
CCAAGGTGGAGATCAAACG

SEQ ID NO: 340 Light DIQMTQSPSSLSASVGDRVTITCRASQDISDYLNWY
Chain QQKPGKAPKLLIYYTSRLHSGVPSRFSGSGSGTDYT
LTISSLQPEDFATYFCQQTHTLPFTFGGGTKVEIKRT
VAAPSVFIFPPSDEQLKSGTASVVCLLNNFYPREAK
VQWKVDNALQSGNSQESVTEQDSKDSTYSLSSTLT
LSKADYEKHKVYACEVTHQGLSSPVTKSFNRGEC SEQ ID NO: 341 DNA GACATCCAGATGACCCAGTCTCCATCCTCCCTGT
Light CTGCATCTGTAGGAGACAGAGTCACCATCACTTG
Chain CAGGGCAAGTCAGGACATTAGCGATTATTTAAA
CTGGTATCAGCAGAAACCAGGGAAAGCCCCTAA
GCTCCTGATCTATTATACATCAAGATTACACTCA
GGGGTCCCATCAAGGTTCAGTGGCAGTGGATCTG
GGACAGATTACACTCTCACCATCAGCAGTCTGCA
ACCTGAAGATTTTGCAACTTACTTCTGTCAACAG
ACTCATACGCTTCCTTTCACGTTCGGCGGAGGGA
CCAAGGTGGAGATCAAACGTACGGTGGCTGCAC
CATCTGTCTTCATCTTCCCGCCATCTGATGAGCA
GTTGAAATCTGGAACTGCCTCTGTTGTGTGCCTG
CTGAATAACTTCTATCCCCGCGAGGCCAAAGTAC
AGTGGAAGGTGGATAACGCCCTCCAATCGGGTA
ACTCCCAGGAGAGTGTCACAGAGCAGGACAGCA
AGGACAGCACCTACAGCCTCAGCAGCACCCTGA
CGCTGAGCAAAGCAGACTACGAGAAACACAAAG
TCTACGCCTGCGAAGTCACCCATCAGGGCCTGAG
CTCGCCCGTCACAAAGAGCTTCAACCGCGGAGA
GTGT
```

2075-16-1

SEQ ID NO: 342 HCDR1 NYWMH
(Kabat)

SEQ ID NO: 343 HCDR2 NIYPGSGNTNYGENFKS
(Kabat)

SEQ ID NO: 344 HCDR3 SAIYYGYDGHYFAMDY
(Kabat)

TABLE 2-continued anti-VP1 Antibodies

SEQ ID NO: 345 HCDR1 GYTFTNY
(Chothia)

SEQ ID NO: 346 HCDR2 YPGSGN
(Chothia)

SEQ ID NO: 347 HCDR3 SAIYYGYDGHYFAMDY
(Chothia)

SEQ ID NO: 348 VH QVQLQQPGSELVRPGASVKLSCKASGYTFTNYWM
HWVKQGHGQGLEWIGNIYPGSGNTNYGENFKSKG
TLTVDTSSSTAYMHLSRLTSEDSAVYYCSRSAIYYG
YDGHYFAMDYWGQGTSVTVSS

SEQ ID NO: 349 LCDR1 KASQDIRKYIA
(Kabat)

SEQ ID NO: 350 LCDR2 YTSTLQS
(Kabat)

SEQ ID NO: 351 LCDR3 LQYDNILFT
(Kabat)

SEQ ID NO: 352 LCDR1 SQDIRKY
(Chothia)

SEQ ID NO: 353 LCDR2 YTS
(Chothia)

SEQ ID NO: 354 LCDR3 YDNILF
(Chothia)

SEQ ID NO: 355 VL DIQMTQSPSSLSASLGGKVTITCKASQDIRKYIAWY
QHKPGKGPRLLINYTSTLQSGIPSRFRGSGSGRDYS
FSISNLEPEDIATYYCLQYDNILFTFGTGTKLEIK 2075-456-4

SEQ ID NO: 356 HCDR1 SCWMN
(Kabat)

SEQ ID NO: 357 HCDR2 RIYPGDGDTKYTEKFKD
(Kabat)

SEQ ID NO: 358 HCDR3 SGSGLPY
(Kabat)

SEQ ID NO: 359 HCDR1 GYSFSSC
(Chothia)

SEQ ID NO: 360 HCDR2 YPGDGD
(Chothia)

SEQ ID NO: 361 HCDR3 SGSGLPY
(Chothia)

SEQ ID NO: 362 VH QVHLQQSGPELVKPGASVTISCKTSGYSFSSCWMN
WVKQRPGQGLEWIGRIYPGDGDTKYTEKFKDKAT
LTADKSSSTAYMQLSSLTSVDSALYFCAISGSGLPY
WGQGTLVTVSE

SEQ ID NO: 363 LCDR1 RASQDIHNYLN
(Kabat)

SEQ ID NO: 364 LCDR2 STSRLHS
(Kabat)

SEQ ID NO: 365 LCDR3 QQTHTLPLT
(Kabat)

SEQ ID NO: 366 LCDR1 SQDIHNY
(Chothia)

SEQ ID NO: 367 LCDR2 STS
(Chothia)

SEQ ID NO: 368 LCDR3 THTLPL
(Chothia)

TABLE 2-continued anti-VP1 Antibodies

| SEQ ID NO: 369 VL | DIQMTQTTSSLSASLGDRVTISCRASQDIHNYLNWY<br>QQKPDGTIKLLIYSTSRLHSGVPSRFSGSGSGTHYSL<br>TINNLEQEDIATYFCQQTHTLPLTFGAGTKLELK |

2081-36-8

| SEQ ID NO: 370 HCDR1 (Kabat) | SYWMN |
| SEQ ID NO: 371 HCDR2 (Kabat) | QIYPGNGDTNYNGKFKG |
| SEQ ID NO: 372 HCDR3 (Kabat) | EARQGYHYAMDY |
| SEQ ID NO: 373 HCDR1 (Chothia) | GYAFSSY |
| SEQ ID NO: 374 HCDR2 (Chothia) | YPGNGD |
| SEQ ID NO: 375 HCDR3 (Chothia) | EARQGYHYAMDY |
| SEQ ID NO: 376 VH | QVQLQQSGAGLVRPGSSVKISCKTSGYAFSSYWM<br>NWVKQRPGQGLEWIGQIYPGNGDTNYNGKFKGK<br>ATLTADKSSNTAYIQLNSLTSEDSAVYFCAREARQ<br>GYHYAMDYWGQGTSVTVSL |
| SEQ ID NO: 377 LCDR1 (Kabat) | SASSMINSNYLH |
| SEQ ID NO: 378 LCDR2 (Kabat) | RTSNLAS |
| SEQ ID NO: 379 LCDR3 (Kabat) | QQGSNIFT |
| SEQ ID NO: 380 LCDR1 (Chothia) | SSMINSNY |
| SEQ ID NO: 381 LCDR2 (Chothia) | RTS |
| SEQ ID NO: 382 LCDR3 (Chothia) | GSNIF |
| SEQ ID NO: 383 VL | EIVFTQSPTTMAAFPGEKITITCSASSMINSNYLHWY<br>QQKPGFSPKVLIYRTSNLASGVPARFSGTGSGTSFS<br>LTIGTMEAEDVATYYCQQGSNIFTFGSGTKLEIK |

2081-66-5

| SEQ ID NO: 384 HCDR1 (Kabat) | NSWMN |
| SEQ ID NO: 385 HCDR2 (Kabat) | RIYPGDGDTQYNEKFKG |
| SEQ ID NO: 386 HCDR3 (Kabat) | SRSGLDY |
| SEQ ID NO: 387 HCDR1 (Chothia) | GFTFSNS |
| SEQ ID NO: 388 HCDR2 (Chothia) | YPGDGD |
| SEQ ID NO: 389 HCDR3 (Chothia) | SRSGLDY |
| SEQ ID NO: 390 VH | QVQLQQSGPELVKPGASVRISCKVSGFTFSNSWMN<br>WVKQRPGQGLEWIGRIYPGDGDTQYNEKFKGKAT<br>LTADTSSNTAYIQLNSLTSVDSAVFFCARSRSGLDY<br>WGQGTTLTVSS |
| SEQ ID NO: 391 LCDR1 (Kabat) | RASQDIYNYLN |

TABLE 2-continued anti-VP1 Antibodies

SEQ ID NO: 392 LCDR2 STSRLHS
(Kabat)

SEQ ID NO: 393 LCDR3 HQSHTVPFT
(Kabat)

SEQ ID NO: 394 LCDR1 SQDIYNY
(Chothia)

SEQ ID NO: 395 LCDR2 STS
(Chothia)

SEQ ID NO: 396 LCDR3 SHTVPF
(Chothia)

SEQ ID NO: 397 VL DIQMTQSTSSLSASLGDRVTISCRASQDIYNYLNWF
QQKPDGTVKPLIYSTSRLHSGVSSRFSGSGSGTDYS
LTISNLEREDIATYFCHQSHTVPFTFGSGTKLEIK

2081-38-5

SEQ ID NO: 398 HCDR1 SSWIN
(Kabat)

SEQ ID NO: 399 HCDR2 RIYPGDGDTNYNGKFKG
(Kabat)

SEQ ID NO: 400 HCDR3 HSSGFPH
(Kabat)

SEQ ID NO: 401 HCDR1 GYTFSSS
(Chothia)

SEQ ID NO: 402 HCDR2 YPGDGD
(Chothia)

SEQ ID NO: 403 HCDR3 HSSGFPH
(Chothia)

SEQ ID NO: 404 VH QVQLQQSGPELVKPGASVKISCKASGYTFSSSWIN
WVKQRPGQGLEWIGRIYPGDGDTNYNGKFKGKAT
LTADKSSSTVDMHLSSLTYVDSAVYFCAIHSSGFPH
WGQGTLVTVSA

SEQ ID NO: 405 LCDR1 RTSQDISDYLN
(Kabat)

SEQ ID NO: 406 LCDR2 YTSRLHS
(Kabat)

SEQ ID NO: 407 LCDR3 QQTNTLPFT
(Kabat)

SEQ ID NO: 408 LCDR1 SQDISDY
(Chothia)

SEQ ID NO: 409 LCDR2 YTS
(Chothia)

SEQ ID NO: 410 LCDR3 TNTLPF
(Chothia)

SEQ ID NO: 411 VL DIQMTQTTSSLSASLGGRVTISCRTSQDISDYLNWY
QQKPDGAVKLLIYYTSRLHSGVPSRFSGSGSGTDYS
LTISNLEQEDIATYFCQQTNTLPFTFGGGTKLEIK

2081-25-6

SEQ ID NO: 412 HCDR1 RYWMN
(Kabat)

SEQ ID NO: 413 HCDR2 QIYPGDGDTKYNGKFKD
(Kabat)

SEQ ID NO: 414 HCDR3 YGNYGMDY
(Kabat)

TABLE 2-continued

| anti-VP1 Antibodies |

SEQ ID NO: 415 HCDR1 GYAFSRY
(Chothia)

SEQ ID NO: 416 HCDR2 YPGDGD
(Chothia)

SEQ ID NO: 417 HCDR3 YGNYGMDY
(Chothia)

SEQ ID NO: 418 VH QVQLQQSGAELVRPGSSVKISCKASGYAFSRYWM
NWVKQRPGQGLEWIGQIYPGDGDTKYNGKFKDTA
TLTADKSSSTAYLQLSSLTSEDSAVYFCAKYGNYG
MDYWGQGTSVTVSS

SEQ ID NO: 419 LCDR1 RSSQSLEYGNGNTYLN
(Kabat)

SEQ ID NO: 420 LCDR2 RVSNRFS
(Kabat)

SEQ ID NO: 421 LCDR3 LQFTHVPYT
(Kabat)

SEQ ID NO: 422 LCDR1 SQSLEYGNGNTY
(Chothia)

SEQ ID NO: 423 LCDR2 RVS
(Chothia)

SEQ ID NO: 424 LCDR3 FTHVPY
(Chothia)

SEQ ID NO: 425 VL DAVMTQTPLSLPVSLGDQASISCRSSQSLEYGNGNT
YLNWYLQKPGQSPQLLIYRVSNRFSGVLDRFSGSG
SGTDFTLKISRVEAEDLGVYFCLQFTHVPYTFGGGT
KLEIK 2077-4-1

SEQ ID NO: 426 HCDR1 GYTMN
(Kabat)

SEQ ID NO: 427 HCDR2 LFNPYNGGTRYNQKFKG
(Kabat)

SEQ ID NO: 428 HCDR3 LRNYGIGDDFFDY
(Kabat)

SEQ ID NO: 429 HCDR1 GYSFTGY
(Chothia)

SEQ ID NO: 430 HCDR2 NPYNGG
(Chothia)

SEQ ID NO: 431 HCDR3 LRNYGIGDDFFDY
(Chothia)

SEQ ID NO: 432 VH EVQLQQSGPELVKPGASMKISCKASGYSFTGYTMN
WVKQSHGENLEWIGLFNPYNGGTRYNQKFKGKAT
LTVDKSSSTAYMELLSLTSEDSAVYYCARLRNYGI
GDDFFDYWGQGTTLTVSS

SEQ ID NO: 433 LCDR1 KASQDVGTAVA
(Kabat)

SEQ ID NO: 434 LCDR2 WASTRHT
(Kabat)

SEQ ID NO: 435 LCDR3 QQYSNYPYT
(Kabat)

SEQ ID NO: 436 LCDR1 SQDVGTA
(Chothia)

SEQ ID NO: 437 LCDR2 WAS
(Chothia)

TABLE 2-continued anti-VP1 Antibodies

SEQ ID NO: 438 LCDR3 YSNYPY
(Chothia)

SEQ ID NO: 439 VL    DIVMTQSHKFMSTSVGDRVSITCKASQDVGTAVA
                     WYQQKPGQSPKLLIYWASTRHTGVPDRFTGSGSGT
                     DFTLTISNVQSEDLTDYFCQQYSNYPYTFGGGTKLE
                     IK 2077-7-5

SEQ ID NO: 440 HCDR1 GYTMN
(Kabat)

SEQ ID NO: 441 HCDR2 LFNPYNGGINYNQKFKG
(Kabat)

SEQ ID NO: 442 HCDR3 LRYYGIGDDFFDY
(Kabat)

SEQ ID NO: 443 HCDR1 GYSFTGY
(Chothia)

SEQ ID NO: 444 HCDR2 NPYNGG
(Chothia)

SEQ ID NO: 445 HCDR3 LRYYGIGDDFFDY
(Chothia)

SEQ ID NO: 446 VH    EVQLQQSGPELVKPGASMKISCKASGYSFTGYTMN
                     WVKQSHGKNLEWIGLFNPYNGGINYNQKFKGKAT
                     LTVDKSSSTAYMELLSLTSEDSAVYYCARLRYYGI
                     GDDFFDYWGQGTSLTVSS

SEQ ID NO: 447 LCDR1 KASRDVGTAVA
(Kabat)

SEQ ID NO: 448 LCDR2 WASTRHT
(Kabat)

SEQ ID NO: 449 LCDR3 QQYSNYPYT
(Kabat)

SEQ ID NO: 450 LCDR1 SRDVGTA
(Chothia)

SEQ ID NO: 451 LCDR2 WAS
(Chothia)

SEQ ID NO: 452 LCDR3 YSNYPY
(Chothia)

SEQ ID NO: 453 VL    DIVMTQSHKFMSTSVGDRVSITCKASRDVGTAVA
                     WYQQKPGQSPKLLIYWASTRHTGVPDRFTGSGSGT
                     DFTLTISNVQSEDLADYFCQQYSNYPYTFGGGTKL
                     EMK 2077-10-1

SEQ ID NO: 454 HCDR1 GYTMN
(Kabat)

SEQ ID NO: 455 HCDR2 LFNPYNGGPNYNQKFKG
(Kabat)

SEQ ID NO: 456 HCDR3 LRYYGIGDDFFDY
(Kabat)

SEQ ID NO: 457 HCDR1 GYSFTGY
(Chothia)

SEQ ID NO: 458 HCDR2 NPYNGG
(Chothia)

SEQ ID NO: 459 HCDR3 LRYYGIGDDFFDY
(Chothia)

SEQ ID NO: 460 VH    EVQLQQSGPELVKPGASMKISCKASGYSFTGYTMN
                     WMKQGHGKNLEWIGLFNPYNGGPNYNQKFKGKA

TABLE 2-continued anti-VP1 Antibodies

|  |  |  |
|---|---|---|
|  |  | TLTVDKSSSTAYMELLSLTSEDSAVYYCARLRYYG<br>IGDDFFDYWGQGTTLTVSS |
| SEQ ID NO: 461<br>(Kabat) | LCDR1 | KASQDVGTAVA |
| SEQ ID NO: 462<br>(Kabat) | LCDR2 | WASTRHT |
| SEQ ID NO: 463<br>(Kabat) | LCDR3 | QQYSSYPYT |
| SEQ ID NO: 464<br>(Chothia) | LCDR1 | SQDVGTA |
| SEQ ID NO: 465<br>(Chothia) | LCDR2 | WAS |
| SEQ ID NO: 466<br>(Chothia) | LCDR3 | YSSYPY |
| SEQ ID NO: 467 | VL | DIVMTQSHKFMSTSVGDRVSITCKASQDVGTAVA<br>WYQQKPGQSPKLLIYWASTRHTGVPDRFTGSGSGT<br>DFTLTITNVQSEDLTDYFCQQYSSYPYTFGGGTKLE<br>IK |

2077-26-1

| SEQ ID NO: 468<br>(Kabat) | HCDR1 | GYTMN |
| SEQ ID NO: 469<br>(Kabat) | HCDR2 | LFNPYNGGPSYNQKFKG |
| SEQ ID NO: 470<br>(Kabat) | HCDR3 | LRYYGIGDDFFDY |
| SEQ ID NO: 471<br>(Chothia) | HCDR1 | GYSFTGY |
| SEQ ID NO: 472<br>(Chothia) | HCDR2 | NPYNGG |
| SEQ ID NO: 473<br>(Chothia) | HCDR3 | LRYYGIGDDFFDY |
| SEQ ID NO: 474 | VH | EVQLQQSGPDLVKPGASMKLSCKASGYSFTGYTM<br>NWVKQSHGKNLEWIGLFNPYNGGPSYNQKFKGKA<br>TLTVDKSSSTAYMELLSLTPEDSAVYYCARLRYYG<br>IGDDFFDYWGQGTTLTVSS |
| SEQ ID NO: 475<br>(Kabat) | LCDR1 | KASQDVGTAVA |
| SEQ ID NO: 476<br>(Kabat) | LCDR2 | WASTRHT |
| SEQ ID NO: 477<br>(Kabat) | LCDR3 | QQYSNYPYT |
| SEQ ID NO: 478<br>(Chothia) | LCDR1 | SQDVGTA |
| SEQ ID NO: 479<br>(Chothia) | LCDR2 | WAS |
| SEQ ID NO: 480<br>(Chothia) | LCDR3 | YSNYPY |
| SEQ ID NO: 481 | VL | DIVMTQSHKFMSTSVGDRVSITCKASQDVGTAVA<br>WYQEKPGQSPKLLIYWASTRHTGVPDRFTGSGSGT<br>DFTLTISNVQSEDLAYYFCQQYSNYPYTFGGGTKL<br>EIK |

2077-28-2

| SEQ ID NO: 482<br>(Kabat) | HCDR1 | GYTMN |

TABLE 2-continued anti-VP1 Antibodies

SEQ ID NO: 483 HCDR2 LFNPYNGGATYNQRFKG
(Kabat)

SEQ ID NO: 484 HCDR3 LRKYGIGDDFFDY
(Kabat)

SEQ ID NO: 485 HCDR1 GYSFTGY
(Chothia)

SEQ ID NO: 486 HCDR2 NPYNGG
(Chothia)

SEQ ID NO: 487 HCDR3 LRKYGIGDDFFDY
(Chothia)

SEQ ID NO: 488 VH        EVQLQQSGPELVKPGASMKISCKASGYSFTGYTMN
                         WVKQSHGKNLEWIGLFNPYNGGATYNQRFKGKA
                         TLTVDKSSSTAYMDLLSLTSEDSAVYYCTRLRKYG
                         IGDDFFDYWGQGTTLTVSS

SEQ ID NO: 489 LCDR1 KASQDVGTAVA
(Kabat)

SEQ ID NO: 490 LCDR2 WASTRHT
(Kabat)

SEQ ID NO: 491 LCDR3 QQYSTYTYT
(Kabat)

SEQ ID NO: 492 LCDR1 SQDVGTA
(Chothia)

SEQ ID NO: 493 LCDR2 WAS
(Chothia)

SEQ ID NO: 494 LCDR3 YSTYTY
(Chothia)

SEQ ID NO: 495 VL        DIVMTQSHKFMSTSVGDRVSITCKASQDVGTAVA
                         WYQQKPGQSPKLLIYWASTRHTGVPDRFTGSGSGT
                         DFTLTISNVQSEDLADYFCQQYSTYTYTFGGGTKL
                         EIK

P8D11

SEQ ID NO: 508 HCDR1 GFTFNNYWMT
(Combined)

SEQ ID NO: 509 HCDR2 NIKKDGSEKYYVDSVRG
(Combined)

SEQ ID NO: 510 HCDR3 VRSGRYFALDD
(Combined)

SEQ ID NO: 511 LCDR1 GGDNIGSRPVH
(Combined)

SEQ ID NO: 512 LCDR2 DDSNRPS
(Combined)

SEQ ID NO: 513 LCDR3 QVWSSSTDHP
(Combined)

P8D11A

SEQ ID NO: 514 HCDR1 GFTFSNYWMT
(Combined)

SEQ ID NO: 515 HCDR2 NIKKDGSEKYYVDSVRG
(Combined)

SEQ ID NO: 516 HCDR3 VRSGRYFALDD
(Combined)

SEQ ID NO: 517 LCDR1 GGDNIGSRPVH
(Combined)

TABLE 2-continued anti-VP1 Antibodies

SEQ ID NO: 518 LCDR2 DDSNRPS
(Combined)

SEQ ID NO: 519 LCDR3 QVWSSSTDHP
(Combined)

P8D11B

SEQ ID NO: 520 HCDR1 GFTFKNYWMT
(Combined)

SEQ ID NO: 521 HCDR2 NIKKDGSEKYYVDSVRG
(Combined)

SEQ ID NO: 522 HCDR3 VRSGRYFALDD
(Combined)

SEQ ID NO: 523 LCDR1 GGDNIGSRPVH
(Combined)

SEQ ID NO: 524 LCDR2 DDSNRPS
(Combined)

SEQ ID NO: 525 LCDR3 QVWSSSTDHP
(Combined)

P8D11C

SEQ ID NO: 526 HCDR1 GFTFQNYWMT
(Combined)

SEQ ID NO: 527 HCDR2 NIKKDGSEKYYVDSVRG
(Combined)

SEQ ID NO: 528 HCDR3 VRSGRYFALDD
(Combined)

SEQ ID NO: 529 LCDR1 GGDNIGSRPVH
(Combined)

SEQ ID NO: 530 LCDR2 DDSNRPS
(Combined)

SEQ ID NO: 531 LCDR3 QVWSSSTDHP
(Combined)

P8D11D

SEQ ID NO: 532 HCDR1 GFTFNNYWMT
(Combined)

SEQ ID NO: 533 HCDR2 NIKKDGSEKYYVDSVRG
(Combined)

SEQ ID NO: 534 HCDR3 VRSGRYFALDD
(Combined)

SEQ ID NO: 535 LCDR1 GGDNIGSRPVH
(Combined)

SEQ ID NO: 536 LCDR2 DDSNRPS
(Combined)

SEQ ID NO: 537 LCDR3 QVWSSSTDHP
(Combined)

P8D11E

SEQ ID NO: 538 HCDR1 GFTFNNYWMT
(Combined)

SEQ ID NO: 539 HCDR2 NIKKDGSEKYYVDSVRG
(Combined)

SEQ ID NO: 540 HCDR3 VRSGRYFALDD
(Combined)

TABLE 2-continued anti-VP1 Antibodies

SEQ ID NO: 541 LCDR1 GGDNIGSRPVH
(Combined)

SEQ ID NO:

246, 266, 286, 306, 322, 342, 356, 370, 384, 398, 412, 426, 440, 454, 468, and 482; a heavy chain CDR2 comprising an amino acid sequence selected from the group consisting of SEQ ID NOs: 7, 27, 47, 67, 87, 107, 127, 147, 167, 187, 207, 227, 247, 267, 287, 307, 323, 343, 357, 371, 385, 399, 413, 427, 441, 455, 469, and 483; a heavy chain CDR3 comprising an amino acid sequence selected from the group consisting of SEQ ID NOs: 8, 28, 48, 68, 88, 108, 128, 148, 168, 188, 208, 228, 248, 268, 288, 308, 324, 344, 358, 372, 386, 400, 414, 428, 442, 456, 470, and 484; a light chain CDR1 comprising an amino acid sequence selected from the group consisting of SEQ ID NOs: 16, 36, 56, 76, 96, 116, 136, 156, 176, 196, 216, 236, 256, 276, 296, 314, 332, 349, 363, 377, 391, 405, 419, 433, 447, 461, 475 and 489; a light chain CDR2 comprising an amino acid sequence selected from the group consisting of SEQ ID NOs: 17, 37, 57, 77, 97, 117, 137, 157, 177, 197, 217, 237, 257, 277, 297, 315, 333, 350, 364, 378, 392, 406, 420, 434, 448, 462, 476 and 490; and a light chain CDR3 comprising an amino acid sequence selected from the group consisting of SEQ ID NOs: 18, 38, 58, 78, 98, 118, 138, 158, 178, 198, 218, 238, 258, 278, 298, 316, 334, 351, 365, 379, 393, 407, 421, 435, 449, 463, 477 and 491; wherein the antibody specifically binds to VP1.

In certain aspects, an antibody that specifically binds to VP1 is an antibody or antibody fragment (e.g., antigen binding fragment) that is described in Table 2.

1. Identification of Epitopes and Antibodies that Bind to the Same Epitope

The present disclosure provides antibodies and antibody fragments (e.g., antigen binding fragments) that bind to an epitope of VP1. In certain aspects the antibodies and antibody fragments can bind to the same epitope within all four BKV serotypes and/or JCV.

The present disclosure also provides antibodies and antibody fragments (e.g., antigen binding fragments) that bind to the same epitope as do the anti-VP1 antibodies described in Table 2. Additional antibodies and antibody fragments (e.g., antigen binding fragments) can therefore be identified based on their ability to cross-compete (e.g., to competitively inhibit the binding of, in a statistically significant manner) with other antibodies in binding assays. The ability of a test antibody to inhibit the binding of antibodies and antibody fragments (e.g., antigen binding fragments) of the present disclosure to VP1 (e.g., human BKV or JCV VP1) demonstrates that the test antibody can compete with that antibody or antibody fragment (e.g., antigen binding fragments) for binding to VP1; such an antibody may, according to non-limiting theory, bind to the same or a related (e.g., a structurally similar or spatially proximal) epitope on VP1 as the antibody or antibody fragment (e.g., antigen binding fragments) with which it competes. In a certain aspect, the antibody that binds to the same epitope on VP1 as the antibodies or antibody fragments (e.g., antigen binding fragments) of the present disclosure is a human or humanized monoclonal antibody. Such human or humanized monoclonal antibodies can be prepared and isolated as described herein.

2. Further Alteration of the Framework of Fc Region

The present disclosure disclosed specific anti-VP1 antibodies. These antibodies comprise modified antibodies or antigen binding fragments thereof that further comprise modifications to framework residues within VH and/or VL, e.g. to improve the properties of the antibody. Typically such framework modifications are made to decrease the immunogenicity of the antibody. For example, one approach is to "back-mutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "back-mutated" to the germline sequence by, for example, site-directed mutagenesis. Such "back-mutated" antibodies are also intended to be encompassed.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in U.S. Patent Publication No. 2003/0153043 by Carr et al.

In addition or alternative to modifications made within the framework or CDR regions, antibodies can be engineered to include modifications within the Fc region, typically to alter one or more functional properties of the antibody, such as serum half-life, complement fixation, Fc receptor binding, and/or antigen-dependent cellular cytotoxicity. Furthermore, an antibody can be chemically modified (e.g., one or more chemical moieties can be attached to the antibody) or be modified to alter its glycosylation, again to alter one or more functional properties of the antibody. Each of these aspects is described in further detail below.

In one aspect, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another aspect, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other aspects, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in, e.g., U.S. Pat. Nos. 5,624,821 and 5,648,260, both by Winter et al.

In another aspect, one or more amino acids selected from amino acid residues can be replaced with a different amino acid residue such that the antibody has altered C1q binding and/or reduced or abolished complement dependent cytotoxicity (CDC). This approach is described in, e.g., U.S. Pat. No. 6,194,551 by Idusogie et al.

In another aspect, one or more amino acid residues are altered to thereby alter the ability of the antibody to fix complement. This approach is described in, e.g., the PCT Publication WO 94/29351 by Bodmer et al. In a specific aspect, one or more amino acids of an antibody or antigen binding fragment thereof of the present disclosure are replaced by one or more allotypic amino acid residues, for the IgG1 subclass and the kappa isotype. Allotypic amino acid residues also include, but are not limited to, the constant region of the heavy chain of the IgG1, IgG2, and IgG3 subclasses as well as the constant region of the light chain of the kappa isotype as described by Jefferis et al., MAbs. 1:332-338 (2009).

In yet another aspect, the Fc region is modified to increase the ability of the antibody to mediate antibody dependent cellular cytotoxicity (ADCC) and/or to increase the affinity of the antibody for an Fcγ receptor by modifying one or more amino acids. This approach is described in, e.g., the PCT Publication WO 00/42072 by Presta. Moreover, the binding sites on human IgG1 for FcγR1, FcγRII, FcγRIII and FcRn have been mapped and variants with improved binding have been described (see Shields et al., J. Biol. Chem. 276:6591-6604, 2001).

In still another aspect, the glycosylation of an antibody is modified. For example, an aglycosylated antibody can be made (i.e., the antibody lacks glycosylation). Glycosylation can be altered to, for example, increase the affinity of the antibody for "antigen." Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in, e.g., U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn (297)-linked carbohydrates, also resulting in hypofucosylation of antibodies expressed in that host cell (see also Shields et al., (2002) J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., Nat. Biotech. 17:176-180, 1999).

In another aspect, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In order to minimize the ADCC activity of an antibody, specific mutations in the Fc region result in "Fc silent" antibodies that have minimal interaction with effector cells. In general, the "IgG Fc region" is used to define the C-terminal region of an immunoglobulin heavy chain, including native sequence Fc region and variant Fc regions. The human IgG heavy chain Fc region is generally defined as comprising the amino acid residue from position C226 or from P230 to the carboxyl-terminus of the IgG antibody. The numbering of residues in the Fc region is that of the EU index of Kabat. The C-terminal lysine (residue K447) of the Fc region may be removed, for example, during production or purification of the antibody.

Silenced effector functions can be obtained by mutation in the Fc region of the antibodies and have been described in the art: LALA and N297A (Strohl, W., 2009, Curr. Opin. Biotechnol. vol. 20(6):685-691); and D265A (Baudino et al., 2008, J. Immunol. 181: 6664-69) see also Heusser et al., WO2012065950. Examples of silent Fc lgG1 antibodies are the LALA mutant comprising L234A and L235A mutation in the lgG1 Fc amino acid sequence. Another example of a silent lgG1 antibody is the DAPA (D265A, P329A) mutation (U.S. Pat. No. 6,737,056). Another silent lgG1 antibody comprises the N297A mutation, which results in aglycosylated/non-glycosylated antibodies.

Fc silent antibodies result in no or low ADCC activity, meaning that an Fc silent antibody exhibits an ADCC activity that is below 50% specific cell lysis (low ADCC activity), or that is below 1% specific cell lysis (no ADCC activity).

3. Production of the Anti-VP1 Antibodies

Anti-VP1 antibodies and antibody fragments (e.g., antigen binding fragments) thereof can be produced by any means known in the art, including but not limited to, recombinant expression, chemical synthesis, and enzymatic digestion of antibody tetramers, whereas full-length monoclonal antibodies can be obtained by, e.g., hybridoma or recombinant production. Recombinant expression can be from any appropriate host cells known in the art, for example, mammalian host cells, bacterial host cells, yeast host cells, insect host cells, etc.

The disclosure further provides polynucleotides encoding the antibodies described herein, e.g., polynucleotides encoding heavy or light chain variable regions or segments comprising the complementarity determining regions as described herein. In some aspects, the polynucleotide encoding the heavy chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 13, 33, 53, 73, 93, 113, 133, 153, 173, 193, 213, 233, 253, 273 and 293. In some aspects, the polynucleotide encoding the light chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs:23, 43, 63, 83, 103, 123, 143, 163, 183, 203, 223, 243, 263, 283 and 303.

In some aspects, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO: 15, 35, 55, 75, 95, 115, 135, 155, 175, 195, 215, 235, 255, 275 and 295. In some aspects, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO: 25, 45, 65, 85, 105, 125, 145, 165, 185, 205, 225, 245, 265, 285 and 305.

The polynucleotides of the present disclosure can encode only the variable region sequence of an anti-VP1 antibody. They can also encode both a variable region and a constant region of the antibody. Some of the polynucleotide sequences encode a polypeptide that comprises variable regions of both the heavy chain and the light chain of one of an exemplified anti-VP1 antibody. Some other polynucleotides encode two polypeptide segments that respectively are substantially identical to the variable regions of the heavy chain and the light chain of one of the mouse antibodies.

The polynucleotide sequences can be produced by de novo solid-phase DNA synthesis or by PCR mutagenesis of an existing sequence (e.g., sequences as described in the Examples below) encoding an anti-VP1 antibody or its binding fragment. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the present disclosure are expression vectors and host cells for producing the anti-VP1 antibodies described above. Various expression vectors can be employed to express the polynucleotides encoding the anti-VP1 antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the anti-VP1 polynucleotides and polypeptides in mammalian (e.g., human) cells include pThioHis A, B & C, pcDNA3.1/His, pEBVHis A, B & C (Invitrogen, San Diego, Calif.), MPSV vectors, and numerous other vectors known in the art for expressing other proteins. Useful viral vectors include vectors based on retroviruses, adenoviruses, adeno-associated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an anti-VP1 antibody chain or fragment. In some aspects, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under non-inducing conditions without biasing the population for coding sequences whose expression products are better tolerated by the host cells. In addition to promoters, other regulatory elements may also be required or desired for efficient expression of an anti-VP1 antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted anti-VP1 antibody sequences. More often, the inserted anti-VP1 antibody sequences are linked to a signal sequences before inclusion in the vector. Vectors to be used to receive sequences encoding anti-VP1 antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the anti-VP1 antibody chains can be either prokaryotic or eukaryotic. *E. coli* is one prokaryotic host useful for cloning and expressing the polynucleotides of the present disclosure. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express anti-VP1 polypeptides. Insect cells in combination with baculovirus vectors can also be used.

In other aspects, mammalian host cells are used to express and produce the anti-VP1 polypeptides of the present disclosure. For example, they can be either a hybridoma cell line expressing endogenous immunoglobulin genes (e.g., the myeloma hybridoma clones as described in the Examples) or a mammalian cell line harboring an exogenous expression vector. These include any normal mortal or normal or abnormal immortal animal or human cell. For example, a number of suitable host cell lines capable of secreting intact immunoglobulins have been developed, including the CHO cell lines, various COS cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer (see, e.g., Queen et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express anti-VP1 antibody chains or binding fragments can be prepared using expression vectors which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Therapeutic and Diagnostic Uses

The antibodies, antibody fragments (e.g., antigen binding fragments) of the present disclosure are useful in a variety of applications including, but not limited to, polyoma viral infection and disease. In certain aspects, the antibodies, antibody fragments (e.g., antigen binding fragments), and are useful for neutralizing BKV or JCV infection and the prevention or treatment of BK virus nephropathy, for example, BKVAN). The methods of use can be in vitro, ex vivo, or in vivo methods.

In one aspect, the antibodies, antibody fragments (e.g., antigen binding fragments), are useful for detecting the presence of BKV in a biological sample. The term "detecting" as used herein encompasses quantitative or qualitative detection. In certain aspects, a biological sample comprises a cell or tissue. In certain aspects, such tissues include normal and/or cancerous tissues that express BKV at higher levels relative to other tissues.

In one aspect, the present disclosure provides a method of detecting the presence of BKV in a biological sample. In certain aspects, the method comprises contacting the biological sample with an anti-VP1 antibody under conditions permissive for binding of the antibody to the antigen, and detecting whether a complex is formed between the antibody and the antigen. The biological sample can include, without limitation, urine or blood samples.

Also included is a method of diagnosing a disorder associated with expression of BKV or JCV virus. In certain aspects, the method comprises contacting a test cell with an anti-VP1 antibody; determining the level of expression (either quantitatively or qualitatively) of BK virus in the test cell by detecting binding of the anti-VP1 antibody to the BK virus; and comparing the level of infection in the test cell with the level of infection of BK virus in a control cell (e.g., with a normal cell of the same tissue origin as the test cell or a non-BK virus infected cell), wherein a higher level of presence of BK virus in the test cell as compared to the control cell indicates the presence of a disorder associated with infection with BK virus. In certain aspects, the test cell is obtained from an individual suspected of having a BK virus infection.

In certain aspects, a method of diagnosis or detection, such as those described above, comprises detecting binding of an anti-VP1 antibody to a BKV infected cell. An exemplary assay for detecting binding of an anti-VP1 antibody to a BKV infected cell is a "FACS" assay.

Certain other methods can be used to detect binding of anti-VP1 antibodies. Such methods include, but are not limited to, antigen-binding assays that are well known in the art, such as Western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain aspects, anti-VP1 antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction.

In certain aspects, anti-VP1 antibodies are immobilized on an insoluble matrix. Immobilization entails separating the anti-VP1 antibody from any BKV or JCV proteins that remains free in solution. This conventionally is accomplished by either insolubilizing the anti-VP1 antibody before the assay procedure, as by adsorption to a water-insoluble matrix or surface (Bennich et al, U.S. Pat. No. 3,720,760), or by covalent coupling (for example, using glutaraldehyde cross-linking), or by insolubilizing the anti-VP1 antibody after formation of a complex between the anti-VP1 antibody and BKV or JCV protein, e.g., by immunoprecipitation.

Any of the above aspects of diagnosis or detection can be carried out using an anti-VP1 antibody of the present disclosure in place of or in addition to another anti-VP1 antibody.

In one aspect, the disclosure provides for a method of treating, reducing the likelihood of or ameliorating a disease comprising administering the antibodies, antibody fragments (e.g., antigen binding fragments), to a patient, thereby treating the disease. In certain aspects, the disease treated with the antibodies, antibody fragments (e.g., antigen binding fragments), is BK viral or JC viral infection. Examples of BKV and JCV diseases which can be treated and/or prevented include, but are not limited to, nephropathy, hemorrhagic cystitis, Progressive Multifocal Leukoencephalopathy (PML), interstitial kidney disease, ureteral stenosis, granule cell neuronopathy (GCN), vasculitis, colitis, retinitis, meningitis, and immune reconstitution inflammatory syndrome (IRIS). In certain aspects, the infection is characterized by BKV or JCV expressing cells to which the anti-VP1 antibodies, antibody fragments (e.g., antigen binding fragments) can specifically bind.

The present disclosure provides for methods of treating BK viral infection and BKVAN comprising administering a therapeutically effective amount of the antibodies, antibody fragments (e.g., antigen binding fragments). In certain aspects, the subject is a human.

In certain aspects, the method of reducing BK viral infection comprises administering to a subject a therapeutically effective amount of antibodies or antibody fragments (e.g., antigen binding fragments). In certain aspects, the subject is a human. In certain aspects, the subject is immunosuppressed. For immunosuppresed subjects, the amount of immunosuppression can be increased or decreased due to the therapeutic effects of the anti-VP1 antibodies.

In certain aspects, the transplanted tissue is infected with BK virus to which the anti-VP1 antibody binds. As the incidence of BK infection in the general population is high, there is a high probability that in the case of kidney transplantation, the patient accepting the kidney is BK virus positive or the donor providing the kidney is BK virus positive or both are BK virus positive. In order to prevent BKVAN, anti-VP1 antibodies can be administered to the kidney transplant recipient, before and/or after the kidney transplant procedure, depending on the seropositivity of the kidney donor or transplant recipient. In another aspect, the anti-VP1 antibodies can be administered to the patient when virus is detected in the urine (viruria), or when virus is detected in the blood (viremia).

For the treatment of BK or JCV viral infection, the appropriate dosage of the antibodies, or antibody fragments (e.g., antigen binding fragments), depend on various factors, such as the type of infection to be treated, the severity and course of the infection, the responsiveness of the infection, the generation of viral resistance to therapy, previous therapy, patient's clinical history, and so on. The antibody can be administered one time or over a series of treatments lasting from several days to several months, or until a cure is effected or a diminution of the infection is achieved (e.g., reduction in viruria or viral damage to the kidney). Optimal dosing schedules can be calculated from measurements of drug accumulation in the body of the patient and will vary depending on the relative potency of an individual antibody or antibody fragment (e.g., antigen binding fragment). In certain aspects, dosage is from 0.01 mg to 10 mg (e.g., 0.01 mg, 0.05 mg, 0.1 mg, 0.5 mg, 1 mg, 2 mg, 3 mg, 4 mg, 5 mg, 7 mg, 8 mg, 9 mg, or 10 mg) per kg of body weight, and can be given once or more daily, weekly, monthly or yearly. In certain aspects, the antibody or antibody fragment (e.g., antigen binding fragment), of the present disclosure is given once every two weeks or once every three weeks. The treating physician can estimate repetition rates for dosing based on measured half-life and concentrations of the antibody in bodily fluids or tissues.

Combination Therapy

In certain instances, the antibody or antibody fragment (e.g., antigen binding fragment), of the present disclosure is combined with other therapeutic agents, such as other antiviral agents, anti-allergic agents, anti-nausea agents (or anti-emetics), pain relievers, cytoprotective agents, immunosuppressants and combinations thereof.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect.

The term "combination therapy" refers to the administration of two or more therapeutic agents to treat a therapeutic condition or infection described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In one aspect, the present disclosure provides a method of treating BKV or JCV infection by administering to a subject in need thereof an antibody in together with immunosuppressant therapies. The anti-VP1 antibodies will act prophylactically to neutralize BKV or JCV primary infection or viral reactivation resulting from the immunosuppressant therapy prior to or post-transplantation. Examples of immunosuppressant therapy include, but are not limited to; a monophosphate dehydrogenase inhibitor, a purine synthesis inhibitor, a calcineurin inhibitor or an mTOR inhibitor. Specific examples of immunosuppressive therapeutics include but are not limited to; mycophenolate mofetil (MMF), mycophenolate sodium, azathioprine, tacrolimus, sirolimus and cyclosporine.

Pharmaceutical Compositions

To prepare pharmaceutical or sterile compositions including anti-VP1 antibodies, the antibodies of the present disclosure are mixed with a pharmaceutically acceptable carrier or excipient. The compositions can additionally contain one or more other therapeutic agents that are suitable for neutralizing BKV or JCV infection.

Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman et al., Goodman and Gilman's The Pharmacological Basis of Therapeutics, McGraw-Hill, New York, N.Y., 2001; Gennaro, Remington: The Science and Practice of Pharmacy, Lippincott, Williams, and Wilkins, New York, N.Y., 2000; Avis, et al. (eds.), Pharmaceutical Dosage Forms: Parenteral Medications, Marcel Dekker, N Y, 1993; Lieberman, et al. (eds.), Pharmaceutical Dosage Forms: Tablets, Marcel Dekker, N Y, 1990; Lieberman, et al. (eds.) Pharmaceutical Dosage Forms: Disperse Systems, Marcel Dekker, N Y, 1990; Weiner and Kotkoskie, Excipient Toxicity and Safety, Marcel Dekker, Inc., New York, N.Y., 2000).

In a specific aspect, the anti-VP1 antibody is a lyophilisate in a vial containing the antibody. The lyophilisate can be reconstituted with water or a pharmaceutical carrier suitable for injection. For subsequent intravenous administration, the obtained solution will usually be further diluted into a carrier solution.

The antibodies disclosed herein are useful in the neutralization of BKV or JCV in tissue transplant patients who can be immunosuppressed, so a pharmaceutical carrier of sucrose and human albumin as used previously in bone marrow transplant patients receiving CytoGam® can be used (DeRienzo et al. Pharmacotherapy 2000; 20:1175-8). Alternatively, the anti-VP1 antibodies can be introduced into transplant patients via a pharmaceutical carrier as described for another anti-viral antibody, Synagis®, as described in WO2003/105894. In this publication, the pharmaceutical carrier was comprised of histidine and/or glycine, a saccharide (e.g. sucrose) and a polyol (e.g. polysorbate).

Selecting an administration regimen for a therapeutic depends on several factors, including the severity of the infection, the level of symptoms, and the accessibility of the target cells in the biological matrix. In certain aspects, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, Antibody Therapy, Bios Scientific Pub. Ltd, Oxfordshire, UK, 1996; Kresina (ed.), Monoclonal Antibodies, Cytokines and Arthritis, Marcel Dekker, New York, N.Y., 1991; Bach (ed.), Monoclonal Antibodies and Peptide Therapy in Autoimmune Diseases, Marcel Dekker, New York, N.Y., 1993; Baert et al., New Engl. J. Med. 348:601-608, 2003; Milgrom et al., New Engl. J. Med. 341:1966-1973, 1999; Slamon et al., New Engl. J. Med. 344:783-792, 2001; Beniaminovitz et al., New Engl. J. Med. 342:613-619, 2000; Ghosh et al., New Engl. J. Med. 348:24-32, 2003; Lipsky et al., New Engl. J. Med. 343:1594-1602, 2000).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., infusion reactions.

Actual dosage levels of the active ingredients in the pharmaceutical compositions with the anti-VP1 antibodies can be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the neutralizing activity of the antibodies, the route of administration, the time of administration, the half-life of the antibody in the patient, the duration of the treatment, other drugs, compounds and/or materials used in combination with the particular compositions employed, the age, sex, weight, condition, general health and prior medical history of the patient being treated, and like factors known in the medical arts.

Compositions comprising antibodies or fragments thereof can be provided by continuous infusion, or by doses at intervals of, e.g., one day, one week, or 1-7 times per week. Doses can be provided intravenously, subcutaneously, topically, orally, nasally, rectally, intramuscular, intracerebrally, or by inhalation. A specific dose protocol is one involving the maximal dose or dose frequency that avoids significant undesirable side effects.

For the antibodies described herein, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. The dosage of the antibodies or fragments thereof can be calculated using the patient's weight in kilograms (kg) multiplied by the dose to be administered in mg/kg.

Doses of the antibodies then can be repeated and the administrations may be separated by at least 1 day, 2 days, 3 days, 5 days, 10 days, 15 days, 30 days, 45 days, 2 months, 75 days, 3 months, or at least 6 months.

An effective amount for a particular patient may vary depending on factors such as the condition being treated, the overall health of the patient, the method, route and dose of administration and the severity of side effects (see, e.g., Maynard et al., A Handbook of SOPs for Good Clinical Practice, Interpharm Press, Boca Raton, Fla., 1996; Dent, Good Laboratory and Good Clinical Practice, Urch Publ., London, UK, 2001).

The route of administration may be by, e.g., topical or cutaneous application, injection or infusion by intravenous, intraperitoneal, intracerebral, intramuscular, intraocular, intraarterial, intracerebrospinal, intralesional, or by sustained release systems or an implant (see, e.g., Sidman et al., Biopolymers 22:547-556, 1983; Langer et al., J. Biomed. Mater. Res. 15:167-277, 1981; Langer, Chem. Tech. 12:98-105, 1982; Epstein et al., Proc. Natl. Acad. Sci. USA 82:3688-3692, 1985; Hwang et al., Proc. Natl. Acad. Sci. USA 77:4030-4034, 1980; U.S. Pat. Nos. 6,350,466 and 6,316,024). Where necessary, the composition may also include a solubilizing agent or a local anesthetic such as lidocaine to ease pain at the site of the injection, or both. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

A composition of the present disclosure can also be administered via one or more routes of administration using one or more of a variety of methods known in the art. As will be appreciated by the skilled artisan, the route and/or mode of administration will vary depending upon the desired results. Selected routes of administration for the antibodies include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the present disclosure can be administered via a non-parenteral route, such as a topical, epidermal or mucosal route of administration, for example, intranasally, orally, vaginally, rectally, sublingually or topically. In one aspect, the antibodies of the present disclosure are administered by infusion. In another aspect, the antibodies are administered subcutaneously.

If the antibodies of the present disclosure are administered in a controlled release or sustained release system, a pump may be used to achieve controlled or sustained release (see Langer, supra; Sefton, CRC Crit. Ref Biomed. Eng. 14:20, 1987; Buchwald et al., Surgery 88:507, 1980; Saudek et al., N. Engl. J. Med. 321:574, 1989). Polymeric materials can be used to achieve controlled or sustained release of the therapies of the antibodies (see e.g., Medical Applications of Controlled Release, Langer and Wise (eds.), CRC Pres., Boca Raton, Fla., 1974; Controlled Drug Bioavailability, Drug Product Design and Performance, Smolen and Ball (eds.), Wiley, New York, 1984; Ranger and Peppas, J. Macromol. Sci. Rev. Macromol. Chem. 23:61, 1983; see also Levy et al., Science 228:190, 1985; During et al., Ann. Neurol. 25:351, 1989; Howard et al., J. Neurosurg. 7 1:105, 1989; U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly (methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one aspect, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138, 1984).

Controlled release systems are discussed in the review by Langer, Science 249:1527-1533, 1990). Any technique known to one of skill in the art can be used to produce sustained release formulations comprising one or more antibodies of the present disclosure. See, e.g., U.S. Pat. No. 4,526,938, PCT publication WO 91/05548, PCT publication WO 96/20698, Ning et al., Radiotherapy & Oncology 39:179-189, 1996; Song et al., PDA Journal of Pharmaceutical Science & Technology 50:372-397, 1995; Cleek et al., Pro. Int'l. Symp. Control. Rel. Bioact. Mater. 24:853-854, 1997; and Lam et al., Proc. Int'l. Symp. Control Rel. Bioact. Mater. 24:759-760, 1997, each of which is incorporated herein by reference in their entirety.

If the antibodies of the disclosure are administered topically, they can be formulated in the form of an ointment, cream, transdermal patch, lotion, gel, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the compositions comprising the antibodies are administered intranasally, it can be formulated in an aerosol form, spray, mist or in the form of drops. In particular, prophylactic or therapeutic agents for use according to the present disclosure can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., an immunosuppressant, a cytokine, steroid, chemotherapeutic agent, antibiotic, or radiation, are known in the art (see, e.g., Hardman et al., (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%; at least 40%, or at least 50%.

Additional therapies (e.g., prophylactic or therapeutic agents), which can be administered in combination with the anti-VP1 antibodies may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the anti-VP1 antibodies of the present disclosure. The two or more therapies may be administered within one same patient visit.

In certain aspects, anti-VP1 antibodies can be formulated to ensure proper distribution in vivo. For example, the blood-brain barrier (BBB) excludes many highly hydrophilic compounds. To ensure that the anti-VP1 antibodies cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade, (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (Bloeman et al., (1995) FEBS Lett. 357:140; Owais et al., (1995) Antimicrob. Agents Chemother. 39:180); surfactant protein A receptor (Briscoe et al., (1995) Am. J. Physiol. 1233:134); p 120 (Schreier et al, (1994) J. Biol. Chem. 269:9090); see also K. Keinanen; M. L. Laukkanen (1994) FEBS Lett. 346:123; J. J. Killion; I. J. Fidler (1994) Immunomethods 4:273.

The present disclosure provides protocols for the administration of pharmaceutical composition comprising antibodies alone or in combination with other therapies to a subject in need thereof. The combination therapies (e.g., prophylactic or therapeutic agents) can be administered concomitantly or sequentially to a subject. The therapy (e.g., prophylactic or therapeutic agents) of the combination therapies can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the disclosure can be administered to a subject concurrently. The term "concurrently" is not limited to the administration of therapies (e.g., prophylactic or therapeutic agents) at exactly the same time, but rather it is meant that a pharmaceutical composition comprising antibodies or fragments thereof are administered to a subject in a sequence and within a time interval such that the antibodies can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various aspects, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other aspects, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

EXAMPLES

Example 1: Generation of Anti-VP1 Antibodies

B cells expressing anti-VP antibodies were lysed and the VH (heavy) and VL (light) chains were sequenced by RT-PCR and analyzed to identify critical post translational modification (PTM) sites. Plasmids of the VH and VL chains were then transfected in a CHO mammalian cell line in an IgG1 back bone vector for expression of the full IgG1 antibodies.

Methods for generation of monoclonal antibodies using hybridoma technology are known in the art (Antibody Methods and Protocols, Methods in Molecular Biology vol. 901, 2012, Chapter 7: 117). Briefly, female Balb/c mice were immunized with VLPs from BKV serotype I, serotype IV, and JCV (either individually or in combination) using various prime-boost strategies, doses of immunogen, and adjuvants (including but not limited to Freund's adjuvant and MF59 adjuvant). Supernatant of successfully fused (growing) hybridomas were screened for the presence of anti-VP1 antibodies by ELISA, then for functional activity in neutralization assays. CDRs from select murine IgGs were humanized by grafting onto human framework acceptor templates, cloned into mammalian IgG1 backbone expression vectors and transfected in a CHO mammalian cell line for expression of the full IgG1 antibodies.

Methods for generation of monoclonal antibodies using phage display technology are known in the art (Antibody Methods and Protocols, Methods in Molecular Biology vol. 901, 2012, Chapter 3: 33). Briefly, a human B-cell antibody library in scFv format with Vκ was screened for anti-VP1 antibodies by solution panning with streptavidin-coupled magnetic beads complexed with biotinylated BKV serotype IV VLPs over 3 rounds of selection with increasing stringency. Isolates were first expressed as scFv and screened for binding to both BKV serotype IV VLPs and pentamers by ELISA. Select isolates were then cloned and expressed as IgG1, reanalyzed for binding to VP1 (serotype I and IV) by ELISA and for functional activity in neutralization assays, and transfected in a CHO mammalian cell line for expression of the full IgG1 antibodies.

A summary of the anti-VP1 antibodies is provided in Table 3.

TABLE 3

| anti-VP1 antibodies | |
|---|---|
| Antibody | |
| P165E2 | |
| NEG447 | P165E2 changes: germlined/affinity matured for serotype IV; VH (T35S, E43A, A73T, S74N), VL (R17K, G61D, A86V) resulted in no significant change in affinity or activity. |

TABLE 3-continued anti-VP1 antibodies

| Antibody | |
|---|---|
| NEG447A | P165E2 changes: germlined NEG447; VL (L10V, V86D) resulted in ~3-fold greater affinity and ~8-fold more potent activity (EC90) on serotype II, ~10-fold greater affinity for serotype IV |
| P7G11 | |
| P7G11A | P7G11 variant: germlined P7G11; VH (A12V, S23T, I69V, M71I, T85S) resulted in ~150-fold greater affinity for serotype II, ~14-fold greater affinity for serotype IV |
| P8D11 | |
| P8D11A | P8D11 change to remove post-translational modification: N30S in HCDR1 resulted in no significant change in affinity or activity |
| P8D11B | P8D11 change to remove post-translational modification: N30K in HCDR1 resulted in no significant change in affinity or activity |
| P8D11C | P8D11 change to remove post-translational modification: N30Q in HCDR1 resulted in no significant change in affinity or activity |
| P8D11D | P8D11 change in Heavy Chain framework 1 region to fix proteolysis/clipping liability (V5Q, G9P, T10G) resulted in no significant change in affinity or activity |
| P8D11E | P8D11 change in Heavy Chain framework 1 region to fix proteolysis/clipping liability (T10G) resulted in no significant change in affinity or activity |
| P46F4 | |
| EBB-C1975-B5 | phage display |
| EBB-C1975-A3 | phage display |
| EBB-C1975-A7 | phage display |
| EBB-C1975-E7 | phage display |
| 2081-20-8 | mouse hybridoma |
| 2075-16-1 | mouse hybridoma |
| 2075-456-4 | mouse hybridoma |
| 2081-36-8 | mouse hybridoma |
| 2081-66-5 | mouse hybridoma |
| 2081-38-5 | mouse hybridoma |
| 2081-25-6 | mouse hybridoma |
| 2077-4-1 | mouse hybridoma |
| 2077-7-5 | mouse hybridoma |
| 2077-10 1 | mouse hybridoma |
| 2077-26-1 | mouse hybridoma |
| 2077-28-2 | mouse hybridoma |

Example 2: Affinity Maturation of Anti-VP1 Antibodies

The anti-VP1 antibodies were affinity matured in yeast by error-prone PCR or CDR-directed mutagenesis. VP1 proteins from each of the four serotypes of BKV (as shown in Table 4) were used as the antigen in up to three rounds of selection by FACS analysis. VH (heavy) and/or VL (light) chains with enhanced binding affinity to VP1 by FACS analysis were then cloned into mammalian IgG1 backbone expression vectors and transfected in a CHO mammalian cell line for expression of the full IgG1 antibodies.

TABLE 4

| Name | VP1 protein | SEQ ID NO |
|---|---|---|
| Serotype 1, amino acids 66-145 | FSLKLSAENDFSSDSPERKMLPCYSTARIPLP LNNEDLTCGNLLMWEAVTVQTEVIGITSML NLHAGSQKVHEHGGGKPI | (SEQ ID NO: 496) |
| Serotype II, amino acids 66-145 | YSLKLTAENAFDSDSPDKKMLPCYSTARIPL PNLNEDLTCGNLLMWEAVTVKTEVIGITSM LNLHAGSQKVHENGGGKPV | (SEQ ID NO: 497) |
| Serotype III, amino acids 66-145 | YSQHLSAENAFDSDSPDKKMLPCYSTARIPL PNLNEDLTCGNLLMWEAVTVKTEVIGITSM LNLHAGSQKVHENGGGKPV | (SEQ ID NO: 498) |
| Serotype IV, amino acids 66-145 | YSLRLTAETAFDSDSPDRKMLPCYSTARIPLP NLNEDLTCGNLLMWEAVTVKTEVIGITSML NLHAGSQKVHENGGGKPI | (SEQ ID NO: 499) |

Example 3: BK Virus and Virus-Like Particle (VLP) Generation

Genomic clones of BKV serotype I were obtained from ATCC (pBR322-BKV MM, cat #45026; pBR322-BKV Dunlop, cat #45025). Infectious genomic clones of chimeric viruses for serotype II, III and IV were generated using the cloning strategy described previously (Broekema et al, Virology 2010 407:368-373). Briefly, unique restriction sites (SacII, PmlI) were introduced into BKV serotype I genomes flanking the VP1-VP2-VP3 coding region using site-directed mutagenesis. The coding region for VP1 from serotype II isolate SB (GenBank Accession CAA79596.1), serotype III isolate AS (GenBank Accession AAA46882.1) and serotype IV strain ITA-4 (GenBank Accession BAF75132) were synthesized in the context of VP2/VP3 coding region from the serotype I isolates (Genewiz, La Jolla, Calif.), such that the synthesized fragments encompassed the SacII-PmlI region to be used for swap combinations as described in Broekema et al., supra. The resulting chimeric genomic clones were then used to generate high titer infectious viral stocks in primary renal proximal tubule epithelial (RPTE) cells (ATCC, cat # PCS-400-010) as previously described (Abend et al, J. Virology 2007 81:272-279).

VLPs representing each of the four BKV serotypes were generated by expression of VP1 in Sf9 insect cells and extracted from frozen cell pellets from 1 L cultures by microtip sonication (3×45 second pulses, rest 5 min between pulses on ice), isolation by pelleting VLPs through a 20% sucrose cushion (116,000 g for 2.5 hours), and purification by anion exchange with a 5 ml GE HiTrap Q HP column (GE Healthcare, Pittsburgh, Pa.) followed by purification using a 10 ml Capto™ Core700 (GE Healthcare, Pittsburgh, Pa.) resin-based size exclusion column, and finally purification on a GE Sephacryl S500 26/60 (GE Healthcare, Pittsburgh, Pa.) size exclusion column. The prepared VLPs were used in ELISA and SPR based binding assays in Examples 6 and 7.

Example 4: Purification of BKV VP1 Pentamers

VP1 proteins from each of the four serotypes of BKV (sequences shown in Table 5 below) were cloned with N terminal GST-6xHis-TEV sequences and subcloned into pGEX destination vector (GE Healthcare, Pittsburgh, Pa.). GST fusion proteins were expressed in *E. coli*, extracted from cell pellets using a microfluidizer (15,000 PSI), and purified by immobilized metal ion affinity chromatography (IMAC) using a 20 ml nickel sepharose 6 Fast Flow column (GE Healthcare, Pittsburgh, Pa.). The GST-6×His-TEV tag was cleaved by overnight incubation with TEV protease and final purification was performed using a 5 ml His-Trap Fast Flow column (GE Heathcare, Pittsburgh, Pa.), followed by Superdex 200 26/60 size exclusion column (GE Heathcare, Pittsburgh, Pa.).

TABLE 5

| BKV Serotype | VP1 Sequence | SEQ ID NO. |
|---|---|---|
| Serotype I, amino acids 30-297 | KGGVEVLEVKTGVDAITEVECFLNPEMGDPDENLRGFSLKLSAENDF SSDSPERKMLPCYSTARIPLPNLNEDLTCGNLLMWEAVTVQTEVIGIT SMLNLHAGSQKVHEHGGGKPIQGSNFHFFAVGGDPLEMQGVLMNYR TKYPEGTITPKNPTAQSQVMNTDHKAYLDKNNAYPVECWIPDPSRNE NTRYFGTFTGGENVPPVLHVTNTATTVLLDEQGVGPLCKADSLYVSA ADICGLFTNSSGTQQWRGLARYFKIRLRKRSVK | SEQ ID NO: 502 |
| Serotype II, amino acids 30-297 | KGGVEVLEVKTGVDAITEVECFLNPEMGDPDDNLRGYSLKLTAENAF DSDSPDKKMLPCYSTARIPLPNLNEDLTCGNLLMWEAVTVKTEVIGIT SMLNLHAGSQKVHENGGGKPVQGSNFHFFAVGGDPLEMQGVLMNY RTKYPQGTITPKNPTAQSQVMNTDHKAYLDKNNAYPVECWIPDPSRN ENTRYFGTYTGGENVPPVLHVTNTATTVLLDEQGVGPLCKADSLYVS AADICGLFTNSSGTQQWRGLARYFKIRLRKRSVK | SEQ ID NO: 503 |
| Serotype III, amino acids 30-297 | KGGVEVLEVKTGVDAITEVECFLNPEMGDPDDHLRGYSQHLSAENAF DSDSPDKKMLPCYSTARIPLPNLNEDLTCGNLLMWEAVTVKTEVIGIT SMLNLHAGSQKVHENGGGKPVQGSNFHFFAVGGDPLEMQGVLMNY RTKYPQGTITPKNPTAQSQVMNTDHKAYLDKNNAYPVECWIPDPSKN ENTRYFGTYTGGENVPPVLHVTNTATTVLLDEQGVGPLCKADSLYVS AADICGLFTNSSGTQQWRGLARYFKIRLRKRSVK | SEQ ID NO: 504 |
| Serotype IV, amino acids 30-297 | KGGVEVLEVKTGVDAITEVECFLNPEMGDPDNDLRGYSLRLTAETAF DSDSPDRKMLPCYSTARIPLPNLNEDLTCGNLLMWEAVTVKTEVIGIT SMLNLHAGSQKVHENGGGKPIQGSNFHFFAVGGDPLEMQGVLMNYR TKYPEGTVTPKNPTAQSQVMNTDHKAYLDKNNAYPVECWIPDPSRN ENTRYFGTYTGGENVPPVLHVTNTATTVLLDEQGVGPLCKADSLYVS AADICGLFTNSSGTQQWRGLPRYFKIRLRKRSVK | SEQ ID NO: 505 |

Example 5: Affinity Measurements of Anti-VP1 Antibodies (SET Assay)

Solution equilibration titration (SET) assay was used to determine the interaction affinities ($K_D$) of antibodies with BKV VP1 pentamers from all four serotypes. Antibodies were assayed at 1 pM concentration (constant), VP1 pentamers were serially diluted from a starting concentration of 10 nM. Antibody:VP1 pentamer solution was incubated overnight, then assayed for unbound antibody using an MSD array plate (Meso Scale Discovery Cat # L21XA, Rockville Md.) coated with VP1 pentamer. The $K_D$ was determined by fitting the plot with a 1:1 fit model (according to Piehler et al. J. Immunol. Methods. 1997; 201(2):189-206).

In SET assays, $K_D$ values were similar for anti-VP1 antibodies binding to BKV serotype I pentamers, ranging from 0.9 to 5.0 pM. P8D11 and derivatives of P8D11 had comparable $K_D$ values for binding to BKV serotype II, III, and IV pentamers, and when compared to the other antibodies, had at least 3.5-fold greater affinity on serotype II pentamers and 47-fold greater affinity on serotype IV pentamers. This is shown in FIG. 1A-1D. In addition, P8D11 and derivatives of P8D11 demonstrated binding affinity ranging from 2.5 to 6.0 pM on serotype III pentamers, whereas the other antibodies had no detectable binding to serotype III pentamers within the tested conditions. A summary of SET affinity data for these anti-VP1 antibodies is found in FIG. 2.

Example 6: Binding of Anti-VP1 Antibodies to VP1 Pentamers and VLPs (ELISA)

The binding of anti-VP1 antibodies to VP1 pentamers and VLPs were analyzed by ELISA. Briefly, Immulon 2HB plates (VWR, 62402-972) were coated with 100 ng/well BKV VLPs or VP1 pentamers overnight. Antibodies were serially diluted in PBS with 0.5% BSA and allowed to bind antigen-coated plates for 2 h. Plates were washed with PBS and then incubated with secondary antibody (HRP-conjugated rabbit anti-human IgG, Southern Biotech #6140-05) diluted 1:6000 in 0.5% BSA in PBS for 1 h. Plates were washed with PBS and tetramethylbenzidine (TMB) microwell peroxidase substrate (KPL, 52-00-03 1 L) was used to develop the reactions.

Figure 4:
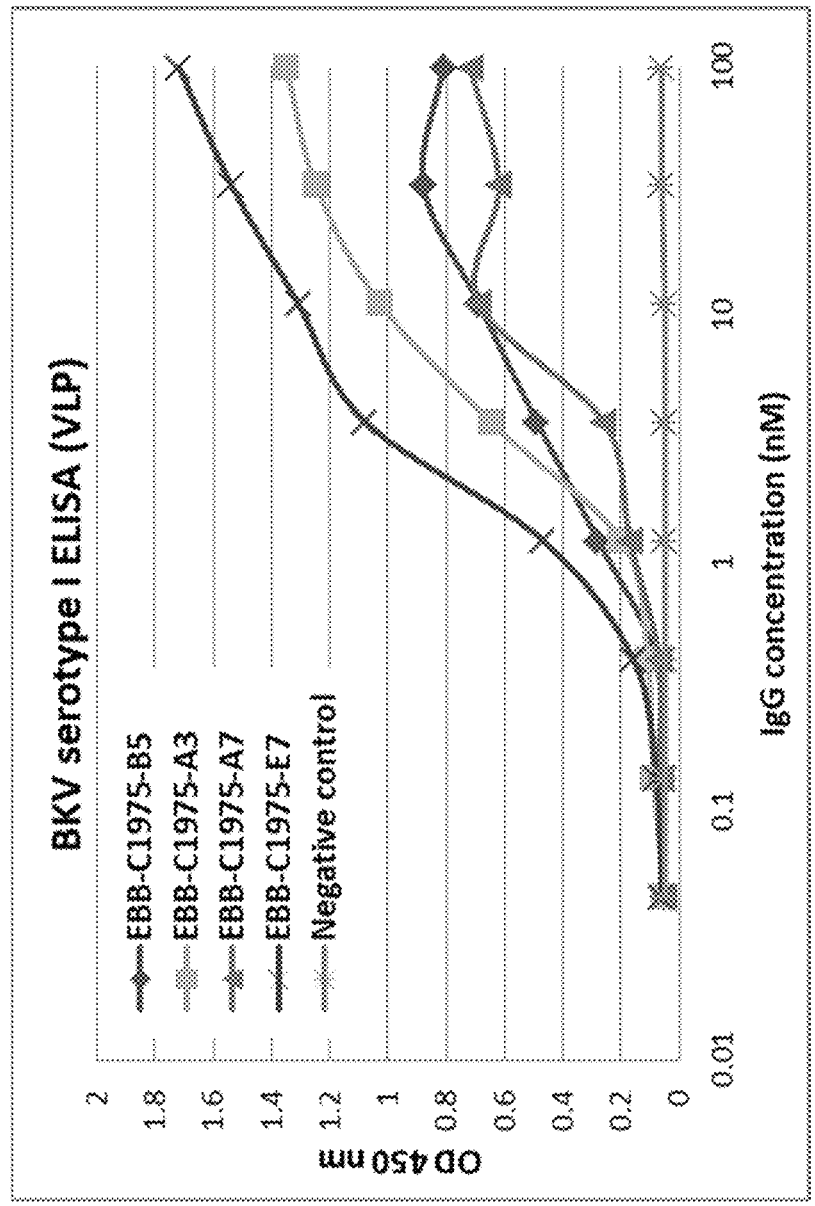
FIG. 4 is a graph of anti-VP1 antibodies binding to BKV serotype I VLPs as measured by ELISA.
Figure 5:
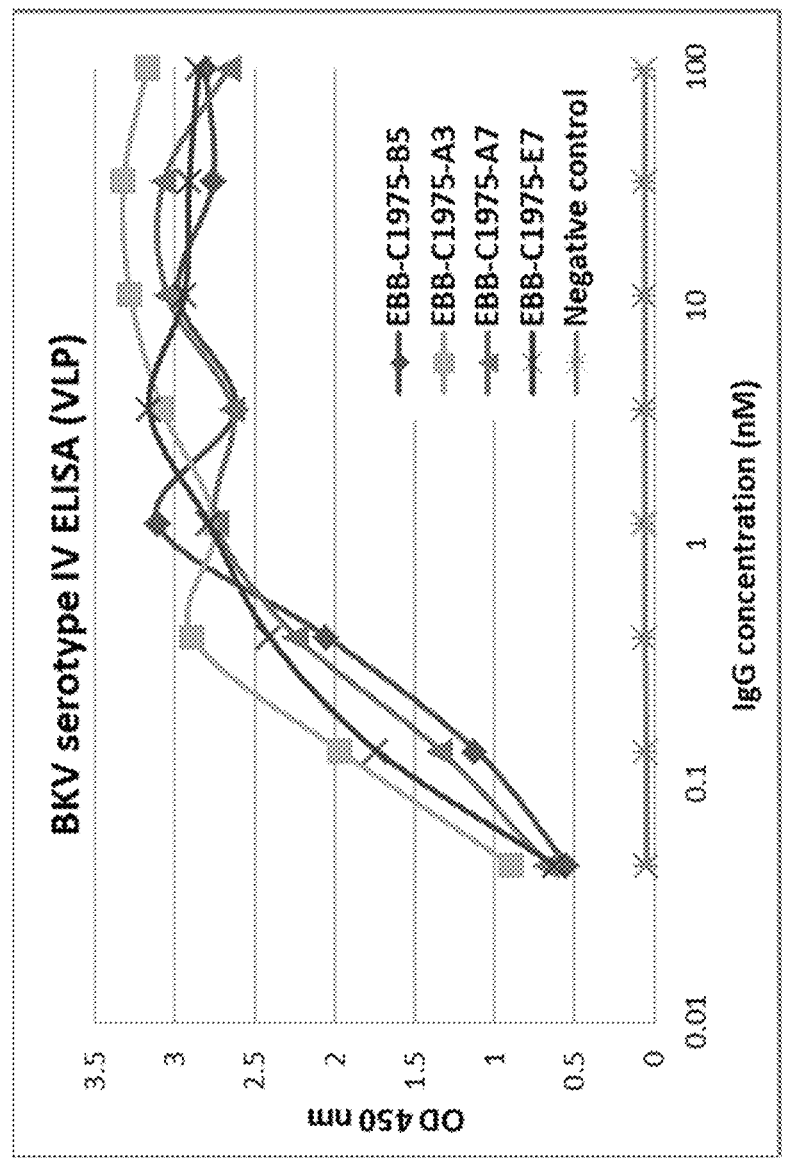
FIG. 5 is a graph of anti-VP1 antibodies binding to BKV serotype IV VLPs as measured by ELISA.
Figure 6:
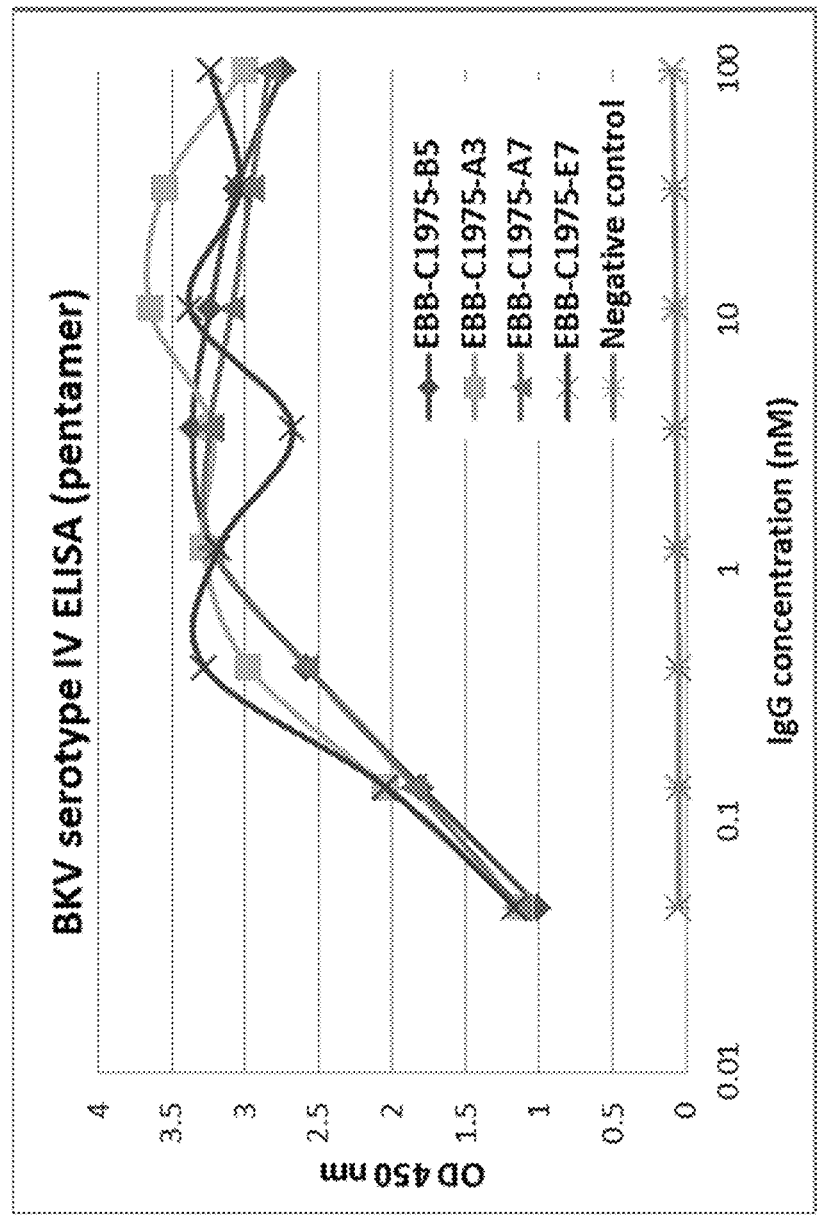
FIG. 6 is a graph of anti-VP1 antibodies binding to BKV serotype IV VP1 pentamers as measured by ELISA.
Figure 8:
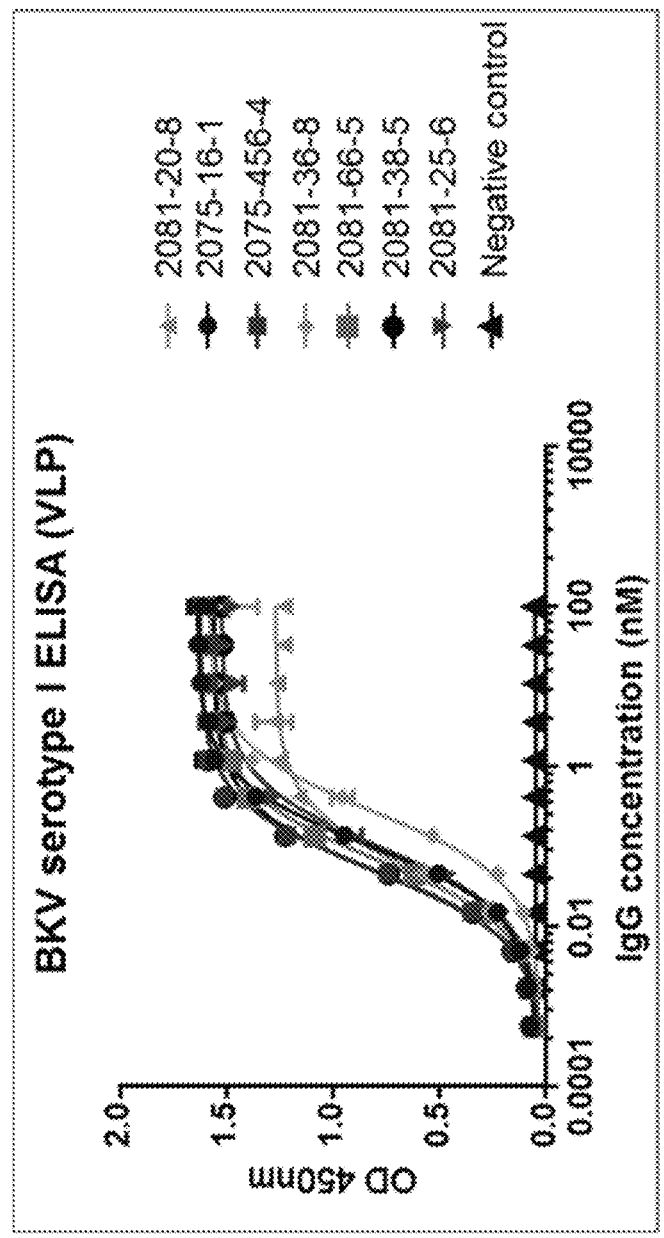
FIG. 8 is a graph of anti-VP1 antibodies binding to BKV serotype I VLPs as measured by ELISA.
Figure 10:
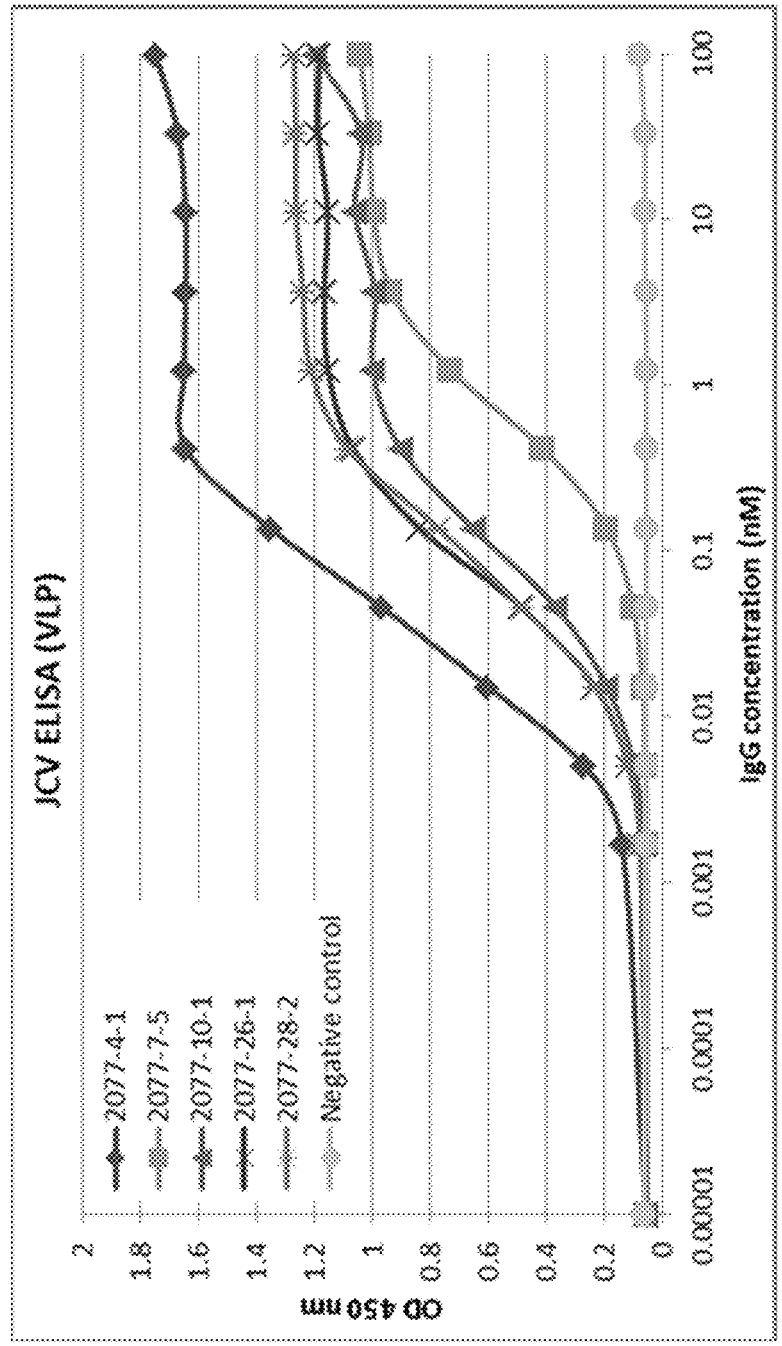
FIG. 10 is a graph of anti-VP1 antibodies binding to JC virus VLPs as measured by ELISA.

The anti-VP1 antibodies EBB-C1975-A3, A7, E7, and B5 showed similar binding to VLPs (IC50s ranging from 0.044 to 0.1 nM) or VP1 pentamers (IC50s ranging from 0.026 to 0.078 nM) from BKV serotype IV, but reduced and more variable binding activity to serotype I VLPs (IC50s ranging from 4.32 to 85.7 nM). This data is shown graphically in FIGS. 4-6 and summarized in FIG. 7. In contrast, anti-VP1 antibodies from the 2081 and 2075 series showed enhanced binding activity to serotype I VLPs, with IC50s ranging from 0.046 to 0.267 nM and this data is shown in FIGS. 8 and 9. The JCV-specific anti-VP1 antibodies of the 2077 series demonstrated binding activity to JCV VLPs ranging from 0.034 to 0.651 nM and this data is provided in FIGS. 10 and 11.

Example 7: Binding of Anti-VP1 Antibodies to VP1 Pentamers and VLPs by SPR

The binding of anti-VP1 antibodies to VP1 pentamers and VLPs were analyzed by surface plasmon resonance (SPR). Briefly, biotinylated Protein A is immobilized on a streptavidin-coated SPR chip surface, and anti-VP1 antibodies are captured on the resulting surface by binding to Protein A. BKV VP1 pentamers or VLPs are then flowed over the surface and allowed to bind anti-VP1 antibodies during the association phase, followed by a buffer wash during the dissociation phase.

Figure 3A:
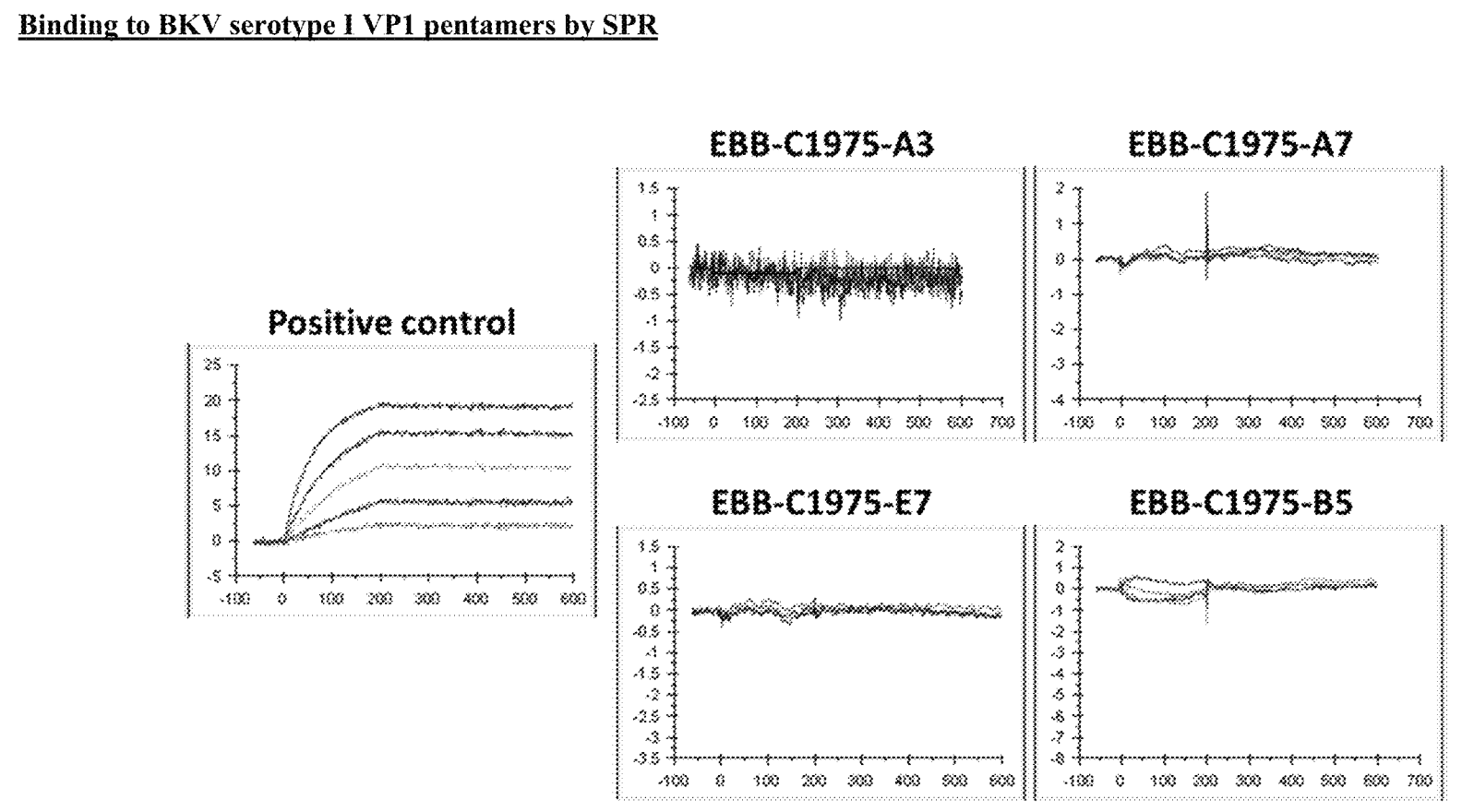
Figure 3B:
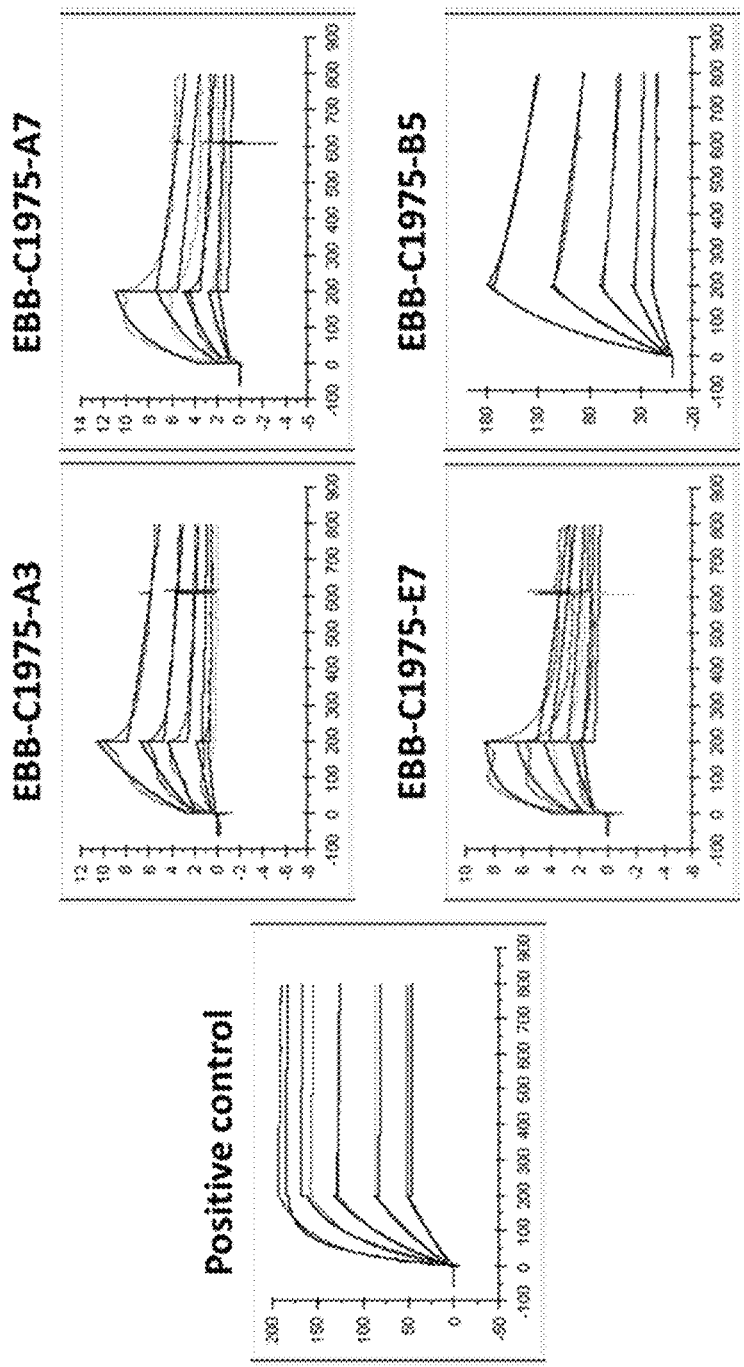
Figure 3C:
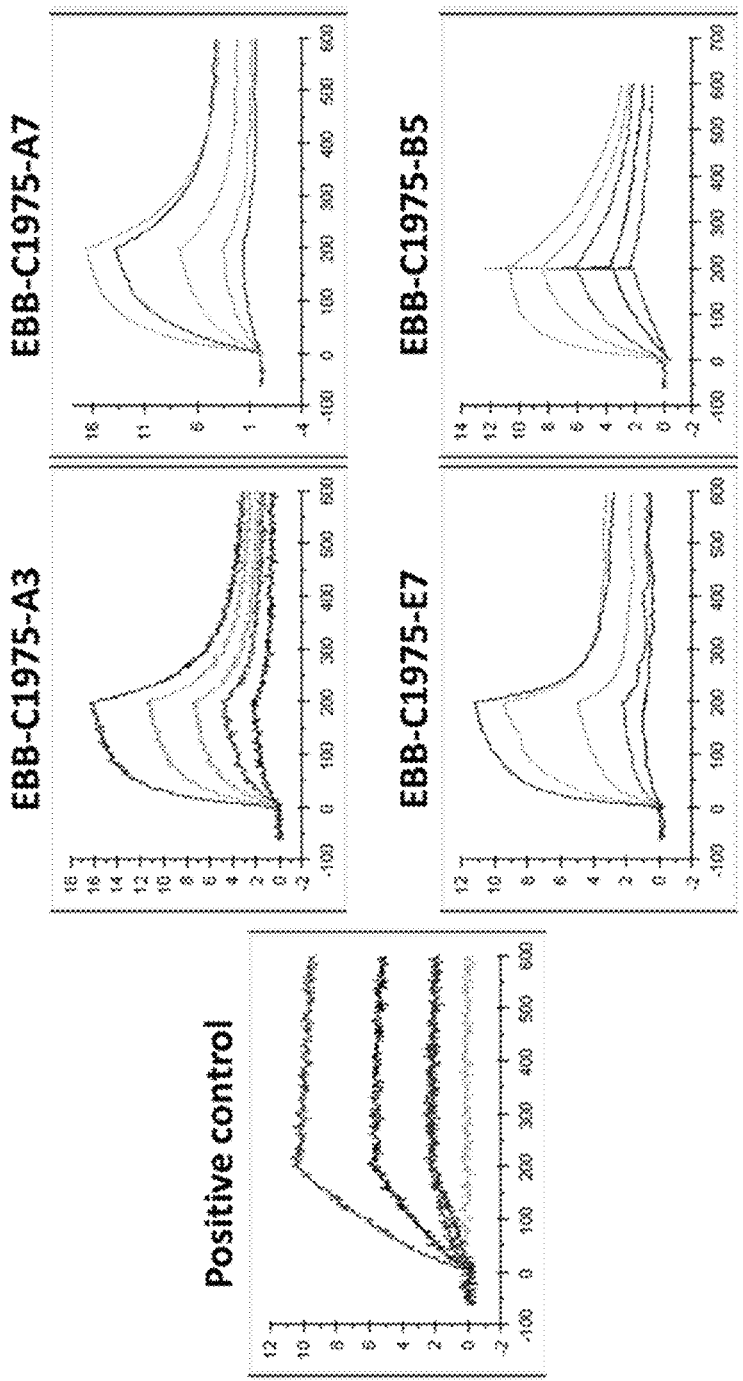
Figure 3D:
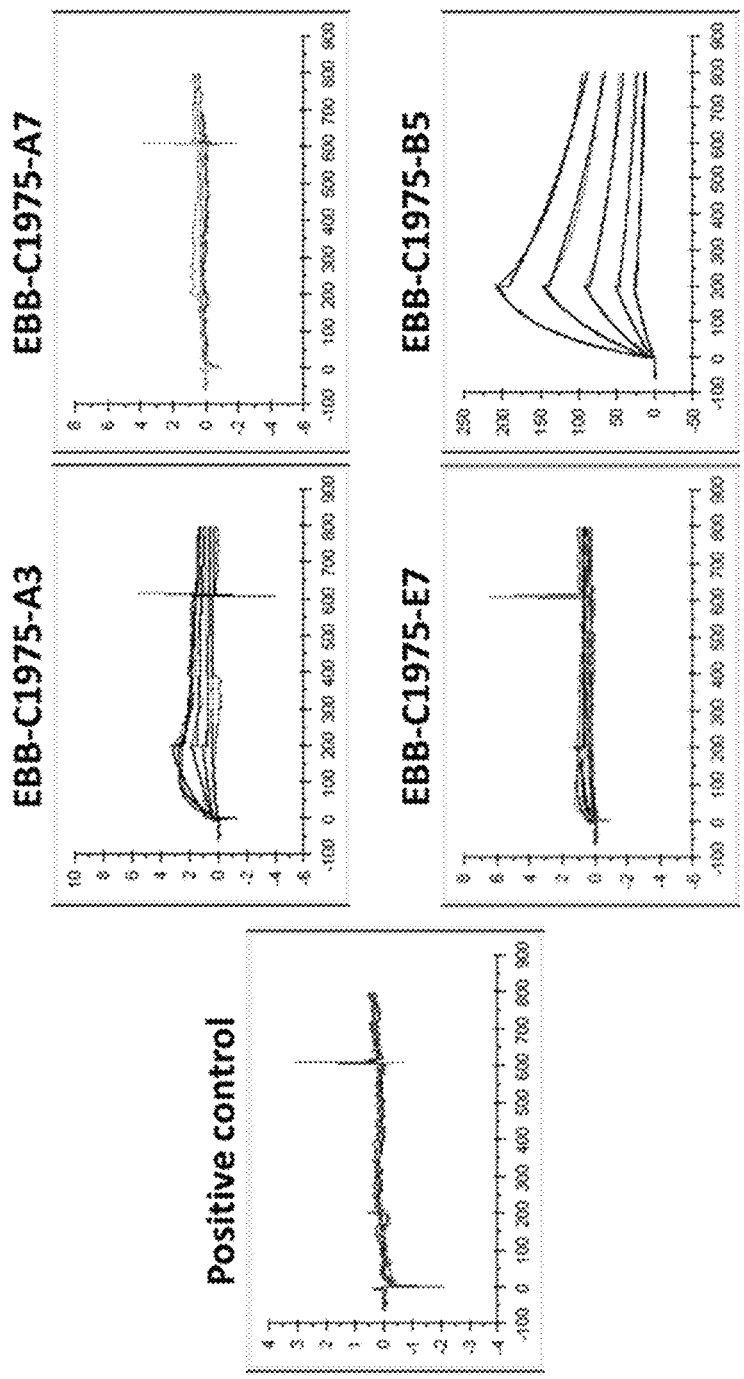
Figure 3E:
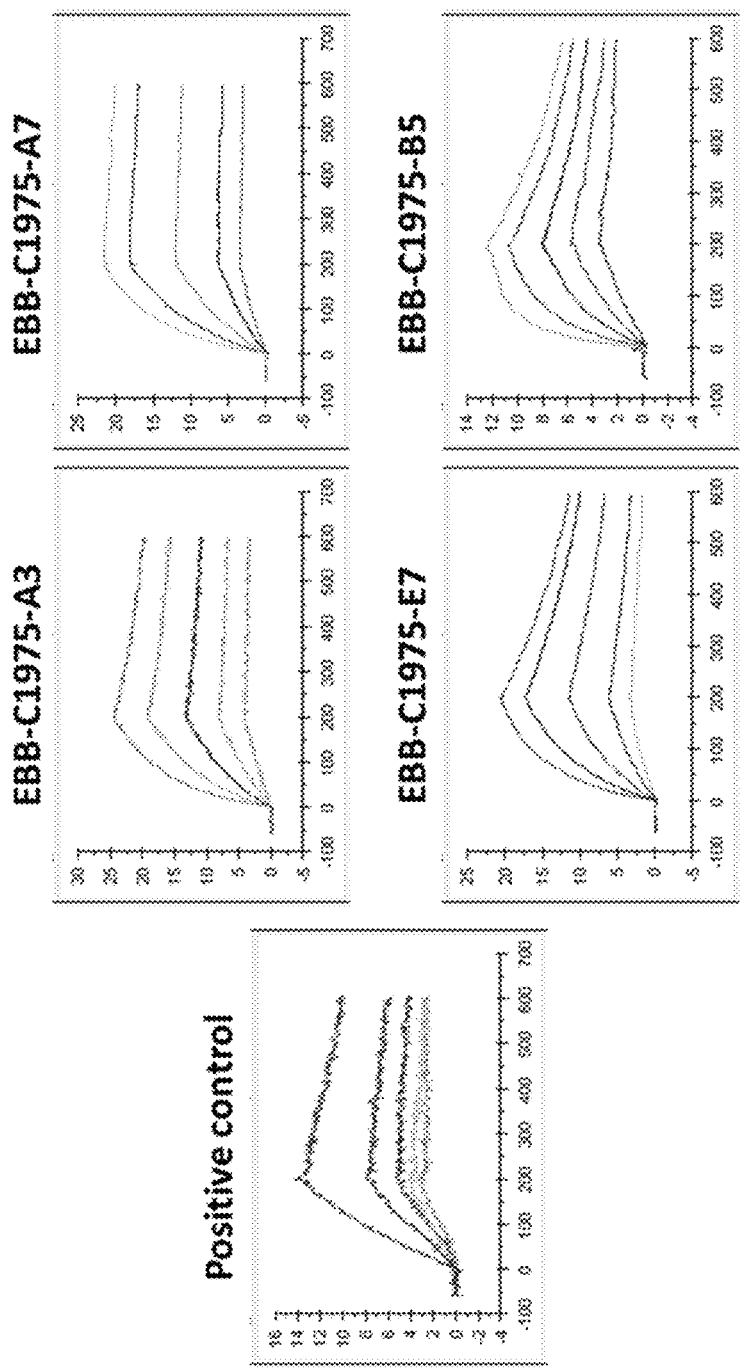

SPR was used to evaluate binding of anti-VP1 antibodies EBB-C1975-A3, A7, E7, and B5 to the four serotypes of BKV, relative to a positive control (P165E2). All four antibodies had very similar binding profiles to VP1 pentamers: no binding to serotype I and III pentamers, atypical binding to serotype II pentamers (large bulk shift and no return to baseline), and binding to serotype IV pentamers similar to P165E2 but with lower affinity (FIGS. 3A, 3C and 3E). For VLPs, EBB-C1975-A3, A7, and E7 shared similar binding profiles: atypical binding to serotype I VLPs and no binding to serotype III VLPs. However, EBB-C1975-B5 binding profile was distinct with significant binding to serotype I and III VLPs, demonstrating binding to a different epitope on VP1 (FIGS. 3B and 3D).

Figure 13A:
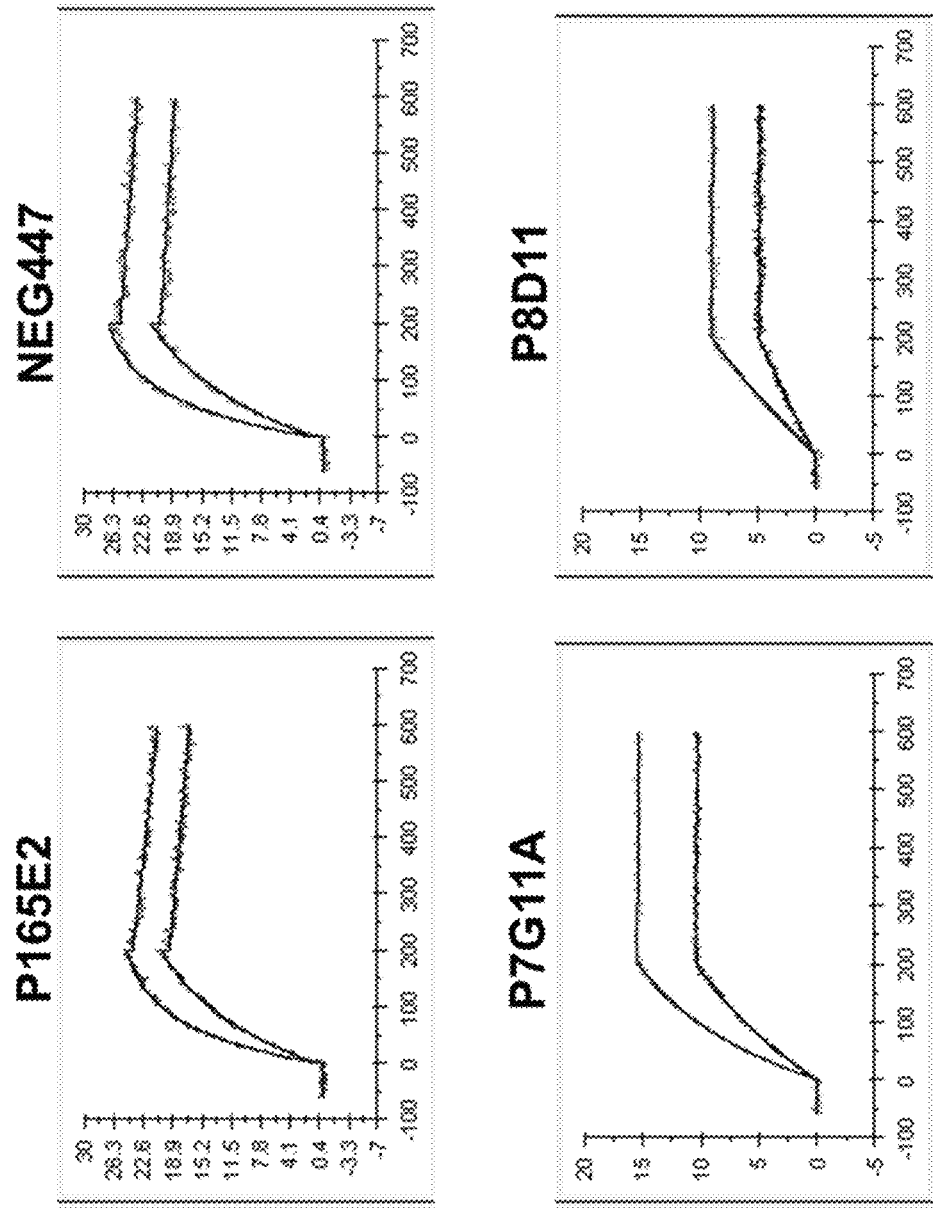
FIG. 13A-13F graphically represents binding of anti-VP1 antibodies to wild type BKV serotype I VP1 pentamers by Biacore, but that point mutations in the VP1 can disrupt binding.
Figure 13B:
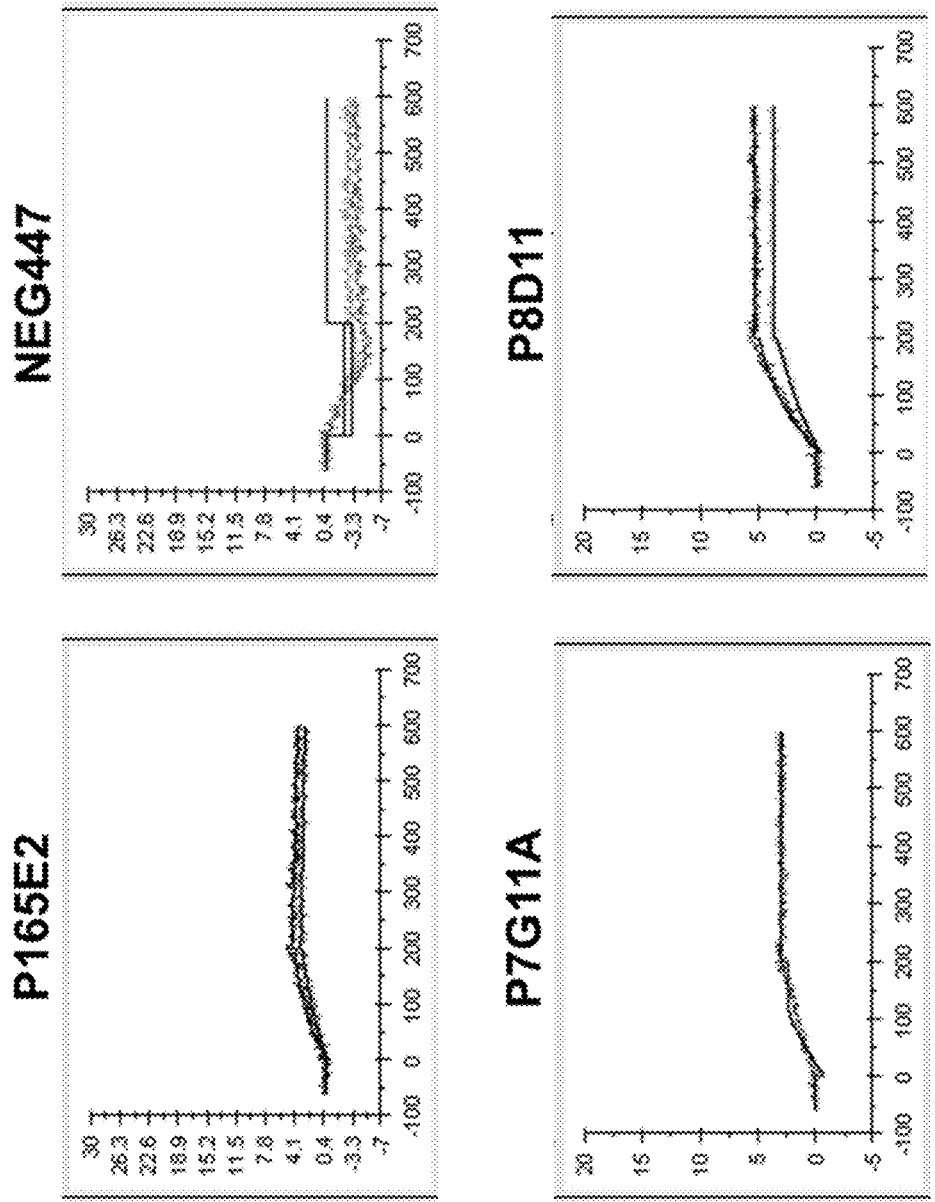
Figure 13C:
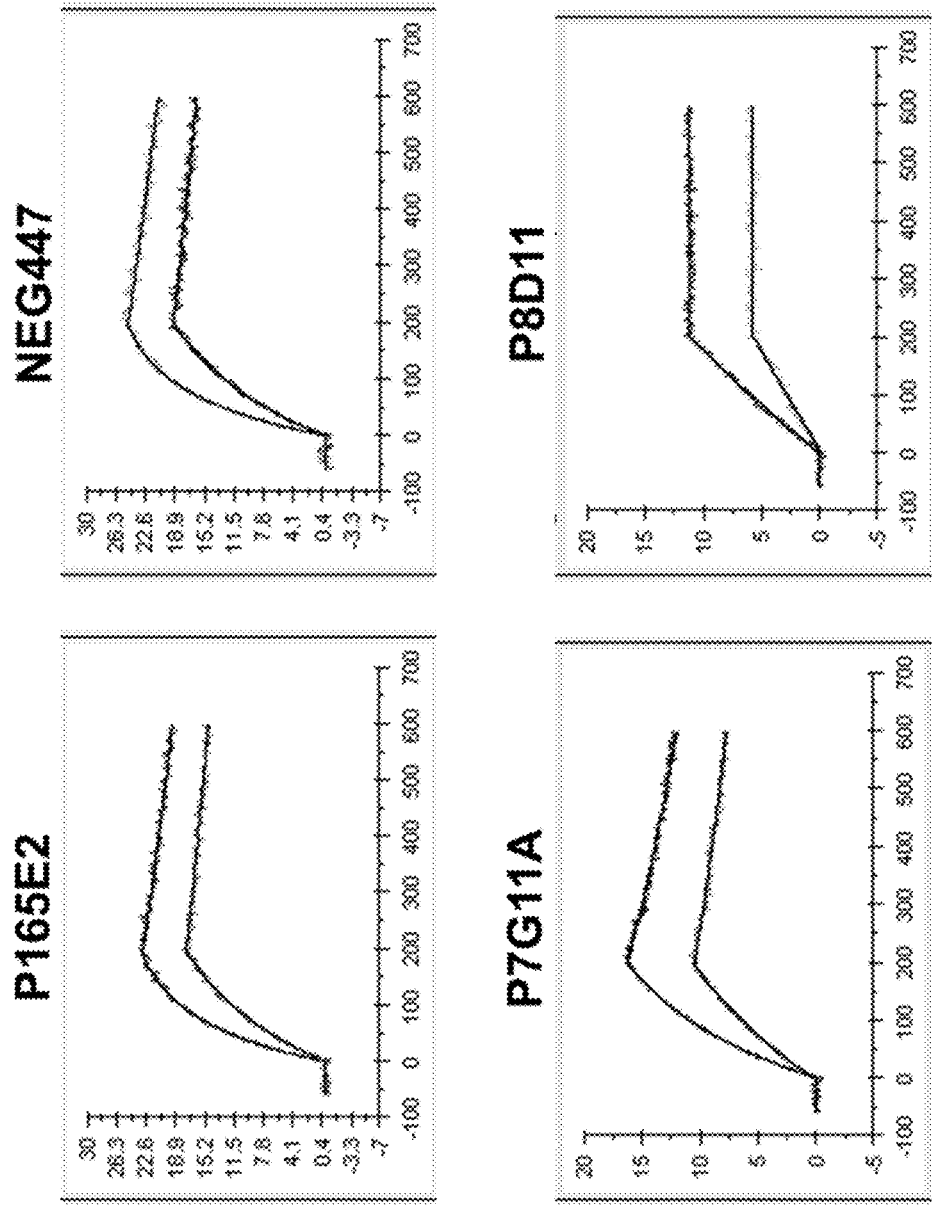
Figure 13D:
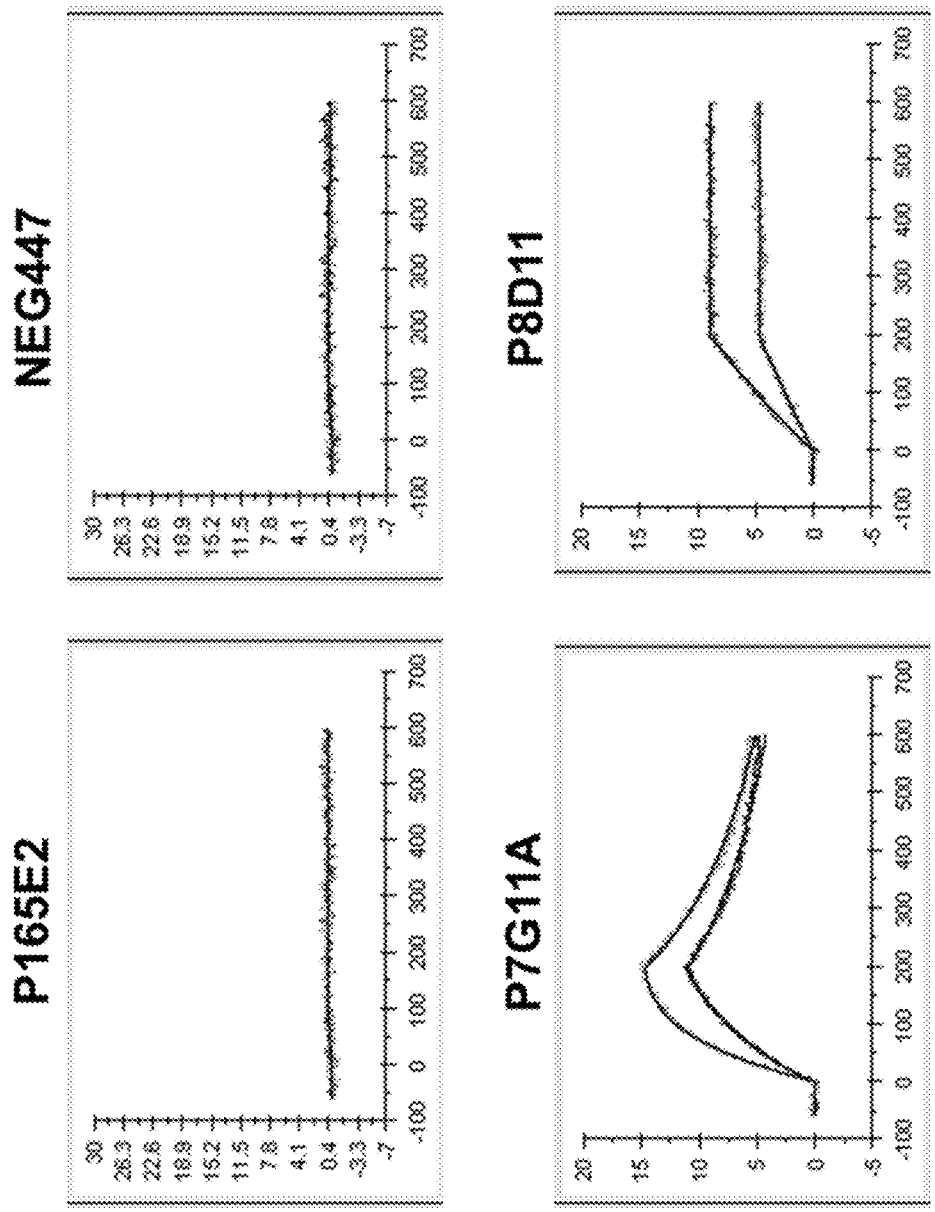
Figure 13E:
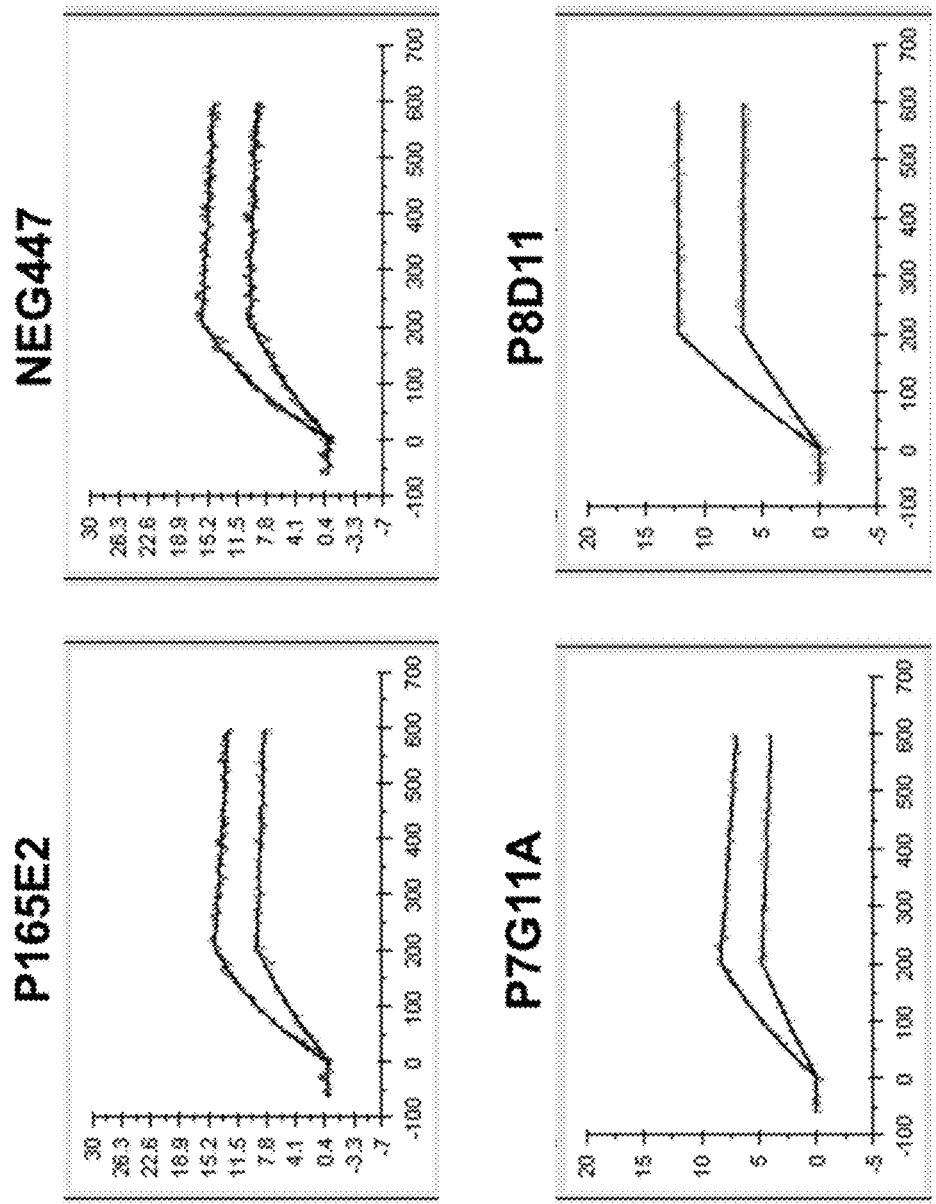
Figure 13F:
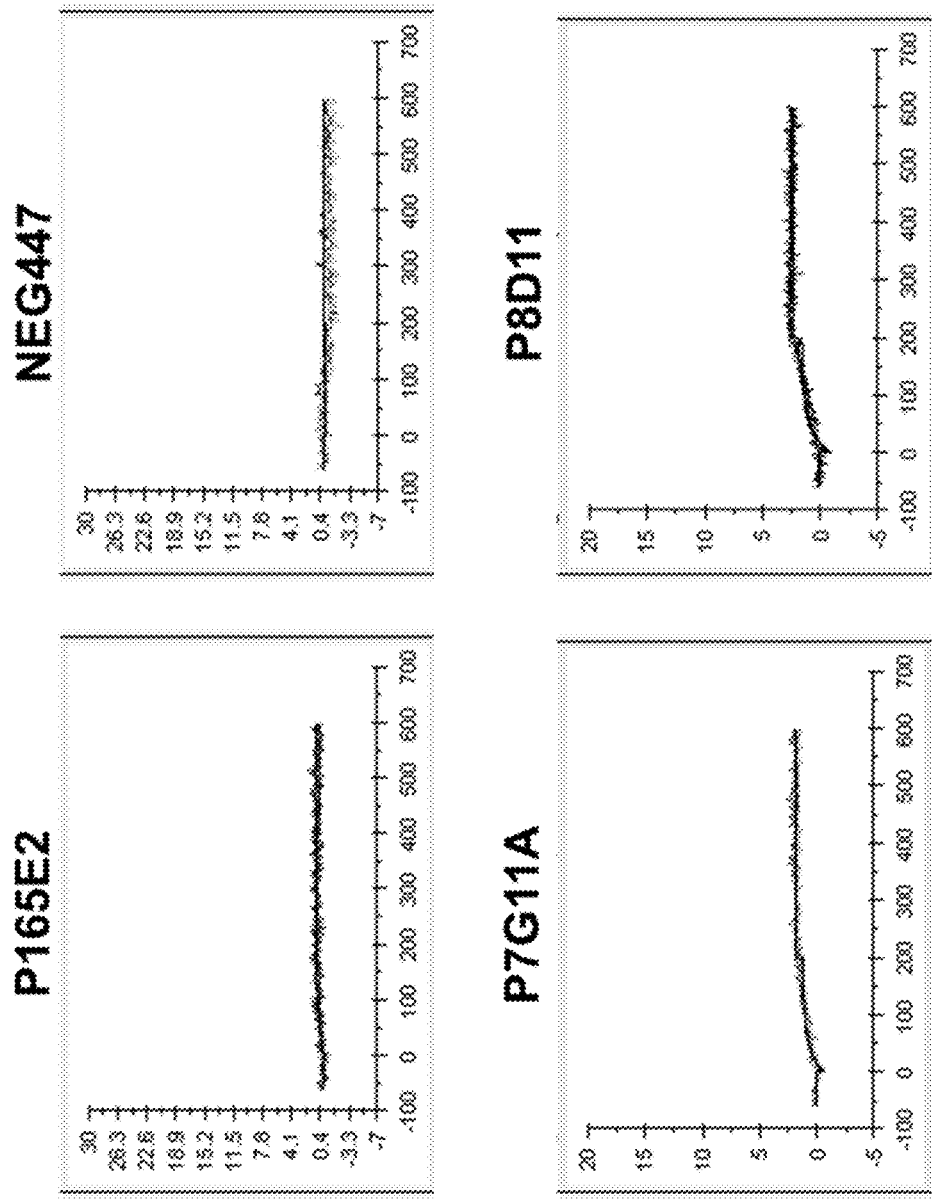
Figure 15:
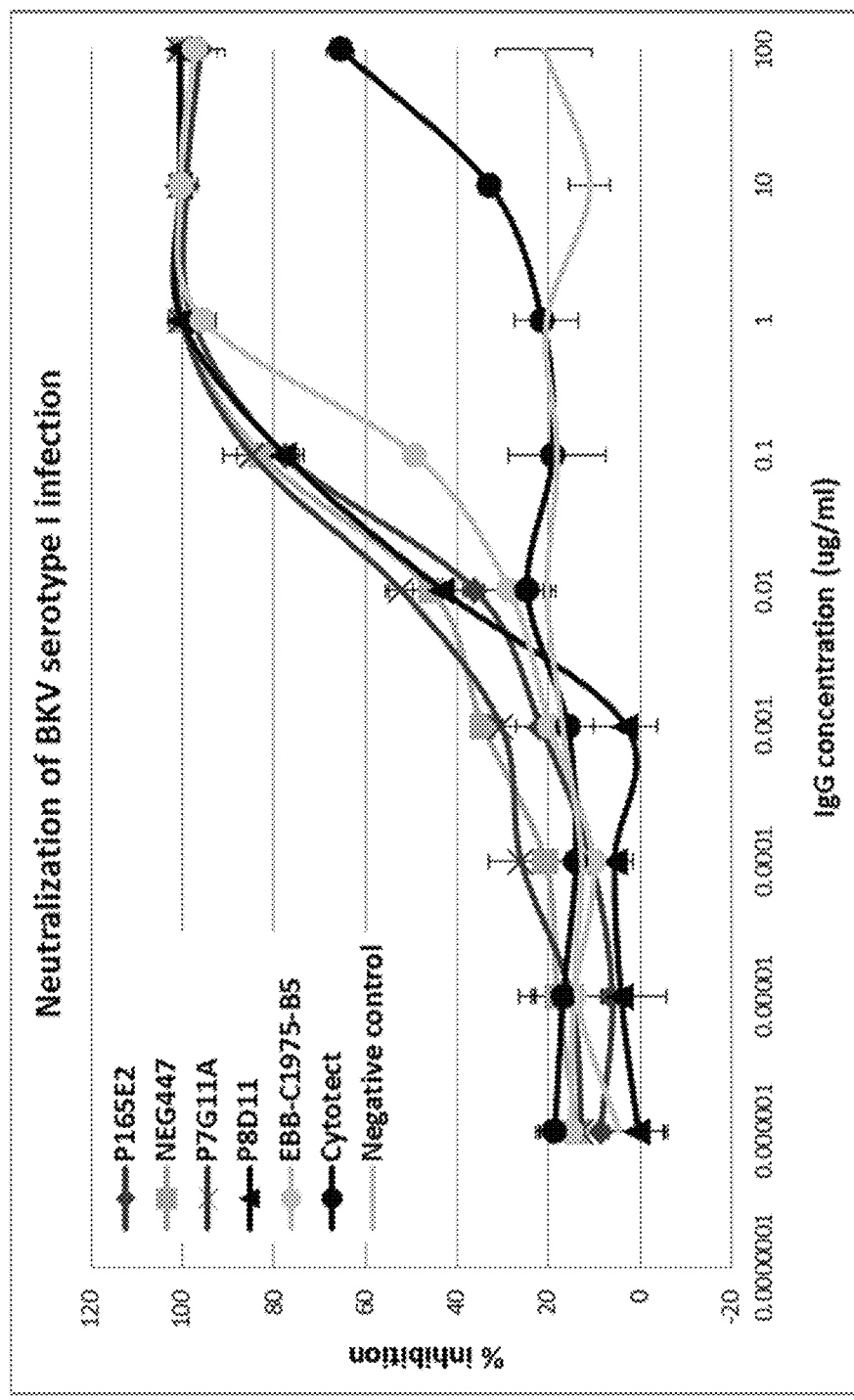
FIG. 15 is a graph of anti-VP1 antibodies neutralizing BKV serotype I infection.
Figure 16:
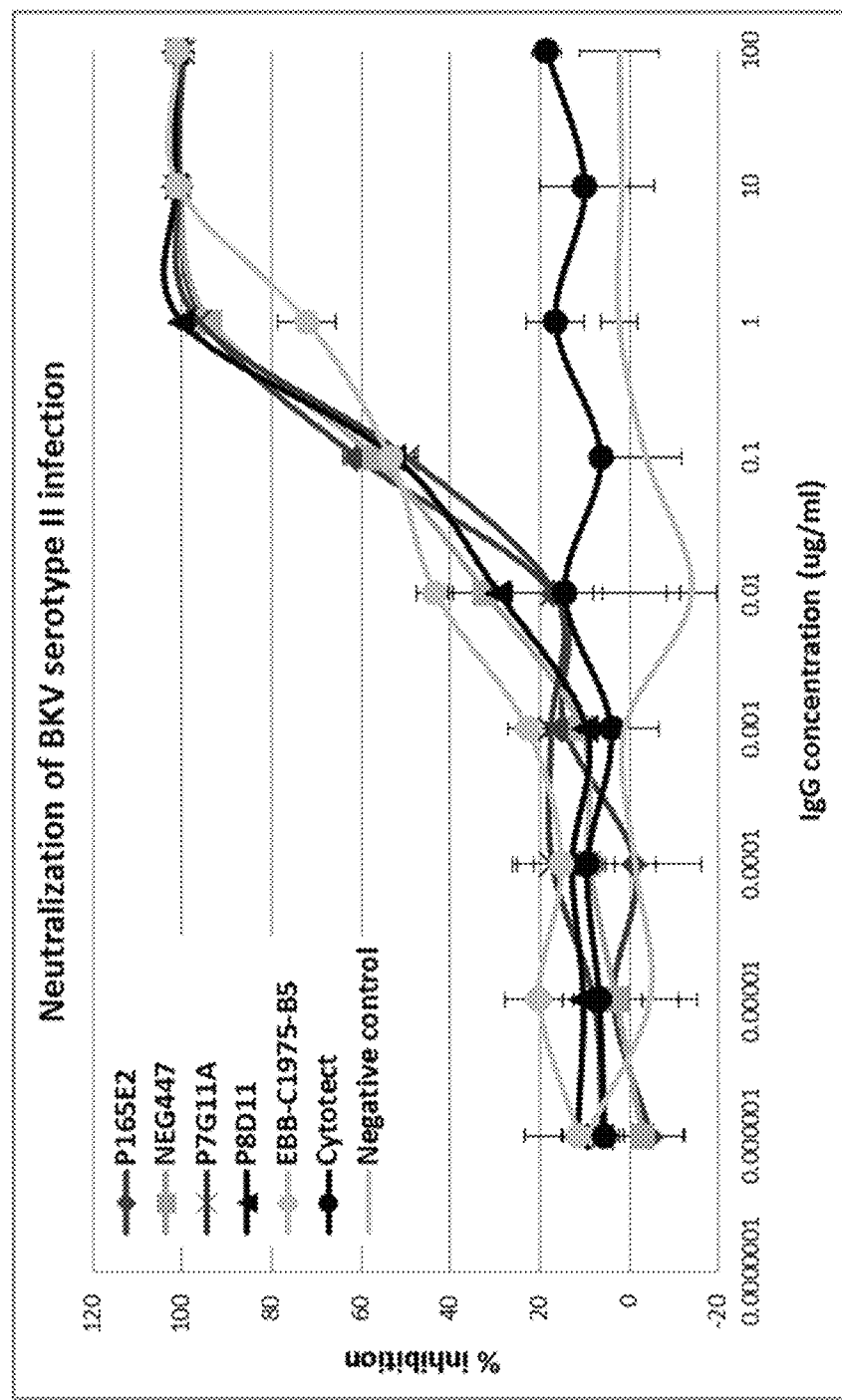
FIG. 16 is a graph of anti-VP1 antibodies neutralizing BKV serotype II infection.
Figure 17:
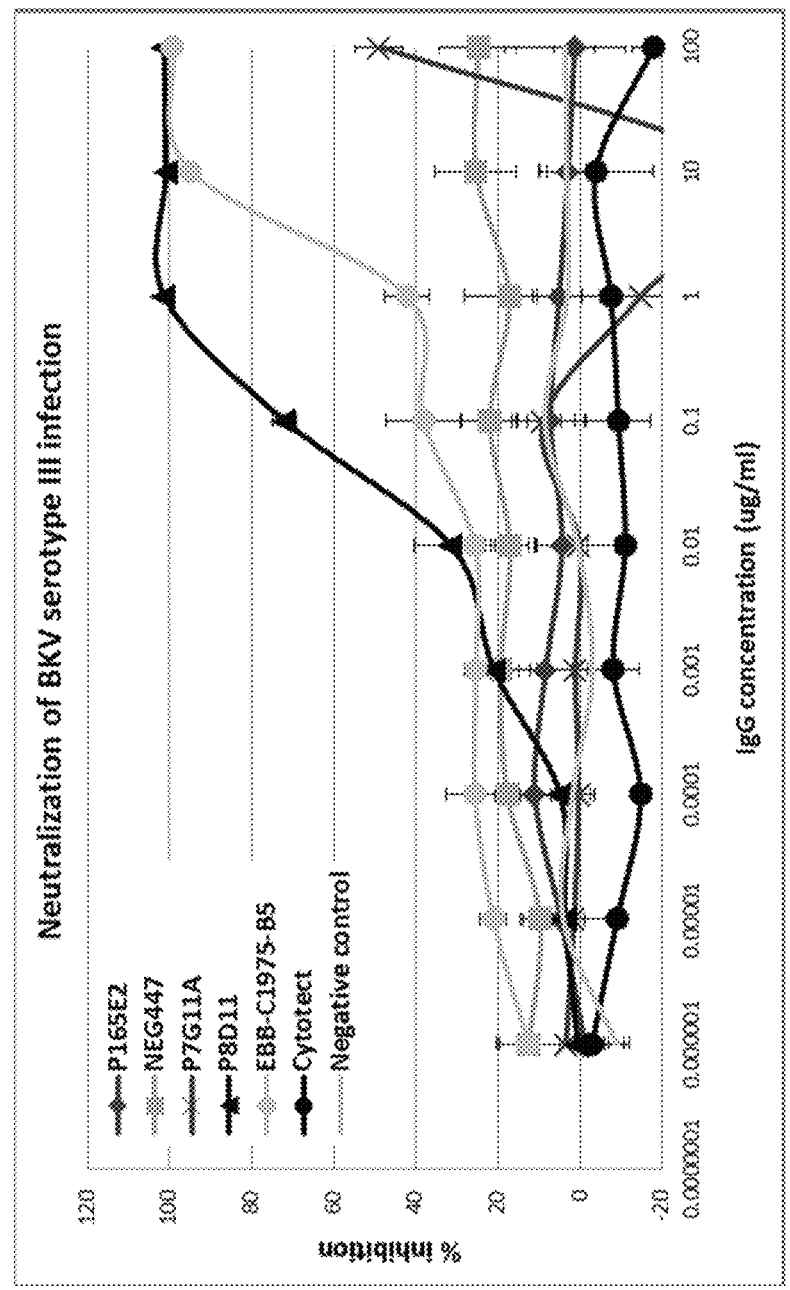
FIG. 17 is a graph of anti-VP1 antibodies neutralizing BKV serotype III infection.
Figure 18:
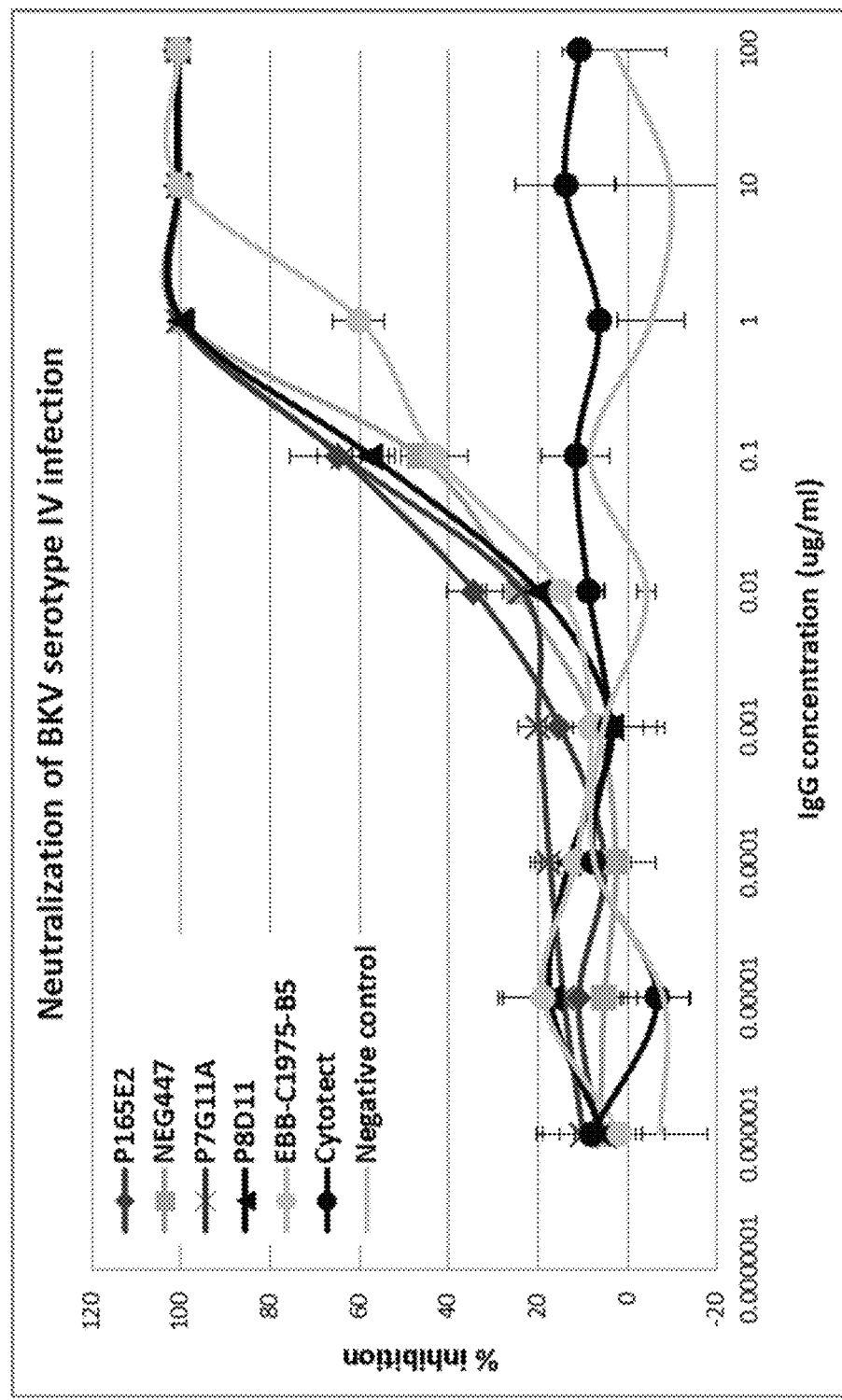
FIG. 18 is a graph of anti-VP1 antibodies neutralizing BKV serotype IV infection.
Figure 20:
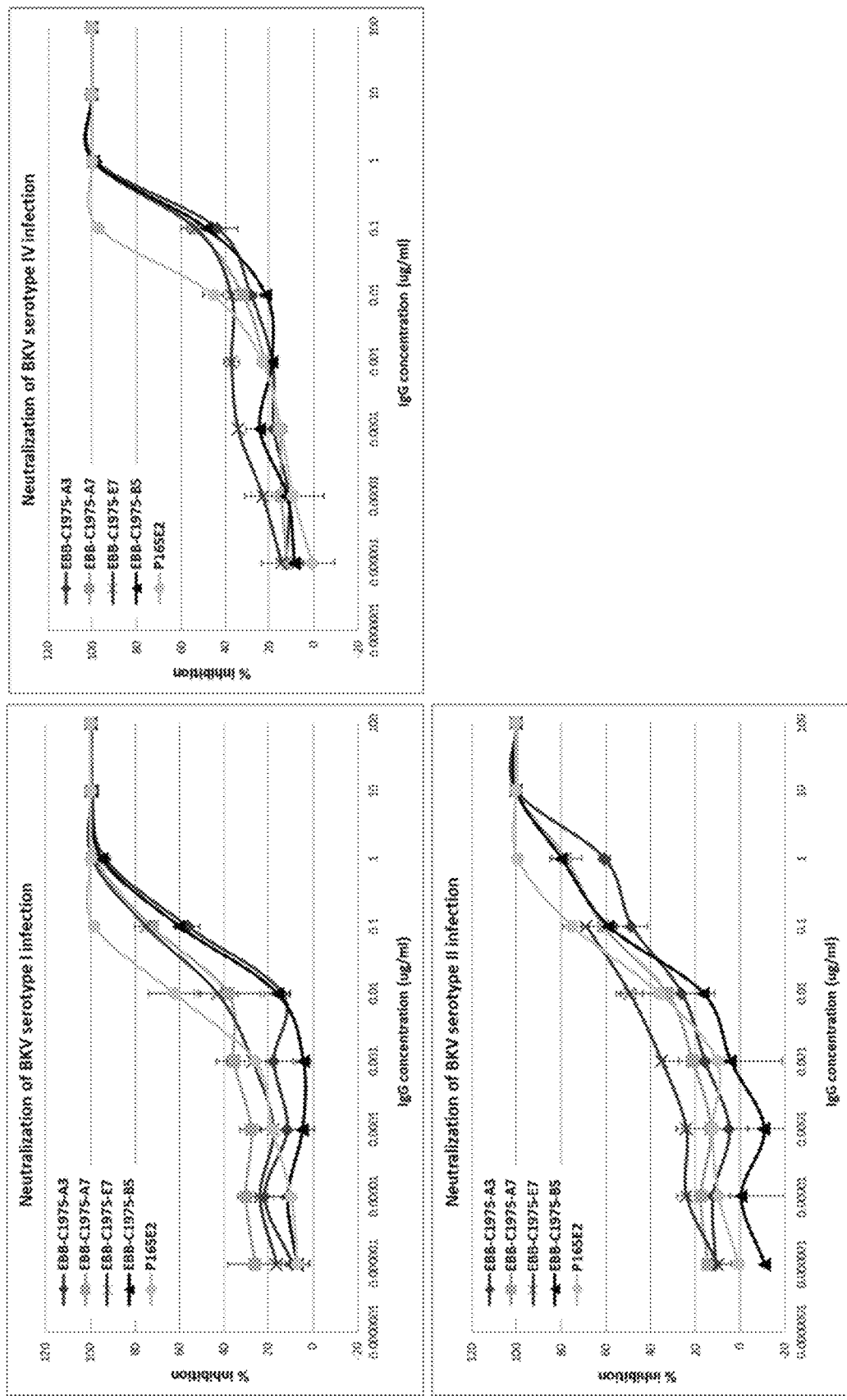
FIG. 20 is a graph of anti-VP1 antibodies neutralizing infection with BKV serotypes I, II, and IV.
Figure 22:
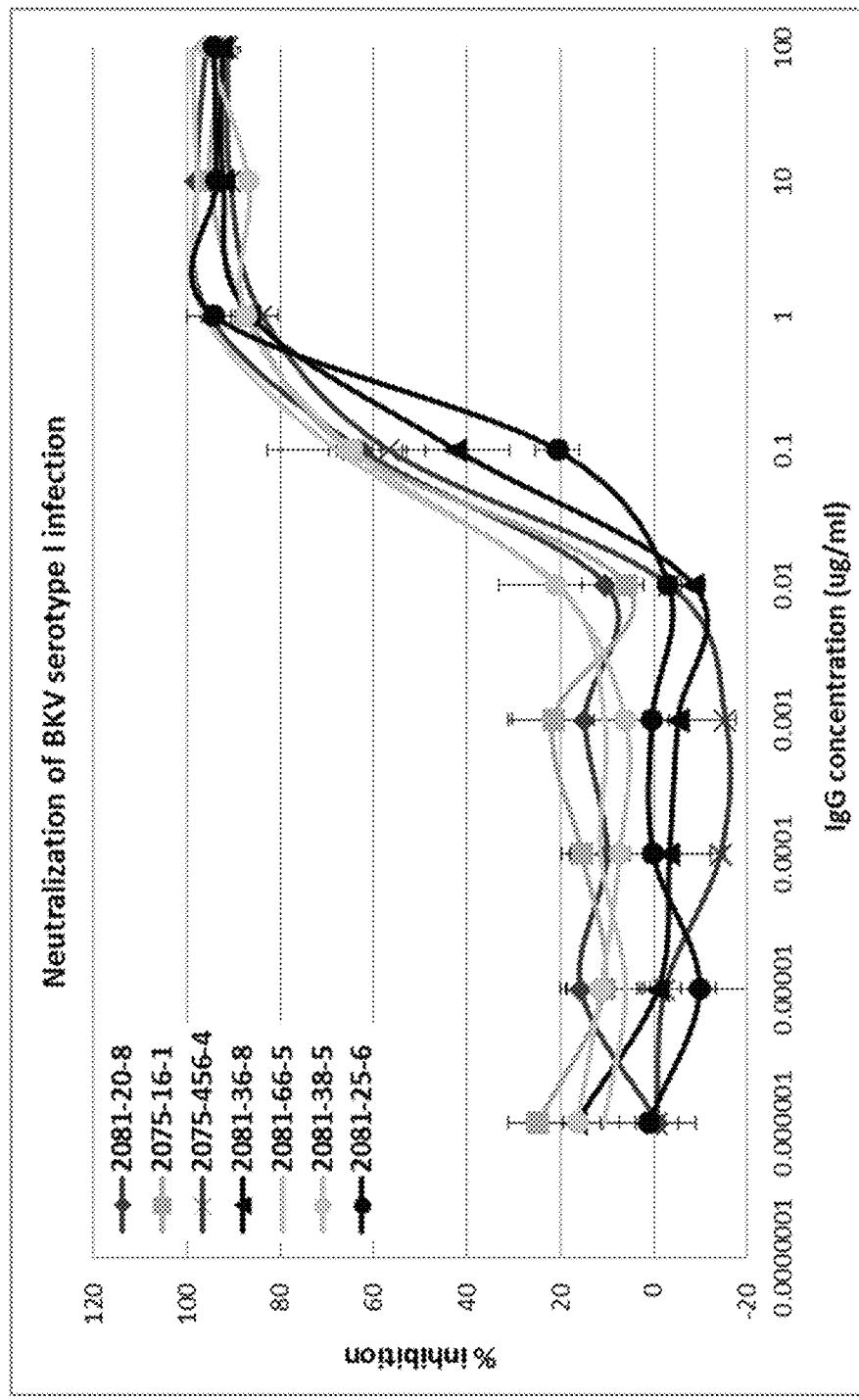
FIG. 22 is a graph of anti-VP1 antibodies neutralizing infection with BKV serotype I.

SPR was also used to characterize binding of anti-VP1 antibodies P165E2, NEG447, P7G11A, and P8D11 to VP1 pentamers by scanning alanine mutagenesis (FIGS. 13A-F and FIG. 14). All anti-VP1 antibodies showed reduced binding to F66A and I145A VP1 mutants, due to an overall impact of the mutation on VP1 pentamer structure (FIGS. 13B and 13F). In addition, K69A and E82A impacted binding of P165E2, NEG447, and P7G11A (FIGS. 13D and 13E).

Example 8: Anti-VP1 Antibodies Bind to a Conformational Epitope

To determine if the anti-VP1 antibodies bind a conformational epitope, Western blots of denatured protein by SDS-PAGE and dot blots of protein in native conformation were used. Briefly, BKV serotype I or IV VP1-pentamer were run on SDS-PAGE and transferred to nitrocellulose membrane (Western blot) or spotted directly onto nitrocellulose membrane (dot blot). Both membranes were incubated with anti-VP1 antibodies followed by anti-human IgG secondary antibody conjugated to infrared fluorescing dyes for detection using the Licor Odyssey system.

Commercially available positive control antibody (Abcam 53977) known to recognize a linear epitope detected both the denatured and non-denatured VP1. However, P165E2, P7G11 and P8D11 failed to detect denatured VP1 on the Western blot and only recognized native VP1 on the dot blot, indicating that these antibodies bind to a conformational (non-linear) epitope of VP1 (FIGS. 12A and 12B).

To further characterize the epitope of anti-VP1 antibodies, scanning alanine mutagenesis was performed for residues, primarily in the VP1 BC loop, known to be exposed on the virion surface and within a major interaction site for cell surface receptors. These mutant VP1 pentamers were assayed for binding to P8D11 and P7G11A in surface plasmon resonance (SPR) studies as described above in Example 7. Mutations at several positions impacted binding of P7G11A (F66A, K69A, E82A, I145A) (FIGS. 13A-F and FIG. 14). However, mutations at only two sites resulted in reduction of P8D11 binding (F66A, I145A) (FIG. 14). As the mutations at F66 and I145 resulted in a loss of binding of all antibodies tested, without being bound by any one theory, it is likely that these mutations result in a general disruption of the VP1 pentamer structure. All other VP1 pentamers with BC loop mutations tested retained P8D11 binding. In contrast, hydrogen-deuterium exchange studies have identified a protected region within the EF loop of VP1 upon binding of P8D11 Fab fragment. Follow-up scanning alanine mutagenesis studies confirm that key contact residues for P8D11 binding within this region include Y169, R170 and K172, with D/E175, K181, N182, T184 and Q186 to M190 being important residues as determined by deuterium exchange ((YRXKXX(D/E)XXXXXKNXTXQ) (SEQ ID NO: 500)). This is further described in Example 14 through Example 17.

Example 9: Neutralization of BK Virus by Anti-VP1 Antibodies

Infectious BKV serotype I and chimeric viruses representing serotype II, III, and IV were pre-incubated with purified antibodies for 1 hour to allow for binding and neutralization. Primary renal proximal tubule epithelial (RPTE) cells (ATCC, cat # PCS-400-010) were then exposed to the virus-antibody mixture for 4 hours, replaced with fresh medium, and incubated for 48 hours to allow for viral entry and gene expression. Cells were fixed with 4% paraformaldehyde and analyzed by immunofluorescence to detect TAg expression (Calbiochem DP02, pAb416 mouse anti-SV40 TAg antibody). The immunofluorescence was analyzed by high content image analysis using the Cellomics ArrayScan® VTI HCS Reader to quantify the percent of BKV-infected cells (TAg-positive, DAP1-positive), with data presented as percent inhibition of infection relative to untreated control wells.

As shown in FIGS. 15-23, anti-VP1 antibodies neutralized infection by BKV, including the subset of antibodies that neutralize infection by all four serotypes of BKV (I-IV). These anti-VP1 antibodies specifically include P8D11, the modifications of P8D11, and EBB-C1975-B5.

Example 10: Neutralization of JC Virus by Anti-VP1 Virus Antibodies

The infectious JCV isolates Mad-1 and Mad-4, have identical VP1 sequences (GenBank Accession NP_043511).

Figure 24:
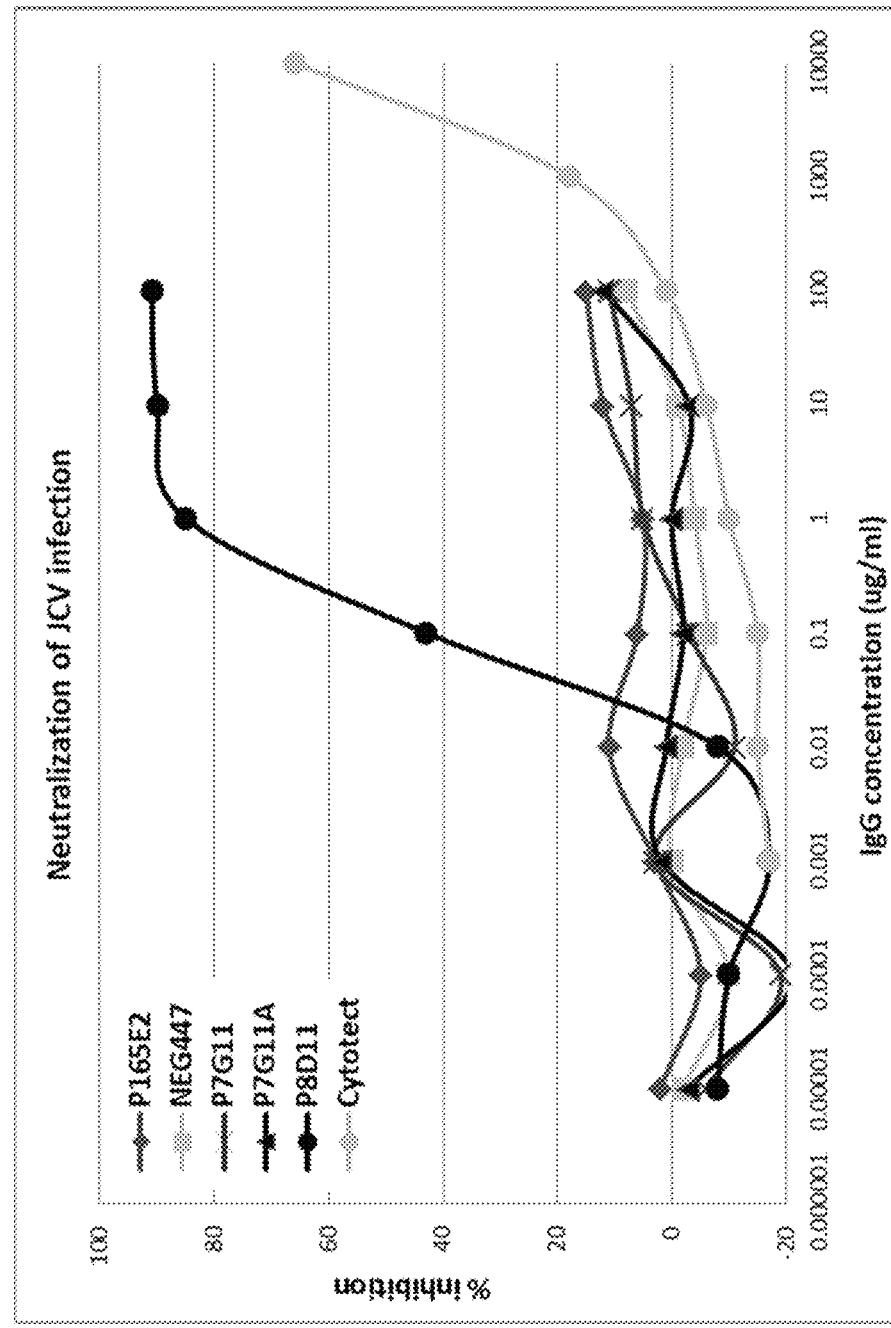
FIG. 24 is a graph of anti-VP1 antibodies neutralizing infection with JCV.
Figure 25:
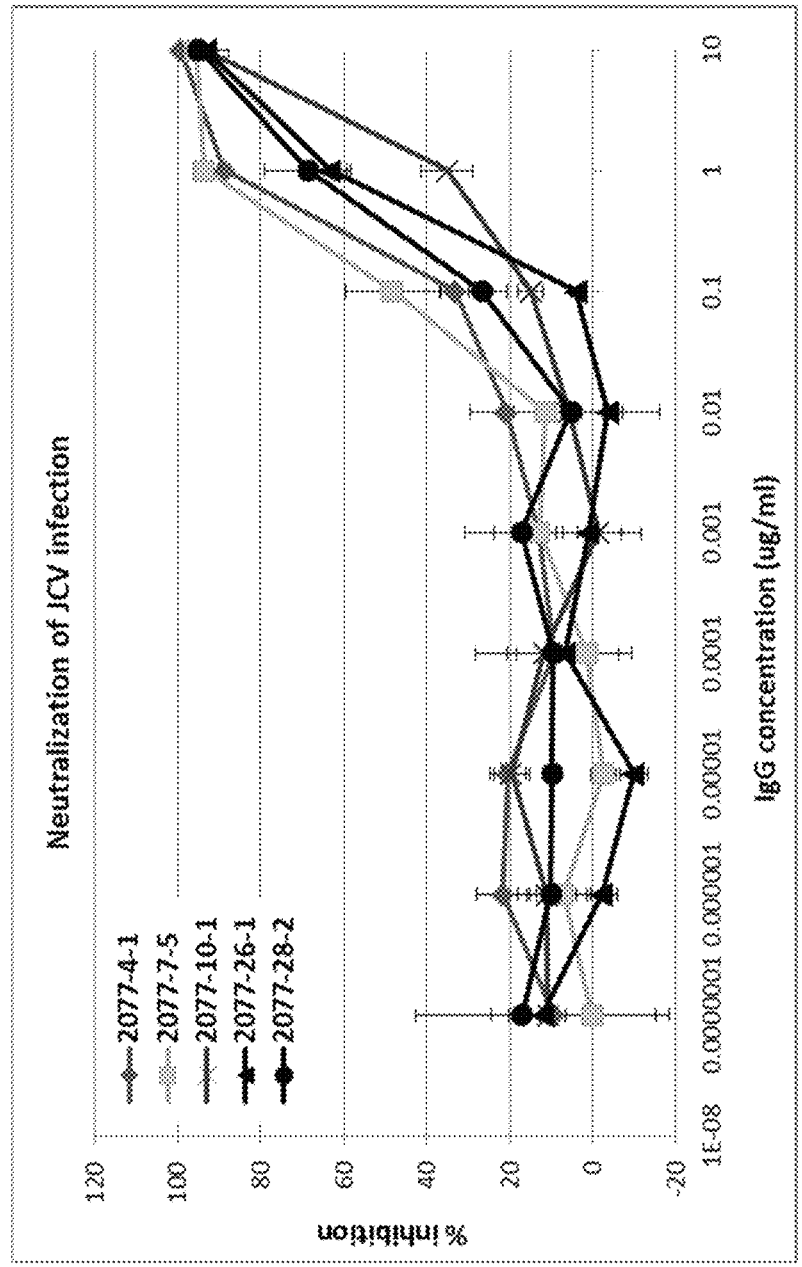
FIG. 25 is a graph of anti-VP1 antibodies neutralizing infection with JCV.

These JCV isolates were pre-incubated with purified antibodies for 1 hour to allow for binding and neutralization. COS7 cells (African green monkey kidney fibroblast-like cell line expressing SV40 TAg, ATCC cat # CRL-1651) were then exposed to the virus-antibody mixture for 4 hours, replaced with fresh medium, and incubated for 72 hours to allow for viral entry and gene expression. Cells were fixed with 4% paraformaldehyde and analyzed by immunofluorescence to detect JCV VP1 expression (Abcam 53977, rabbit polyclonal anti-SV40 VP1 antibody). The assay was analyzed by high content image analysis using the Cellomics ArrayScan® VTI HCS Reader (Thermo Fisher, Waltham Mass.) to quantify the percent of JCV-infected cells (VP1-positive, DAP1-positive), with data presented as percent inhibition of infection relative to untreated control wells. As shown in FIGS. 24-26, a subset of anti-VP1 antibodies neutralize infection by JCV, including P8D11 and the 2077-series of antibodies.

Example 11: Viral Resistance

Resistance selection experiments with P8D11 antibodies were carried out in renal proximal tubular epithelial (RPTE) cell cultures infected with BKV serotype I or serotype IV. In serotype I studies, no viral breakthrough was observed in cultures with P8D11 out to 6 passages (84 days) and thus no resistance-associated variants (RAVs) were identified. No further passaging past this point was done, as no virus could be detected. In contrast, viral breakthrough was detected at passage 3 (day 42) with another antibody. Sequencing of BKV VP1 from these cultures identified a resistance-associated variant (RAV) with 20 amino acid changes throughout VP1, with no changes clustering around specific amino acids in the VP1 sequence. Subsequent phenotypic characterization of this pooled RAV virus showed a complete loss of neutralization activity (>7,692-fold shift in EC50) when compared to wild-type virus, but little change (3.9 fold) in the EC50 of P8D11. In addition, the VP1 mutant E82K was identified as a RAV during selection with another anti-VP1 antibody (see Example 8), and characterization of a cloned E82K mutant virus showed this variant conferred a 15,880-fold shift in EC50 when compared to wild-type virus, but showed no cross-resistance to P8D11.

Similarly, in BKV serotype IV cultures, resistance was not detected with P8D11 after 6 passages (84 days). Again, No further passaging past this point was done, as no virus could be detected. However, resistance to a different anti-BK antibody was selected as early as passage 1 (day 14). Changes in amino acids L68R and E73K were identified as change-from-reference mutations and conferred 600- and 227-fold shifts in EC50 values respectively, but displayed no cross-resistance to P8D11. In summary, P8D11 has a high barrier-to-resistance and maintains neutralizing activity against resistant variants for both serotypes I and IV.

Example 12: Toxicity

Because VP1 is an exogenous, non-human target that is not expressed on the cell surface, the anti-VP1 antibodies disclosed herein constitute a low risk for toxicity in human. A TCR study demonstrated there was no staining of 42 human tissues and blood smears by P8D11, supporting the absence of anti-VP1 antibody cross-reactivity with human proteins. The anti-VP1 antibodies have shown no antibody-dependent cell-mediated cytotoxicity (ADCC) in vitro, consistent with the fact that VP1 protein is not expressed on the host cell surface.

Example 13: SET Affinity Assay of P8D11 on JCV VLPs

Progressive Multifocal Leukoencephalopathy (PML) is a rare, but frequently fatal infection of the brain of immuno-compromised patients by JC virus. The major capsid protein (VP1) of JC virus, is involved in binding sialic acid receptors on the surface of host cells. Certain mutations in the VP1, such as at amino acids L55 and S269, abolish sialic acid recognition and play a role in PML pathogenesis (Chen et al., mAbs 2015; 7(4), 681-692). These two mutations occur frequently in PML patients (Gorelik et al., J. Infect. Dis. 2011 204:103-114 and Reid et al., J. Infect. Dis. 2011; 204:237-244). The antibodies of the disclosure were tested to see if they bound to the mutated JCV VLPs with mutations at those positions. Binding of the anti-VP1 antibodies to these VLPs would indicate that JC virus carrying these common VP1 mutations would not be resistant to therapy.

Two series of twenty-two serial dilution of VLP were prepared in sample buffer. Two constant concentrations of the P8D11 antibody were added. The concentration of P8D11 antibody used was either 9 nM or 1 pM. The concentration range of JCV consensus ranged from 105 µg/ml-72 pg/ml. The concentration range of JCV L55F mutant was 300 µg/ml-143 pg/ml. The concentration range of JCV S269F mutant was 300 µg/ml-143 pg/ml. A volume of 60 µl of each VLP:antibody mix was distributed in duplicates to a 384-well polypropylene microtiter plate (PP MTP). Sample buffer served as negative control and a sample containing no antigen as positive control (Bmax). The plate was sealed and incubated over night (o/n) at room temperature (RT). A 384-well standard MSD array plate was coated o/n with 2 and 0.002 µg/ml of BKV-VP1 serotype I pentameric protein. After three times washing with 50 µl/well washing buffer, the plate was blocked with 50 µl/well blocking buffer for 1 hour at RT. After washing, a volume of 30 µl/well of each VLP:antibody mix was transferred from the PP MTP to the coated MSD plate and incubated for 20 min at RT. After an additional wash step, 30 µl of detection antibody (diluted 1:2000) in sample buffer was added to each well and incubated for 30 min at RT. The MSD plate was washed and 35 µl/well of read buffer was added and incubated for 5 min. ECL signals were measured with the MSD SECTOR Imager 6000.

The reagents used were: Bovine serum albumin (BSA), (VWR Cat #422351S), Phosphate-buffered saline (PBS) 10×, (Teknova Cat # P0195), MSD Read Buffer T 4×, (Meso Scale Discovery Cat # R92TC-1), Tris-buffered saline (TBS) 20×, (Teknova Cat # T1680), Tween-20, (VWR Cat #437082Q). The buffers used were; Blocking buffer: 1×PBS+5% (w/v) BSA, Coating buffer: 1×PBS, Sample buffer: 1×PBS+0.5% (w/v) BSA+0.02% (v/v) Tween-20, Wash buffer: 1×TBS+0.05% (v/v) Tween-20 and Read buffer: 1×MSD Read Buffer.

A solution equilibrium titration (SET) assay was used to determine the interaction affinities ($K_D$) of P8D11 with JCV VLPs as described in Example 5. P8D11 antibody was assayed at either 9 nM or 1 pM concentrations (constant) and JCV VLPs were serially diluted as follows: consensus VLPs ranged from 105 µg/ml-72 pg/ml, and L55F and S269F mutant VLPs both ranged from 300 µg/ml-143 pg/ml. Antibody:VP1 pentamer solution was incubated overnight, then assayed for unbound antibody using an MSD array plate (Meso Scale Discovery, Cat # L21XA, Rockville Md.) coated with VP1 pentamer. The $K_D$ was determined by fitting the plot with a 1:1 fit model (according to Piehler et al. J. Immunol. Methods. 1997; 201(2):189-206). The analysis was performed by using KinExA® Pro and n-Curve Analysis softwares from Sapidyne (Boise Id.).

FIG. 27 depicts the results of the SET assay in tabular form. This data provides the affinity determination ($K_D$) of P8D11 antibody to consensus JCV VLPs and VLPs containing VP1 mutations commonly associated with PML. P8D11 showed binding affinities to all JCV VLPs in the low nanomolar range. However, the binding affinity to the L55F mutant was approximately 2-fold lower than the affinity for wild type (consensus) and S269F mutant VLPs. Therefore, this indicates that the P8D11 antibody would still be an effective therapy against either wild type JC virus or JC virus with mutations commonly associated with PML.

Example 14: Deuterium Exchange Study (P8D11 Fab in Complex with BKV VP1 Pentamers) for Epitope Mapping Deuterium exchange mass spectrometry (HDx-MS) measures the deuterium uptake on the amide backbone of a protein. These measurements are sensitive to the amide's solvent accessibility and to changes in the hydrogen bonding network of the backbone amides. HDx-MS is often used to compare proteins in two different states, such as apo and ligand-bound, and coupled with rapid digestion with pepsin. In such experiments one can locate regions, typically of 10 to 15 amino acids, that show differential deuterium uptake between two different states. Regions that are protected are either directly involved in ligand binding or allosterically affected by binding of the antibody to the ligand.

In these experiments, the deuterium uptake of BKV VP1 protein (SEQ ID NO:502), was measured in the absence and presence of P8D11 Fab fragment. Regions in VP1 that show a decrease in deuterium uptake upon binding of the Fab fragment are likely to be involved in the epitope; however, due to the nature of the measurement it is also possible to detect changes remote from the direct binding site (allosteric effects). In general, the regions that have the greatest amount of protection are involved in direct binding.

The epitope mapping experiments are performed on a Waters Synapt® G2 HDx-MS platform, which includes LEAP® robot system, nanoACQUITY® UPLC System, and Synapt® G2 mass spectrometer. In this method, triplicate control experiments are carried out as follows. BKV serotype I VP1 pentamer is diluted into 110 μl of 95% deuterated PBS buffer (pH 7.4) and incubated at room temperature on a bench rotator for 25 minutes (% D=85.5%). Deuterium exchange is quenched by 1:1 dilution with cold quench buffer (6M Urea and 1M TCEP pH=2.5) on ice for 5 min. After quenching the tube is transferred onto a LEAP system (Thermo box is set at 2° C.) and the quenched sample is injected by the LEAP system onto the UPLC system for analysis. The UPLC system incorporates an immobilized pepsin column 2.1 mm×30 mm (Life Technologies 2-3131-00) that is maintained at 12° C. An 8-minute 2 to 35% acetonitrile gradient and Waters UPLC CSH C18 1.0×100 mm column is used for separation. Next, triplicate experiments are carried out using the antibody. The P8D11 Fab fragment is immobilized on Protein G agarose beads (Thermo Scientific Cat #22851) using standard techniques. Briefly, the antibody is centrifuged to remove a storage buffer. Then 200 μl of PBS buffer (pH 7.4) and a concentration of VP1 pentamers are added to the immobilized P8D11 Fab fragment and incubated for 30 min at room temperature. After incubation, the complex is centrifuged and washed with 200 μl PBS buffer and centrifuged again. For deuterium exchange, 200 μl of deuterated PBS is added to the antigen-antibody complex for incubation at room temperature for 25 minutes (% D=85.5%). Deuterium buffer is then removed, and immediately, 125 μl ice cold quench buffer is added. After quenching for 5 minutes, the column is centrifuged and the flow-through is transferred into a prechilled HPLC vial. The sample is analyzed using the same on-line pepsin digestion/LC-MS setup as the control experiment.

Figure 28:
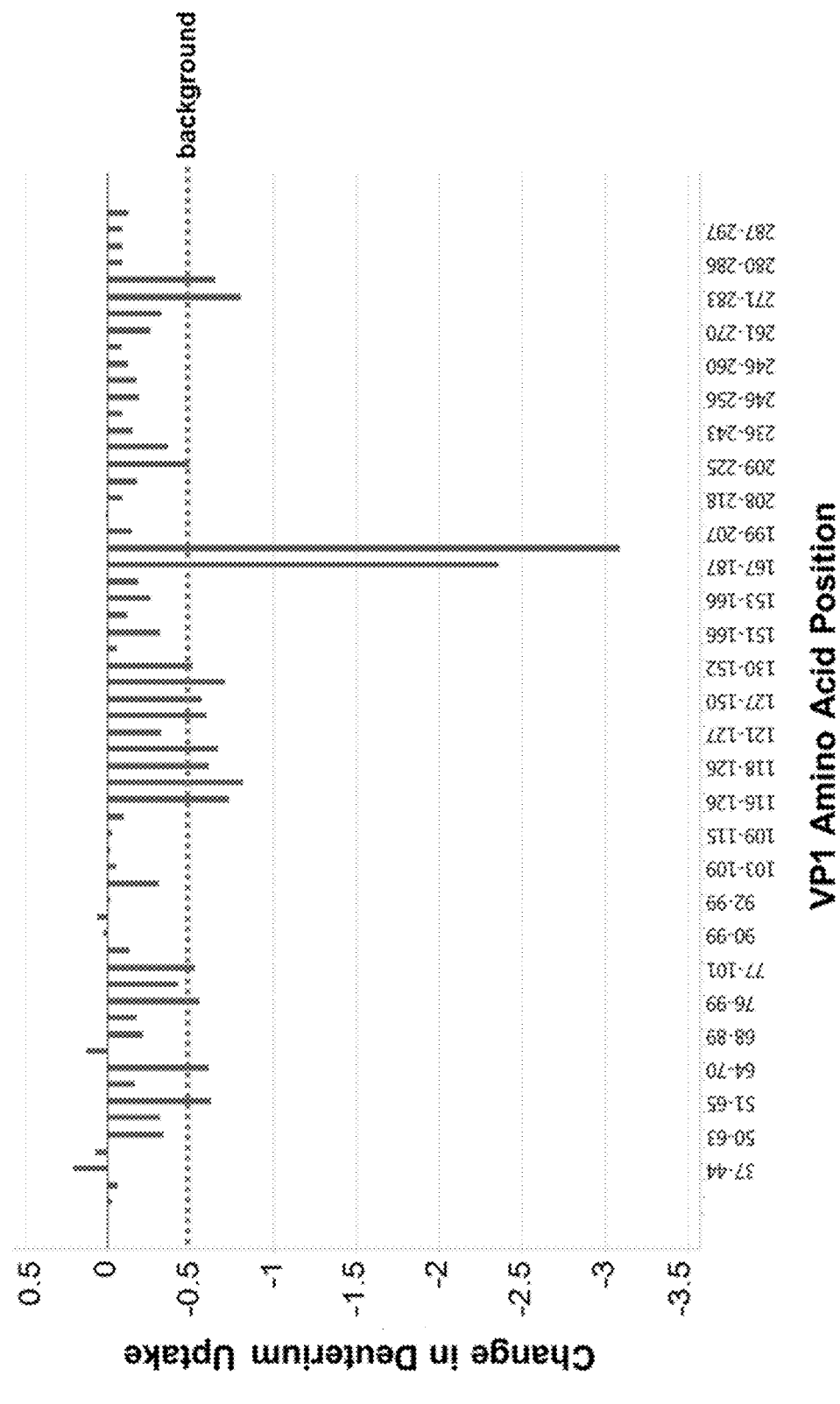
FIG. 28 is deuterium exchange epitope mapping of a P8D11 Fab bound to BKV VP1 pentamers.

The results of these measurements are summarized in FIG. 28. FIG. 28 shows the baseline corrected differences between the control and P8D11 antibody bound sample divided by the standard error in the measurement. In this plot the more negative value indicates a greater amount of protection in a given region upon binding of P8D11 Fab fragment to BKV serotype I VP1 pentamer. We observe the most significant amounts of protection in amino acids 168-190 of the VP1 protein upon binding of P8D11 Fab fragment. This region of the EF loop is highly conserved across all four serotypes of BK virus and JC virus, as can be seen with the sequences bolded and underlined in Table 1 ((NYRTKYPXGTXXPKNXTXQSQVM) (SEQ ID NO:501)).

In conclusion, the deuterium mapping data indicate that P8D11 antibody binds to an epitope within the EF loop of BKV VP1. This region is highly conserved across all four BKV serotypes and JC virus, and thus supports the result that P8D11 has neutralizing activity across all four BKV serotypes and JC virus.

Example 15: Targeted Alanine Scanning and SPR for Epitope Mapping of P8D11

Biacore surface plasmon resonance (SPR) was used to characterize the binding of anti-VP1 antibodies to VP1 pentamers generated for epitope mapping by scanning alanine mutagenesis. Experiments were performed at 25° C. in phosphate buffered saline (PBS) supplemented with 0.005% Tween 20 detergent (Calbiochem #655206) and run on a Biacore T-200 instrument (GE Healthcare Life Sciences). Biotinylated protein A (Sigma # P2165) was immobilized onto a Series S streptavidin sensor chip to approximately 1200 response units (RUs) and remaining free streptavidin sites were blocked with biotin-PEG (Pierce EZ-Link # PI21346). Antibodies were captured onto the prepared protein A sensor chip with a 4 second injection at a flow rate of 30 μl/minute. Antibodies were immobilized at 20-40 RUs on flowcells 2, 3 and 4, leaving flowcell 1 as a reference cell without any antibody. VP1 pentamers were then injected over the chip for 200 seconds at 100 μl/min followed by injections of buffer to monitor dissociation. Between each pentamer and pentamer concentration, the sensor chip surface was regenerated with an injection of 25 mM NaOH for 60 seconds at 30 μl/minute to remove antibodies before re-capture of antibodies onto the protein A surfaces for the next cycle. Data analysis was done in the GE BiaEvaluation software where double reference subtraction was applied. Assessment of the effect of alanine mutagenesis on VP1 pentamer binding was achieved by comparison of the binding RU levels and shapes of the binding curves compared to those of the wildtype pentamer.

Figure 29C:
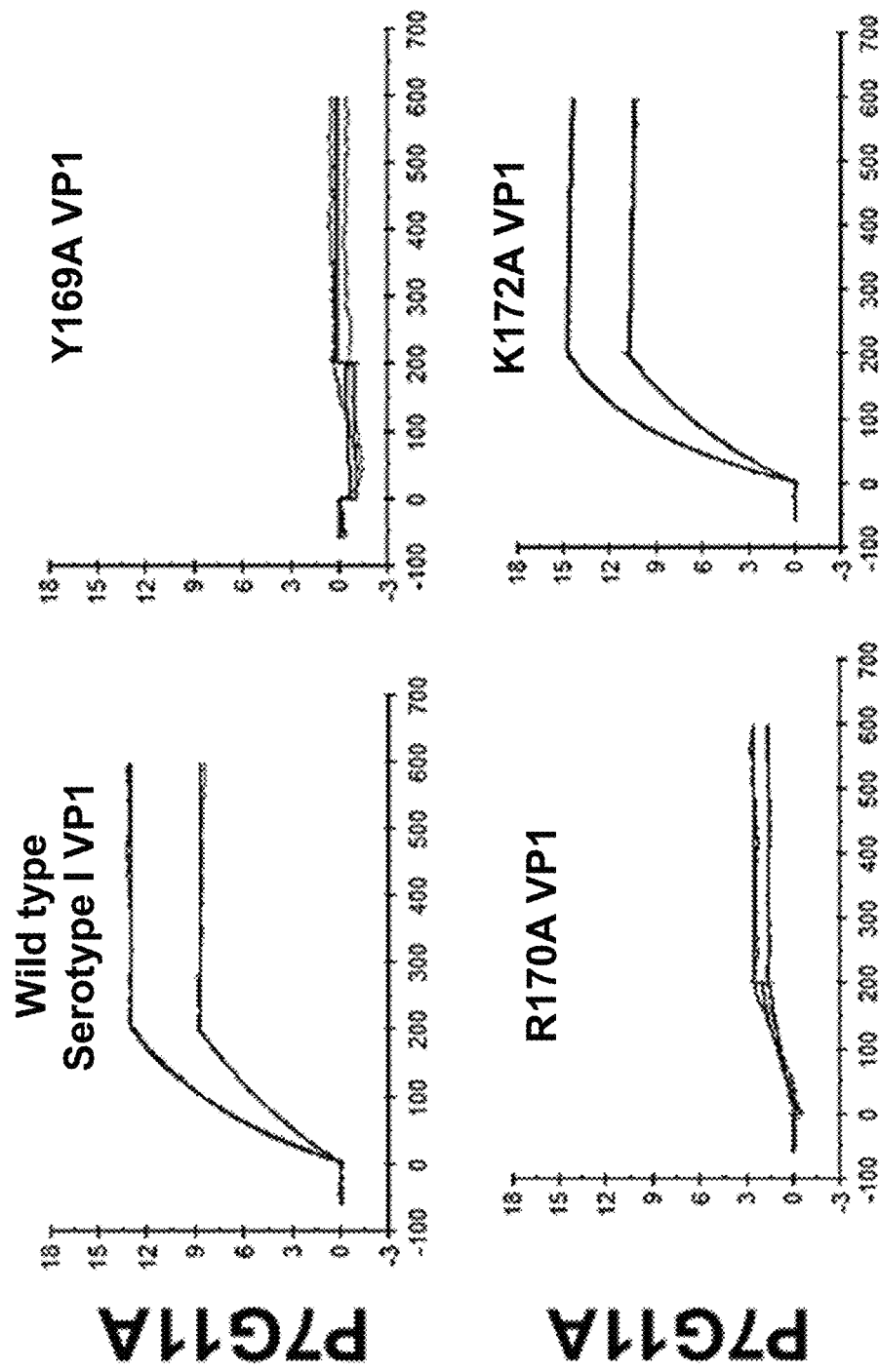
Figure 30:
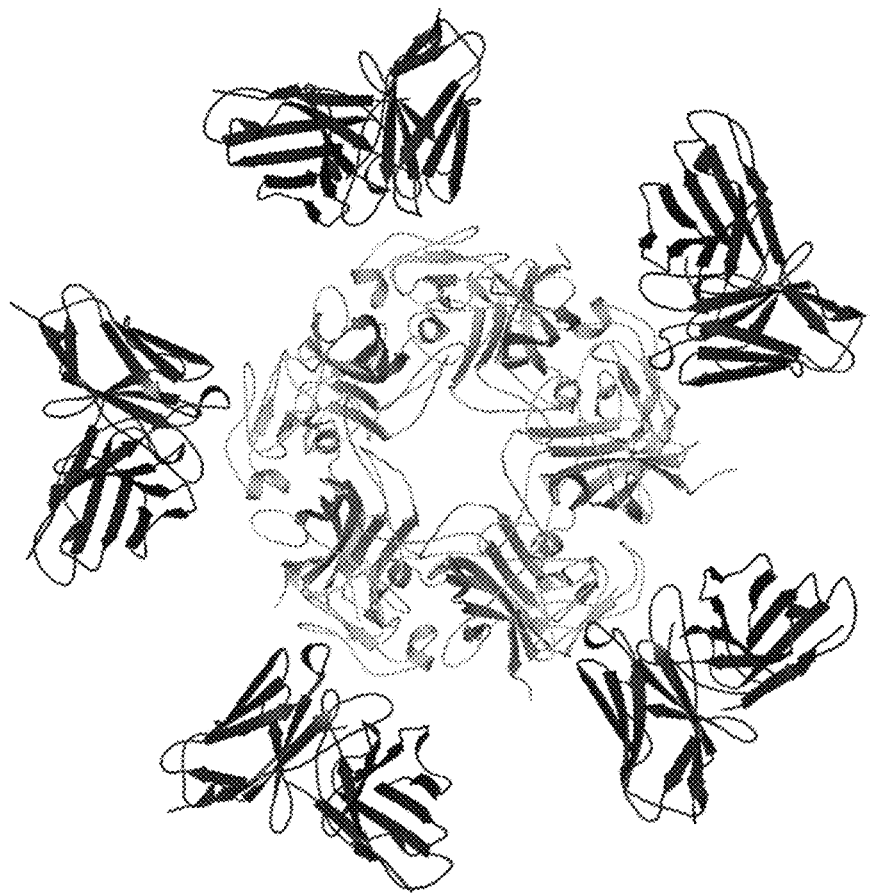
FIG. 30 is an X-ray crystal structure of P8D11 in complex with BKV VP1 pentamer.
Figure 31B:
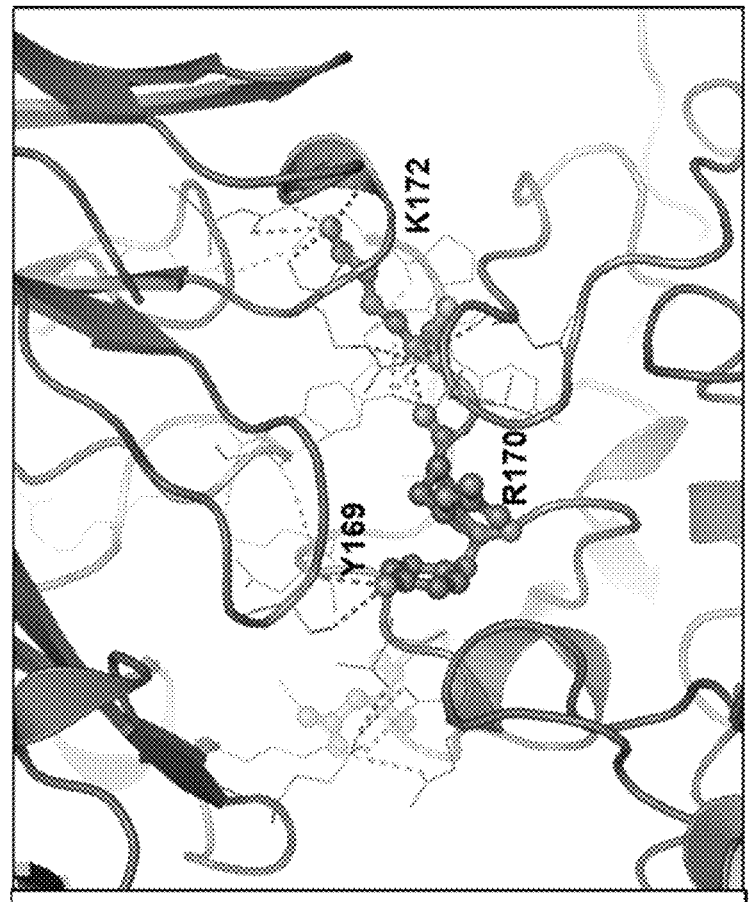
FIG. 31A-B is a graphical representation of how P8D11 contacts the residues of the VP1 pentamer.
Figure 31A:
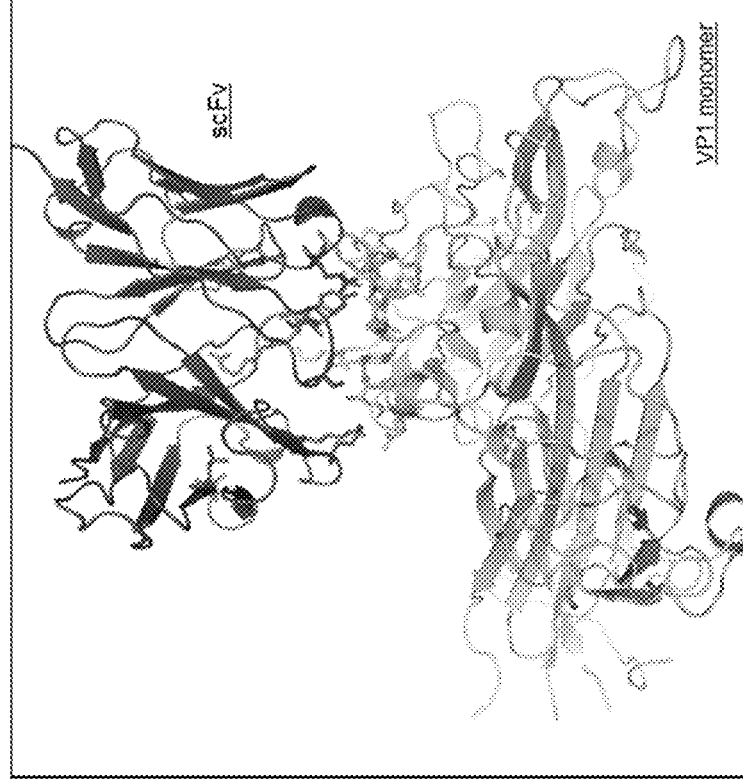

As discussed previously, the epitopes for antibodies P8D11 and P7G11A are conformational and non-contiguous (FIGS. 12A-B). Here, single mutations to alanine at Y169, R170 and K172 in the EF loop of BKV VP1 abolishes binding of P8D11 (FIGS. 29A and 29B). Mutations at Y169 and R170 also abolish binding of the P7G11A antibody, however binding of this antibody is not affected by changes at position K172 of the EF loop of BKV VP1 (FIGS. 29A and 29C).

Example 16: Epitope Mapping by X-Ray Crystallography

The crystal structure of the scFv chain of the antibody P8D11 bound to the BKV major capsid protein VP1 in its pentameric form was determined. As detailed below, a 5.5:1 solution of scFv:BKV-VP1 pentamer was used to produce a crystallographically suitable complex composed of five scFv chains bound to each pentamer. Protein crystallography was then employed to generate an atomic resolution structure and define the epitope.

Crystallization and Structure Determination

The P8D11 scFv/BKV-VP1 complex was concentrated to 5.2 mg/ml and screened for crystallization. Crystals for data collection were grown by hanging drop vapor diffusion at 18° C. Crystals were grown by mixing 1.0 µl of the complex with 1.0 µl of reservoir solution containing 25% (w/v) PEG3350, 0.2 M magnesium chloride and 0.1M Bis-Tris pH 7.0, and equilibrating the drop against 350 µl of the same reservoir solution. Crystals grew overnight and continued to grow for a few days. Before data collection, the crystals were transferred to 75% of reservoir solutions plus 25% glycerol and flash cooled in liquid nitrogen.

Diffraction data were collected in-house on a Rigaku FRE+ copper source and an R-axis X-ray detector. Data was processed and scaled using Autoproc (Global Phasing, LTD). The data of BKV-VP1 was processed to 2.66 Å in space group P42212 with cell dimensions a=224.4 Å, b=224.4 Å, c=144.04 Å, alpha=90°, beta=90°, gamma=90°. The structure of the complex was solved by molecular replacement using Phaser (McCoy et al., (2007) J. Appl. Cryst. 40:658-674) with a BKV-VP1 pentamer as the search model. The final model was built in COOT (Emsley & Cowtan (2004) Acta Cryst. D60:2126-2132) and refined with Buster (Global Phasing, LTD, Cambridge, UK). The Rwork and Rfree values are 17.1% and 21.4%, respectively; and root-mean-square (r.m.s) deviation values of bond lengths and bond angles are 0.010 Å and 1.18°, respectively.

Residues of BKV-VP1-Pentamer that are in contact with the P8D11 scFv, the types of interactions, and the buried surface areas are all identified by PISA (Krissinel et al., (2007) J Mol Biol. 372:774-97) and listed in Table 6 below. It was found the each monomer of the VP1-pentamer contains a single isolated epitope for the P8D11 antibody. Thus five scFv domains bind to each pentamer at five chemically and sterically equivalent positions. Details for the interactions at each epitope are essentially identical so that only one scFv/VP1-epitope interface is analyzed here.

Epitopes of P8D1-scFv on BKV-VP1

Overall Structure

The overall folding of each polyomavirus VP1-pentmer structure is highly homologous at the level of tertiary structure. Primary sequences are well conserved with identity as at 69-85%. Each pentamer is composed of five monomers, each of which is composed by a three-strand β sheet stacking against another five-strand β sheet and then a four-strand β sheet. The P8D11 scFv is a VH-VL fusion protein with a 20 amino acid linker between VH and VL domains. As shown in FIG. 30, the VH-VL fusion protein binds to an epitope located on the lateral, exterior surface of the BKV-VP1-pentamer.

Epitope of P8D11

The crystal structure of the BKV-VP1/P8D11 complex is used to identify the P8D11 epitope on BKV-VP1. The interaction surface on VP1 by P8D11-scFv is formed by several continuous and discontinuous (i.e. noncontiguous) sequences: namely residues 77-80, 169-186, and 191-192, as detailed in Table 6. These residues form the three-dimensional conformational epitope that is recognized by the P8D11-scFv (FIG. 31A-B). This epitope defined by crystallography is in good agreement with that defined by hydrogen deuterium exchange mass spectrometry (HDx-MS), in which residues 168-190 are substantially protected by P8D11-Fab (FIG. 28). There is also good agreement with the Alanine scan that was done on the key amino acids of the epitope (FIG. 29A-C) which showed that TYR169, ARG170 and LYS172 are contact residues which are part of the epitope of the P8D11 antibody.

P8D11-scFv epitope on BKV-VP1. All residues of BKV-VP1 that are in contact with P8D11-scFv in the crystal structure are identified by PISA, listed and sorted by their buried surface area by P8D11-scFv. Types of interaction are also listed where applicable.

TABLE 6

| | Hydrogen bond | Salt Bridge | ASA* | BSA* |
|---|---|---|---|---|
| Anti-VP1 scFv residue | | | | |
| ASN31 | 0 | 0 | 72.36 | 1.11 |
| TYR32 | 0 | 0 | 60.89 | 6.59 |
| TRP33 | 0 | 0 | 42.56 | 39.19 |
| LYS52 | 2 | 0 | 66.84 | 59.49 |
| LYS53 | 0 | 1 | 89.76 | 40.27 |
| ASP54 | 0 | 0 | 100.58 | 3.42 |
| SER56 | 0 | 0 | 78.38 | 5.60 |
| GLU57 | 2 | 0 | 63.29 | 46.19 |
| TRY59 | 0 | 0 | 55.86 | 13.29 |
| VAL99 | 0 | 0 | 19.54 | 17.42 |
| ARG100 | 1 | 0 | 97.42 | 14.49 |
| GLY102 | 1 | 0 | 45.24 | 23.46 |
| ARG103 | 5 | 0 | 190.68 | 157.62 |
| TYR104 | 4 | 0 | 68.25 | 63.79 |
| PHE105 | 0 | 0 | 37.94 | 32.69 |
| ASN526 | 0 | 0 | 84.174 | 16.28 |
| GLY528 | 1 | 0 | 27.52 | 11.48 |
| SER529 | 0 | 0 | 62.31 | 55.68 |
| ARG530 | 4 | 0 | 83.56 | 70.86 |
| PRO531 | 0 | 0 | 14.77 | 13.77 |
| ASP549 | 0 | 0 | 21.15 | 4.11 |
| ASP550 | 0 | 2 | 37.36 | 16.62 |
| SER551 | 0 | 0 | 68.46 | 11.52 |
| ASN552 | 1 | 0 | 65.13 | 28.37 |
| TRP590 | 0 | 0 | 51.46 | 50.45 |
| SER591 | 0 | 0 | 40.49 | 16.66 |
| SER592 | 0 | 0 | 51.90 | 25.61 |
| SER593 | 2 | 0 | 45.01 | 33.37 |
| VP1 Pentamer residue | | | | |
| SER77 | 1 | 0 | 74.90 | 25.99 |
| SER78 | 0 | 0 | 73.45 | 46.46 |
| ASP79 | 1 | 0 | 36.90 | 2.33 |
| SER80 | 0 | 0 | 63.82 | 20.03 |
| TYR169 | 2 | 0 | 66.99 | 44.33 |
| ARG170 | 1 | 0 | 117.97 | 54.91 |
| THR171 | 1 | 0 | 12.44 | 9.58 |
| LYS172 | 2 | 2 | 142.87 | 121.15 |
| TYR173 | 3 | 0 | 33.81 | 24.25 |
| PRO174 | 1 | 0 | 27.18 | 4.61 |
| GLU175 | 1 | 0 | 165.93 | 61.70 |
| GLY176 | 0 | 0 | 30.62 | 0.58 |

TABLE 6-continued

| | Hydrogen bond | Salt Bridge | ASA* | BSA* |
|---|---|---|---|---|
| THR177 | 1 | 0 | 21.14 | 13.74 |
| ILE178 | 0 | 0 | 63.25 | 0.67 |
| THR179 | 2 | 0 | 29.52 | 22.67 |
| PRO180 | 0 | 0 | 11.34 | 7.66 |
| LYS181 | 2 | 0 | 164.73 | 85.21 |
| ASN182 | 1 | 0 | 111.76 | 104.95 |
| PRO183 | 0 | 0 | 50.84 | 49.34 |
| THR184 | 1 | 0 | 67.62 | 67.45 |
| ALA185 | 0 | 0 | 61.12 | 6.85 |
| GLN186 | 1 | 0 | 103.62 | 42.67 |
| ASN191 | 2 | 0 | 13.15 | 12.56 |
| THR192 | 0 | 0 | 89.19 | 1.87 |
| ASP193 | 0 | 1 | 123.11 | 71.49 |

*ASA: Accessible Surface Area
*BSA: Buried Surface Area

Example 18: Formulation

The anti-VP1 antibodies described herein are monoclonal antibodies, IgG1 isotype with lambda light chain, and can be lyophilized. These antibodies are soluble and stable in a histidine-sucrose formulation buffer for 4 weeks. In addition, anti-VP1 antibodies were soluble at >200 mg/ml as minimally formulated drug substance (e.g., in histidine buffer in the absence of stabilizers).

For subsequent intravenous administration, the obtained solution will usually be further diluted into a carrier solution to the ready-to-use antibody solution for infusion.

Important stability-indicating analytical methods to select the most stable formulation encompassed, amongst others, size-exclusion chromatography to determine aggregation levels, subvisible particulate matter testing, and potency testing.

It is understood that the examples and aspects described herein are for illustrative purposes only and that various modifications or changes in light thereof will be suggested to persons skilled in the art and are to be included within the spirit and purview of this application and scope of the appended claims.

SEQUENCE LISTING

```
<160> NUMBER OF SEQ ID NOS: 543

<210> SEQ ID NO 1
<211> LENGTH: 362
<212> TYPE: PRT
<213> ORGANISM: Polyomavirus

<400> SEQUENCE: 1

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
        35                  40                  45

Glu Cys Phe Leu Asn Pro Glu Met Gly Asp Pro Asp Glu Asn Leu Arg
    50                  55                  60

Gly Phe Ser Leu Lys Leu Ser Ala Glu Asn Asp Phe Ser Ser Asp Ser
65                  70                  75                  80

Pro Glu Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Gln Thr Glu Val Ile Gly Ile Thr Ser Met Leu Asn
        115                 120                 125

Leu His Ala Gly Ser Gln Lys Val His Glu His Gly Gly Gly Lys Pro
    130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
        195                 200                 205

Trp Ile Pro Asp Pro Ser Arg Asn Glu Asn Thr Arg Tyr Phe Gly Thr
    210                 215                 220
```

```
Phe Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
            245                 250                 255

Ala Asp Ser Leu Tyr Val Ser Ala Ala Asp Ile Cys Gly Leu Phe Thr
            260                 265                 270

Asn Ser Ser Gly Thr Gln Gln Trp Arg Gly Leu Ala Arg Tyr Phe Lys
            275                 280                 285

Ile Arg Leu Arg Lys Arg Ser Val Lys Asn Pro Tyr Pro Ile Ser Phe
            290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Glu Val Arg Val Phe Asp
                325                 330                 335

Gly Thr Glu Arg Leu Pro Gly Asp Pro Asp Met Ile Arg Tyr Ile Asp
                340                 345                 350

Lys Gln Gly Gln Leu Gln Thr Lys Met Leu
                355                 360

<210> SEQ ID NO 2
<211> LENGTH: 362
<212> TYPE: PRT
<213> ORGANISM: Polyomavirus

<400> SEQUENCE: 2

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
            35                  40                  45

Glu Cys Phe Leu Asn Pro Glu Met Gly Asp Pro Asp Asp Asn Leu Arg
    50                  55                  60

Gly Tyr Ser Leu Lys Leu Thr Ala Glu Asn Ala Phe Asp Ser Asp Ser
65                  70                  75                  80

Pro Asp Lys Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Ile Gly Ile Thr Ser Met Leu Asn
            115                 120                 125

Leu His Ala Gly Ser Gln Lys Val His Glu Asn Gly Gly Lys Pro
130                 135                 140

Val Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Gln Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
            195                 200                 205

Trp Ile Pro Asp Pro Ser Arg Asn Glu Asn Thr Arg Tyr Phe Gly Thr
    210                 215                 220

Tyr Thr Gly Gly Glu Asn Val Pro Pro Val Leu His Val Thr Asn Thr
```

```
             225                 230                 235                 240
Ala Thr Thr Val Leu Leu Asp Glu Gln Gly Val Gly Pro Leu Cys Lys
                    245                 250                 255

Ala Asp Ser Leu Tyr Val Ser Ala Ala Asp Ile Cys Gly Leu Phe Thr
                260                 265                 270

Asn Ser Ser Gly Thr Gln Gln Trp Arg Gly Leu Ala Arg Tyr Phe Lys
                275                 280                 285

Ile Arg Leu Arg Lys Arg Ser Val Lys Asn Pro Tyr Pro Ile Ser Phe
            290                 295                 300

Leu Leu Ser Asp Leu Ile Asn Arg Arg Thr Gln Lys Val Asp Gly Gln
305                 310                 315                 320

Pro Met Tyr Gly Met Glu Ser Gln Val Glu Glu Val Arg Val Phe Asp
                325                 330                 335

Gly Thr Glu Gln Leu Pro Gly Asp Pro Asp Met Ile Arg Tyr Ile Asp
                340                 345                 350

Arg Gln Gly Gln Leu Gln Thr Lys Met Val
            355                 360

<210> SEQ ID NO 3
<211> LENGTH: 362
<212> TYPE: PRT
<213> ORGANISM: Polyomavirus

<400> SEQUENCE: 3

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
                20                  25                  30

Val Glu Val Leu Glu Val Lys Thr Gly Val Asp Ala Ile Thr Glu Val
            35                  40                  45

Glu Cys Phe Leu Asn Pro Glu Met Gly Asp Pro Asp Asp His Leu Arg
50                  55                  60

Gly Tyr Ser Gln His Leu Ser Ala Glu Asn Ala Phe Asp Ser Asp Ser
65                  70                  75                  80

Pro Asp Lys Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Ile Gly Ile Thr Ser Met Leu Asn
            115                 120                 125

Leu His Ala Gly Ser Gln Lys Val His Glu Asn Gly Gly Gly Lys Pro
130                 135                 140

Val Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Gln Gly
                165                 170                 175

Thr Ile Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
            195                 200                 205

Trp Ile Pro Asp Pro Ser Lys Asn Glu Asn Thr Arg Tyr Phe Gly Thr
        210                 215                 220

Tyr Thr Gly Gly Glu Asn Val Pro Pro Val Leu His Val Thr Asn Thr
225                 230                 235                 240
```

Ala Thr Thr Val Leu Leu Asp Glu Gln Gly Val Gly Pro Leu Cys Lys
            245                 250                 255

Ala Asp Ser Leu Tyr Val Ser Ala Asp Ile Cys Gly Leu Phe Thr
            260                 265                 270

Asn Ser Ser Gly Thr Gln Gln Trp Arg Gly Leu Ala Arg Tyr Phe Lys
            275                 280                 285

Ile Arg Leu Arg Lys Arg Ser Val Lys Asn Pro Tyr Pro Ile Ser Phe
290             295                 300

Leu Leu Ser Asp Leu Ile Asn Arg Arg Thr Gln Lys Val Asp Gly Gln
305                 310                 315                 320

Pro Met Tyr Gly Met Glu Ser Gln Val Glu Glu Val Arg Val Phe Asp
                325                 330                 335

Gly Thr Glu Gln Leu Pro Gly Asp Pro Asp Met Ile Arg Tyr Ile Asp
                340                 345                 350

Arg Gln Gly Gln Leu Gln Thr Lys Met Val
                355                 360

<210> SEQ ID NO 4
<211> LENGTH: 362
<212> TYPE: PRT
<213> ORGANISM: Polyomavirus

<400> SEQUENCE: 4

Met Ala Pro Thr Lys Arg Lys Gly Glu Cys Pro Gly Ala Ala Pro Lys
1               5                   10                  15

Lys Pro Lys Glu Pro Val Gln Val Pro Lys Leu Leu Ile Lys Gly Gly
            20                  25                  30

Val Glu Val Leu Glu Val Lys Thr Gly Val Asp Ala Ile Thr Glu Val
            35                  40                  45

Glu Cys Phe Leu Asn Pro Glu Met Gly Asp Pro Asp Asn Asp Leu Arg
50                  55                  60

Gly Tyr Ser Leu Arg Leu Thr Ala Glu Thr Ala Phe Asp Ser Asp Ser
65                  70                  75                  80

Pro Asp Arg Lys Met Leu Pro Cys Tyr Ser Thr Ala Arg Ile Pro Leu
                85                  90                  95

Pro Asn Leu Asn Glu Asp Leu Thr Cys Gly Asn Leu Leu Met Trp Glu
            100                 105                 110

Ala Val Thr Val Lys Thr Glu Val Ile Gly Ile Thr Ser Met Leu Asn
            115                 120                 125

Leu His Ala Gly Ser Gln Lys Val His Glu Asn Gly Gly Gly Lys Pro
130                 135                 140

Ile Gln Gly Ser Asn Phe His Phe Phe Ala Val Gly Gly Asp Pro Leu
145                 150                 155                 160

Glu Met Gln Gly Val Leu Met Asn Tyr Arg Thr Lys Tyr Pro Glu Gly
                165                 170                 175

Thr Val Thr Pro Lys Asn Pro Thr Ala Gln Ser Gln Val Met Asn Thr
            180                 185                 190

Asp His Lys Ala Tyr Leu Asp Lys Asn Asn Ala Tyr Pro Val Glu Cys
            195                 200                 205

Trp Ile Pro Asp Pro Ser Arg Asn Glu Asn Thr Arg Tyr Phe Gly Thr
210                 215                 220

Tyr Thr Gly Gly Glu Asn Val Pro Pro Val Leu His Val Thr Asn Thr
225                 230                 235                 240

Ala Thr Thr Val Leu Leu Asp Glu Gln Gly Val Gly Pro Leu Cys Lys
                245                 250                 255

```
Ala Asp Ser Leu Tyr Val Ser Ala Ala Asp Ile Cys Gly Leu Phe Thr
        260                 265                 270

Asn Ser Ser Gly Thr Gln Gln Trp Arg Gly Leu Pro Arg Tyr Phe Lys
275                 280                 285

Ile Arg Leu Arg Lys Arg Ser Val Lys Asn Pro Tyr Pro Ile Ser Phe
        290                 295                 300

Leu Leu Ser Asp Leu Ile Asn Arg Arg Thr Gln Arg Val Asp Gly Gln
305                 310                 315                 320

Pro Met Tyr Gly Met Glu Ser Gln Val Glu Val Arg Val Phe Asp
                325                 330                 335

Gly Thr Glu Gln Leu Pro Gly Asp Pro Asp Met Ile Arg Tyr Ile Asp
        340                 345                 350

Arg Gln Gly Gln Leu Gln Thr Lys Met Val
        355                 360

<210> SEQ ID NO 5
<211> LENGTH: 354
<212> TYPE: PRT
<213> ORGANISM: Orthopolyomavirus

<400> SEQUENCE: 5

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
                20                  25                  30

Gly Val Asp Ser Ile Thr Glu Val Glu Cys Phe Leu Thr Pro Glu Met
            35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
                100                 105                 110

Ile Gly Val Thr Thr Leu Met Asn Val His Ser Asn Gly Gln Ala Thr
            115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
```

```
                260                 265                 270
Arg Gly Leu Ser Arg Tyr Phe Lys Val Gln Leu Arg Lys Arg Val
            275                 280                 285

Lys Asn Pro Tyr Pro Ile Ser Phe Leu Leu Thr Asp Leu Ile Asn Arg
        290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                325                 330                 335

Pro Asp Met Met Arg Tyr Val Asp Arg Tyr Gly Gln Leu Gln Thr Lys
            340                 345                 350

Met Leu

<210> SEQ ID NO 6
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Asn Tyr Trp Met Thr
1               5

<210> SEQ ID NO 7
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Asn Ile Lys Lys Asp Gly Ser Glu Lys Tyr Tyr Val Asp Ser Val Arg
1               5                   10                  15

Gly

<210> SEQ ID NO 8
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Val Arg Ser Gly Arg Tyr Phe Ala Leu Asp Asp
1               5                   10

<210> SEQ ID NO 9
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gly Phe Thr Phe Asn Asn Tyr
```

```
<210> SEQ ID NO 10
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Lys Lys Asp Gly Ser Glu
1               5

<210> SEQ ID NO 11
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Val Arg Ser Gly Arg Tyr Phe Ala Leu Asp Asp
1               5                   10

<210> SEQ ID NO 12
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Thr Phe Asn Asn Tyr
            20                  25                  30

Trp Met Thr Trp Val Arg Gln Ala Pro Gly Lys Gly Leu Glu Trp Val
        35                  40                  45

Ala Asn Ile Lys Lys Asp Gly Ser Glu Lys Tyr Tyr Val Asp Ser Val
    50                  55                  60

Arg Gly Arg Phe Thr Ile Ser Arg Asp Asn Ala Lys Asn Ser Leu Phe
65                  70                  75                  80

Leu Gln Met Asn Ser Leu Arg Pro Glu Asp Thr Ala Val Tyr Phe Cys
                85                  90                  95

Ala Thr Val Arg Ser Gly Arg Tyr Phe Ala Leu Asp Asp Trp Gly Gln
            100                 105                 110

Gly Thr Leu Val Thr Val Ser Ser
        115                 120

<210> SEQ ID NO 13
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 13
```

```
caggtgcagc tggtggaatc aggcggcaca ctggtgcagc ctggcggtag cctgagactg    60
agctgcgctg ctagtggctt cacctttaac aactactgga tgacctgggt taggcaggcc   120
cctggtaaag gcctcgagtg ggtggcaaat atcaagaagg acggtagcga gaagtactac   180
gtggactcag tcagaggccg gttcactatc tctaggata acgctaagaa tagcctgttc   240
ctgcagatga actcactgag gcccgaggat accgccgtct acttctgtgc taccgtcaga   300
tcaggccgct acttcgccct ggacgactgg ggtcaaggca cactggtcac cgtgtctagc   360
```

<210> SEQ ID NO 14
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Thr Phe Asn Asn Tyr
            20                  25                  30

Trp Met Thr Trp Val Arg Gln Ala Pro Gly Lys Gly Leu Glu Trp Val
        35                  40                  45

Ala Asn Ile Lys Lys Asp Gly Ser Glu Lys Tyr Tyr Val Asp Ser Val
    50                  55                  60

Arg Gly Arg Phe Thr Ile Ser Arg Asp Asn Ala Lys Asn Ser Leu Phe
65                  70                  75                  80

Leu Gln Met Asn Ser Leu Arg Pro Glu Asp Thr Ala Val Tyr Phe Cys
                85                  90                  95

Ala Thr Val Arg Ser Gly Arg Tyr Phe Ala Leu Asp Asp Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

```
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 15
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 15
caggtgcagc tggtggaatc aggcggcaca ctggtgcagc tggcggtag  cctgagactg      60 agctgcgctg ctagtggctt cacctttaac aactactgga tgacctgggt taggcaggcc     120
cctggtaaag gcctcgagtg ggtggcaaat atcaagaagg acggtagcga agagtactac     180
gtggactcag tcagaggccg gttcactatc tctagggata cgctaagaa tagcctgttc     240 ctgcagatga actcactgag gcccgaggat accgccgtct acttctgtgc taccgtcaga     300
tcaggccgct acttcgccct ggacgactgg ggtcaaggca cactggtcac cgtgtctagc     360
gctagcacta agggcccaag tgtgtttccc ctggcccca gcagcaagtc tacttccggc      420
ggaactgctg ccctgggttg cctggtgaag gactacttcc ccgagcccgt gacagtgtcc     480
tggaactctg ggctctgac ttccggcgtg cacaccttcc ccgccgtgct gcagagcagc      540
ggcctgtaca gcctgagcag cgtggtgaca gtgccctcca gctctctggg aacccagacc     600
tatatctgca acgtgaacca caagcccagc aacaccaagg tggacaagag agtggagccc     660
aagagctgcg acaagaccca cacctgcccc cctgcccag ctccagaact gctgggaggg      720
ccttccgtgt tcctgttccc ccccaagccc aaggacaccc tgatgatcag caggaccccc     780
gaggtgacct gcgtggtggt ggacgtgtcc cacgaggacc cagaggtgaa gttcaactgg     840
tacgtggacg gcgtggaggt gcacaacgcc aagaccaagc cagagagga gcagtacaac      900 agcacctaca gggtggtgtc cgtgctgacc gtgctgcacc aggactggct gaacggcaaa     960
gaatacaagt gcaaagtctc caacaaggcc ctgccagccc caatcgaaaa gacaatcagc    1020
```

```
aaggccaagg gccagccacg ggagccccag gtgtacaccc tgccccccag ccgggaggag    1080
atgaccaaga accaggtgtc cctgacctgt ctggtgaagg gcttctaccc cagcgatatc    1140
gccgtggagt gggagagcaa cggccagccc gagaacaact acaagaccac ccccccagtg    1200
ctggacagcg acggcagctt cttcctgtac agcaagctga ccgtggacaa gtccaggtgg    1260
cagcagggca acgtgttcag ctgcagcgtg atgcacgagg ccctgcacaa ccactacacc    1320
cagaagtccc tgagcctgag ccccggcaag                                    1350
```

```
<210> SEQ ID NO 16
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Gly Gly Asp Asn Ile Gly Ser Arg Pro Val His
1               5                   10

<210> SEQ ID NO 17
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Asp Asp Ser Asn Arg Pro Ser
1               5

<210> SEQ ID NO 18
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Gln Val Trp Ser Ser Ser Thr Asp His Pro
1               5                   10

<210> SEQ ID NO 19
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Asp Asn Ile Gly Ser Arg Pro
1               5

<210> SEQ ID NO 20
<211> LENGTH: 3
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 20

Asp Asp Ser
1

<210> SEQ ID NO 21
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Trp Ser Ser Ser Thr Asp His
1               5

<210> SEQ ID NO 22
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Gln Ser Val Leu Thr Gln Pro Pro Ser Val Ser Val Ala Pro Gly Lys
1               5                   10                  15

Thr Ala Arg Ile Thr Cys Gly Gly Asp Asn Ile Gly Ser Arg Pro Val
            20                  25                  30

His Trp Tyr Gln Gln Lys Pro Gly Gln Ala Pro Ile Leu Val Val Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Ser Ser Ser Thr Asp His
                85                  90                  95

Pro Phe Gly Gly Gly Thr Lys Val Thr Val Leu
            100                 105

<210> SEQ ID NO 23
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 23
cagtcagtcc tgactcagcc ccctagcgtc agcgtggccc ctggtaaaac cgctagaatc      60
acctgtggcg gcgataatat cggctctagg cccgtgcact ggtatcagca gaagcccggt     120
caagccccta tcctggtggt ctacgacgac tctaatagac ctagcggaat ccccgagcgg     180
tttagcggct ctaattctgg taataccgct accctgacta tctctagggt ggaagccggc     240
gacgaggccg actactactg tcaagtctgg tctagctcta ccgatcaccc cttcggcgga     300
ggcactaagg ttacagtgct g                                               321
```

<210> SEQ ID NO 24
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 24

```
Gln Ser Val Leu Thr Gln Pro Pro Ser Val Ser Val Ala Pro Gly Lys
1               5                   10                  15

Thr Ala Arg Ile Thr Cys Gly Gly Asp Asn Ile Gly Ser Arg Pro Val
            20                  25                  30

His Trp Tyr Gln Gln Lys Pro Gly Gln Ala Pro Ile Leu Val Val Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Ser Ser Ser Thr Asp His
                85                  90                  95

Pro Phe Gly Gly Gly Thr Lys Val Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210
```

<210> SEQ ID NO 25
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 25

| | | |
|---|---|---|
| cagtcagtcc tgactcagcc ccctagcgtc agcgtggccc ctggtaaaac cgctagaatc | 60 |
| acctgtggcg gcgataatat cggctctagg cccgtgcact ggtatcagca gaagcccggt | 120 |
| caagccccta tcctggtggt ctacgacgac tctaatagac tagcggaat ccccgagcgg | 180 |
| tttagcggct ctaattctgg taataccgct accctgacta tctctagggt ggaagccggc | 240 |
| gacgaggccg actactactg tcaagtctgg tctagctcta ccgatcaccc cttcggcgga | 300 |
| ggcactaagg ttacagtgct gggtcaacct aaggctgccc ccagcgtgac cctgttcccc | 360 |

```
cccagcagcg aggagctgca ggccaacaag gccaccctgg tgtgcctgat cagcgacttc    420
tacccaggcg ccgtgaccgt ggcctggaag gccgacagca gccccgtgaa ggccggcgtg    480
gagaccacca ccccagcaa gcagagcaac aacaagtacg ccgccagcag ctacctgagc    540 ctgaccccg agcagtggaa gagccacagg tcctacagct gccaggtgac ccacgagggc    600
agcaccgtgg aaaagaccgt ggccccaacc gagtgcagc                           639
```

```
<210> SEQ ID NO 26
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Asn Tyr Trp Met Thr
1               5

<210> SEQ ID NO 27
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Asn Ile Lys Lys Asp Gly Ser Glu Lys Tyr Tyr Val Asp Ser Val Arg
1               5                   10                  15

Gly

<210> SEQ ID NO 28
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Val Arg Ser Gly Arg Tyr Phe Ala Leu Asp Asp
1               5                   10

<210> SEQ ID NO 29
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Gly Phe Thr Phe Ser Asn Tyr
1               5

<210> SEQ ID NO 30
<211> LENGTH: 6
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 30

Lys Lys Asp Gly Ser Glu
1               5

<210> SEQ ID NO 31
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Val Arg Ser Gly Arg Tyr Phe Ala Leu Asp Asp
1               5                   10

<210> SEQ ID NO 32
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Thr Trp Val Arg Gln Ala Pro Gly Lys Gly Leu Glu Trp Val
        35                  40                  45

Ala Asn Ile Lys Lys Asp Gly Ser Glu Lys Tyr Tyr Val Asp Ser Val
    50                  55                  60

Arg Gly Arg Phe Thr Ile Ser Arg Asp Asn Ala Lys Asn Ser Leu Phe
65                  70                  75                  80

Leu Gln Met Asn Ser Leu Arg Pro Glu Asp Thr Ala Val Tyr Phe Cys
                85                  90                  95

Ala Thr Val Arg Ser Gly Arg Tyr Phe Ala Leu Asp Asp Trp Gly Gln
            100                 105                 110

Gly Thr Leu Val Thr Val Ser Ser
        115                 120

<210> SEQ ID NO 33
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 33
caggtgcagc tggtggaatc aggcggcaca ctggtgcagc ctggcggtag cctgagactg     60
agctgcgctg ctagtggctt caccttctct aactactgga tgacctgggt caggcaggcc    120
cctggtaaag gcctcgagtg gtggcaaat atcaagaagg acggtagcga agaagtactac    180 gtggactcag tcagaggccg gttcactatc tctagggata cgctaagaa tagcctgttc    240
```

```
ctgcagatga actcactgag gcccgaggat accgccgtct acttctgtgc taccgtcaga    300
tcaggccgct acttcgccct ggacgactgg ggtcaaggca cactggtcac cgtgtctagc    360
```

<210> SEQ ID NO 34
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

```
Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Thr Trp Val Arg Gln Ala Pro Gly Lys Gly Leu Glu Trp Val
        35                  40                  45

Ala Asn Ile Lys Lys Asp Gly Ser Glu Lys Tyr Tyr Val Asp Ser Val
    50                  55                  60

Arg Gly Arg Phe Thr Ile Ser Arg Asp Asn Ala Lys Asn Ser Leu Phe
65                  70                  75                  80

Leu Gln Met Asn Ser Leu Arg Pro Glu Asp Thr Ala Val Tyr Phe Cys
                85                  90                  95

Ala Thr Val Arg Ser Gly Arg Tyr Phe Ala Leu Asp Asp Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

```
Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 35
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 35
caggtgcagc tggtggaatc aggcggcaca ctggtgcagc ctggcggtag cctgagactg      60
agctgcgctg ctagtggctt caccttctct aactactgga tgacctgggt caggcaggcc     120
cctggtaaag gctcgagtg gtggcaaat atcaagaagg acggtagcga gaagtactac      180
gtggactcag tcagaggccg gttcactatc tctagggata cgctaagaa tagcctgttc      240 ctgcagatga actcactgag gcccgaggat accgccgtct acttctgtgc taccgtcaga     300
tcaggccgct acttcgccct ggacgactgg ggtcaaggca ctggtcac cgtgtctagc      360 gctagcacta agggcccaag tgtgtttccc ctggccccca gcagcaagtc tacttccggc     420
ggaactgctg ccctgggttg cctggtgaag gactacttcc ccgagcccgt gacagtgtcc     480
tggaactctg ggctctgac ttccggcgtg cacaccttcc ccgccgtgct gcagagcagc     540
ggcctgtaca gcctgagcag cgtggtgaca gtgccctcca gctctctggg aacccagacc     600
tatatctgca acgtgaacca caagcccagc aacaccaagg tggacaagag agtggagccc     660
aagagctgcg acaagaccca cacctgcccc cctgcccag ctccagaact gctgggaggg     720
ccttccgtgt tcctgttccc ccccaagccc aaggacaccc tgatgatcag caggaccccc     780
gaggtgacct gcgtggtggt ggacgtgtcc cacgaggacc cagaggtgaa gttcaactgg     840
tacgtggacg gcgtggaggt gcacaacgcc aagaccaagc cagagagga gcagtacaac     900 agcacctaca gggtggtgtc cgtgctgacc gtgctgcacc aggactggct gaacggcaaa     960
gaatacaagt gcaaagtctc caacaaggcc ctgccagccc caatcgaaaa gacaatcagc    1020
aaggccaagg gccagccacg ggagcccag gtgtacaccc tgcccccag ccggaggag    1080 atgaccaaga accaggtgtc cctgacctgt ctggtgaagg gcttctaccc cagcgatatc    1140
gccgtggagt gggagagcaa cggccagccc gagaacaact acaagaccac ccccccagtg    1200
ctggacagcg acggcagctt cttcctgtac agcaagctga ccgtggacaa gtccaggtgg    1260
cagcagggca acgtgttcag ctgcagcgtg atgcacgagg ccctgcacaa ccactacacc    1320
```
cagaagtccc tgagcctgag ccccggcaag    1350

<210> SEQ ID NO 36
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Gly Gly Asp Asn Ile Gly Ser Arg Pro Val His
1               5                   10

<210> SEQ ID NO 37
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Asp Asp Ser Asn Arg Pro Ser
1               5

<210> SEQ ID NO 38
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Gln Val Trp Ser Ser Ser Thr Asp His Pro
1               5                   10

<210> SEQ ID NO 39
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Asp Asn Ile Gly Ser Arg Pro
1               5

<210> SEQ ID NO 40
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Asp Asp Ser
1

<210> SEQ ID NO 41
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Trp Ser Ser Ser Thr Asp His
1               5

<210> SEQ ID NO 42
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Gln Ser Val Leu Thr Gln Pro Pro Ser Val Ser Val Ala Pro Gly Lys
1               5                   10                  15

Thr Ala Arg Ile Thr Cys Gly Gly Asp Asn Ile Gly Ser Arg Pro Val
            20                  25                  30

His Trp Tyr Gln Gln Lys Pro Gly Gln Ala Pro Ile Leu Val Val Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Ser Ser Thr Asp His
                85                  90                  95

Pro Phe Gly Gly Gly Thr Lys Val Thr Val Leu
            100                 105

<210> SEQ ID NO 43
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 43
cagtcagtcc tgactcagcc ccctagcgtc agcgtggccc ctggtaaaac cgctagaatc      60
acctgtggcg gcgataatat cggctctagg cccgtgcact ggtatcagca gaagcccggt     120
caagccccta tcctggtggt ctacgacgac tctaatagac tagcggaat ccccgagcgg     180 tttagcggct ctaattctgg taataccgct accctgacta tctctagggt ggaagccggc    240
gacgaggccg actactactg tcaagtctgg tctagctcta ccgatcaccc cttcggcgga    300
ggcactaagg ttacagtgct g                                               321

<210> SEQ ID NO 44
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 44

Gln Ser Val Leu Thr Gln Pro Pro Ser Val Ser Val Ala Pro Gly Lys
1               5                   10                  15

Thr Ala Arg Ile Thr Cys Gly Gly Asp Asn Ile Gly Ser Arg Pro Val
            20                  25                  30

His Trp Tyr Gln Gln Lys Pro Gly Gln Ala Pro Ile Leu Val Val Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Ser Ser Ser Thr Asp His
                85                  90                  95

Pro Phe Gly Gly Gly Thr Lys Val Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 45
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 45
cagtcagtcc tgactcagcc ccctagcgtc agcgtggccc ctggtaaaac cgctagaatc      60
acctgtggcg gcgataatat cggctctagg cccgtgcact ggtatcagca gaagcccggt     120
caagccccta tcctggtggt ctacgacgac tctaatagac ctagcggaat ccccgagcgg     180
tttagcggct ctaattctgg taataccgct accctgacta tctctagggt ggaagcggc     240 gacgaggccg actactactg tcaagtctgg tctagctcta ccgatcaccc cttcggcgga     300
ggcactaagg ttacagtgct gggtcaacct aaggctgccc cagcgtgac cctgttcccc      360 cccagcagcg aggagctgca ggccaacaag gccaccctgg tgtgcctgat cagcgacttc     420
tacccaggcg ccgtgaccgt ggcctggaag gccgacagca gccccgtgaa ggccggcgtg     480
gagaccacca ccccccagca agcagagcaac aacaagtacg ccgccagcag ctacctgagc     540
ctgacccccg agcagtggaa gagccacagg tcctacagct gccaggtgac ccacgagggc     600
agcaccgtgg aaaagaccgt ggccccaacc gagtgcagc                              639

```
<210> SEQ ID NO 46
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Asn Tyr Trp Met Thr
1               5

<210> SEQ ID NO 47
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Asn Ile Lys Lys Asp Gly Ser Glu Lys Tyr Tyr Val Asp Ser Val Arg
1               5                   10                  15

Gly

<210> SEQ ID NO 48
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Val Arg Ser Gly Arg Tyr Phe Ala Leu Asp Asp
1               5                   10

<210> SEQ ID NO 49
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Gly Phe Thr Phe Lys Asn Tyr
1               5

<210> SEQ ID NO 50
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Lys Lys Asp Gly Ser Glu
1               5
```

```
<210> SEQ ID NO 51
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Val Arg Ser Gly Arg Tyr Phe Ala Leu Asp Asp
1               5                   10

<210> SEQ ID NO 52
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Thr Phe Lys Asn Tyr
            20                  25                  30

Trp Met Thr Trp Val Arg Gln Ala Pro Gly Lys Gly Leu Glu Trp Val
        35                  40                  45

Ala Asn Ile Lys Lys Asp Gly Ser Glu Lys Tyr Tyr Val Asp Ser Val
    50                  55                  60

Arg Gly Arg Phe Thr Ile Ser Arg Asp Asn Ala Lys Asn Ser Leu Phe
65                  70                  75                  80

Leu Gln Met Asn Ser Leu Arg Pro Glu Asp Thr Ala Val Tyr Phe Cys
                85                  90                  95

Ala Thr Val Arg Ser Gly Arg Tyr Phe Ala Leu Asp Asp Trp Gly Gln
            100                 105                 110

Gly Thr Leu Val Thr Val Ser Ser
        115                 120

<210> SEQ ID NO 53
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 53
caggtgcagc tggtggaatc aggcggcaca ctggtgcagc ctggcggtag cctgagactg      60
agctgcgctg ctagtggctt cacctttaag aactactgga tgacctgggt caggcaggcc     120
cctggtaaag gcctcgagtg gtggcaaat atcaagaagg acggtagcga gaagtactac     180
gtggactcag tcagaggccg gttcactatc tctagggata acgctaagaa tagcctgttc     240
ctgcagatga actcactgag gcccgaggat accgccgtct acttctgtgc taccgtcaga     300
tcaggccgct acttcgccct ggacgactgg ggtcaaggca cactggtcac cgtgtctagc     360

<210> SEQ ID NO 54
<211> LENGTH: 450
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 54

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Thr Phe Lys Asn Tyr
            20                  25                  30

Trp Met Thr Trp Val Arg Gln Ala Pro Gly Lys Gly Leu Glu Trp Val
        35                  40                  45

Ala Asn Ile Lys Lys Asp Gly Ser Glu Lys Tyr Tyr Val Asp Ser Val
    50                  55                  60

Arg Gly Arg Phe Thr Ile Ser Arg Asp Asn Ala Lys Asn Ser Leu Phe
65                  70                  75                  80

Leu Gln Met Asn Ser Leu Arg Pro Glu Asp Thr Ala Val Tyr Phe Cys
                85                  90                  95

Ala Thr Val Arg Ser Gly Arg Tyr Phe Ala Leu Asp Asp Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380
```

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 55
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 55
caggtgcagc tggtggaatc aggcggcaca ctggtgcagc ctggcggtag cctgagactg      60
agctgcgctg ctagtggctt cacctttaag aactactgga tgacctgggt caggcaggcc    120
cctggtaaag gcctcgagtg ggtggcaaat atcaagaagg acggtagcga aagtactac      180 gtggactcag tcagaggccg gttcactatc tctagggata cgctaagaa tagcctgttc     240 ctgcagatga actcactgag gcccgaggat accgccgtct acttctgtgc taccgtcaga    300
tcaggccgct acttcgccct ggacgactgg ggtcaaggca cactggtcac cgtgtctagc    360
gctagcacta agggcccaag tgtgtttccc ctggccccca gcagcaagtc tacttccggc    420
ggaactgctg ccctgggttg cctggtgaag gactacttcc ccgagcccgt gacagtgtcc    480
tggaactctg gggctctgac ttccggcgtg cacaccttcc ccgccgtgct gcagagcagc    540
ggcctgtaca gcctgagcag cgtggtgaca gtgcctcca gctctctggg aacccagacc    600
tatatctgca acgtgaacca caagcccagc aacaccaagg tggacaagag agtggagccc    660
aagagctgcg acaagaccca cacctgcccc cctgcccag ctccagaact gctgggaggg      720
ccttccgtgt tcctgttccc ccccaagccc aaggacaccc tgatgatcag caggaccccc    780
gaggtgacct gcgtggtggt ggacgtgtcc acgaggacc agaggtgaa gttcaactgg       840 tacgtggacg gcgtggaggt gcacaacgcc aagaccaagc ccagagagga gcagtacaac    900
agcacctaca gggtggtgtc cgtgctgacc gtgctgcacc aggactggct gaacggcaaa    960
gaatacaagt gcaaagtctc caacaaggcc ctgccagccc caatcgaaaa gacaatcagc   1020
aaggccaagg gccagccacg ggagcccag gtgtacaccc tgccccccag ccggaggag      1080 atgaccaaga accaggtgtc cctgacctgt ctggtgaagg gcttctaccc cagcgatatc    1140
gccgtggagt gggagagcaa cggccagccc gagaacaact acaagaccac cccccagtg     1200 ctggacagcg acggcagctt cttcctgtac agcaagctga ccgtggacaa gtccaggtgg   1260
cagcagggca acgtgttcag ctgcagcgtg atgcacgagg ccctgcacaa ccactacacc   1320
cagaagtccc tgagcctgag ccccggcaag                                    1350

<210> SEQ ID NO 56
<211> LENGTH: 11
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 56

Gly Gly Asp Asn Ile Gly Ser Arg Pro Val His
1               5                   10

<210> SEQ ID NO 57
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Asp Asp Ser Asn Arg Pro Ser
1               5

<210> SEQ ID NO 58
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Gln Val Trp Ser Ser Ser Thr Asp His Pro
1               5                   10

<210> SEQ ID NO 59
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Asp Asn Ile Gly Ser Arg Pro
1               5

<210> SEQ ID NO 60
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Asp Asp Ser
1

<210> SEQ ID NO 61
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 61

Trp Ser Ser Ser Thr Asp His
1               5

<210> SEQ ID NO 62
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Gln Ser Val Leu Thr Gln Pro Pro Ser Val Ser Val Ala Pro Gly Lys
1               5                   10                  15

Thr Ala Arg Ile Thr Cys Gly Gly Asp Asn Ile Gly Ser Arg Pro Val
            20                  25                  30

His Trp Tyr Gln Gln Lys Pro Gly Gln Ala Pro Ile Leu Val Val Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Ser Ser Thr Asp His
                85                  90                  95

Pro Phe Gly Gly Gly Thr Lys Val Thr Val Leu
            100                 105

<210> SEQ ID NO 63
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 63
cagtcagtcc tgactcagcc ccctagcgtc agcgtggccc ctggtaaaac cgctagaatc      60
acctgtggcg gcgataatat cggctctagg cccgtgcact ggtatcagca gaagcccggt     120
caagccccta tcctggtggt ctacgacgac tctaatagac ctagcggaat ccccgagcgg     180
tttagcggct ctaattctgg taataccgct accctgacta tctctagggt ggaagccggc     240
gacgaggccg actactactg tcaagtctgg tctagctcta ccgatcaccc cttcggcgga     300
ggcactaagg ttacagtgct g                                               321

<210> SEQ ID NO 64
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Gln Ser Val Leu Thr Gln Pro Pro Ser Val Ser Val Ala Pro Gly Lys
1               5                   10                  15

Thr Ala Arg Ile Thr Cys Gly Gly Asp Asn Ile Gly Ser Arg Pro Val
            20                  25                  30

-continued

His Trp Tyr Gln Gln Lys Pro Gly Gln Ala Pro Ile Leu Val Val Tyr
             35                  40                  45

Asp Asp Ser Asn Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Ser Ser Thr Asp His
                 85                  90                  95

Pro Phe Gly Gly Gly Thr Lys Val Thr Val Leu Gly Gln Pro Lys Ala
                100                 105                 110

Ala Pro Ser Val Thr Leu Phe Pro Pro Ser Ser Glu Glu Leu Gln Ala
            115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 65
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 65
cagtcagtcc tgactcagcc ccctagcgtc agcgtggccc ctggtaaaac cgctagaatc      60
acctgtggcg gcgataatat cggctctagg cccgtgcact ggtatcagca gaagcccggt     120
caagccccta tcctggtggt ctacgacgac tctaatagac ctagcggaat ccccgagcgg     180
tttagcggct ctaattctgg taataccgct accctgacta tctctagggt ggaagccggc     240
gacgaggccg actactactg tcaagtctgg tctagctcta ccgatcaccc cttcggcgga     300
ggcactaagg ttacagtgct gggtcaacct aaggctgccc ccagcgtgac cctgttcccc     360
cccagcagcg aggagctgca ggccaacaag gccaccctgg tgtgcctgat cagcgacttc     420
tacccaggcg ccgtgaccgt ggcctggaag gccgacagca gccccgtgaa ggccggcgtg     480
gagaccacca cccccagcaa gcagagcaac aacaagtacg ccgccagcag ctacctgagc     540
ctgacccccg agcagtggaa gagccacagg tcctacagct gccaggtgac ccacgagggc     600
agcaccgtgg aaaagaccgt ggccccaacc gagtgcagc                            639

<210> SEQ ID NO 66
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 66

Asn Tyr Trp Met Thr
1               5

<210> SEQ ID NO 67
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Asn Ile Lys Lys Asp Gly Ser Glu Lys Tyr Tyr Val Asp Ser Val Arg
1               5                   10                  15

Gly

<210> SEQ ID NO 68
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Val Arg Ser Gly Arg Tyr Phe Ala Leu Asp Asp
1               5                   10

<210> SEQ ID NO 69
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Gly Phe Thr Phe Gln Asn Tyr
1               5

<210> SEQ ID NO 70
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Lys Lys Asp Gly Ser Glu
1               5

<210> SEQ ID NO 71
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Val Arg Ser Gly Arg Tyr Phe Ala Leu Asp Asp
1               5                   10

<210> SEQ ID NO 72
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Gln Val Gln Leu Val Glu Ser Gly Gly Thr Leu Val Gln Pro Gly Gly
1               5                   10                  15

Ser Leu Arg Leu Ser Cys Ala Ala Ser Gly Phe Thr Phe Gln Asn Tyr
                20                  25                  30

Trp Met Thr Trp Val Arg Gln Ala Pro Gly Lys Gly Leu Glu Trp Val
            35                  40                  45

Ala Asn Ile Lys Lys Asp Gly Ser Glu Lys Tyr Tyr Val Asp Ser Val
        50                  55                  60

Arg Gly Arg Phe Thr Ile Ser Arg Asp Asn Ala Lys Asn Ser Leu Phe
65                  70                  75                  80

Leu Gln Met Asn Ser Leu Arg Pro Glu Asp Thr Ala Val Tyr Phe Cys
                85                  90                  95

Ala Thr Val Arg Ser Gly Arg Tyr Phe Ala Leu Asp Asp Trp Gly Gln
            100                 105                 110

Gly Thr Leu Val Thr Val Ser Ser
            115                 120

<210> SEQ ID NO 73
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 73
caggtgcagc tggtggaatc aggcggcaca ctggtgcagc ctggcggtag cctgagactg     60
agctgcgccg ctagtggatt cacctttcag aactactgga tgacctgggt cagacaggcc    120
cctggtaaag gcctcgagtg gtggcaaat  atcaagaagg acggtagcga aagtactac    180 gtggactcag tcagaggccg gttcactatc tctagggata acgctaagaa tagcctgttc    240
ctgcagatga actcactgag gcccgaggat accgccgtct acttctgtgc taccgtcaga    300
tcaggccgct acttcgccct ggacgactgg ggtcaaggca cactggtcac cgtgtctagc    360

<210> SEQ ID NO 74
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Gln Val Gln Leu Val Glu Ser Gly Gly Thr Leu Val Gln Pro Gly Gly
1               5                   10                  15

```
Ser Leu Arg Leu Ser Cys Ala Ala Ser Gly Phe Thr Phe Gln Asn Tyr
         20                  25                  30

Trp Met Thr Trp Val Arg Gln Ala Pro Gly Lys Gly Leu Glu Trp Val
         35                  40                  45

Ala Asn Ile Lys Lys Asp Gly Ser Glu Lys Tyr Tyr Val Asp Ser Val
     50                  55                  60

Arg Gly Arg Phe Thr Ile Ser Arg Asp Asn Ala Lys Asn Ser Leu Phe
65                   70                  75                  80

Leu Gln Met Asn Ser Leu Arg Pro Glu Asp Thr Ala Val Tyr Phe Cys
                 85                  90                  95

Ala Thr Val Arg Ser Gly Arg Tyr Phe Ala Leu Asp Asp Trp Gly Gln
             100                 105                 110

Gly Thr Leu Val Thr Val Ser Ser Ala Ser Thr Lys Gly Pro Ser Val
         115                 120                 125

Phe Pro Leu Ala Pro Ser Ser Lys Ser Thr Ser Gly Gly Thr Ala Ala
     130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
             180                 185                 190

Ser Ser Ser Leu Gly Thr Gln Thr Tyr Ile Cys Asn Val Asn His Lys
         195                 200                 205

Pro Ser Asn Thr Lys Val Asp Lys Arg Val Glu Pro Lys Ser Cys Asp
     210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                 245                 250                 255

Ser Arg Thr Pro Glu Val Thr Cys Val Val Val Asp Val Ser His Glu
             260                 265                 270

Asp Pro Glu Val Lys Phe Asn Trp Tyr Val Asp Gly Val Glu Val His
         275                 280                 285

Asn Ala Lys Thr Lys Pro Arg Glu Glu Gln Tyr Asn Ser Thr Tyr Arg
     290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                 325                 330                 335

Lys Thr Ile Ser Lys Ala Lys Gly Gln Pro Arg Glu Pro Gln Val Tyr
             340                 345                 350

Thr Leu Pro Pro Ser Arg Glu Glu Met Thr Lys Asn Gln Val Ser Leu
         355                 360                 365

Thr Cys Leu Val Lys Gly Phe Tyr Pro Ser Asp Ile Ala Val Glu Trp
     370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                 405                 410                 415

Lys Ser Arg Trp Gln Gln Gly Asn Val Phe Ser Cys Ser Val Met His
             420                 425                 430
```

Glu Ala Leu His Asn His Tyr Thr Gln Lys Ser Leu Ser Leu Ser Pro
            435                 440                 445

Gly Lys
    450

<210> SEQ ID NO 75
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 75
caggtgcagc tggtggaatc aggcggcaca ctggtgcagc ctggcggtag cctgagactg      60
agctgcgccg ctagtggatt cacctttcag aactactgga tgacctgggt cagacaggcc     120
cctggtaaag cctcgagtg gtggcaaat atcaagaagg acggtagcga aagtactac        180 gtggactcag tcagaggccg gttcactatc tctaggata acgctaagaa tagcctgttc      240
ctgcagatga actcactgag gcccgaggat accgccgtct acttctgtgc taccgtcaga     300
tcaggccgct acttcgccct ggacgactgg ggtcaaggca cactggtcac cgtgtctagc     360
gctagcacta agggcccaag tgtgtttccc ctggcccca gcagcaagtc tacttccggc      420
ggaactgctg ccctggggtg cctggtgaag gactacttcc ccgagcccgt gacagtgtcc     480
tggaactctg ggctctgac ttccggcgtg cacaccttcc cgccgtgct gcagagcagc       540 ggcctgtaca gcctgagcag cgtggtgaca gtgcctcca gctctctggg aacccagacc      600
tatatctgca acgtgaacca caagcccagc aacaccaagg tggacaagag agtggagccc     660
aagagctgcg acaagaccca cacctgcccc cctgcccag ctccagaact gctgggaggg      720
ccttccgtgt tcctgttccc ccccaagccc aaggacaccc tgatgatcag caggaccccc    780
gaggtgacct gctggtggt ggacgtgtcc cacgaggacc cagaggtgaa gttcaactgg      840
tacgtggacg gcgtggaggt gcacaacgcc aagaccaagc ccagagagga gcagtacaac    900
agcacctaca gggtggtgtc cgtgctgacc gtgctgcacc aggactggct gaacggcaaa    960
gaatacaagt gcaaagtctc caacaaggcc ctgccagccc caatcgaaaa gacaatcagc   1020
aaggccaagg gccagccacg ggagcccag gtgtacaccc tgccccccag ccggaggag     1080 atgaccaaga accaggtgtc cctgacctgt ctggtgaagg gcttctaccc cagcgatatc    1140
gccgtggagt gggagagcaa cggccagccc gagaacaact acaagaccac cccccagtg     1200 ctggacagcg acggcagctt cttcctgtac agcaagctga ccgtggacaa gtccaggtgg    1260
cagcagggca acgtgttcag ctgcagcgtg atgcacgagg ccctgcacaa ccactacacc    1320
cagaagtccc tgagcctgag ccccggcaag                                      1350

<210> SEQ ID NO 76
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Gly Gly Asp Asn Ile Gly Ser Arg Pro Val His
1               5                   10

```
<210> SEQ ID NO 77
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Asp Asp Ser Asn Arg Pro Ser
1               5

<210> SEQ ID NO 78
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Gln Val Trp Ser Ser Ser Thr Asp His Pro
1               5                   10

<210> SEQ ID NO 79
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Asp Asn Ile Gly Ser Arg Pro
1               5

<210> SEQ ID NO 80
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Asp Asp Ser
1

<210> SEQ ID NO 81
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Trp Ser Ser Ser Thr Asp His
1               5

<210> SEQ ID NO 82
<211> LENGTH: 107
<212> TYPE: PRT
```

<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 82

Gln Ser Val Leu Thr Gln Pro Pro Ser Val Ser Val Ala Pro Gly Lys
1               5                   10                  15

Thr Ala Arg Ile Thr Cys Gly Gly Asp Asn Ile Gly Ser Arg Pro Val
            20                  25                  30

His Trp Tyr Gln Gln Lys Pro Gly Gln Ala Pro Ile Leu Val Val Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Ser Ser Thr Asp His
                85                  90                  95

Pro Phe Gly Gly Gly Thr Lys Val Thr Val Leu
            100                 105

<210> SEQ ID NO 83
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 83
cagtcagtcc tgactcagcc ccctagcgtc agcgtggccc ctggtaaaac cgctagaatc      60
acctgtggcg gcgataatat cggctctagg cccgtgcact ggtatcagca gaagcccggt     120
caagccccta tcctggtggt ctacgacgac tctaatagac ctagcggaat ccccgagcgg     180
tttagcggct ctaattctgg taataccgct accctgacta tctctagggt ggaagccggc     240
gacgaggccg actactactg tcaagtctgg tctagctcta ccgatcaccc cttcggcgga     300
ggcactaagg ttacagtgct g                                              321

<210> SEQ ID NO 84
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 84

Gln Ser Val Leu Thr Gln Pro Pro Ser Val Ser Val Ala Pro Gly Lys
1               5                   10                  15

Thr Ala Arg Ile Thr Cys Gly Gly Asp Asn Ile Gly Ser Arg Pro Val
            20                  25                  30

His Trp Tyr Gln Gln Lys Pro Gly Gln Ala Pro Ile Leu Val Val Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

```
Asp Glu Ala Asp Tyr Tyr Cys Gln Val Trp Ser Ser Thr Asp His
                85                  90                  95

Pro Phe Gly Gly Gly Thr Lys Val Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210
```

<210> SEQ ID NO 85
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 85

```
cagtcagtcc tgactcagcc ccctagcgtc agcgtggccc tggtaaaac cgctagaatc        60 acctgtggcg gcgataatat cggctctagg cccgtgcact ggtatcagca gaagcccggt       120
caagccccta tcctggtggt ctacgacgac tctaatagac ctagcggaat ccccgagcgg       180
tttagcggct ctaattctgg taataccgct accctgacta tctctagggt ggaagccggc       240
gacgaggccg actactactg tcaagtctgg tctagctcta ccgatcaccc cttcggcgga       300
ggcactaagg ttacagtgct gggtcaacct aaggctgccc ccagcgtgac cctgttcccc       360
cccagcagcg aggagctgca ggccaacaag gccaccctgg tgtgcctgat cagcgacttc       420
tacccaggcg ccgtgaccgt ggcctggaag gccgacagca gccccgtgaa ggccggcgtg       480
gagaccacca ccccccagca acagagcaac aacaagtacg ccgccagcag ctacctgagc       540 ctgaccccccg agcagtggaa gagccacagg tcctacagct gccaggtgac ccacgagggc       600
agcaccgtgg aaaagaccgt ggccccaacc gagtgcagc                              639
```

<210> SEQ ID NO 86
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

```
Asn Tyr Trp Met Thr
1               5
```

<210> SEQ ID NO 87

```
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Asn Ile Lys Lys Asp Gly Ser Glu Lys Tyr Tyr Val Asp Ser Val Arg
1               5                   10                  15

Gly

<210> SEQ ID NO 88
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Val Arg Ser Gly Arg Tyr Phe Ala Leu Asp Asp
1               5                   10

<210> SEQ ID NO 89
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Gly Phe Thr Phe Asn Asn Tyr
1               5

<210> SEQ ID NO 90
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Lys Lys Asp Gly Ser Glu
1               5

<210> SEQ ID NO 91
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Val Arg Ser Gly Arg Tyr Phe Ala Leu Asp Asp
1               5                   10

<210> SEQ ID NO 92
<211> LENGTH: 120
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92
```

Gln Val Gln Leu Gln Glu Ser Gly Pro Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Trp Met Thr Trp Val Arg Gln Ala Pro Gly Lys Gly Leu Glu Trp Val
        35                  40                  45

Ala Asn Ile Lys Lys Asp Gly Ser Glu Lys Tyr Tyr Val Asp Ser Val
    50                  55                  60

Arg Gly Arg Phe Thr Ile Ser Arg Asp Asn Ala Lys Asn Ser Leu Phe
65                  70                  75                  80

Leu Gln Met Asn Ser Leu Arg Pro Glu Asp Thr Ala Val Tyr Phe Cys
                85                  90                  95

Ala Thr Val Arg Ser Gly Arg Tyr Phe Ala Leu Asp Asp Trp Gly Gln
            100                 105                 110

Gly Thr Leu Val Thr Val Ser Ser
        115                 120

```
<210> SEQ ID NO 93
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 93
caggtgcagc tgcaggaatc aggcccagga ctggtgcagc ctggcggtag cctgagactg    60
agctgcgctg ctagtggctt cacctttaac aactactgga tgacctgggt ccgccaggcc   120
cctggcaaag gcctggagtg gtggcaaat atcaagaagg acggtagcga agaagtactac  180 gtggactcag tcagaggccg gttcactatc tctagggata acgctaagaa tagcctgttc   240
ctgcagatga actcactgag gcccgaggat accgccgtct acttctgtgc taccgtcaga   300
tcaggccgct acttcgccct ggacgactgg ggccagggca ccctggtcac cgtgtcttcc   360

<210> SEQ ID NO 94
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94
```

Gln Val Gln Leu Gln Glu Ser Gly Pro Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Trp Met Thr Trp Val Arg Gln Ala Pro Gly Lys Gly Leu Glu Trp Val
        35                  40                  45

Ala Asn Ile Lys Lys Asp Gly Ser Glu Lys Tyr Tyr Val Asp Ser Val
    50                  55                  60

Arg Gly Arg Phe Thr Ile Ser Arg Asp Asn Ala Lys Asn Ser Leu Phe
 65                  70                  75                  80

Leu Gln Met Asn Ser Leu Arg Pro Glu Asp Thr Ala Val Tyr Phe Cys
             85                  90                  95

Ala Thr Val Arg Ser Gly Arg Tyr Phe Ala Leu Asp Asp Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly Lys
450

<210> SEQ ID NO 95
<211> LENGTH: 1350

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 95

```
caggtgcagc tgcaggaatc aggcccagga ctggtgcagc ctggcggtag cctgagactg      60
agctgcgctg ctagtggctt caccttTaac aactactgga tgacctgggt ccgccaggcc     120
cctggcaaag gcctggagtg ggtggcaaat atcaagaagg acggtagcga aagtactac      180
gtggactcag tcagaggccg gttcactatc tctagggata cgctaagaa tagcctgttc      240
ctgcagatga actcactgag gcccgaggat accgccgtct acttctgtgc taccgtcaga     300
tcaggccgct acttcgccct ggacgactgg ggccagggca ccctggtcac cgtgtcttcc     360
gctagcacta agggcccaag tgtgtttccc ctggccccca gcagcaagtc tacttccggc     420
ggaactgctg ccctgggttg cctggtgaag gactacttcc ccgagcccgt gacagtgtcc     480
tggaactctg ggctctgac ttccggcgtg cacaccttcc ccgccgtgct gcagagcagc      540
ggcctgtaca gcctgagcag cgtggtgaca gtgccctcca gctctctggg aacccagacc     600
tatatctgca acgtgaacca caagcccagc aacaccaagg tggacaagag agtggagccc     660
aagagctgcg acaagaccca cacctgcccc cctgcccag ctccagaact gctgggaggg      720
ccttccgtgt tcctgttccc ccccaagccc aaggacaccc tgatgatcag caggaccccc     780
gaggtgacct gcgtggtggt ggacgtgtcc cacgaggacc cagaggtgaa gttcaactgg     840
tacgtggacg gcgtggaggt gcacaacgcc aagaccaagc cagagagga gcagtacaac      900
agcacctaca gggtggtgtc cgtgctgacc gtgctgcacc aggactggct gaacggcaaa     960
gaatacaagt gcaaagtctc caacaaggcc ctgccagccc aatcgaaaa gacaatcagc      1020
aaggccaagg ccagccacg ggagcccag gtgtacaccc tgcccccag ccgggaggag        1080
atgaccaaga accaggtgtc cctgacctgt ctggtgaagg gcttctaccc cagcgatatc    1140
gccgtggagt gggagagcaa cggccagccc gagaacaact acaagaccac ccccccagtg    1200
ctggacagcg acggcagctt cttcctgtac agcaagctga ccgtggacaa gtccaggtgg    1260
cagcagggca acgtgttcag ctgcagcgtg atgcacgagg ccctgcacaa ccactacacc    1320
cagaagtccc tgagcctgag ccccggcaag                                    1350
```

<210> SEQ ID NO 96
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Gly Gly Asp Asn Ile Gly Ser Arg Pro Val His
1               5                   10

<210> SEQ ID NO 97
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

-continued

```
<400> SEQUENCE: 97

Asp Asp Ser Asn Arg Pro Ser
1               5

<210> SEQ ID NO 98
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Gln Val Trp Ser Ser Ser Thr Asp His Pro
1               5                   10

<210> SEQ ID NO 99
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Asp Asn Ile Gly Ser Arg Pro
1               5

<210> SEQ ID NO 100
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Asp Asp Ser
1

<210> SEQ ID NO 101
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Trp Ser Ser Ser Thr Asp His
1               5

<210> SEQ ID NO 102
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 102

Gln Ser Val Leu Thr Gln Pro Pro Ser Val Ser Val Ala Pro Gly Lys
```

```
1               5                   10                  15
Thr Ala Arg Ile Thr Cys Gly Gly Asp Asn Ile Gly Ser Arg Pro Val
            20                  25                  30

His Trp Tyr Gln Gln Lys Pro Gly Gln Ala Pro Ile Leu Val Val Tyr
            35                  40                  45

Asp Asp Ser Asn Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Ser Ser Thr Asp His
                85                  90                  95

Pro Phe Gly Gly Gly Thr Lys Val Thr Val Leu
            100                 105
```

<210> SEQ ID NO 103
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 103

```
cagtcagtcc tgactcagcc ccctagcgtc agcgtggccc ctggtaaaac cgctagaatc    60
acctgtggcg gcgataatat cggctctagg cccgtgcact ggtatcagca gaagcccggt   120
caagccccta tcctggtggt ctacgacgac tctaatagac tagcggaat ccccgagcgg    180
tttagcggct ctaattctgg taataccgct accctgacta tctctagggt ggaagccggc   240
gacgaggccg actactactg tcaagtctgg tctagctcta ccgatcaccc cttcggcgga   300
ggcactaagg ttacagtgct g                                             321
```

<210> SEQ ID NO 104
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 104

```
Gln Ser Val Leu Thr Gln Pro Pro Ser Val Ser Val Ala Pro Gly Lys
1               5                   10                  15

Thr Ala Arg Ile Thr Cys Gly Gly Asp Asn Ile Gly Ser Arg Pro Val
            20                  25                  30

His Trp Tyr Gln Gln Lys Pro Gly Gln Ala Pro Ile Leu Val Val Tyr
            35                  40                  45

Asp Asp Ser Asn Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Ser Ser Thr Asp His
                85                  90                  95

Pro Phe Gly Gly Gly Thr Lys Val Thr Val Leu Gly Gln Pro Lys Ala
            100                 105                 110

Ala Pro Ser Val Thr Leu Phe Pro Pro Ser Ser Glu Glu Leu Gln Ala
        115                 120                 125
```

Asn Lys Ala Thr Leu Val Cys Leu Ile Ser Asp Phe Tyr Pro Gly Ala
            130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 105
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 105
cagtcagtcc tgactcagcc ccctagcgtc agcgtggccc ctggtaaaac cgctagaatc      60
acctgtggcg gcgataatat cggctctagg cccgtgcact ggtatcagca gaagcccggt     120
caagccccta tcctggtggt ctacgacgac tctaatagac ctagcggaat ccccgagcgg     180
tttagcggct ctaattctgg taataccgct accctgacta tctctagggt ggaagccggc     240
gacgaggccg actactactg tcaagtctgg tctagctcta ccgatcaccc cttcggcgga     300
ggcactaagg ttacagtgct gggtcaacct aaggctgccc cagcgtgac cctgttcccc      360 cccagcagcg aggagctgca ggccaacaag gccaccctgg tgtgcctgat cagcgacttc     420
tacccaggcg ccgtgaccgt ggcctggaag gccgacagca gccccgtgaa ggccggcgtg     480
gagaccacca ccccccagcaa gcagagcaac aacaagtacg ccgccagcag ctacctgagc     540
ctgacccccg agcagtggaa gagccacagg tcctacagct gccaggtgac ccacgagggc     600
agcaccgtgg aaaagaccgt ggcccccaacc gagtgcagc                           639

<210> SEQ ID NO 106
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Asn Tyr Trp Met Thr
1               5

<210> SEQ ID NO 107
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Asn Ile Lys Lys Asp Gly Ser Glu Lys Tyr Tyr Val Asp Ser Val Arg
1               5                   10                  15

Gly

<210> SEQ ID NO 108
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Val Arg Ser Gly Arg Tyr Phe Ala Leu Asp Asp
1               5                   10

<210> SEQ ID NO 109
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Gly Phe Thr Phe Asn Asn Tyr
1               5

<210> SEQ ID NO 110
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Lys Lys Asp Gly Ser Glu
1               5

<210> SEQ ID NO 111
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

Val Arg Ser Gly Arg Tyr Phe Ala Leu Asp Asp
1               5                   10

<210> SEQ ID NO 112
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

Gln Val Gln Leu Val Glu Ser Gly Gly Gly Leu Val Gln Pro Gly Gly

```
                1               5                   10                  15
            Ser Leu Arg Leu Ser Cys Ala Ala Ser Gly Phe Thr Phe Asn Asn Tyr
                            20                  25                  30

Trp Met Thr Trp Val Arg Gln Ala Pro Gly Lys Gly Leu Glu Trp Val
                        35                  40                  45

Ala Asn Ile Lys Lys Asp Gly Ser Glu Lys Tyr Tyr Val Asp Ser Val
                    50                  55                  60

Arg Gly Arg Phe Thr Ile Ser Arg Asp Asn Ala Lys Asn Ser Leu Phe
            65                  70                  75                  80

Leu Gln Met Asn Ser Leu Arg Pro Glu Asp Thr Ala Val Tyr Phe Cys
                            85                  90                  95

Ala Thr Val Arg Ser Gly Arg Tyr Phe Ala Leu Asp Asp Trp Gly Gln
                        100                 105                 110

Gly Thr Leu Val Thr Val Ser Ser
                        115                 120

<210> SEQ ID NO 113
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 113
caggtgcagc tggtggaatc aggcggcgga ctggtgcagc ctggcggtag cctgagactg      60
agctgcgctg ctagtggctt cacctttaac aactactgga tgacctgggt taggcaggcc     120
cctggtaaag gcctcgagtg ggtggcaaat atcaagaagg acggtagcga agagtactac     180
gtggactcag tcagaggccg gttcactatc tctagggata cgctaagaa tagcctgttc      240 ctgcagatga actcactgag gcccgaggat accgccgtct acttctgtgc taccgtcaga     300
tcaggccgct acttcgccct ggacgactgg ggtcaaggca cactggtcac cgtgtctagc     360

<210> SEQ ID NO 114
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 114

Gln Val Gln Leu Val Glu Ser Gly Gly Gly Leu Val Gln Pro Gly Gly
            1               5                   10                  15

Ser Leu Arg Leu Ser Cys Ala Ala Ser Gly Phe Thr Phe Asn Asn Tyr
                            20                  25                  30

Trp Met Thr Trp Val Arg Gln Ala Pro Gly Lys Gly Leu Glu Trp Val
                        35                  40                  45

Ala Asn Ile Lys Lys Asp Gly Ser Glu Lys Tyr Tyr Val Asp Ser Val
                    50                  55                  60

Arg Gly Arg Phe Thr Ile Ser Arg Asp Asn Ala Lys Asn Ser Leu Phe
            65                  70                  75                  80

Leu Gln Met Asn Ser Leu Arg Pro Glu Asp Thr Ala Val Tyr Phe Cys
                            85                  90                  95

Ala Thr Val Arg Ser Gly Arg Tyr Phe Ala Leu Asp Asp Trp Gly Gln
                        100                 105                 110
```

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 115
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 115

```
caggtgcagc tggtggaatc aggcggcgga ctggtgcagc tggcggtag cctgagactg    60
agctgcgctg ctagtggctt cacctttaac aactactgga tgacctgggt taggcaggcc   120
cctggtaaag gcctcgagtg ggtggcaaat atcaagaagg acggtagcga gaagtactac   180
gtggactcag tcagaggccg gttcactatc tctagggata cgctaagaa tagcctgttc    240
ctgcagatga actcactgag gcccgaggat accgccgtct acttctgtgc taccgtcaga   300
tcaggccgct acttcgccct ggacgactgg ggtcaaggca cactggtcac cgtgtctagc   360
gctagcacta agggcccaag tgtgtttccc ctggccccca gcagcaagtc tacttccggc   420
ggaactgctg ccctgggttg cctggtgaag gactacttcc ccgagcccgt gacagtgtcc   480
tggaactctg ggctctgac ttccggcgtg cacaccttcc ccgccgtgct gcagagcagc    540
ggcctgtaca gcctgagcag cgtggtgaca gtgccctcca gctctctggg aacccagacc   600
tatatctgca acgtgaacca caagcccagc aacaccaagg tggacaagag agtggagccc   660
aagagctgcg acaagaccca cacctgcccc cctgcccag ctccagaact gctgggaggg    720
ccttccgtgt tcctgttccc ccccaagccc aaggacaccc tgatgatcag caggaccccc   780
gaggtgacct gcgtggtggt ggacgtgtcc cacgaggacc cagaggtgaa gttcaactgg   840
tacgtggacg gcgtggaggt gcacaacgcc aagaccaagc ccagagagga gcagtacaac   900
agcacctaca gggtggtgtc cgtgctgacc gtgctgcacc aggactggct gaacggcaaa   960
gaatacaagt gcaaagtctc caacaaggcc ctgccagccc caatcgaaaa gacaatcagc  1020
aaggccaagg gccagccacg ggagcccag gtgtacaccc tgcccccag ccgggaggag    1080
atgaccaaga accaggtgtc cctgacctgt ctggtgaagg gcttctaccc cagcgatatc  1140
gccgtggagt gggagagcaa cggccagccc gagaacaact acaagaccac cccccagtg   1200
ctggacagcg acggcagctt cttcctgtac agcaagctga ccgtggacaa gtccaggtgg  1260
cagcagggca acgtgttcag ctgcagcgtg atgcacgagg ccctgcacaa ccactacacc  1320
cagaagtccc tgagcctgag ccccggcaag                                   1350
```

<210> SEQ ID NO 116
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic peptide"

<400> SEQUENCE: 116

Gly Gly Asp Asn Ile Gly Ser Arg Pro Val His
1               5                   10

<210> SEQ ID NO 117
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic peptide"

<400> SEQUENCE: 117

Asp Asp Ser Asn Arg Pro Ser
1               5

<210> SEQ ID NO 118
<211> LENGTH: 10

-continued

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Gln Val Trp Ser Ser Ser Thr Asp His Pro
1               5                   10

<210> SEQ ID NO 119
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Asp Asn Ile Gly Ser Arg Pro
1               5

<210> SEQ ID NO 120
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

Asp Asp Ser
1

<210> SEQ ID NO 121
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Trp Ser Ser Ser Thr Asp His
1               5

<210> SEQ ID NO 122
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

Gln Ser Val Leu Thr Gln Pro Pro Ser Val Ser Val Ala Pro Gly Lys
1               5                   10                  15

Thr Ala Arg Ile Thr Cys Gly Gly Asp Asn Ile Gly Ser Arg Pro Val
            20                  25                  30

His Trp Tyr Gln Gln Lys Pro Gly Gln Ala Pro Ile Leu Val Val Tyr
        35                  40                  45

Asp Asp Ser Asn Arg Pro Ser Gly Ile Pro Glu Arg Phe Ser Gly Ser
```

```
            50                  55                  60
Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Ser Ser Thr Asp His
                 85                  90                  95

Pro Phe Gly Gly Gly Thr Lys Val Thr Val Leu
            100                 105
```

<210> SEQ ID NO 123
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 123

```
cagtcagtcc tgactcagcc ccctagcgtc agcgtggccc ctggtaaaac cgctagaatc      60
acctgtggcg gcgataatat cggctctagg cccgtgcact ggtatcagca gaagcccggt     120
caagccccta tcctggtggt ctacgacgac tctaatagac ctagcggaat ccccgagcgg     180
tttagcggct ctaattctgg taataccgct accctgacta tctctagggt ggaagccggc     240
gacgaggccg actactactg tcaagtctgg tctagctcta ccgatcaccc cttcggcgga     300
ggcactaagg ttacagtgct g                                               321
```

<210> SEQ ID NO 124
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 124

```
Gln Ser Val Leu Thr Gln Pro Pro Ser Val Ser Val Ala Pro Gly Lys
  1               5                  10                  15

Thr Ala Arg Ile Thr Cys Gly Gly Asp Asn Ile Gly Ser Arg Pro Val
                 20                  25                  30

His Trp Tyr Gln Gln Lys Pro Gly Gln Ala Pro Ile Leu Val Val Tyr
             35                  40                  45

Asp Asp Ser Asn Arg Pro Ser Gly Ile Pro Glu Arg Phe Ser Gly Ser
         50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Ser Ser Thr Asp His
                 85                  90                  95

Pro Phe Gly Gly Gly Thr Lys Val Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175
```

```
Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210
```

<210> SEQ ID NO 125
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic polynucleotide"

<400> SEQUENCE: 125

| | | |
|---|---|---|
| cagtcagtcc tgactcagcc ccctagcgtc agcgtggccc ctggtaaaac cgctagaatc | 60 |
| acctgtggcg gcgataatat cggctctagg cccgtgcact ggtatcagca gaagcccggt | 120 |
| caagccccta tcctggtggt ctacgacgac tctaatagac ctagcggaat ccccgagcgg | 180 |
| tttagcggct ctaattctgg taataccgct accctgacta tctctagggt ggaagccggc | 240 |
| gacgaggccg actactactg tcaagtctgg tctagctcta ccgatcaccc cttcggcgga | 300 |
| ggcactaagg ttacagtgct gggtcaacct aaggctgccc ccagcgtgac cctgttcccc | 360 |
| cccagcagcg aggagctgca ggccaacaag gccaccctgg tgtgcctgat cagcgacttc | 420 |
| tacccaggcg ccgtgaccgt ggcctggaag gccgacagca gccccgtgaa ggccggcgtg | 480 |
| gagaccacca cccccagcaa gcagagcaac aacaagtacg ccgccagcag ctacctgagc | 540 |
| ctgaccccg agcagtggaa gagccacagg tcctacagct gccaggtgac ccacgagggc | 600 |
| agcaccgtgg aaaagaccgt ggccccaacc gagtgcagc | 639 |

<210> SEQ ID NO 126
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic peptide"

<400> SEQUENCE: 126

```
Arg Asp Tyr Trp Thr
1               5
```

<210> SEQ ID NO 127
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic peptide"

<400> SEQUENCE: 127

```
Asn Ile Tyr Tyr Ser Gly Ser Thr Asn Tyr Asn Pro Ser Leu Lys Ser
1               5                   10                  15
```

<210> SEQ ID NO 128
<211> LENGTH: 16
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 128

Val Pro Gly Cys Ser Ser Thr Ser Cys Ile Asp Gly Trp Phe Asp Pro
1               5                   10                  15

<210> SEQ ID NO 129
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 129

Gly Gly Ser Ile Ser Arg Asp
1               5

<210> SEQ ID NO 130
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 130

Tyr Tyr Ser Gly Ser
1               5

<210> SEQ ID NO 131
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 131

Val Pro Gly Cys Ser Ser Thr Ser Cys Ile Asp Gly Trp Phe Asp Pro
1               5                   10                  15

<210> SEQ ID NO 132
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 132

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Arg Asp
                20                  25                  30

Tyr Trp Thr Trp Val Arg Gln Pro Pro Gly Glu Gly Leu Glu Trp Ile
            35                  40                  45

Gly Asn Ile Tyr Tyr Ser Gly Ser Thr Asn Tyr Asn Pro Ser Leu Lys
        50                  55                  60
```

Ser Arg Val Thr Ile Ser Val Ala Ala Ser Lys Lys Gln Phe Ser Leu
65                  70                  75                  80

Lys Leu Thr Ser Val Thr Ala Ala Asp Thr Ala Val Tyr Tyr Cys Ala
                85                  90                  95

Arg Val Pro Gly Cys Ser Ser Thr Ser Cys Ile Asp Gly Trp Phe Asp
            100                 105                 110

Pro Trp Gly Gln Gly Ile Leu Val Thr Val Ser Ser
        115                 120

<210> SEQ ID NO 133
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 133
caggtgcagc tgcaagaatc aggccctggc ctggtcaagc ctagcgagac actgagcctg      60
acctgcaccg tcagcggcgg ctctatctct aggtgactact ggacctgggt ccgacagcct    120
cctggcgagg gcctcgagtg gatcggtaat atctactata gcggctctac taactataac    180
cctagcctga agtctagggt cacaattagc gtggccgcct ctaagaagca gtttagcctg    240
aagctgacta gcgtgaccgc cgctgacacc gccgtctact actgcgctag agtgcccggc    300
tgctctagca ctagctgtat cgacggctgg tttgacccct ggggtcaagg gatcctggtc    360
accgtgtcta gc                                                        372

<210> SEQ ID NO 134
<211> LENGTH: 454
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 134

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Arg Asp
                20                  25                  30

Tyr Trp Thr Trp Val Arg Gln Pro Pro Gly Glu Gly Leu Glu Trp Ile
            35                  40                  45

Gly Asn Ile Tyr Tyr Ser Gly Ser Thr Asn Tyr Asn Pro Ser Leu Lys
        50                  55                  60

Ser Arg Val Thr Ile Ser Val Ala Ala Ser Lys Lys Gln Phe Ser Leu
65                  70                  75                  80

Lys Leu Thr Ser Val Thr Ala Ala Asp Thr Ala Val Tyr Tyr Cys Ala
                85                  90                  95

Arg Val Pro Gly Cys Ser Ser Thr Ser Cys Ile Asp Gly Trp Phe Asp
            100                 105                 110

Pro Trp Gly Gln Gly Ile Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

-continued

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 135
<211> LENGTH: 1362
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 135
caggtgcagc tgcaagaatc aggccctggc ctggtcaagc ctagcgagac actgagcctg      60
acctgcaccg tcagcggcgg ctctatctct agggactact ggacctgggt ccgacagcct     120
cctggcgagg gcctcgagtg gatcggtaat atctactata gcggctctac taactataac     180
cctagcctga agtctagggt cacaattagc gtggccgcct ctaagaagca gtttagcctg     240
aagctgacta gcgtgaccgc cgctgacacc gccgtctact actgcgctag agtgcccggc     300

```
tgctctagca ctagctgtat cgacggctgg tttgacccctt ggggtcaagg gatcctggtc    360
accgtgtcta gcgctagcac taagggccca agtgtgtttc cctggccccc agcagcaag     420 tctacttccg gcggaactgc tgccctgggt tgcctggtga aggactactt ccccgagccc    480
gtgacagtgt cctggaactc tggggctctg acttccggcg tgcacaccctt ccccgccgtg    540 ctgcagagca gcggcctgta cagcctgagc agcgtggtga cagtgccctc agctctctg     600 ggaacccaga cctatatctg caacgtgaac cacaagccca gcaacaccaa ggtggacaag    660
agagtggagc ccaagagctg cgacaagacc cacacctgcc ccccctgccc agctccagaa    720
ctgctgggag gccttccgt gttcctgttc cccccaagc caaggacac cctgatgatc       780 agcaggaccc ccgaggtgac ctgcgtggtg gtggacgtgt cccacgagga cccagaggtg    840
aagttcaact ggtacgtgga cggcgtggag gtgcacaacg ccaagaccaa gcccagagag    900
gagcagtaca acagcaccta cagggtggtg tccgtgctga ccgtgctgca ccaggactgg    960
ctgaacggca agaatacaa gtgcaaagtc tccaacaagg ccctgccagc cccaatcgaa   1020
aagacaatca gcaaggccaa gggccagcca cgggagcccc aggtgtacac cctgccccc    1080 agccgggagg agatgaccaa gaaccaggtg tccctgacct gtctggtgaa gggcttctac   1140
cccagcgata tcgccgtgga gtgggagagc aacggccagc ccgagaacaa ctacaagacc   1200
acccccccag tgctggacag cgacggcagc ttcttcctgt acagcaagct gaccgtggac   1260
aagtccaggt ggcagcaggg caacgtgttc agctgcagcg tgatgcacga ggccctgcac   1320
aaccactaca cccagaagtc cctgagcctg agccccggca ag                      1362
```

<210> SEQ ID NO 136
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

Ser Gly Ser Ser Ser Asn Ile Gly Asn Thr Tyr Val Ser
1               5                   10

<210> SEQ ID NO 137
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

Asp Asn Asn Lys Arg Pro Ser
1               5

<210> SEQ ID NO 138
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

```
Gly Thr Trp Asp Ser Ser Leu Ser Ala Trp Val
1               5                   10

<210> SEQ ID NO 139
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 139

Ser Ser Ser Asn Ile Gly Asn Thr Tyr
1               5

<210> SEQ ID NO 140
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 140

Asp Asn Asn
1

<210> SEQ ID NO 141
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 141

Trp Asp Ser Ser Leu Ser Ala Trp
1               5

<210> SEQ ID NO 142
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 142

Gln Ser Val Leu Thr Gln Pro Pro Ser Leu Ser Ala Ala Pro Gly Gln
1               5                   10                  15

Arg Val Thr Ile Ser Cys Ser Gly Ser Ser Ser Asn Ile Gly Asn Thr
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Gly Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Ala Tyr Tyr Cys Gly Thr Trp Asp Ser Ser Leu
                85                  90                  95

Ser Ala Trp Val Phe Gly Gly Gly Thr Arg Leu Thr Val Leu
```

<210> SEQ ID NO 143
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 143

```
cagtcagtcc tgactcagcc ccctagcctg agcgccgctc ccggtcaaag agtgactatt      60
agctgtagcg gctctagctc taatatcggt aatacctacg tcagctggta tcagcagctg     120
cccggcaccg cccctaagct gctgatctac gataacaaca agcggcctag cggaatccct     180
ggtcgcttta gcggatctaa atcaggcact agcgctaccc tgggaatcac cggcctgcag     240
accggcgacg aagccgccta ctactgcggc acctgggact ctagtctgag cgcctgggtg     300
ttcggcggag gcactagact gaccgtgctg                                      330
```

<210> SEQ ID NO 144
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 144

Gln Ser Val Leu Thr Gln Pro Pro Ser Leu Ser Ala Ala Pro Gly Gln
1               5                   10                  15

Arg Val Thr Ile Ser Cys Ser Gly Ser Ser Ser Asn Ile Gly Asn Thr
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Gly Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Ala Tyr Tyr Cys Gly Thr Trp Asp Ser Ser Leu
                85                  90                  95

Ser Ala Trp Val Phe Gly Gly Gly Thr Arg Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 145
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 145

```
cagtcagtcc tgactcagcc ccctagcctg agcgccgctc ccggtcaaag agtgactatt      60
agctgtagcg gctctagctc taatatcggt aataccacg tcagctggta tcagcagctg     120
cccggcaccg cccctaagct gctgatctac gataacaaca agcggcctag cggaatccct    180
ggtcgcttta gcggatctaa atcaggcact agcgctaccc tgggaatcac cggcctgcag    240
accggcgacg aagccgccta ctactgcggc acctgggact ctagtctgag cgcctgggtg    300
ttcggcggag gcactagact gaccgtgctg ggtcaaccta aggctgcccc cagcgtgacc    360
ctgttccccc ccagcagcga ggagctgcag gccaacaagg ccaccctggt gtgcctgatc    420
agcgacttct acccaggcgc cgtgaccgtg gcctggaagg ccgacagcag ccccgtgaag    480
gccggcgtgg agaccaccac ccccagcaag cagagcaaca caagtacgc cgccagcagc     540
tacctgagcc tgaccccga gcagtggaag agccacaggt cctacagctg ccaggtgacc    600
cacgagggca gcaccgtgga aaagaccgtg gccccaaccg agtgcagc                 648
```

<210> SEQ ID NO 146
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 146

Arg Asp Tyr Trp Ser
1               5

<210> SEQ ID NO 147
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 147

Asn Ile Tyr Tyr Ser Gly Ser Thr Asn Tyr Asn Pro Ser Leu Lys Ser
1               5                   10                  15

<210> SEQ ID NO 148
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 148

Val Pro Gly Cys Ser Ser Thr Ser Cys Ile Asp Gly Trp Phe Asp Pro
1               5                   10                  15

<210> SEQ ID NO 149
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 149

Gly Gly Ser Ile Ser Arg Asp
1               5

<210> SEQ ID NO 150
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 150

Tyr Tyr Ser Gly Ser
1               5

<210> SEQ ID NO 151
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 151

Val Pro Gly Cys Ser Ser Thr Ser Cys Ile Asp Gly Trp Phe Asp Pro
1               5                   10                  15

<210> SEQ ID NO 152
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 152

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Arg Asp
            20                  25                  30

Tyr Trp Ser Trp Val Arg Gln Pro Pro Gly Ala Gly Leu Glu Trp Ile
        35                  40                  45

Gly Asn Ile Tyr Tyr Ser Gly Ser Thr Asn Tyr Asn Pro Ser Leu Lys
    50                  55                  60

Ser Arg Val Thr Ile Ser Val Ala Thr Asn Lys Lys Gln Phe Ser Leu
65                  70                  75                  80

Lys Leu Thr Ser Val Thr Ala Ala Asp Thr Ala Val Tyr Tyr Cys Ala
                85                  90                  95

Arg Val Pro Gly Cys Ser Ser Thr Ser Cys Ile Asp Gly Trp Phe Asp
            100                 105                 110

Pro Trp Gly Gln Gly Ile Leu Val Thr Val Ser Ser
        115                 120

<210> SEQ ID NO 153
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 153
caggtgcagc tgcaagaatc aggccctggc ctggtcaagc ctagcgagac actgagcctg      60
acctgcaccg tcagcggcgg ctctatctct agggactact ggtcctgggt ccgacaacct     120
cctggcgctg gcctcgagtg gatcggtaat atctactata cggctctac taactataac      180 cctagcctga agtctagggt cacaattagt gtggctacta acaagaagca gtttagcctg     240
aagctgacta gcgtgaccgc cgctgacacc gccgtctact actgcgctag agtgcccggc     300
tgctctagca ctagctgtat cgacggttgg tttgaccctt ggggtcaagg gatcctggtc     360
accgtgtcta gc                                                         372

<210> SEQ ID NO 154
<211> LENGTH: 454
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 154

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Arg Asp
            20                  25                  30

Tyr Trp Ser Trp Val Arg Gln Pro Pro Gly Ala Gly Leu Glu Trp Ile
        35                  40                  45

Gly Asn Ile Tyr Tyr Ser Gly Ser Thr Asn Tyr Asn Pro Ser Leu Lys
    50                  55                  60

Ser Arg Val Thr Ile Ser Val Ala Thr Asn Lys Lys Gln Phe Ser Leu
65                  70                  75                  80

Lys Leu Thr Ser Val Thr Ala Ala Asp Thr Ala Val Tyr Tyr Cys Ala
                85                  90                  95

Arg Val Pro Gly Cys Ser Ser Thr Ser Cys Ile Asp Gly Trp Phe Asp
            100                 105                 110

Pro Trp Gly Gln Gly Ile Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
            210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp Gly
        275                 280                 285
Val Glu Val His Asn Ala Lys Thr Lys Pro Arg Glu Glu Gln Tyr Asn
    290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Ser Arg Glu Glu Met Thr Lys Asn
        355                 360                 365
Gln Val Ser Leu Thr Cys Leu Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
        435                 440                 445
Ser Leu Ser Pro Gly Lys
    450

<210> SEQ ID NO 155
<211> LENGTH: 1362
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 155
caggtgcagc tgcaagaatc aggccctggc ctggtcaagc ctagcgagac actgagcctg     60
acctgcaccg tcagcggcgg ctctatctct agggactact ggtcctgggt ccgacaacct    120
cctggcgctg gcctcgagtg gatcggtaat atctactata gcggctctac taactataac    180
cctagcctga agtctagggt cacaattagt gtggctacta caagaagca gtttagcctg    240 aagctgacta gcgtgaccgc cgctgacacc gccgtctact actgcgctag agtgcccggc    300
tgctctagca ctagctgtat cgacggttgg tttgaccctt ggggtcaagg gatcctggtc    360
accgtgtcta gcgctagcac taagggccca agtgtgtttc ccctggcccc cagcagcaag    420
tctacttccg gcgcgaactgc tgccctgggt gcctggtga aggactactt ccccgagccc    480
gtgacagtgt cctggaactc tggggctctg acttccggcg tgcacacctt ccccgccgtg    540

```
ctgcagagca gcggcctgta cagcctgagc agcgtggtga cagtgccctc cagctctctg      600
ggaacccaga cctatatctg caacgtgaac cacaagccca gcaacaccaa ggtggacaag      660
agagtggagc ccaagagctg cgacaagacc cacacctgcc cccctgccc  agctccagaa     720 ctgctgggag gccttccgt  gttcctgttc cccccaagc  ccaaggacac cctgatgatc     780
agcaggaccc ccgaggtgac ctgcgtggtg gtggacgtgt cccacgagga cccagaggtg      840
aagttcaact ggtacgtgga cggcgtggag gtgcacaacg ccaagaccaa gcccagagag      900
gagcagtaca acagcaccta cagggtggtg tccgtgctga ccgtgctgca ccaggactgg      960
ctgaacggca agaatacaa  gtgcaaagtc tccaacaagg ccctgccagc cccaatcgaa     1020
aagacaatca gcaaggccaa gggccagcca cgggagcccc aggtgtacac cctgccccc    1080 agccgggagg agatgaccaa gaaccaggtg tccctgacct gtctggtgaa ggcttctac     1140 cccagcgata tcgccgtgga gtgggagagc aacggccagc cgagaacaa  ctacaagacc    1200 accccccag  tgctggacag cgacggcagc ttcttcctgt acagcaagct gaccgtggac     1260
aagtccaggt ggcagcaggg caacgtgttc agctgcagcg tgatgcacga ggccctgcac     1320
aaccactaca cccagaagtc cctgagcctg agccccggca ag                        1362
```

<210> SEQ ID NO 156
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 156

Ser Gly Ser Ser Ser Asn Ile Gly Asn Thr Tyr Val Ser
1               5                   10

<210> SEQ ID NO 157
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 157

Asp Asn Asn Lys Arg Pro Ser
1               5

<210> SEQ ID NO 158
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 158

Gly Thr Trp Asp Ser Ser Leu Ser Ala Trp Val
1               5                   10

<210> SEQ ID NO 159
<211> LENGTH: 9
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 159

Ser Ser Ser Asn Ile Gly Asn Thr Tyr
1               5

<210> SEQ ID NO 160
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 160

Asp Asn Asn
1

<210> SEQ ID NO 161
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 161

Trp Asp Ser Ser Leu Ser Ala Trp
1               5

<210> SEQ ID NO 162
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 162

Gln Ser Val Leu Thr Gln Pro Pro Ser Leu Ser Ala Ala Pro Gly Gln
1               5                   10                  15

Lys Val Thr Ile Ser Cys Ser Gly Ser Ser Ser Asn Ile Gly Asn Thr
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Val Tyr Tyr Cys Gly Thr Trp Asp Ser Ser Leu
                85                  90                  95

Ser Ala Trp Val Phe Gly Gly Gly Thr Arg Leu Thr Val Leu
            100                 105                 110

<210> SEQ ID NO 163
<211> LENGTH: 330
<212> TYPE: DNA
<213> ORGANISM: Artificial Sequence
<220> FEATURE:
<221> NAME/KEY: source
```

<223> OTHER INFORMATION: /note="Description of Artificial Sequence:
      Synthetic polynucleotide"

<400> SEQUENCE: 163

```
cagtcagtcc tgactcagcc ccctagcctg agcgccgctc ccggtcaaaa agtgactatt    60
agctgtagcg gctctagctc taatatcggt aataccctacg tcagctggta tcagcagctg   120
cccggcaccg ccctaagct gctgatctac gataacaaca agcggcctag cggaatcccc    180
gataggttta gcggatctaa gtcaggcact agcgctaccc tgggaatcac cggcctgcag   240
accggcgacg aggccgtcta ctactgcggc acctgggact ctagtctgag cgcctgggtg   300
ttcggcggag gcactagact gaccgtgctg                                    330
```

<210> SEQ ID NO 164
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 164

Gln Ser Val Leu Thr Gln Pro Pro Ser Leu Ser Ala Ala Pro Gly Gln
1               5                   10                  15

Lys Val Thr Ile Ser Cys Ser Gly Ser Ser Ser Asn Ile Gly Asn Thr
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Val Tyr Tyr Cys Gly Thr Trp Asp Ser Ser Leu
                85                  90                  95

Ser Ala Trp Val Phe Gly Gly Gly Thr Arg Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 165
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 165

```
cagtcagtcc tgactcagcc ccctagcctg agcgccgctc ccggtcaaaa agtgactatt        60
agctgtagcg gctctagctc taatatcggt aataccctacg tcagctggta tcagcagctg      120
cccggcaccg cccctaagct gctgatctac gataacaaca agcggcctag cggaatcccc       180
gataggttta gcggatctaa gtcaggcact agcgctaccc tgggaatcac cggcctgcag       240
accggcgacg aggccgtcta ctactgcggc acctgggact ctagtctgag cgcctgggtg       300
ttcggcggag cactagact gaccgtgctg ggtcaaccta aggctgcccc cagcgtgacc        360
ctgttccccc ccagcagcga ggagctgcag gccaacaagg ccaccctggt gtgcctgatc       420
agcgacttct acccaggcgc cgtgaccgtg gcctggaagg ccgacagcag ccccgtgaag       480
gccggcgtgg agaccaccac ccccagcaag cagagcaaca acaagtacgc cgccagcagc       540
tacctgagcc tgaccccccga gcagtggaag agccacaggt cctacagctg ccaggtgacc      600
cacgagggca gcaccgtgga aaagaccgtg gccccaaccg agtgcagc                    648
```

<210> SEQ ID NO 166
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 166

Arg Asp Tyr Trp Ser
1               5

<210> SEQ ID NO 167
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 167

Asn Ile Tyr Tyr Ser Gly Ser Thr Asn Tyr Asn Pro Ser Leu Lys Ser
1               5                   10                  15

<210> SEQ ID NO 168
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 168

Val Pro Gly Cys Ser Ser Thr Ser Cys Ile Asp Gly Trp Phe Asp Pro
1               5                   10                  15

<210> SEQ ID NO 169
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 169

Gly Gly Ser Ile Ser Arg Asp
1               5

<210> SEQ ID NO 170
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 170

Tyr Tyr Ser Gly Ser
1               5

<210> SEQ ID NO 171
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 171

Val Pro Gly Cys Ser Ser Thr Ser Cys Ile Asp Gly Trp Phe Asp Pro
1               5                   10                  15

<210> SEQ ID NO 172
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 172

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Arg Asp
            20                  25                  30

Tyr Trp Ser Trp Val Arg Gln Pro Pro Gly Ala Gly Leu Glu Trp Ile
        35                  40                  45

Gly Asn Ile Tyr Tyr Ser Gly Ser Thr Asn Tyr Asn Pro Ser Leu Lys
    50                  55                  60

Ser Arg Val Thr Ile Ser Val Ala Thr Asn Lys Lys Gln Phe Ser Leu
65                  70                  75                  80

Lys Leu Thr Ser Val Thr Ala Ala Asp Thr Ala Val Tyr Tyr Cys Ala
                85                  90                  95

Arg Val Pro Gly Cys Ser Ser Thr Ser Cys Ile Asp Gly Trp Phe Asp
            100                 105                 110

Pro Trp Gly Gln Gly Ile Leu Val Thr Val Ser Ser
        115                 120

<210> SEQ ID NO 173
<211> LENGTH: 372
<212> TYPE: DNA
<213> ORGANISM: Artificial Sequence
<220> FEATURE:

<221> NAME/KEY: source
<223> OTHER INFORMATION: /note="Description of Artificial Sequence: Synthetic polynucleotide"

<400> SEQUENCE: 173

```
caggtgcaat tgcaggaaag cggccctggc ctcgtgaagc ccagcgagac actgagcctg      60
acctgtaccg tgtccggcgg cagcatcagc agagactact ggagctgggt tcgccagcct     120
ccaggcgcag gactggaatg gatcggcaac atctactaca gcggcagcac caactacaac     180
cccagcctga agtccagagt gaccatcagc gtggccacaa acaagaaaca gttctccctg     240
aagctgacca gcgtgacagc cgccgatacc gccgtgtact actgcgccag agtgcctggc     300
tgtagcagca ccagctgcat cgacggatgg ttcgacccct ggggccaggg cattctcgtg     360
accgtcagct ca                                                         372
```

<210> SEQ ID NO 174
<211> LENGTH: 454
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 174

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Arg Asp
            20                  25                  30

Tyr Trp Ser Trp Val Arg Gln Pro Pro Gly Ala Gly Leu Glu Trp Ile
        35                  40                  45

Gly Asn Ile Tyr Tyr Ser Gly Ser Thr Asn Tyr Asn Pro Ser Leu Lys
    50                  55                  60

Ser Arg Val Thr Ile Ser Val Ala Thr Asn Lys Lys Gln Phe Ser Leu
65                  70                  75                  80

Lys Leu Thr Ser Val Thr Ala Ala Asp Thr Ala Val Tyr Tyr Cys Ala
                85                  90                  95

Arg Val Pro Gly Cys Ser Ser Thr Ser Cys Ile Asp Gly Trp Phe Asp
            100                 105                 110

Pro Trp Gly Gln Gly Ile Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255
```

```
    Thr Leu Met Ile Ser Arg Thr Pro Glu Val Thr Cys Val Val Val Asp
                    260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
        290                 295                 300

Ser Thr Tyr Arg Val Val Ser Val Leu Thr Val Leu His Gln Asp Trp
    305                 310                 315                 320

Leu Asn Gly Lys Glu Tyr Lys Cys Lys Val Ser Asn Lys Ala Leu Pro
                    325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
    385                 390                 395                 400

Thr Pro Pro Val Leu Asp Ser Asp Gly Ser Phe Phe Leu Tyr Ser Lys
                    405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Lys
        450
```

<210> SEQ ID NO 175
<211> LENGTH: 1362
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 175

```
caggtgcaat tgcaggaaag cggccctggc ctcgtgaagc ccagcgagac actgagcctg      60
acctgtaccg tgtccggcgg cagcatcagc agagactact ggagctgggt tcgccagcct     120
ccaggcgcag gactggaatg gatcggcaac atctactaca gcggcagcac caactacaac     180
cccagcctga agtccagagt gaccatcagc gtggccacaa acaagaaaca gttctccctg     240
aagctgacca gcgtgacagc cgccgatacc gccgtgtact actgcgccag agtgcctggc     300
tgtagcagca ccagctgcat cgacggatgg ttcgacccct ggggccaggg cattctcgtg     360
accgtcagct cagctagcac caagggcccc agcgtgttcc ccctggcccc cagcagcaag     420
agcaccagcg gcggcacagc cgccctgggc tgcctggtga aggactactt ccccgagccc     480
gtgaccgtgt cctggaacag cggagccctg acctccggcg tgcacacctt ccccgccgtg     540
ctgcagagca gcggcctgta cagcctgtcc agcgtggtga cagtgcccag cagcagcctg     600
ggcacccaga cctacatctg caacgtgaac cacaagccca gcaacaccaa ggtggacaag     660
agagtggagc ccaagagctg cgacaagacc cacacctgcc cccctgccc agccccagag     720 ctgctgggcg gaccctccgt gttcctgttc cccccaagc caaggacac cctgatgatc     780 agcaggaccc ccgaggtgac ctgcgtggtg gtggacgtga gccacgagga cccagaggtg     840
```

```
aagttcaact ggtacgtgga cggcgtggag gtgcacaacg ccaagaccaa gcccagagag    900
gagcagtaca acagcaccta cagggtggtg tccgtgctga ccgtgctgca ccaggactgg    960
ctgaacggca aggaatacaa gtgcaaggtc tccaacaagg ccctgccagc ccccatcgaa   1020
aagaccatca gcaaggccaa gggccagcca cgggagcccc aggtgtacac cctgcccccc   1080
tcccgggagg agatgaccaa gaaccaggtg tccctgacct gtctggtgaa gggcttctac   1140
cccagcgaca tcgccgtgga gtgggagagc aacggccagc ccgagaacaa ctacaagacc   1200 accccccag tgctggacag cgacggcagc ttcttcctgt acagcaagct gaccgtggac   1260
aagtccaggt ggcagcaggg caacgtgttc agctgcagcg tgatgcacga ggccctgcac   1320
aaccactaca cccagaagag cctgagcctg tcccccggca ag                      1362
```

<210> SEQ ID NO 176
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 176

Ser Gly Ser Ser Ser Asn Ile Gly Asn Thr Tyr Val Ser
1               5                   10

<210> SEQ ID NO 177
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 177

Asp Asn Asn Lys Arg Pro Ser
1               5

<210> SEQ ID NO 178
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 178

Gly Thr Trp Asp Ser Ser Leu Ser Ala Trp Val
1               5                   10

<210> SEQ ID NO 179
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 179

Ser Ser Ser Asn Ile Gly Asn Thr Tyr
1               5

<210> SEQ ID NO 180
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 180

Asp Asn Asn
1

<210> SEQ ID NO 181
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 181

Trp Asp Ser Ser Leu Ser Ala Trp
1               5

<210> SEQ ID NO 182
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 182

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Thr
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Arg Leu Thr Val Leu
            100                 105                 110

<210> SEQ ID NO 183
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 183
caaagcgtgc tgacccagcc tcctagcgtg tctgctgccc ctggccagaa ggtgaccatc      60
agctgtagcg gcagcagctc caacatcggc aacacctacg tgtcctggta tcagcagctg     120

```
cccggcaccg ccccaaaact gctgatctac gacaacaaca agcggcccag cggcatcccc    180
gatagatttt ctggcagcaa gagcggcacc agcgccaccc tgggaatcac aggactgcag    240 acagggacg aggccgatta ctactgtggc acctgggatt ctagcctgag cgcctgggtg     300
ttcggcggag gcacaagact gacagtgctg                                     330
```

<210> SEQ ID NO 184
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 184

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Thr
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Arg Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 185
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 185

```
caaagcgtgc tgacccagcc tcctagcgtg tctgctgccc ctggccagaa ggtgaccatc    60
agctgtagcg gcagcagctc caacatcggc aacacctacg tgtcctggta tcagcagctg    120
cccggcaccg ccccaaaact gctgatctac gacaacaaca agcggcccag cggcatcccc    180
```

```
gatagatttt ctggcagcaa gagcggcacc agcgccaccc tgggaatcac aggactgcag    240
acaggggacg aggccgatta ctactgtggc acctgggatt ctagcctgag cgcctgggtg    300
ttcggcggag gcacaagact gacagtgctg ggtcagccta aggccgctcc ctccgtgacc    360
ctgttccccc ccagctccga ggaactgcag gccaacaagg ccaccctggt gtgcctgatc    420
agcgacttct accctggcgc cgtgaccgtg gcctggaagg ccgacagcag ccccgtgaag    480
gccggcgtgg agacaaccac ccccagcaag cagagcaaca caagtacgc cgccagcagc    540 tacctgagcc tgaccccga gcagtggaag agccacagaa gctacagctg ccaggtcacc    600
cacgagggca gcaccgtgga gaaaaccgtg gcccccaccg agtgcagc                648
```

<210> SEQ ID NO 186
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 186

```
Ser Gly Gly Tyr Ser Trp Ser
1               5
```

<210> SEQ ID NO 187
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 187

```
Tyr Ile Tyr Tyr Arg Gly Thr Thr Tyr Tyr Asn Pro Ser Leu Lys Ser
1               5                   10                  15
```

<210> SEQ ID NO 188
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 188

```
Ala Leu Thr His Leu Val Gly Val Gly Trp Phe Asp Pro
1               5                   10
```

<210> SEQ ID NO 189
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 189

```
Gly Gly Ser Ile Ser Ser Gly Gly Tyr
1               5
```

<210> SEQ ID NO 190

<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 190

Tyr Tyr Arg Gly Thr
1               5

<210> SEQ ID NO 191
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 191

Ala Leu Thr His Leu Val Gly Val Gly Trp Phe Asp Pro
1               5                   10

<210> SEQ ID NO 192
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 192

Gln Val Gln Leu Gln Glu Ser Gly Pro Gly Leu Ala Lys Pro Ser Gln
1               5                   10                  15

Thr Leu Ser Leu Thr Cys Ser Val Ser Gly Gly Ser Ile Ser Ser Gly
            20                  25                  30

Gly Tyr Ser Trp Ser Trp Ile Arg Gln Pro Pro Gly Lys Gly Leu Glu
        35                  40                  45

Tyr Ile Gly Tyr Ile Tyr Tyr Arg Gly Thr Thr Tyr Tyr Asn Pro Ser
    50                  55                  60

Leu Lys Ser Arg Ile Thr Met Ser Val Asp Thr Ser Asn Asn Gln Ile
65                  70                  75                  80

Ser Leu Lys Leu Thr Ser Val Thr Ala Ala Asp Thr Ala Val Tyr Tyr
                85                  90                  95

Cys Ala Arg Ala Leu Thr His Leu Val Gly Val Gly Trp Phe Asp Pro
            100                 105                 110

Trp Gly Gln Gly Thr Met Val Thr Val Ser Ser
        115                 120

<210> SEQ ID NO 193
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 193
caggtgcagc tgcaagaatc aggccctggc ctggctaagc ctagtcagac cctgagcctg      60
acctgtagcg tcagcggagg ctctatctct agcggcggct atagctggtc ctggattaga     120

-continued

```
cagcccccag gtaaaggcct cgagtatatc ggctatatct actataggg cactacctac      180 tataaccta gcctgaagtc taggatcact atgagcgtgg acacctctaa caatcagatt       240
agcctgaagc tgactagcgt gaccgccgct gacaccgccg tctactactg cgctagagcc      300
ctgactcacc tcgttggagt gggctggttt gaccttggg gtcaaggcac tatggtcacc       360
gtgtctagc                                                              369
```

<210> SEQ ID NO 194
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 194

```
Gln Val Gln Leu Gln Glu Ser Gly Pro Gly Leu Ala Lys Pro Ser Gln
1               5                   10                  15

Thr Leu Ser Leu Thr Cys Ser Val Ser Gly Gly Ser Ile Ser Ser Gly
            20                  25                  30

Gly Tyr Ser Trp Ser Trp Ile Arg Gln Pro Pro Gly Lys Gly Leu Glu
        35                  40                  45

Tyr Ile Gly Tyr Ile Tyr Tyr Arg Gly Thr Thr Tyr Tyr Asn Pro Ser
    50                  55                  60

Leu Lys Ser Arg Ile Thr Met Ser Val Asp Thr Ser Asn Asn Gln Ile
65                  70                  75                  80

Ser Leu Lys Leu Thr Ser Val Thr Ala Ala Asp Thr Ala Val Tyr Tyr
                85                  90                  95

Cys Ala Arg Ala Leu Thr His Leu Val Gly Val Gly Trp Phe Asp Pro
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300
```

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 195
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 195
caggtgcagc tgcaagaatc aggccctggc ctggctaagc ctagtcagac cctgagcctg      60
acctgtagcg tcagcggagg ctctatctct agcggcggct atagctggtc ctggattaga     120
cagcccccag gtaaaggcct cgagtatatc ggctatatct actataggqg cactacctac     180 tataacccta gcctgaagtc taggatcact atgagcgtgg acacctctaa caatcagatt     240
agcctgaagc tgactagcgt gaccgccgct gacaccgccg tctactactg cgctagagcc     300
ctgactcacc tcgttggagt gggctggttt gaccctgggg tcaaggcac tatggtcacc     360 gtgtctagcg ctagcactaa gggcccaagt gtgtttcccc tggccccag cagcaagtct     420 acttccggcg gaactgctgc cctgggttgc ctggtgaagg actacttccc cgagcccgtg     480
acagtgtcct ggaactctgg ggctctgact tccggcgtgc acaccttccc cgccgtgctg     540
cagagcagcg gcctgtacag cctgagcagc gtggtgacag tgccctccag ctctctggga     600
acccagacct atatctgcaa cgtgaaccac aagcccagca caccaaggt ggacaagaga     660 gtggagccca gagctgcga caagacccac acctgccccc cctgcccagc tccagaactg     720
ctgggagggc cttccgtgtt cctgttcccc ccaagcccaa ggacaccct gatgatcagc     780 aggaccccgg aggtgacctg cgtggtggtg gacgtgtccc acgaggaccc agaggtgaag     840
ttcaactggt acgtggacgg cgtggaggtg cacaacgcca agaccaagcc agagaggag     900 cagtacaaca gcacctacag ggtggtgtcc gtgctgaccg tgctgcacca ggactggctg     960
aacggcaaag aatacaagtg caaagtctcc aacaaggccc tgccagcccc aatcgaaaag    1020
acaatcagca aggccaaggg ccagccacgg gagcccagg tgtacaccct gccccccagc    1080

```
cgggaggaga tgaccaagaa ccaggtgtcc ctgacctgtc tggtgaaggg cttctacccc    1140
agcgatatcg ccgtggagtg ggagagcaac ggccagcccg agaacaacta caagaccacc    1200
cccccagtgc tggacagcga cggcagcttc ttcctgtaca gcaagctgac cgtggacaag    1260
tccaggtggc agcagggcaa cgtgttcagc tgcagcgtga tgcacgaggc cctgcacaac    1320
cactacaccc agaagtccct gagcctgagc cccggcaag                           1359
```

<210> SEQ ID NO 196
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 196

Ser Gly Gly Ser Ser Asn Leu Gly Ser Asn Tyr Val Ser
1               5                   10

<210> SEQ ID NO 197
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 197

Asp Asn Asn Lys Arg Pro Ser
1               5

<210> SEQ ID NO 198
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 198

Gly Thr Trp Asp Gly Ser Leu Ser Ala Trp Val
1               5                   10

<210> SEQ ID NO 199
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 199

Gly Ser Ser Asn Leu Gly Ser Asn Tyr
1               5

<210> SEQ ID NO 200
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 200

Asp Asn Asn
1

<210> SEQ ID NO 201
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 201

Trp Asp Gly Ser Leu Ser Ala Trp
1               5

<210> SEQ ID NO 202
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 202

Gln Ser Val Leu Thr Gln Pro Pro Ser Val Ser Ala Ala Pro Gly Gln
1               5                   10                  15

Lys Val Thr Ile Ser Cys Ser Gly Gly Ser Ser Asn Leu Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Gly Ser Leu
                85                  90                  95

Ser Ala Trp Val Phe Gly Gly Gly Thr Lys Val Thr Val Leu
            100                 105                 110

<210> SEQ ID NO 203
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 203
cagtcagtcc tgactcagcc ccctagcgtc agcgccgctc ccggtcaaaa agtgactatt      60
agctgtagcg gcggctcctc taacctgggc tctaactacg tcagctggta tcagcagctg     120
cccggcaccg cccctaagct gctgatctac gataacaaca agcggcctag cggaatcccc     180
gataggttta gcggctctaa gtcaggcact agcgctaccc tgggaatcac cggcctgcag     240
accggcgacg aggccgacta ctactgtggc acctgggacg gtagcctgag cgcctgggtg     300
ttcggcggag gcactaaagt cacagtgctg                                      330

<210> SEQ ID NO 204
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 204

```
Gln Ser Val Leu Thr Gln Pro Pro Ser Val Ser Ala Ala Pro Gly Gln
1               5                   10                  15

Lys Val Thr Ile Ser Cys Ser Gly Gly Ser Ser Asn Leu Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Gly Ser Leu
                85                  90                  95

Ser Ala Trp Val Phe Gly Gly Gly Thr Lys Val Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 205
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 205

```
cagtcagtcc tgactcagcc ccctagcgtc agcgccgctc ccggtcaaaa agtgactatt    60
agctgtagcg gcggctcctc taacctgggc tctaactacg tcagctggta tcagcagctg   120
cccggcaccg cccctaagct gctgatctac gataacaaca gcggcctagc ggaatccccc   180
gataggttta gcggctctaa gtcaggcact agcgctaccc tgggaatcac cggcctgcag   240
accggcgacg aggccgacta ctactgtggc acctgggacg gtagcctgag cgcctgggtg   300
ttcggcggag gcactaaagt cacagtgctg ggtcaaccta aggctgcccc cagcgtgacc   360
ctgttccccc ccagcagcga ggagctgcag gccaacaagg ccaccctggt gtgcctgatc   420
```

```
agcgacttct acccaggcgc cgtgaccgtg gcctggaagg ccgacagcag ccccgtgaag    480
gccggcgtgg agaccaccac ccccagcaag cagagcaaca acaagtacgc cgccagcagc    540
tacctgagcc tgaccccga  gcagtggaag agccacaggt cctacagctg ccaggtgacc    600
cacgagggca gcaccgtgga aaagaccgtg gccccaaccg agtgcagc                 648
```

```
<210> SEQ ID NO 206
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 206

Ser Gly Gly Tyr Ser Trp Ser
1               5

<210> SEQ ID NO 207
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 207

Tyr Ile Tyr Tyr Arg Gly Thr Thr Tyr Tyr Asn Pro Ser Leu Lys Ser
1               5                   10                  15

<210> SEQ ID NO 208
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 208

Ala Leu Thr His Leu Val Gly Val Gly Trp Phe Asp Pro
1               5                   10

<210> SEQ ID NO 209
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 209

Gly Gly Ser Ile Ser Ser Gly Gly Tyr
1               5

<210> SEQ ID NO 210
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 210
```

Tyr Tyr Arg Gly Thr
1               5

<210> SEQ ID NO 211
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 211

Ala Leu Thr His Leu Val Gly Val Gly Trp Phe Asp Pro
1               5                   10

<210> SEQ ID NO 212
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 212

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Ser Trp Ser Trp Ile Arg Gln Pro Pro Gly Lys Gly Leu Glu
        35                  40                  45

Tyr Ile Gly Tyr Ile Tyr Tyr Arg Gly Thr Thr Tyr Tyr Asn Pro Ser
    50                  55                  60

Leu Lys Ser Arg Val Thr Ile Ser Val Asp Thr Ser Asn Asn Gln Ile
65                  70                  75                  80

Ser Leu Lys Leu Ser Ser Val Thr Ala Ala Asp Thr Ala Val Tyr Tyr
                85                  90                  95

Cys Ala Arg Ala Leu Thr His Leu Val Gly Val Gly Trp Phe Asp Pro
            100                 105                 110

Trp Gly Gln Gly Thr Met Val Thr Val Ser Ser
        115                 120

<210> SEQ ID NO 213
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 213
caggtgcagc tgcaagaatc aggccctggc ctggtcaagc ctagtcagac cctgagcctg      60
acctgcaccg tcagcggagg ctctatctct agcggcggct atagctggtc ctggattaga     120
cagcccccag gtaaaggcct cgagtatatc ggctatatct actataggg cactacctac      180 tataacccta gcctgaagtc tagggtcaca attagcgtgg acacctctaa caatcagatt     240
agcctgaagc tgtctagcgt gaccgccgct gacaccgccg tctactactg cgctagagcc     300
ctgactcacc tcgtcggagt gggctggttt gaccccttggg gtcaaggcac tatggtcacc     360

```
gtgtctagc                                                    369
```

<210> SEQ ID NO 214
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 214

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Ser Trp Ser Trp Ile Arg Gln Pro Pro Gly Lys Gly Leu Glu
        35                  40                  45

Tyr Ile Gly Tyr Ile Tyr Tyr Arg Gly Thr Thr Tyr Tyr Asn Pro Ser
    50                  55                  60

Leu Lys Ser Arg Val Thr Ile Ser Val Asp Thr Ser Asn Asn Gln Ile
65                  70                  75                  80

Ser Leu Lys Leu Ser Ser Val Thr Ala Ala Asp Thr Ala Val Tyr Tyr
                85                  90                  95

Cys Ala Arg Ala Leu Thr His Leu Val Gly Val Gly Trp Phe Asp Pro
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

```
Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
        450
```

<210> SEQ ID NO 215
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 215

```
caggtgcagc tgcaagaatc aggccctggc ctggtcaagc ctagtcagac cctgagcctg     60
acctgcaccg tcagcggagg ctctatctct agcggcggct atagctggtc ctggattaga    120
cagccccag gtaaaggcct cgagtatatc ggctatatct actatagggg cactacctac     180
tataacccta gcctgaagtc tagggtcaca attagcgtgg acacctctaa caatcagatt    240
agcctgaagc tgtctagcgt gaccgccgct gacaccgccg tctactactg cgctagagcc    300
ctgactcacc tcgtcggagt gggctggttt gacccttggg gtcaaggcac tatggtcacc    360
gtgtctagcg ctagcactaa gggcccaagt gtgtttcccc tggcccccag cagcaagtct    420
acttccggcg gaactgctgc cctgggttgc ctggtgaagg actacttccc cgagcccgtg    480
acagtgtcct ggaactctgg ggctctgact tccggcgtgc acaccttccc cgccgtgctg    540
cagagcagcg gcctgtacag cctgagcagc gtggtgacag tgccctccag ctctctggga    600
acccagacct atatctgcaa cgtgaaccac aagcccagca caccaaggt ggacaagaga     660
gtggagccca gagctgcga caagacccac acctgccccc cctgcccagc tccagaactg    720
ctgggagggc cttccgtgtt cctgttcccc ccaagcccca aggacaccct gatgatcagc    780
aggaccccg aggtgacctg cgtggtggtg gacgtgtccc acgaggaccc agaggtgaag    840
ttcaactggt acgtggacgg cgtggaggtg cacaacgcca agaccaagcc agagaggag    900
cagtacaaca gcacctacag ggtggtgtcc gtgctgaccg tgctgcacca ggactggctg    960
aacggcaaag aatacaagtg caaagtctcc aacaaggccc tgccagcccc aatcgaaaag   1020
acaatcagca aggccaaggg ccagccacgg gagcccagg tgtacaccct gccccccagc    1080
cgggaggaga tgaccaagaa ccaggtgtcc ctgacctgtc tggtgaaggg cttctacccc    1140
agcgatatcg ccgtggagtg ggagagcaac ggccagcccg agaacaacta caagaccacc    1200
ccccagtgc tggacagcga cggcagcttc ttcctgtaca gcaagctgac cgtggacaag    1260
tccaggtggc agcagggcaa cgtgttcagc tgcagcgtga tgcacgaggc cctgcacaac    1320
cactacaccc agaagtccct gagcctgagc cccggcaag                            1359
```

```
<210> SEQ ID NO 216
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 216

Ser Gly Gly Ser Ser Asn Leu Gly Ser Asn Tyr Val Ser
1               5                   10

<210> SEQ ID NO 217
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 217

Asp Asn Asn Lys Arg Pro Ser
1               5

<210> SEQ ID NO 218
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 218

Gly Thr Trp Asp Gly Ser Leu Ser Ala Trp Val
1               5                   10

<210> SEQ ID NO 219
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 219

Gly Ser Ser Asn Leu Gly Ser Asn Tyr
1               5

<210> SEQ ID NO 220
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 220

Asp Asn Asn
1

<210> SEQ ID NO 221
<211> LENGTH: 8
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 221

Trp Asp Gly Ser Leu Ser Ala Trp
1               5

<210> SEQ ID NO 222
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 222

Gln Ser Val Leu Thr Gln Pro Pro Ser Val Ser Ala Ala Pro Gly Gln
1               5                   10                  15

Lys Val Thr Ile Ser Cys Ser Gly Gly Ser Ser Asn Leu Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Gly Ser Leu
                85                  90                  95

Ser Ala Trp Val Phe Gly Gly Gly Thr Lys Val Thr Val Leu
            100                 105                 110

<210> SEQ ID NO 223
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 223
cagtcagtcc tgactcagcc ccctagcgtc agcgccgctc ccggtcaaaa agtgactatt      60
agctgtagcg gcggctcctc taacctgggc tctaactacg tcagctggta tcagcagctg     120
cccggcaccg cccctaagct gctgatctac gataacaaca gcggcctag cggaatcccc      180 gataggttta gcggctctaa gtcaggcact agcgctaccc tgggaatcac cggcctgcag     240
accggcgacg aggccgacta ctactgtggc acctgggacg gtagcctgag cgcctgggtg     300
ttcggcggag gcactaaagt cacagtgctg                                      330

<210> SEQ ID NO 224
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

<400> SEQUENCE: 224

Gln Ser Val Leu Thr Gln Pro Pro Ser Val Ser Ala Ala Pro Gly Gln
1               5                   10                  15

Lys Val Thr Ile Ser Cys Ser Gly Gly Ser Ser Asn Leu Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Gly Ser Leu
                85                  90                  95

Ser Ala Trp Val Phe Gly Gly Gly Thr Lys Val Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
        210                 215

<210> SEQ ID NO 225
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 225
cagtcagtcc tgactcagcc ccctagcgtc agcgccgctc ccggtcaaaa agtgactatt      60
agctgtagcg gcggctcctc taacctgggc tctaactacg tcagctggta tcagcagctg     120
cccggcaccg cccctaagct gctgatctac gataacaaca gcggcctag cggaatcccc      180 gataggttta gcggctctaa gtcaggcact agcgctaccc tgggaatcac cggcctgcag     240
accggcgacg aggccgacta ctactgtggc acctgggacg gtagcctgag cgcctgggtg     300
ttcggcggag gcactaaagt cacagtgctg ggtcaaccta aggctgcccc cagcgtgacc     360
ctgttccccc ccagcagcga ggagctgcag gccaacaagg ccaccctggt gtgcctgatc     420
agcgacttct acccaggcgc cgtgaccgtg gcctggaagg ccgacagcag ccccgtgaag     480
gccggcgtgg agaccaccac ccccagcaag cagagcaaca acaagtacgc cgccagcagc     540
tacctgagcc tgacccccga gcagtggaag agccacaggt cctacagctg ccaggtgacc     600
cacgagggca gcaccgtgga aaagaccgtg gccccaaccg agtgcagc                  648

```
<210> SEQ ID NO 226
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 226

Ala Tyr Tyr Trp Thr
1               5

<210> SEQ ID NO 227
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 227

Tyr Ile Ser His Ser Gly Ser Thr Asn Tyr Asn Pro Ser Leu Lys Ser
1               5                   10                  15

<210> SEQ ID NO 228
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 228

Leu Gly Asp Thr Ala Ser Leu Ser Arg Phe Tyr Tyr Tyr Ile Asp Val
1               5                   10                  15

<210> SEQ ID NO 229
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 229

Gly Gly Ser Thr Ser Ala Tyr
1               5

<210> SEQ ID NO 230
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 230

Ser His Ser Gly Ser
1               5

<210> SEQ ID NO 231
<211> LENGTH: 16
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 231

Leu Gly Asp Thr Ala Ser Leu Ser Arg Phe Tyr Tyr Tyr Ile Asp Val
1               5                   10                  15

<210> SEQ ID NO 232
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 232

Gln Val Gln Leu Val Gln Ser Gly Pro Gly Leu Val Lys Pro Ser Glu
1               5                   10                  15

Thr Leu Ser Leu Thr Cys Thr Val Ser Gly Gly Ser Thr Ser Ala Tyr
                20                  25                  30

Tyr Trp Thr Trp Ile Arg Gln Pro Pro Gly Lys Gly Leu Glu Trp Ile
            35                  40                  45

Gly Tyr Ile Ser His Ser Gly Ser Thr Asn Tyr Asn Pro Ser Leu Lys
        50                  55                  60

Ser Arg Val Thr Ile Ser Ala Asp Thr Ser Lys Asn Gln Leu Ser Leu
65                  70                  75                  80

Lys Val Asn Ser Val Thr Ala Ala Asp Thr Ala Val Tyr Tyr Cys Ala
                85                  90                  95

Arg Leu Gly Asp Thr Ala Ser Leu Ser Arg Phe Tyr Tyr Tyr Ile Asp
            100                 105                 110

Val Trp Gly Lys Gly Thr Thr Val Thr Val Ser Ser
        115                 120

<210> SEQ ID NO 233
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 233
caggtgcagc tggtgcagtc tggcccagga ctggtgaagc cttcggagac cctgtccctc    60
acctgcactg tctctggtgg ctccaccagt gcttactact ggacctggat tcggcagccc   120
ccagggaagg gactggagtg gattgggtat atctctcaca gtgggagcac caactacaac   180
ccctccctca gagtcgagt caccatatca gcagacacgt ccaagaacca gctctccctg   240
aaggtgaact ctgtgaccgc cgcagacacg gccgtgtatt actgtgcgag acttggggat   300
acagcttcac ttagccgctt ctactactac attgacgtct ggggcaaagg gaccacggtc   360
accgtctcct ca                                                      372

<210> SEQ ID NO 234
<211> LENGTH: 454
<212> TYPE: PRT
<213> ORGANISM: Artificial Sequence
<220> FEATURE:
<221> NAME/KEY: source
```

<223> OTHER INFORMATION: /note="Description of Artificial Sequence: Synthetic polypeptide"

<400> SEQUENCE: 234

```
Gln Val Gln Leu Val Gln Ser Gly Pro Gly Leu Val Lys Pro Ser Glu
1               5                   10                  15
Thr Leu Ser Leu Thr Cys Thr Val Ser Gly Gly Ser Thr Ser Ala Tyr
            20                  25                  30
Tyr Trp Thr Trp Ile Arg Gln Pro Pro Gly Lys Gly Leu Glu Trp Ile
        35                  40                  45
Gly Tyr Ile Ser His Ser Gly Ser Thr Asn Tyr Asn Pro Ser Leu Lys
    50                  55                  60
Ser Arg Val Thr Ile Ser Ala Asp Thr Ser Lys Asn Gln Leu Ser Leu
65                  70                  75                  80
Lys Val Asn Ser Val Thr Ala Ala Asp Thr Ala Val Tyr Tyr Cys Ala
                85                  90                  95
Arg Leu Gly Asp Thr Ala Ser Leu Ser Arg Phe Tyr Tyr Tyr Ile Asp
            100                 105                 110
Val Trp Gly Lys Gly Thr Thr Val Thr Val Ser Ser Ala Ser Thr Lys
        115                 120                 125
Gly Pro Ser Val Phe Pro Leu Ala Pro Ser Ser Lys Ser Thr Ser Gly
    130                 135                 140
Gly Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
            180                 185                 190
Val Thr Val Pro Ser Ser Ser Leu Gly Thr Gln Thr Tyr Ile Cys Asn
        195                 200                 205
Val Asn His Lys Pro Ser Asn Thr Lys Val Asp Lys Arg Val Glu Pro
    210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp Gly
        275                 280                 285
Val Glu Val His Asn Ala Lys Thr Lys Pro Arg Glu Glu Gln Tyr Asn
    290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Ser Arg Glu Glu Met Thr Lys Asn
        355                 360                 365
Gln Val Ser Leu Thr Cys Leu Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
```

Thr Pro Pro Val Leu Asp Ser Asp Gly Ser Phe Phe Leu Tyr Ser Lys
             405                 410                 415

Leu Thr Val Asp Lys Ser Arg Trp Gln Gln Gly Asn Val Phe Ser Cys
         420                 425                 430

Ser Val Met His Glu Ala Leu His Asn His Tyr Thr Gln Lys Ser Leu
         435                 440                 445

Ser Leu Ser Pro Gly Lys
    450

<210> SEQ ID NO 235
<211> LENGTH: 1362
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 235
caggtgcagc tggtgcagtc tggcccagga ctggtgaagc cttcggagac cctgtccctc      60
acctgcactg tctctggtgg ctccaccagt gcttactact ggacctggat tcggcagccc     120
ccagggaagg gactggagtg gattgggtat atctctcaca gtgggagcac caactacaac     180
ccctccctca gagtcgagt caccatatca gcagacacgt ccaagaacca gctctccctg     240
aaggtgaact ctgtgaccgc cgcagacacg gccgtgtatt actgtgcgag acttggggat     300
acagcttcac ttagccgctt ctactactac attgacgtct ggggcaaagg gaccacggtc     360
accgtctcct cagctagcac caagggccca tcggtcttcc ccctggcacc ctcctccaag     420
agcacctctg ggggcacagc ggccctgggc tgcctggtca aggactactt ccccgaaccg     480
gtgacggtgt cgtggaactc aggcgccctg accagcggcg tgcacacctt cccggctgtc     540
ctacagtcct caggactcta ctccctcagc agcgtggtga ccgtgccctc agcagcttg     600 ggcacccaga cctacatctg caacgtgaat cacaagccca gcaacaccaa ggtggacaag     660
agagttgagc ccaaatcttg tgacaaaact cacacatgcc caccgtgccc agcacctgaa     720
ctcctggggg gaccgtcagt cttcctcttc cccccaaaac ccaaggacac cctcatgatc     780
tcccggaccc ctgaggtcac atgcgtggtg gtggacgtga gccacgaaga ccctgaggtc     840
aagttcaact ggtacgtgga cggcgtggag gtgcataatg ccaagacaaa gccgcgggag     900
gagcagtaca acagcacgta ccgtgtggtc agcgtcctca ccgtcctgca ccaggactgg     960
ctgaatggca aggagtacaa gtgcaaggtc tccaacaaag ccctcccagc ccccatcgag    1020
aaaaccatct ccaaagccaa agggcagccc cgagaaccac aggtgtacac cctgccccca    1080
tcccgggagg agatgaccaa gaaccaggtc agcctgacct gcctggtcaa aggcttctat    1140
cccagcgaca tcgccgtgga gtgggagagc aatgggcagc cggagaacaa ctacaagacc    1200
acgcctcccg tgctggactc cgacggctcc ttcttcctct acagcaagct caccgtggac    1260
aagagcaggt ggcagcaggg gaacgtcttc tcatgctccg tgatgcatga ggctctgcac    1320
aaccactaca cgcagaagag cctctccctg tctccgggta aa                       1362

<210> SEQ ID NO 236
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 236

Arg Ala Ser Gln Ser Val Ser Ser Asn Tyr Leu Ala
1               5                   10

<210> SEQ ID NO 237
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 237

Gly Ala Ser Ser Arg Ala Thr
1               5

<210> SEQ ID NO 238
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 238

Gln Gln Tyr Gly Ser Ser Pro Pro Tyr Thr
1               5                   10

<210> SEQ ID NO 239
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 239

Ser Gln Ser Val Ser Ser Asn Tyr
1               5

<210> SEQ ID NO 240
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 240

Gly Ala Ser
1

<210> SEQ ID NO 241
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 241

Tyr Gly Ser Ser Pro Pro Tyr
1               5

<210> SEQ ID NO 242
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 242

Glu Ile Val Met Thr Gln Ser Pro Asp Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Glu Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Tyr Thr Phe Gly Gln Gly Thr Arg Leu Glu Ile Lys
            100                 105

<210> SEQ ID NO 243
<211> LENGTH: 328
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 243
gaaattgtaa tgacgcagtc tccagacacc ctgtctttgt ctccagggga aagagccacc      60
ctctcctgca gggccagtca gagtgttagc agcaactact tagcctggta ccagcagaaa     120
cctggcgagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcacctcc gtacactttt     300
ggccagggga cacgactgga gattaaac                                         328

<210> SEQ ID NO 244
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 244

Glu Ile Val Met Thr Gln Ser Pro Asp Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Glu Ala Pro Arg Leu Leu

```
            35                  40                  45
Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Pro Tyr Thr Phe Gly Gln Gly Thr Arg Leu Glu Ile Lys Arg Thr Val
                100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 245
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 245
gaaattgtaa tgacgcagtc tccagacacc ctgtctttgt ctccagggga aagagccacc      60
ctctcctgca gggccagtca gagtgttagc agcaactact tagcctggta ccagcagaaa     120
cctggcgagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcacctcc gtacactttt     300
ggccagggga cacgactgga gattaaacgt acggtggctg caccatctgt cttcatcttc     360
ccgccatctg atgagcagtt gaaatctgga actgcctctg ttgtgtgcct gctgaataac     420
ttctatcccc gcgaggccaa agtacagtgg aaggtggata acgccctcca atcgggtaac     480
tcccaggaga gtgtcacaga gcaggacagc aaggacagca cctacagcct cagcagcacc     540
ctgacgctga gcaaagcaga ctacgagaaa cacaaagtct acgcctgcga agtcacccat     600
cagggcctga gctcgcccgt cacaaagagc ttcaaccgcg gagagtgt                  648

<210> SEQ ID NO 246
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 246

Arg Asn Tyr Met Ser
1               5

<210> SEQ ID NO 247
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 247

Gly Ile Tyr Ser Gly Gly Ser Thr Tyr Tyr Ala Asp Ser Val Lys Gly
1               5                   10                  15

<210> SEQ ID NO 248
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 248

Glu Asp Glu Phe Trp Ser Gly Tyr Ser Ala Gly Val Asp
1               5                   10

<210> SEQ ID NO 249
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 249

Gly Phe Thr Val Arg Arg Asn
1               5

<210> SEQ ID NO 250
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 250

Tyr Ser Gly Gly Ser
1               5

<210> SEQ ID NO 251
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 251

Glu Asp Glu Phe Trp Ser Gly Tyr Ser Ala Gly Val Asp
1               5                   10
```

<210> SEQ ID NO 252
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 252

Glu Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Val Arg Arg Asn
            20                  25                  30

Tyr Met Ser Trp Val Arg Gln Ala Pro Gly Lys Gly Leu Glu Trp Val
        35                  40                  45

Ser Gly Ile Tyr Ser Gly Gly Ser Thr Tyr Tyr Ala Asp Ser Val Lys
    50                  55                  60

Gly Arg Phe Thr Ile Ser Arg Asp Tyr Ser Lys Asn Thr Leu Ser Leu
65                  70                  75                  80

Gln Met Asn Thr Leu Arg Val Glu Asp Thr Ala Val Tyr Phe Cys Ala
                85                  90                  95

Arg Glu Asp Glu Phe Trp Ser Gly Tyr Ser Ala Gly Val Asp Trp Gly
            100                 105                 110

Gln Gly Thr Leu Val Thr Val Ser Ser
        115                 120

<210> SEQ ID NO 253
<211> LENGTH: 364
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 253
gaggtgcagc tggtggagac tggaggaggc ttggtccagc cggggggggtc cctgagactc    60 tcatgtgcag cctctggatt caccgtcaga cgcaattaca tgagttgggt ccgccaggct   120
ccggggaagg gactggagtg gtctcaggg atctacagtg gtggtagcac atactacgca   180
gactccgtga agggccgatt caccatctcc agagactatt ccaagaacac actgtctctt   240
caaatgaaca ccctgagagt cgaggacacg gccgtgtatt tctgtgcgag agaagacgaa   300
ttttggagcg gtattccgc tggggtcgac tggggccagg gaaccctggt caccgtctcc   360
tcag                                                                364

<210> SEQ ID NO 254
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 254

Glu Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Val Arg Arg Asn

-continued

```
                20                  25                  30
Tyr Met Ser Trp Val Arg Gln Ala Pro Gly Lys Gly Leu Glu Trp Val
                35                  40                  45
Ser Gly Ile Tyr Ser Gly Ser Thr Tyr Tyr Ala Asp Ser Val Lys
        50                  55                  60
Gly Arg Phe Thr Ile Ser Arg Asp Tyr Ser Lys Asn Thr Leu Ser Leu
 65                  70                  75                  80
Gln Met Asn Thr Leu Arg Val Glu Asp Thr Ala Val Tyr Phe Cys Ala
                85                  90                  95
Arg Glu Asp Glu Phe Trp Ser Gly Tyr Ser Ala Gly Val Asp Trp Gly
                100                 105                 110
Gln Gly Thr Leu Val Thr Val Ser Ser Ala Ser Thr Lys Gly Pro Ser
                115                 120                 125
Val Phe Pro Leu Ala Pro Ser Ser Lys Ser Thr Ser Gly Gly Thr Ala
                130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
                195                 200                 205
Lys Pro Ser Asn Thr Lys Val Asp Lys Arg Val Glu Pro Lys Ser Cys
                210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
                275                 280                 285
His Asn Ala Lys Thr Lys Pro Arg Glu Glu Gln Tyr Asn Ser Thr Tyr
                290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Glu Glu Met Thr Lys Asn Gln Val Ser
                355                 360                 365
Leu Thr Cys Leu Val Lys Gly Phe Tyr Pro Ser Asp Ile Ala Val Glu
                370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
                435                 440                 445
```

Pro Gly Lys
   450

<210> SEQ ID NO 255
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 255

```
gaggtgcagc tggtggagac tggaggaggc ttggtccagc cgggggggtc cctgagactc    60
tcatgtgcag cctctggatt caccgtcaga cgcaattaca tgagttgggt ccgccaggct   120
ccggggaagg gactggagtg ggtctcaggg atctacagtg gtggtagcac atactacgca   180
gactccgtga agggccgatt caccatctcc agagactatt ccaagaacac actgtctctt   240
caaatgaaca ccctgagagt cgaggacacg gccgtgtatt tctgtgcgag agaagacgaa   300
ttttggagcg ggtattccgc tggggtcgac tggggccagg gaaccctggt caccgtctcc   360
tcagctagca ccaagggccc atcggtcttc ccctggcac cctcctccaa gagcacctct   420
gggggcacag cggccctggg ctgcctggtc aaggactact ccccgaacc ggtgacggtg    480 tcgtggaact caggcgccct gaccagcggc gtgcacacct tcccggctgt cctacagtcc   540
tcaggactct actccctcag cagcgtggtg accgtgccct ccagcagctt gggcacccag   600
acctacatct gcaacgtgaa tcacaagccc agcaacacca aggtggacaa gagagttgag   660
cccaaatctt gtgacaaaac tcacacatgc ccaccgtgcc cagcacctga actcctgggg   720
ggaccgtcag tcttcctctt ccccccaaaa cccaaggaca ccctcatgat ctcccggacc   780
cctgaggtca catgcgtggt ggtggacgtg agccacgaag accctgaggt caagttcaac   840
tggtacgtgg acggcgtgga ggtgcataat gccaagacaa agccgcggga ggagcagtac   900
aacagcacgt accgtgtggt cagcgtcctc accgtcctgc accaggactg gctgaatggc   960
aaggagtaca agtgcaaggt ctccaacaaa gccctcccag cccccatcga gaaaaccatc  1020
tccaaagcca agggcagcc cgagaaccca caggtgtaca ccctgccccc atcccgggag  1080
gagatgacca agaaccaggt cagcctgacc tgcctggtca aaggcttcta tcccagcgac  1140
atcgccgtgg agtgggagag caatgggcag ccggagaaca actacaagac cacgcctccc  1200
gtgctggact ccgacggctc cttcttcctc tacagcaagc tcaccgtgga caagagcagg  1260
tggcagcagg ggaacgtctt ctcatgctcc gtgatgcatg aggctctgca caaccactac  1320
acgcagaaga gcctctccct gtctccgggt aaa                               1353
```

<210> SEQ ID NO 256
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 256

Arg Ala Ser Gln Ser Ile Ser Ser Tyr Leu Asn
1               5                   10

<210> SEQ ID NO 257

```
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 257

Ala Ala Ser Ser Leu Gln Ser
1               5

<210> SEQ ID NO 258
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 258

Gln Gln Ser Tyr Asn Thr Pro Arg Thr
1               5

<210> SEQ ID NO 259
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 259

Ser Gln Ser Ile Ser Ser Tyr
1               5

<210> SEQ ID NO 260
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 260

Ala Ala Ser
1

<210> SEQ ID NO 261
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 261

Ser Tyr Asn Thr Pro Arg
1               5

<210> SEQ ID NO 262
<211> LENGTH: 107
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"

<400> SEQUENCE: 262

Asp Ile Arg Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Thr Pro Arg
                85                  90                  95

Thr Phe Gly Gln Gly Thr Lys Val Glu Ile Lys
            100                 105

<210> SEQ ID NO 263
<211> LENGTH: 323
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 263
gacatccggt tgacccagtc tccatcctcc ctgtctgcat ctgtaggaga cagagtcacc      60
atcacttgcc gggcaagtca gagcattagc agctatttga attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacaata cccctcgaac gttcggccaa    300
gggaccaagg tggagatcaa acg                                            323

<210> SEQ ID NO 264
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 264

Asp Ile Arg Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Thr Pro Arg
```

```
                    85                  90                  95
Thr Phe Gly Gln Gly Thr Lys Val Glu Ile Lys Arg Thr Val Ala Ala
                    100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 265
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 265
gacatccggt tgacccagtc tccatcctcc ctgtctgcat ctgtaggaga cagagtcacc     60
atcacttgcc gggcaagtca gagcattagc agctatttga attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacaata cccctcgaac gttcggccaa    300
gggaccaagg tggagatcaa acgtacggtg gctgcaccat ctgtcttcat cttcccgcca    360
tctgatgagc agttgaaatc tggaactgcc tctgttgtgt gcctgctgaa taacttctat    420 cccgcgagg ccaaagtaca gtggaaggtg ataacgccc tccaatcggg taactcccag     480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac cgcggagagt gt                       642

<210> SEQ ID NO 266
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 266

Arg Asn Tyr Met Ser
1               5

<210> SEQ ID NO 267
<211> LENGTH: 16
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 267

Gly Ile Tyr Ser Gly Gly Ser Thr Tyr Tyr Ala Asp Ser Val Lys Gly
1               5                   10                  15

<210> SEQ ID NO 268
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 268

Glu Asp Glu Phe Trp Ser Gly Tyr Ser Ala Gly Val Asp
1               5                   10

<210> SEQ ID NO 269
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 269

Gly Phe Thr Val Ser Arg Asn
1               5

<210> SEQ ID NO 270
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 270

Tyr Ser Gly Gly Ser
1               5

<210> SEQ ID NO 271
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 271

Glu Asp Glu Phe Trp Ser Gly Tyr Ser Ala Gly Val Asp
1               5                   10

<210> SEQ ID NO 272
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 272

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Arg Asn
            20                  25                  30

Tyr Met Ser Trp Val Arg Gln Ala Pro Gly Lys Gly Leu Glu Trp Val
        35                  40                  45

Ser Gly Ile Tyr Ser Gly Gly Ser Thr Tyr Tyr Ala Asp Ser Val Lys
    50                  55                  60

Gly Arg Phe Thr Ile Ser Arg Asp Tyr Ser Lys Asn Thr Leu Ser Leu
65                  70                  75                  80

Gln Met Asn Thr Leu Arg Val Glu Asp Thr Ala Val Tyr Phe Cys Ala
                85                  90                  95

Arg Glu Asp Glu Phe Trp Ser Gly Tyr Ser Ala Gly Val Asp Trp Gly
            100                 105                 110

Gln Gly Thr Leu Val Thr Val Ser Ser
        115                 120
```

<210> SEQ ID NO 273
<211> LENGTH: 365
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 273

```
caggtgcagc tggtggaatc tgaggaggc ttggtccagc ctgggggtc cctgagactc      60
tcatgtgcag cctctggatt caccgtcagt cgcaattaca tgagttgggt ccgccaggct    120
ccggggaagg gactggagtg gtctcaggg atttacagtg gtggtagcac atactacgca    180
gactccgtga agggccgatt caccatctcc agagactatt ccaagaacac actgtctctt    240
caaatgaaca ccctgagagt cgaggacacg gccgtgtatt tctgtgcgag agaagacgaa    300
ttttggagtg gtattccgc tggggtcgac tggggccagg gaaccctggt caccgtctcc    360
tcagc                                                               365
```

<210> SEQ ID NO 274
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 274

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Arg Asn
            20                  25                  30

Tyr Met Ser Trp Val Arg Gln Ala Pro Gly Lys Gly Leu Glu Trp Val
        35                  40                  45

Ser Gly Ile Tyr Ser Gly Gly Ser Thr Tyr Tyr Ala Asp Ser Val Lys
    50                  55                  60

Gly Arg Phe Thr Ile Ser Arg Asp Tyr Ser Lys Asn Thr Leu Ser Leu
```

```
            65                  70                  75                  80
        Gln Met Asn Thr Leu Arg Val Glu Asp Thr Ala Val Tyr Phe Cys Ala
                        85                  90                  95

Arg Glu Asp Glu Phe Trp Ser Gly Tyr Ser Ala Gly Val Asp Trp Gly
                        100                 105                 110

Gln Gly Thr Leu Val Thr Val Ser Ala Ser Thr Lys Gly Pro Ser
                        115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
        145                 150                 155                 160

Ser Trp Asn Ser Gly Ala Leu Thr Ser Gly Val His Thr Phe Pro Ala
                        165                 170                 175

Val Leu Gln Ser Ser Gly Leu Tyr Ser Leu Ser Ser Val Val Thr Val
                        180                 185                 190

Pro Ser Ser Ser Leu Gly Thr Gln Thr Tyr Ile Cys Asn Val Asn His
                        195                 200                 205

Lys Pro Ser Asn Thr Lys Val Asp Lys Arg Val Glu Pro Lys Ser Cys
        210                 215                 220

Asp Lys Thr His Thr Cys Pro Pro Cys Pro Ala Pro Glu Leu Leu Gly
        225                 230                 235                 240

Gly Pro Ser Val Phe Leu Phe Pro Pro Lys Pro Lys Asp Thr Leu Met
                        245                 250                 255

Ile Ser Arg Thr Pro Glu Val Thr Cys Val Val Val Asp Val Ser His
                        260                 265                 270

Glu Asp Pro Glu Val Lys Phe Asn Trp Tyr Val Asp Gly Val Glu Val
                        275                 280                 285

His Asn Ala Lys Thr Lys Pro Arg Glu Glu Gln Tyr Asn Ser Thr Tyr
                        290                 295                 300

Arg Val Val Ser Val Leu Thr Val Leu His Gln Asp Trp Leu Asn Gly
        305                 310                 315                 320

Lys Glu Tyr Lys Cys Lys Val Ser Asn Lys Ala Leu Pro Ala Pro Ile
                        325                 330                 335

Glu Lys Thr Ile Ser Lys Ala Lys Gly Gln Pro Arg Glu Pro Gln Val
                        340                 345                 350

Tyr Thr Leu Pro Pro Ser Arg Glu Glu Met Thr Lys Asn Gln Val Ser
                        355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
        385                 390                 395                 400

Val Leu Asp Ser Asp Gly Ser Phe Phe Leu Tyr Ser Lys Leu Thr Val
                        405                 410                 415

Asp Lys Ser Arg Trp Gln Gln Gly Asn Val Phe Ser Cys Ser Val Met
                        420                 425                 430

His Glu Ala Leu His Asn His Tyr Thr Gln Lys Ser Leu Ser Leu Ser
                        435                 440                 445

Pro Gly Lys
                450

<210> SEQ ID NO 275
<211> LENGTH: 1353
<212> TYPE: DNA
<213> ORGANISM: Artificial Sequence
```

<220> FEATURE:
<221> NAME/KEY: source
<223> OTHER INFORMATION: /note="Description of Artificial Sequence: Synthetic polynucleotide"

<400> SEQUENCE: 275

```
caggtgcagc tggtggaatc tggaggaggc ttggtccagc ctgggggtc cctgagactc      60
tcatgtgcag cctctggatt caccgtcagt cgcaattaca tgagttgggt ccgccaggct    120
ccggggaagg gactggagtg ggtctcaggg atttacagtg gtggtagcac atactacgca    180
gactccgtga agggccgatt caccatctcc agagactatt ccaagaacac actgtctctt    240
caaatgaaca ccctgagagt cgaggacacg gccgtgtatt tctgtgcgag agaagacgaa    300
ttttggagtg ggtattccgc tggggtcgac tggggccagg gaaccctggt caccgtctcc    360
tcagctagca ccaagggccc atcggtcttc cccctggcac cctcctccaa gagcacctct    420
gggggcacag cggccctggg ctgcctggtc aaggactact ccccgaaccc ggtgacggtg    480
tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gagagttgag    660
cccaaatctt gtgacaaaac tcacacatgc ccaccgtgcc cagcacctga actcctgggg    720
ggaccgtcag tcttcctctt ccccccaaaa cccaaggaca ccctcatgat ctcccggacc    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcccag cccccatcga gaaaaccatc   1020
tccaaagcca agggcagcc cgagaacca caggtgtaca ccctgccccc atcccgggag   1080
gagatgacca gaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaa                                1353
```

<210> SEQ ID NO 276
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 276

Arg Ala Ser Gln Ser Ile Ser Ser Tyr Leu Asn
1               5                   10

<210> SEQ ID NO 277
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 277

```
Ala Ala Ser Ser Leu Gln Ser
1               5

<210> SEQ ID NO 278
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 278

Gln Gln Ser Tyr Ser Thr Pro Arg Thr
1               5

<210> SEQ ID NO 279
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 279

Ser Gln Ser Ile Ser Ser Tyr
1               5

<210> SEQ ID NO 280
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 280

Ala Ala Ser
1

<210> SEQ ID NO 281
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 281

Ser Tyr Ser Thr Pro Arg
1               5

<210> SEQ ID NO 282
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 282

Asp Ile Arg Met Thr Gln Ser Pro Ser Ser Leu Ser Ala Ser Val Gly
1               5                   10                  15
```

```
Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Thr Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Arg
                 85                  90                  95

Thr Phe Gly Gln Gly Thr Lys Val Glu Ile Lys
             100                 105
```

<210> SEQ ID NO 283
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 283

```
gacatccgga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctacgctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctcggac gttcggccaa   300
gggaccaagg tggagatcaa ac                                            322
```

<210> SEQ ID NO 284
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 284

```
Asp Ile Arg Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Thr Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Arg
                 85                  90                  95

Thr Phe Gly Gln Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
```

```
                130             135             140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 285
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 285
gacatccgga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctacgctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta cccctcggac gttcggccaa     300
gggaccaagg tggagatcaa acgtacggtg gctgcaccat ctgtcttcat cttcccgcca     360
tctgatgagc agttgaaatc tggaactgcc tctgttgtgt gcctgctgaa taacttctat     420
ccccgcgagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac cgcggagagt gt                        642

<210> SEQ ID NO 286
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 286

Arg Asn Tyr Met Ser
1               5

<210> SEQ ID NO 287
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 287

Gly Ile Tyr Gly Gly Gly Arg Thr Tyr Tyr Ala Glu Ser Val Lys Gly
```

<210> SEQ ID NO 288
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 288

Glu Asp Glu Phe Trp Ser Gly Tyr Ser Ala Gly Val Asp
1               5                   10

<210> SEQ ID NO 289
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 289

Gly Phe Thr Val Ser Arg Asn
1               5

<210> SEQ ID NO 290
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 290

Tyr Gly Gly Gly Arg
1               5

<210> SEQ ID NO 291
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 291

Glu Asp Glu Phe Trp Ser Gly Tyr Ser Ala Gly Val Asp
1               5                   10

<210> SEQ ID NO 292
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 292

Glu Val Gln Leu Leu Glu Ser Gly Gly Gly Leu Val Arg Pro Gly Gly
1               5                   10                  15

Ser Leu Arg Val Ser Cys Ala Ala Ser Gly Phe Thr Val Ser Arg Asn
                20                  25                  30

Tyr Met Ser Trp Val Arg Gln Ala Pro Gly Lys Gly Leu Glu Trp Val
            35                  40                  45

Ser Gly Ile Tyr Gly Gly Gly Arg Thr Tyr Tyr Ala Glu Ser Val Lys
    50                  55                  60

Gly Arg Phe Thr Ile Ser Arg Asp Tyr Ser Lys Asn Thr Leu Phe Leu
65                  70                  75                  80

Gln Met Asn Thr Leu Arg Val Glu Asp Thr Ala Leu Tyr Phe Cys Ala
                85                  90                  95

Arg Glu Asp Glu Phe Trp Ser Gly Tyr Ser Ala Gly Val Asp Trp Gly
            100                 105                 110

Gln Gly Thr Leu Val Thr Val Ser Ser
            115                 120

<210> SEQ ID NO 293
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 293
gaggtgcagc tgttggagtc cggggggaggc ttggtccggc ctggggggtc cctgagagtc      60
tcatgtgcag cctctggatt caccgtcagt cgcaattaca tgagttgggt ccgccaggct     120
ccggggaagg gactggagtg ggtctcaggg atttacggtg gtggtaggac ttactacgca     180
gagtccgtga agggccgatt caccatctcc agagactatt ccaagaacac actgtttctt     240
caaatgaaca ccctgagagt cgaggacacg gccctgtatt tctgtgcgag agaagacgaa     300
ttttggagtg gtattctgc tggggtcgac tggggccagg gaaccctggt cactgtctcc     360
tca                                                                  363

<210> SEQ ID NO 294
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 294

Glu Val Gln Leu Leu Glu Ser Gly Gly Gly Leu Val Arg Pro Gly Gly
1               5                   10                  15

Ser Leu Arg Val Ser Cys Ala Ala Ser Gly Phe Thr Val Ser Arg Asn
            20                  25                  30

Tyr Met Ser Trp Val Arg Gln Ala Pro Gly Lys Gly Leu Glu Trp Val
            35                  40                  45

Ser Gly Ile Tyr Gly Gly Gly Arg Thr Tyr Tyr Ala Glu Ser Val Lys
    50                  55                  60

Gly Arg Phe Thr Ile Ser Arg Asp Tyr Ser Lys Asn Thr Leu Phe Leu
65                  70                  75                  80

Gln Met Asn Thr Leu Arg Val Glu Asp Thr Ala Leu Tyr Phe Cys Ala
                85                  90                  95

Arg Glu Asp Glu Phe Trp Ser Gly Tyr Ser Ala Gly Val Asp Trp Gly
            100                 105                 110

Gln Gly Thr Leu Val Thr Val Ser Ser Ala Ser Thr Lys Gly Pro Ser

```
            115                 120                 125
Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 295
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 295
gaggtgcagc tgttggagtc cggggggaggc ttggtccggc ctggggggtc cctgagagtc    60
```

```
tcatgtgcag cctctggatt caccgtcagt cgcaattaca tgagttgggt ccgccaggct    120
ccggggaagg gactggagtg ggtctcaggg atttacggtg gtggtaggac ttactacgca    180
gagtccgtga agggccgatt caccatctcc agagactatt ccaagaacac actgtttctt    240
caaatgaaca ccctgagagt cgaggacacg gccctgtatt tctgtgcgag agaagacgaa    300
ttttggagtg ggtattctgc tggggtcgac tggggccagg gaaccctggt cactgtctcc    360
tcagctagca ccaagggccc atcggtcttc cccctggcac cctcctccaa gagcacctct    420
gggggcacag cggccctggg ctgcctggtc aaggactact ccccgaacc ggtgacggtg    480
tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gagagttgag    660
cccaaatctt gtgacaaaac tcacacatgc ccaccgtgcc cagcacctga actcctgggg    720
ggaccgtcag tcttcctctt cccccaaaa cccaaggaca ccctcatgat ctcccggacc    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcccag cccccatcga gaaaaccatc   1020
tccaaagcca aagggcagcc ccgagaacca caggtgtaca ccctgccccc atcccgggag   1080
gagatgacca agaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaa                                1353
```

<210> SEQ ID NO 296
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 296

Arg Ala Ser Gln Ser Ile Ser Ser Tyr Leu Asn
1               5                   10

<210> SEQ ID NO 297
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 297

Ala Ala Ser Thr Leu Gln Thr
1               5

<210> SEQ ID NO 298
<211> LENGTH: 9
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 298

Gln Gln Ser Tyr Asn Thr Pro Arg Thr
1               5

<210> SEQ ID NO 299
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 299

Ser Gln Ser Ile Ser Ser Tyr
1               5

<210> SEQ ID NO 300
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 300

Ala Ala Ser
1

<210> SEQ ID NO 301
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 301

Ser Tyr Asn Thr Pro Arg
1               5

<210> SEQ ID NO 302
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 302

Asp Ile Gln Val Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Glu Pro Gly Lys Ala Pro Lys Leu Leu Ile
        35                  40                  45

Tyr Ala Ala Ser Thr Leu Gln Thr Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Thr Pro Arg
                85                  90                  95

Thr Phe Gly Gln Gly Thr Lys Val Glu Ile Lys
            100                 105

<210> SEQ ID NO 303
<211> LENGTH: 323
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 303
gacatccagg tgacccagtc tccatcctcc ctgtctgcat ctgtaggaga cagagtcacc    60
atcacttgcc gggcaagtca gagcattagc agctatttaa attggtatca gcaggaacca   120
gggaaagccc ctaaactcct gatctacgct gcatccactt tgcaaactgg ggtcccatca   180
cggttcagtg gtagtggatc tgggacagat ttcactctca ccatcagcag tctgcaacct   240
gaagattttg caacttatta ctgtcaacag agttacaata cccctcgaac cttcggccaa   300
gggaccaagg tggaaatcaa acg                                           323

<210> SEQ ID NO 304
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 304

Asp Ile Gln Val Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Glu Pro Gly Lys Ala Pro Lys Leu Leu Ile
        35                  40                  45

Tyr Ala Ala Ser Thr Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Thr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr 180                 185                 190
Ala Cys Glu Val Thr His Gln Gly Leu Ser Ser Pro Val Thr Lys Ser
        195                 200                 205

Phe Asn Arg Gly Glu Cys
    210

<210> SEQ ID NO 305
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 305
gacatccagg tgacccagtc tccatcctcc ctgtctgcat ctgtaggaga cagagtcacc      60
atcacttgcc gggcaagtca gagcattagc agctatttaa attggtatca gcaggaacca     120
gggaaagccc ctaaactcct gatctacgct gcatccactt tgcaaactgg ggtcccatca     180
cggttcagtg gtagtggatc tgggacagat ttcactctca ccatcagcag tctgcaacct     240
gaagattttg caacttatta ctgtcaacag agttacaata cccctcgaac cttcggccaa     300
gggaccaagg tggaaatcaa acgtacggtg gctgcaccat ctgtcttcat cttcccgcca     360
tctgatgagc agttgaaatc tggaactgcc tctgttgtgt gcctgctgaa taacttctat     420
ccccgcgagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac cgcggagagt gt                        642

<210> SEQ ID NO 306
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 306

Asn Gly Gly Tyr Tyr Trp Ser
1               5

<210> SEQ ID NO 307
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 307

Cys Ile His Tyr Ser Gly Gly Thr Tyr Tyr Asn Pro Ser Leu Lys Ser
1               5                   10                  15

<210> SEQ ID NO 308
<211> LENGTH: 14
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 308

Ala Leu Ile Ala Ala Pro Gly Ile Ser Asp Trp Phe Asp Pro
1               5                   10

<210> SEQ ID NO 309
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 309

Gly Gly Ser Ile Ser Asn Gly Gly Tyr
1               5

<210> SEQ ID NO 310
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 310

His Tyr Ser Gly Gly
1               5

<210> SEQ ID NO 311
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 311

Ala Leu Ile Ala Ala Pro Gly Ile Ser Asp Trp Phe Asp Pro
1               5                   10

<210> SEQ ID NO 312
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 312

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Gly
            20                  25                  30

Gly Tyr Tyr Trp Ser Trp Ile Arg Leu His Pro Gly Lys Gly Leu Glu
        35                  40                  45

Trp Ile Gly Cys Ile His Tyr Ser Gly Gly Thr Tyr Tyr Asn Pro Ser
    50                  55                  60

Leu Lys Ser Arg Val Thr Val Ser Leu Asp Thr Ser Lys Asn Gln Phe
65                  70                  75                  80
```

```
Ser Leu Asn Leu Ile Ser Val Thr Ala Ala Asp Thr Ala Ile Tyr Phe
                 85                  90                  95

Cys Ala Arg Ala Leu Ile Ala Ala Pro Gly Ile Ser Asp Trp Phe Asp
            100                 105                 110

Pro Trp Gly Gln Gly Thr Leu Val Thr Val Ser Ser
        115                 120
```

<210> SEQ ID NO 313
<211> LENGTH: 454
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 313

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Gly
            20                  25                  30

Gly Tyr Tyr Trp Ser Trp Ile Arg Leu His Pro Gly Lys Gly Leu Glu
        35                  40                  45

Trp Ile Gly Cys Ile His Tyr Ser Gly Gly Thr Tyr Tyr Asn Pro Ser
50                  55                  60

Leu Lys Ser Arg Val Thr Val Ser Leu Asp Thr Ser Lys Asn Gln Phe
65                  70                  75                  80

Ser Leu Asn Leu Ile Ser Val Thr Ala Ala Asp Thr Ala Ile Tyr Phe
                85                  90                  95

Cys Ala Arg Ala Leu Ile Ala Ala Pro Gly Ile Ser Asp Trp Phe Asp
            100                 105                 110

Pro Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
290                 295                 300
```

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys
    450

<210> SEQ ID NO 314
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 314

Ser Gly Ser Asn Ser Asn Val Gly His Asn Tyr Val Ser
1               5                   10

<210> SEQ ID NO 315
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 315

Asp Asn Asn Lys Arg Pro Ser
1               5

<210> SEQ ID NO 316
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 316

Gly Thr Trp Asp Ser Ser Leu Ser Ala Gly Val
1               5                   10

<210> SEQ ID NO 317
<211> LENGTH: 9
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 317

Ser Asn Ser Asn Val Gly His Asn Tyr
1               5

<210> SEQ ID NO 318
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 318

Asp Asn Asn
1

<210> SEQ ID NO 319
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 319

Trp Asp Ser Ser Leu Ser Ala Gly
1               5

<210> SEQ ID NO 320
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 320

Gln Ser Val Leu Thr Gln Pro Pro Ser Val Ser Ala Ala Pro Gly Gln
1               5                   10                  15

Lys Val Thr Ile Ser Cys Ser Gly Ser Asn Ser Asn Val Gly His Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Gly Gly Thr Lys Val Thr Val Leu
            100                 105                 110

<210> SEQ ID NO 321
<211> LENGTH: 216
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 321

Gln Ser Val Leu Thr Gln Pro Pro Ser Val Ser Ala Ala Pro Gly Gln
1               5                   10                  15

Lys Val Thr Ile Ser Cys Ser Gly Ser Asn Ser Asn Val Gly His Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Gly Gly Thr Lys Val Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 322
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 322

Ser Ser Trp Met Asn
1               5

<210> SEQ ID NO 323
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 323

Arg Ile Tyr Pro Gly Asp Ala Asp Thr Tyr Tyr Ser Gly Lys Phe Lys
1               5                   10                  15
```

Gly

<210> SEQ ID NO 324
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 324

His Ser Ser Gly Phe Thr Tyr
1               5

<210> SEQ ID NO 325
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 325

Gly Tyr Thr Phe Ser Ser Ser
1               5

<210> SEQ ID NO 326
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 326

Tyr Pro Gly Asp Ala Asp
1               5

<210> SEQ ID NO 327
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 327

His Ser Ser Gly Phe Thr Tyr
1               5

<210> SEQ ID NO 328
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 328

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Ser
            20                  25                  30

```
Trp Met Asn Trp Val Arg Gln Ala Pro Gly Gln Arg Leu Glu Trp Met
            35                  40                  45

Gly Arg Ile Tyr Pro Gly Asp Ala Asp Thr Tyr Tyr Ser Gly Lys Phe
 50                      55                  60

Lys Gly Arg Val Thr Ile Thr Ala Asp Ser Ser Ala Arg Thr Ala Tyr
 65                  70                  75                  80

Met Glu Leu Ser Ser Leu Arg Ser Glu Asp Thr Ala Val Tyr Tyr Cys
                85                  90                  95

Ala Ile His Ser Ser Gly Phe Thr Tyr Trp Gly Gln Gly Thr Leu Val
            100                 105                 110

Thr Val Ser Ser
            115
```

\<210\> SEQ ID NO 329  
\<211\> LENGTH: 350  
\<212\> TYPE: DNA  
\<213\> ORGANISM: Artificial Sequence  
\<220\> FEATURE:  
\<221\> NAME/KEY: source  
\<223\> OTHER INFORMATION: /note="Description of Artificial Sequence: Synthetic polynucleotide"

\<400\> SEQUENCE: 329

```
caggtccagc ttgtgcagtc tggggctgag gtgaagaagc ctggggcctc agtgaaggtt     60
tcctgcaagg cttctggcta cattcagc agctcttgga tgaactgggt gcgccaggcc    120
cccggacaaa ggcttgagtg gatgggacgg atctatccag agacgccga tacttactac    180
agtgggaaat tcaagggcag agtcaccatt accgccgaca gctccgcgag aacagcctac    240
atggagctga gcagcctgag atctgaagac acggctgtgt attactgtgc gatccacagc    300
tcgggctta cttactgggg ccagggcacc ctggtcaccg tctcctcagc                350
```

\<210\> SEQ ID NO 330  
\<211\> LENGTH: 446  
\<212\> TYPE: PRT  
\<213\> ORGANISM: Artificial Sequence  
\<220\> FEATURE:  
\<221\> NAME/KEY: source  
\<223\> OTHER INFORMATION: /note="Description of Artificial Sequence: Synthetic polypeptide"

\<400\> SEQUENCE: 330

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Ser Ser Ser
            20                  25                  30

Trp Met Asn Trp Val Arg Gln Ala Pro Gly Gln Arg Leu Glu Trp Met
            35                  40                  45

Gly Arg Ile Tyr Pro Gly Asp Ala Asp Thr Tyr Tyr Ser Gly Lys Phe
 50                      55                  60

Lys Gly Arg Val Thr Ile Thr Ala Asp Ser Ser Ala Arg Thr Ala Tyr
 65                  70                  75                  80

Met Glu Leu Ser Ser Leu Arg Ser Glu Asp Thr Ala Val Tyr Tyr Cys
                85                  90                  95

Ala Ile His Ser Ser Gly Phe Thr Tyr Trp Gly Gln Gly Thr Leu Val
            100                 105                 110

Thr Val Ser Ser Ala Ser Thr Lys Gly Pro Ser Val Phe Pro Leu Ala
            115                 120                 125
```

```
Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 331
<211> LENGTH: 1338
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 331
caggtccagc ttgtgcagtc tggggctgag gtgaagaagc ctggggcctc agtgaaggtt      60
tcctgcaagg cttctggcta tacattcagc agctcttgga tgaactgggt gcgccaggcc     120
cccggacaaa ggcttgagtg gatgggacgg atctatccag agacgccga tacttactac      180 agtgggaaat tcaagggcag agtcaccatt accgccgaca gctccgcgag aacagcctac     240
```

-continued

```
atggagctga gcagcctgag atctgaagac acggctgtgt attactgtgc gatccacagc    300
tcgggcttta cttactgggg ccagggcacc ctggtcaccg tctcctcagc tagcaccaag    360
ggcccatcgg tcttccccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaggtg gacaagagag ttgagcccaa atcttgtgac    660
aaaactcaca catgcccacc gtgcccagca cctgaactcc tggggggacc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
cagccccgag aaccacaggt gtacaccctg cccccatccc gggaggagat gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctacag caagctcacc gtggacaaga gcaggtggca gcaggggaac   1260
gtcttctcat gctccgtgat gcatgaggct ctgcacaacc actacacgca gaagagcctc   1320
tccctgtctc cgggtaaa                                                  1338
```

<210> SEQ ID NO 332
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 332

Arg Ala Ser Gln Asp Ile Ser Asp Tyr Leu Asn
1               5                   10

<210> SEQ ID NO 333
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 333

Tyr Thr Ser Arg Leu His Ser
1               5

<210> SEQ ID NO 334
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 334

Gln Gln Thr His Thr Leu Pro Phe Thr
1               5

<210> SEQ ID NO 335
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 335

Ser Gln Asp Ile Ser Asp Tyr
1               5

<210> SEQ ID NO 336
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 336

Tyr Thr Ser
1

<210> SEQ ID NO 337
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 337

Thr His Thr Leu Pro Phe
1               5

<210> SEQ ID NO 338
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 338

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asp Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Thr His Thr Leu Pro Phe
                85                  90                  95

Thr Phe Gly Gly Gly Thr Lys Val Glu Ile Lys
            100                 105

<210> SEQ ID NO 339
<211> LENGTH: 323
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 339
gacatccaga tgacccagtc tccatcctcc ctgtctgcat ctgtaggaga cagagtcacc    60
atcacttgca gggcaagtca ggacattagc gattatttaa actggtatca gcagaaacca   120
gggaaagccc ctaagctcct gatctattat acatcaagat tacactcagg ggtcccatca   180
aggttcagtg gcagtggatc tgggacagat tacactctca ccatcagcag tctgcaacct   240
gaagattttg caacttactt ctgtcaacag actcatacgc ttcctttcac gttcggcgga   300
gggaccaagg tggagatcaa acg                                            323

<210> SEQ ID NO 340
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 340

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asp Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Thr His Thr Leu Pro Phe
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 341
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 341
gacatccaga tgacccagtc tccatcctcc ctgtctgcat ctgtaggaga cagagtcacc     60
atcacttgca gggcaagtca ggacattagc gattatttaa actggtatca gcagaaacca    120
gggaaagccc ctaagctcct gatctattat acatcaagat tacactcagg ggtcccatca    180
aggttcagtg gcagtggatc tgggacagat tacactctca ccatcagcag tctgcaacct    240
gaagattttg caacttactt ctgtcaacag actcatacgc ttcctttcac gttcggcgga    300
gggaccaagg tggagatcaa acgtacggtg gctgcaccat ctgtcttcat cttcccgcca    360
tctgatgagc agttgaaatc tggaactgcc tctgttgtgt gcctgctgaa taacttctat    420
ccccgcgagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac cgcggagagt gt                       642

<210> SEQ ID NO 342
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 342

Asn Tyr Trp Met His
1               5

<210> SEQ ID NO 343
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 343

Asn Ile Tyr Pro Gly Ser Gly Asn Thr Asn Tyr Gly Glu Asn Phe Lys
1               5                   10                  15

Ser

<210> SEQ ID NO 344
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 344

Ser Ala Ile Tyr Tyr Gly Tyr Asp Gly His Tyr Phe Ala Met Asp Tyr
1               5                   10                  15

<210> SEQ ID NO 345
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 345

Gly Tyr Thr Phe Thr Asn Tyr
1               5

<210> SEQ ID NO 346
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 346

Tyr Pro Gly Ser Gly Asn
1               5

<210> SEQ ID NO 347
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 347

Ser Ala Ile Tyr Tyr Gly Tyr Asp Gly His Tyr Phe Ala Met Asp Tyr
1               5                   10                  15

<210> SEQ ID NO 348
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 348

Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Asn Tyr
            20                  25                  30

Trp Met His Trp Val Lys Gln Gly His Gly Gln Gly Leu Glu Trp Ile
        35                  40                  45

Gly Asn Ile Tyr Pro Gly Ser Gly Asn Thr Asn Tyr Gly Glu Asn Phe
    50                  55                  60

Lys Ser Lys Gly Thr Leu Thr Val Asp Thr Ser Ser Ser Thr Ala Tyr
65                  70                  75                  80

Met His Leu Ser Arg Leu Thr Ser Glu Asp Ser Ala Val Tyr Tyr Cys
                85                  90                  95
```

```
Ser Arg Ser Ala Ile Tyr Tyr Gly Tyr Asp Gly His Tyr Phe Ala Met
            100                 105                 110
Asp Tyr Trp Gly Gln Gly Thr Ser Val Thr Val Ser Ser
        115                 120                 125

<210> SEQ ID NO 349
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 349

Lys Ala Ser Gln Asp Ile Arg Lys Tyr Ile Ala
1               5                   10

<210> SEQ ID NO 350
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 350

Tyr Thr Ser Thr Leu Gln Ser
1               5

<210> SEQ ID NO 351
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 351

Leu Gln Tyr Asp Asn Ile Leu Phe Thr
1               5

<210> SEQ ID NO 352
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 352

Ser Gln Asp Ile Arg Lys Tyr
1               5

<210> SEQ ID NO 353
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 353
```

```
Tyr Thr Ser
1

<210> SEQ ID NO 354
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 354

Tyr Asp Asn Ile Leu Phe
1               5

<210> SEQ ID NO 355
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 355

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Arg Lys Tyr
            20                  25                  30

Ile Ala Trp Tyr Gln His Lys Pro Gly Lys Gly Pro Arg Leu Leu Ile
        35                  40                  45

Asn Tyr Thr Ser Thr Leu Gln Ser Gly Ile Pro Ser Arg Phe Arg Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Ile Leu Phe
                85                  90                  95

Thr Phe Gly Thr Gly Thr Lys Leu Glu Ile Lys
            100                 105

<210> SEQ ID NO 356
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 356

Ser Cys Trp Met Asn
1               5

<210> SEQ ID NO 357
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 357

Arg Ile Tyr Pro Gly Asp Gly Asp Thr Lys Tyr Thr Glu Lys Phe Lys
```

```
1               5                   10                  15

Asp

<210> SEQ ID NO 358
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 358

Ser Gly Ser Gly Leu Pro Tyr
1               5

<210> SEQ ID NO 359
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 359

Gly Tyr Ser Phe Ser Ser Cys
1               5

<210> SEQ ID NO 360
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 360

Tyr Pro Gly Asp Gly Asp
1               5

<210> SEQ ID NO 361
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 361

Ser Gly Ser Gly Leu Pro Tyr
1               5

<210> SEQ ID NO 362
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 362

Gln Val His Leu Gln Gln Ser Gly Pro Glu Leu Val Lys Pro Gly Ala
1               5                   10                  15
```

```
Ser Val Thr Ile Ser Cys Lys Thr Ser Gly Tyr Ser Phe Ser Ser Cys
                20                  25                  30

Trp Met Asn Trp Val Lys Gln Arg Pro Gly Gln Gly Leu Glu Trp Ile
         35                  40                  45

Gly Arg Ile Tyr Pro Gly Asp Gly Asp Thr Lys Tyr Thr Glu Lys Phe
     50                  55                  60

Lys Asp Lys Ala Thr Leu Thr Ala Asp Lys Ser Ser Thr Ala Tyr
 65                  70                  75                  80

Met Gln Leu Ser Ser Leu Thr Ser Val Asp Ser Ala Leu Tyr Phe Cys
                 85                  90                  95

Ala Ile Ser Gly Ser Gly Leu Pro Tyr Trp Gly Gln Gly Thr Leu Val
                100                 105                 110

Thr Val Ser Glu
        115

<210> SEQ ID NO 363
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 363

Arg Ala Ser Gln Asp Ile His Asn Tyr Leu Asn
 1               5                  10

<210> SEQ ID NO 364
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 364

Ser Thr Ser Arg Leu His Ser
 1               5

<210> SEQ ID NO 365
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 365

Gln Gln Thr His Thr Leu Pro Leu Thr
 1               5

<210> SEQ ID NO 366
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 366

Ser Gln Asp Ile His Asn Tyr
```

```
1               5
```

<210> SEQ ID NO 367
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 367

```
Ser Thr Ser
1
```

<210> SEQ ID NO 368
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 368

```
Thr His Thr Leu Pro Leu
1               5
```

<210> SEQ ID NO 369
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 369

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile His Asn Tyr
                20                  25                  30

Leu Asn Trp Tyr Gln Gln Lys Pro Asp Gly Thr Ile Lys Leu Leu Ile
            35                  40                  45

Tyr Ser Thr Ser Arg Leu His Ser Gly Val Pro Ser Arg Phe Ser Gly
        50                  55                  60

Ser Gly Ser Gly Thr His Tyr Ser Leu Thr Ile Asn Asn Leu Glu Gln
65                  70                  75                  80

Glu Asp Ile Ala Thr Tyr Phe Cys Gln Gln Thr His Thr Leu Pro Leu
                85                  90                  95

Thr Phe Gly Ala Gly Thr Lys Leu Glu Leu Lys
            100                 105
```

<210> SEQ ID NO 370
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 370

```
Ser Tyr Trp Met Asn
1               5
```

```
<210> SEQ ID NO 371
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 371

Gln Ile Tyr Pro Gly Asn Gly Asp Thr Asn Tyr Asn Gly Lys Phe Lys
1               5                   10                  15

Gly

<210> SEQ ID NO 372
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 372

Glu Ala Arg Gln Gly Tyr His Tyr Ala Met Asp Tyr
1               5                   10

<210> SEQ ID NO 373
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 373

Gly Tyr Ala Phe Ser Ser Tyr
1               5

<210> SEQ ID NO 374
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 374

Tyr Pro Gly Asn Gly Asp
1               5

<210> SEQ ID NO 375
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 375

Glu Ala Arg Gln Gly Tyr His Tyr Ala Met Asp Tyr
1               5                   10
```

```
<210> SEQ ID NO 376
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 376

Gln Val Gln Leu Gln Gln Ser Gly Ala Gly Leu Val Arg Pro Gly Ser
1               5                   10                  15

Ser Val Lys Ile Ser Cys Lys Thr Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asn Gly Asp Thr Asn Tyr Asn Gly Lys Phe
    50                  55                  60

Lys Gly Lys Ala Thr Leu Thr Ala Asp Lys Ser Ser Asn Thr Ala Tyr
65                  70                  75                  80

Ile Gln Leu Asn Ser Leu Thr Ser Glu Asp Ser Ala Val Tyr Phe Cys
                85                  90                  95

Ala Arg Glu Ala Arg Gln Gly Tyr His Tyr Ala Met Asp Tyr Trp Gly
            100                 105                 110

Gln Gly Thr Ser Val Thr Val Ser Leu
        115                 120

<210> SEQ ID NO 377
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 377

Ser Ala Ser Ser Met Ile Asn Ser Asn Tyr Leu His
1               5                   10

<210> SEQ ID NO 378
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 378

Arg Thr Ser Asn Leu Ala Ser
1               5

<210> SEQ ID NO 379
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 379

Gln Gln Gly Ser Asn Ile Phe Thr
1               5
```

<210> SEQ ID NO 380
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 380

Ser Ser Met Ile Asn Ser Asn Tyr
1               5

<210> SEQ ID NO 381
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 381

Arg Thr Ser
1

<210> SEQ ID NO 382
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 382

Gly Ser Asn Ile Phe
1               5

<210> SEQ ID NO 383
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 383

Glu Ile Val Phe Thr Gln Ser Pro Thr Thr Met Ala Ala Phe Pro Gly
1               5                   10                  15

Glu Lys Ile Thr Ile Thr Cys Ser Ala Ser Ser Met Ile Asn Ser Asn
            20                  25                  30

Tyr Leu His Trp Tyr Gln Gln Lys Pro Gly Phe Ser Pro Lys Val Leu
        35                  40                  45

Ile Tyr Arg Thr Ser Asn Leu Ala Ser Gly Val Pro Ala Arg Phe Ser
    50                  55                  60

Gly Thr Gly Ser Gly Thr Ser Phe Ser Leu Thr Ile Gly Thr Met Glu
65                  70                  75                  80

Ala Glu Asp Val Ala Thr Tyr Tyr Cys Gln Gln Gly Ser Asn Ile Phe
                85                  90                  95

Thr Phe Gly Ser Gly Thr Lys Leu Glu Ile Lys
            100                 105

<210> SEQ ID NO 384
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 384

Asn Ser Trp Met Asn
1               5

<210> SEQ ID NO 385
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 385

Arg Ile Tyr Pro Gly Asp Gly Asp Thr Gln Tyr Asn Glu Lys Phe Lys
1               5                   10                  15

Gly

<210> SEQ ID NO 386
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 386

Ser Arg Ser Gly Leu Asp Tyr
1               5

<210> SEQ ID NO 387
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 387

Gly Phe Thr Phe Ser Asn Ser
1               5

<210> SEQ ID NO 388
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 388

Tyr Pro Gly Asp Gly Asp
1               5

<210> SEQ ID NO 389

```
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 389

Ser Arg Ser Gly Leu Asp Tyr
1               5

<210> SEQ ID NO 390
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 390

Gln Val Gln Leu Gln Gln Ser Gly Pro Glu Leu Val Lys Pro Gly Ala
1               5                   10                  15

Ser Val Arg Ile Ser Cys Lys Val Ser Gly Phe Thr Phe Ser Asn Ser
            20                  25                  30

Trp Met Asn Trp Val Lys Gln Arg Pro Gly Gln Gly Leu Glu Trp Ile
        35                  40                  45

Gly Arg Ile Tyr Pro Gly Asp Gly Asp Thr Gln Tyr Asn Glu Lys Phe
    50                  55                  60

Lys Gly Lys Ala Thr Leu Thr Ala Asp Thr Ser Ser Asn Thr Ala Tyr
65                  70                  75                  80

Ile Gln Leu Asn Ser Leu Thr Ser Val Asp Ser Ala Val Phe Phe Cys
                85                  90                  95

Ala Arg Ser Arg Ser Gly Leu Asp Tyr Trp Gly Gln Gly Thr Thr Leu
            100                 105                 110

Thr Val Ser Ser
        115

<210> SEQ ID NO 391
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 391

Arg Ala Ser Gln Asp Ile Tyr Asn Tyr Leu Asn
1               5                   10

<210> SEQ ID NO 392
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 392

Ser Thr Ser Arg Leu His Ser
1               5
```

<210> SEQ ID NO 393
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 393

His Gln Ser His Thr Val Pro Phe Thr
1               5

<210> SEQ ID NO 394
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 394

Ser Gln Asp Ile Tyr Asn Tyr
1               5

<210> SEQ ID NO 395
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 395

Ser Thr Ser
1

<210> SEQ ID NO 396
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 396

Ser His Thr Val Pro Phe
1               5

<210> SEQ ID NO 397
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 397

Asp Ile Gln Met Thr Gln Ser Thr Ser Ser Leu Ser Ala Ser Leu Gly
1               5                   10                  15

Asp Arg Val Thr Ile Ser Cys Arg Ala Ser Gln Asp Ile Tyr Asn Tyr
            20                  25                  30

Leu Asn Trp Phe Gln Gln Lys Pro Asp Gly Thr Val Lys Pro Leu Ile

```
            35                  40                  45
Tyr Ser Thr Ser Arg Leu His Ser Gly Val Ser Ser Arg Phe Ser Gly
 50                  55                  60

Ser Gly Ser Gly Thr Asp Tyr Ser Leu Thr Ile Ser Asn Leu Glu Arg
 65                  70                  75                  80

Glu Asp Ile Ala Thr Tyr Phe Cys His Gln Ser His Thr Val Pro Phe
                 85                  90                  95

Thr Phe Gly Ser Gly Thr Lys Leu Glu Ile Lys
            100                 105
```

<210> SEQ ID NO 398
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 398

```
Ser Ser Trp Ile Asn
1               5
```

<210> SEQ ID NO 399
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 399

```
Arg Ile Tyr Pro Gly Asp Gly Asp Thr Asn Tyr Asn Gly Lys Phe Lys
1               5                   10                  15

Gly
```

<210> SEQ ID NO 400
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 400

```
His Ser Ser Gly Phe Pro His
1               5
```

<210> SEQ ID NO 401
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 401

```
Gly Tyr Thr Phe Ser Ser Ser
1               5
```

<210> SEQ ID NO 402
<211> LENGTH: 6

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 402

Tyr Pro Gly Asp Gly Asp
1               5

<210> SEQ ID NO 403
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 403

His Ser Ser Gly Phe Pro His
1               5

<210> SEQ ID NO 404
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 404

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Ser Ser Ser
            20                  25                  30

Trp Ile Asn Trp Val Lys Gln Arg Pro Gly Gln Gly Leu Glu Trp Ile
        35                  40                  45

Gly Arg Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Val Asp
65                  70                  75                  80

Met His Leu Ser Ser Leu Thr Tyr Val Asp Ser Ala Val Tyr Phe Cys
                85                  90                  95

Ala Ile His Ser Ser Gly Phe Pro His Trp Gly Gln Gly Thr Leu Val
            100                 105                 110

Thr Val Ser Ala
        115

<210> SEQ ID NO 405
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 405

Arg Thr Ser Gln Asp Ile Ser Asp Tyr Leu Asn
1               5                   10
```

```
<210> SEQ ID NO 406
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 406

Tyr Thr Ser Arg Leu His Ser
1               5

<210> SEQ ID NO 407
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 407

Gln Gln Thr Asn Thr Leu Pro Phe Thr
1               5

<210> SEQ ID NO 408
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 408

Ser Gln Asp Ile Ser Asp Tyr
1               5

<210> SEQ ID NO 409
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 409

Tyr Thr Ser
1

<210> SEQ ID NO 410
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 410

Thr Asn Thr Leu Pro Phe
1               5

<210> SEQ ID NO 411
<211> LENGTH: 107
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 411

Asp Ile Gln Met Thr Gln Thr Thr Ser Ser Leu Ser Ala Ser Leu Gly
1               5                   10                  15

Gly Arg Val Thr Ile Ser Cys Arg Thr Ser Gln Asp Ile Ser Asp Tyr
            20                  25                  30

Leu Asn Trp Tyr Gln Gln Lys Pro Asp Gly Ala Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Thr Asn Thr Leu Pro Phe
                85                  90                  95

Thr Phe Gly Gly Gly Thr Lys Leu Glu Ile Lys
            100                 105

<210> SEQ ID NO 412
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 412

Arg Tyr Trp Met Asn
1               5

<210> SEQ ID NO 413
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 413

Gln Ile Tyr Pro Gly Asp Gly Asp Thr Lys Tyr Asn Gly Lys Phe Lys
1               5                   10                  15

Asp

<210> SEQ ID NO 414
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 414

Tyr Gly Asn Tyr Gly Met Asp Tyr
1               5

<210> SEQ ID NO 415
<211> LENGTH: 7
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 415

Gly Tyr Ala Phe Ser Arg Tyr
1               5

<210> SEQ ID NO 416
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 416

Tyr Pro Gly Asp Gly Asp
1               5

<210> SEQ ID NO 417
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 417

Tyr Gly Asn Tyr Gly Met Asp Tyr
1               5

<210> SEQ ID NO 418
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 418

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Arg Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Lys Tyr Asn Gly Lys Phe
    50                  55                  60

Lys Asp Thr Ala Thr Leu Thr Ala Asp Lys Ser Ser Ser Thr Ala Tyr
65                  70                  75                  80

Leu Gln Leu Ser Ser Leu Thr Ser Glu Asp Ser Ala Val Tyr Phe Cys
                85                  90                  95

Ala Lys Tyr Gly Asn Tyr Gly Met Asp Tyr Trp Gly Gln Gly Thr Ser
            100                 105                 110

Val Thr Val Ser Ser
        115

<210> SEQ ID NO 419
```

```
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 419

Arg Ser Ser Gln Ser Leu Glu Tyr Gly Asn Gly Asn Thr Tyr Leu Asn
1               5                   10                  15

<210> SEQ ID NO 420
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 420

Arg Val Ser Asn Arg Phe Ser
1               5

<210> SEQ ID NO 421
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 421

Leu Gln Phe Thr His Val Pro Tyr Thr
1               5

<210> SEQ ID NO 422
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 422

Ser Gln Ser Leu Glu Tyr Gly Asn Gly Asn Thr Tyr
1               5                   10

<210> SEQ ID NO 423
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 423

Arg Val Ser
1

<210> SEQ ID NO 424
<211> LENGTH: 6
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 424

Phe Thr His Val Pro Tyr
1               5

<210> SEQ ID NO 425
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 425

Asp Ala Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Tyr Gly
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Asn Arg Phe Ser Gly Val Leu
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Phe
                85                  90                  95

Thr His Val Pro Tyr Thr Phe Gly Gly Gly Thr Lys Leu Glu Ile Lys
            100                 105                 110

<210> SEQ ID NO 426
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 426

Gly Tyr Thr Met Asn
1               5

<210> SEQ ID NO 427
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 427

Leu Phe Asn Pro Tyr Asn Gly Gly Thr Arg Tyr Asn Gln Lys Phe Lys
1               5                   10                  15

Gly

<210> SEQ ID NO 428
<211> LENGTH: 13
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 428

Leu Arg Asn Tyr Gly Ile Gly Asp Asp Phe Phe Asp Tyr
1               5                   10

<210> SEQ ID NO 429
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 429

Gly Tyr Ser Phe Thr Gly Tyr
1               5

<210> SEQ ID NO 430
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 430

Asn Pro Tyr Asn Gly Gly
1               5

<210> SEQ ID NO 431
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 431

Leu Arg Asn Tyr Gly Ile Gly Asp Asp Phe Phe Asp Tyr
1               5                   10

<210> SEQ ID NO 432
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 432

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Glu Asn Leu Glu Trp Ile
        35                  40                  45

Gly Leu Phe Asn Pro Tyr Asn Gly Gly Thr Arg Tyr Asn Gln Lys Phe
    50                  55                  60
```

```
Lys Gly Lys Ala Thr Leu Thr Val Asp Lys Ser Ser Thr Ala Tyr
 65                  70                  75                  80

Met Glu Leu Leu Ser Leu Thr Ser Glu Asp Ser Ala Val Tyr Tyr Cys
                 85                  90                  95

Ala Arg Leu Arg Asn Tyr Gly Ile Gly Asp Asp Phe Phe Asp Tyr Trp
            100                 105                 110

Gly Gln Gly Thr Thr Leu Thr Val Ser Ser
            115                 120
```

<210> SEQ ID NO 433
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 433

```
Lys Ala Ser Gln Asp Val Gly Thr Ala Val Ala
1               5                   10
```

<210> SEQ ID NO 434
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 434

```
Trp Ala Ser Thr Arg His Thr
1               5
```

<210> SEQ ID NO 435
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 435

```
Gln Gln Tyr Ser Asn Tyr Pro Tyr Thr
1               5
```

<210> SEQ ID NO 436
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 436

```
Ser Gln Asp Val Gly Thr Ala
1               5
```

<210> SEQ ID NO 437
<211> LENGTH: 3
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 437

Trp Ala Ser
1

<210> SEQ ID NO 438
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 438

Tyr Ser Asn Tyr Pro Tyr
1               5

<210> SEQ ID NO 439
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 439

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Thr Asp Tyr Phe Cys Gln Gln Tyr Ser Asn Tyr Pro Tyr
                85                  90                  95

Thr Phe Gly Gly Gly Thr Lys Leu Glu Ile Lys
            100                 105

<210> SEQ ID NO 440
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 440

Gly Tyr Thr Met Asn
1               5

<210> SEQ ID NO 441
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

```
      Synthetic peptide"

<400> SEQUENCE: 441

Leu Phe Asn Pro Tyr Asn Gly Gly Ile Asn Tyr Asn Gln Lys Phe Lys
1               5                   10                  15

Gly

<210> SEQ ID NO 442
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 442

Leu Arg Tyr Tyr Gly Ile Gly Asp Asp Phe Phe Asp Tyr
1               5                   10

<210> SEQ ID NO 443
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 443

Gly Tyr Ser Phe Thr Gly Tyr
1               5

<210> SEQ ID NO 444
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 444

Asn Pro Tyr Asn Gly Gly
1               5

<210> SEQ ID NO 445
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 445

Leu Arg Tyr Tyr Gly Ile Gly Asp Asp Phe Phe Asp Tyr
1               5                   10

<210> SEQ ID NO 446
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

<400> SEQUENCE: 446

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Phe Asn Pro Tyr Asn Gly Gly Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Leu Arg Tyr Tyr Gly Ile Gly Asp Asp Phe Phe Asp Tyr Trp
            100                 105                 110

Gly Gln Gly Thr Ser Leu Thr Val Ser Ser
        115                 120

<210> SEQ ID NO 447
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 447

Lys Ala Ser Arg Asp Val Gly Thr Ala Val Ala
1               5                   10

<210> SEQ ID NO 448
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 448

Trp Ala Ser Thr Arg His Thr
1               5

<210> SEQ ID NO 449
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 449

Gln Gln Tyr Ser Asn Tyr Pro Tyr Thr
1               5

<210> SEQ ID NO 450
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 450

Ser Arg Asp Val Gly Thr Ala
1               5

<210> SEQ ID NO 451
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 451

Trp Ala Ser
1

<210> SEQ ID NO 452
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 452

Tyr Ser Asn Tyr Pro Tyr
1               5

<210> SEQ ID NO 453
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 453

Asp Ile Val Met Thr Gln Ser His Lys Phe Met Ser Thr Ser Val Gly
1               5                   10                  15

Asp Arg Val Ser Ile Thr Cys Lys Ala Ser Arg Asp Val Gly Thr Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Asn Tyr Pro Tyr
                85                  90                  95

Thr Phe Gly Gly Gly Thr Lys Leu Glu Met Lys
                100                 105

<210> SEQ ID NO 454
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 454

Gly Tyr Thr Met Asn
1               5

<210> SEQ ID NO 455
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 455

Leu Phe Asn Pro Tyr Asn Gly Gly Pro Asn Tyr Asn Gln Lys Phe Lys
1               5                  10                  15

Gly

<210> SEQ ID NO 456
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 456

Leu Arg Tyr Tyr Gly Ile Gly Asp Asp Phe Phe Asp Tyr
1               5                  10

<210> SEQ ID NO 457
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 457

Gly Tyr Ser Phe Thr Gly Tyr
1               5

<210> SEQ ID NO 458
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 458

Asn Pro Tyr Asn Gly Gly
1               5

<210> SEQ ID NO 459
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 459
```

Leu Arg Tyr Tyr Gly Ile Gly Asp Asp Phe Phe Asp Tyr
1               5                   10

<210> SEQ ID NO 460
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 460

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Met Lys Gln Gly His Gly Lys Asn Leu Glu Trp Ile
        35                  40                  45

Gly Leu Phe Asn Pro Tyr Asn Gly Gly Pro Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Leu Arg Tyr Tyr Gly Ile Gly Asp Asp Phe Phe Asp Tyr Trp
            100                 105                 110

Gly Gln Gly Thr Thr Leu Thr Val Ser Ser
        115                 120

<210> SEQ ID NO 461
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 461

Lys Ala Ser Gln Asp Val Gly Thr Ala Val Ala
1               5                   10

<210> SEQ ID NO 462
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 462

Trp Ala Ser Thr Arg His Thr
1               5

<210> SEQ ID NO 463
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 463

Gln Gln Tyr Ser Ser Tyr Pro Tyr Thr
1               5

<210> SEQ ID NO 464
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 464

Ser Gln Asp Val Gly Thr Ala
1               5

<210> SEQ ID NO 465
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 465

Trp Ala Ser
1

<210> SEQ ID NO 466
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 466

Tyr Ser Ser Tyr Pro Tyr
1               5

<210> SEQ ID NO 467
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 467

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Thr Asp Tyr Phe Cys Gln Gln Tyr Ser Ser Tyr Pro Tyr
```

```
                    85                  90                  95
Thr Phe Gly Gly Gly Thr Lys Leu Glu Ile Lys
            100                 105

<210> SEQ ID NO 468
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 468

Gly Tyr Thr Met Asn
1               5

<210> SEQ ID NO 469
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 469

Leu Phe Asn Pro Tyr Asn Gly Gly Pro Ser Tyr Asn Gln Lys Phe Lys
1               5                   10                  15
Gly

<210> SEQ ID NO 470
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 470

Leu Arg Tyr Tyr Gly Ile Gly Asp Asp Phe Phe Asp Tyr
1               5                   10

<210> SEQ ID NO 471
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 471

Gly Tyr Ser Phe Thr Gly Tyr
1               5

<210> SEQ ID NO 472
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 472
```

```
Asn Pro Tyr Asn Gly Gly
1               5
```

<210> SEQ ID NO 473
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 473

```
Leu Arg Tyr Tyr Gly Ile Gly Asp Asp Phe Phe Asp Tyr
1               5                   10
```

<210> SEQ ID NO 474
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 474

```
Glu Val Gln Leu Gln Gln Ser Gly Pro Asp Leu Val Lys Pro Gly Ala
1               5                   10                  15

Ser Met Lys Leu Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Phe Asn Pro Tyr Asn Gly Gly Pro Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Pro Glu Asp Ser Ala Val Tyr Tyr Cys
                85                  90                  95

Ala Arg Leu Arg Tyr Tyr Gly Ile Gly Asp Asp Phe Phe Asp Tyr Trp
            100                 105                 110

Gly Gln Gly Thr Thr Leu Thr Val Ser Ser
        115                 120
```

<210> SEQ ID NO 475
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 475

```
Lys Ala Ser Gln Asp Val Gly Thr Ala Val Ala
1               5                   10
```

<210> SEQ ID NO 476
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 476

Trp Ala Ser Thr Arg His Thr
1               5

<210> SEQ ID NO 477
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 477

Gln Gln Tyr Ser Asn Tyr Pro Tyr Thr
1               5

<210> SEQ ID NO 478
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 478

Ser Gln Asp Val Gly Thr Ala
1               5

<210> SEQ ID NO 479
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 479

Trp Ala Ser
1

<210> SEQ ID NO 480
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 480

Tyr Ser Asn Tyr Pro Tyr
1               5

<210> SEQ ID NO 481
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 481

Asp Ile Val Met Thr Gln Ser His Lys Phe Met Ser Thr Ser Val Gly
1               5                   10                  15
```

```
Asp Arg Val Ser Ile Thr Cys Lys Ala Ser Gln Asp Val Gly Thr Ala
            20                  25                  30

Val Ala Trp Tyr Gln Glu Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Tyr Tyr Phe Cys Gln Gln Tyr Ser Asn Tyr Pro Tyr
                85                  90                  95

Thr Phe Gly Gly Gly Thr Lys Leu Glu Ile Lys
            100                 105
```

<210> SEQ ID NO 482
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 482

```
Gly Tyr Thr Met Asn
1               5
```

<210> SEQ ID NO 483
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 483

```
Leu Phe Asn Pro Tyr Asn Gly Gly Ala Thr Tyr Asn Gln Arg Phe Lys
1               5                   10                  15

Gly
```

<210> SEQ ID NO 484
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 484

```
Leu Arg Lys Tyr Gly Ile Gly Asp Asp Phe Phe Asp Tyr
1               5                   10
```

<210> SEQ ID NO 485
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 485

```
Gly Tyr Ser Phe Thr Gly Tyr
```

```
<210> SEQ ID NO 486
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 486

Asn Pro Tyr Asn Gly Gly
1               5

<210> SEQ ID NO 487
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 487

Leu Arg Lys Tyr Gly Ile Gly Asp Asp Phe Phe Asp Tyr
1               5                  10

<210> SEQ ID NO 488
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 488

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Phe Asn Pro Tyr Asn Gly Gly Ala Thr Tyr Asn Gln Arg Phe
    50                  55                  60

Lys Gly Lys Ala Thr Leu Thr Val Asp Lys Ser Ser Ser Thr Ala Tyr
65                  70                  75                  80

Met Asp Leu Leu Ser Leu Thr Ser Glu Asp Ser Ala Val Tyr Tyr Cys
                85                  90                  95

Thr Arg Leu Arg Lys Tyr Gly Ile Gly Asp Asp Phe Phe Asp Tyr Trp
            100                 105                 110

Gly Gln Gly Thr Thr Leu Thr Val Ser Ser
        115                 120

<210> SEQ ID NO 489
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 489
```

Lys Ala Ser Gln Asp Val Gly Thr Ala Val Ala
1               5                   10

<210> SEQ ID NO 490
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 490

Trp Ala Ser Thr Arg His Thr
1               5

<210> SEQ ID NO 491
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 491

Gln Gln Tyr Ser Thr Tyr Thr Tyr Thr
1               5

<210> SEQ ID NO 492
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 492

Ser Gln Asp Val Gly Thr Ala
1               5

<210> SEQ ID NO 493
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 493

Trp Ala Ser
1

<210> SEQ ID NO 494
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 494

Tyr Ser Thr Tyr Thr Tyr
1               5

<210> SEQ ID NO 495
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 495

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Thr Tyr Thr Tyr
                85                  90                  95

Thr Phe Gly Gly Gly Thr Lys Leu Glu Ile Lys
            100                 105

<210> SEQ ID NO 496
<211> LENGTH: 80
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 496

Phe Ser Leu Lys Leu Ser Ala Glu Asn Asp Phe Ser Ser Asp Ser Pro
1               5                   10                  15

Glu Arg Lys Met Leu Pro Cys Tyr Ser Thr Ala Arg Ile Pro Leu Pro
            20                  25                  30

Asn Leu Asn Glu Asp Leu Thr Cys Gly Asn Leu Leu Met Trp Glu Ala
        35                  40                  45

Val Thr Val Gln Thr Glu Val Ile Gly Ile Thr Ser Met Leu Asn Leu
    50                  55                  60

His Ala Gly Ser Gln Lys Val His Glu His Gly Gly Lys Pro Ile
65                  70                  75                  80

<210> SEQ ID NO 497
<211> LENGTH: 80
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 497

Tyr Ser Leu Lys Leu Thr Ala Glu Asn Ala Phe Asp Ser Asp Ser Pro
1               5                   10                  15

Asp Lys Lys Met Leu Pro Cys Tyr Ser Thr Ala Arg Ile Pro Leu Pro
            20                  25                  30

Asn Leu Asn Glu Asp Leu Thr Cys Gly Asn Leu Leu Met Trp Glu Ala

```
                35                  40                  45
Val Thr Val Lys Thr Glu Val Ile Gly Ile Thr Ser Met Leu Asn Leu
    50                  55                  60

His Ala Gly Ser Gln Lys Val His Glu Asn Gly Gly Lys Pro Val
65                  70                  75                  80

<210> SEQ ID NO 498
<211> LENGTH: 80
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 498

Tyr Ser Gln His Leu Ser Ala Glu Asn Ala Phe Asp Ser Asp Ser Pro
1               5                   10                  15

Asp Lys Lys Met Leu Pro Cys Tyr Ser Thr Ala Arg Ile Pro Leu Pro
                20                  25                  30

Asn Leu Asn Glu Asp Leu Thr Cys Gly Asn Leu Leu Met Trp Glu Ala
            35                  40                  45

Val Thr Val Lys Thr Glu Val Ile Gly Ile Thr Ser Met Leu Asn Leu
    50                  55                  60

His Ala Gly Ser Gln Lys Val His Glu Asn Gly Gly Lys Pro Val
65                  70                  75                  80

<210> SEQ ID NO 499
<211> LENGTH: 80
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 499

Tyr Ser Leu Arg Leu Thr Ala Glu Thr Ala Phe Asp Ser Asp Ser Pro
1               5                   10                  15

Asp Arg Lys Met Leu Pro Cys Tyr Ser Thr Ala Arg Ile Pro Leu Pro
                20                  25                  30

Asn Leu Asn Glu Asp Leu Thr Cys Gly Asn Leu Leu Met Trp Glu Ala
            35                  40                  45

Val Thr Val Lys Thr Glu Val Ile Gly Ile Thr Ser Met Leu Asn Leu
    50                  55                  60

His Ala Gly Ser Gln Lys Val His Glu Asn Gly Gly Lys Pro Ile
65                  70                  75                  80

<210> SEQ ID NO 500
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(6)
<223> OTHER INFORMATION: Any amino acid
```

```
<220> FEATURE:
<221> NAME/KEY: VARIANT
<222> LOCATION: (7)..(7)
<223> OTHER INFORMATION: /replace="Glu"
<220> FEATURE:
<221> NAME/KEY: MISC_FEATURE
<222> LOCATION: (7)..(7)
<223> OTHER INFORMATION: /note="Variant residue given in the sequence
      has no preference with respect to that in the annotation for
      variant position"
<220> FEATURE:
<221> NAME/KEY: MOD_RES
<222> LOCATION: (8)..(12)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (17)..(17)
<223> OTHER INFORMATION: Any amino acid

<400> SEQUENCE: 500

Tyr Arg Xaa Lys Xaa Xaa Asp Xaa Xaa Xaa Xaa Xaa Lys Asn Xaa Thr
1               5                   10                  15

Xaa Gln

<210> SEQ ID NO 501
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (18)..(18)
<223> OTHER INFORMATION: Any amino acid

<400> SEQUENCE: 501

Asn Tyr Arg Thr Lys Tyr Pro Xaa Gly Thr Xaa Xaa Pro Lys Asn Xaa
1               5                   10                  15

Thr Xaa Gln Ser Gln Val Met
            20

<210> SEQ ID NO 502
<211> LENGTH: 268
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 502

Lys Gly Gly Val Glu Val Leu Glu Val Lys Thr Gly Val Asp Ala Ile
1               5                   10                  15
```

Thr Glu Val Glu Cys Phe Leu Asn Pro Glu Met Gly Asp Pro Asp Glu
            20                  25                  30

Asn Leu Arg Gly Phe Ser Leu Lys Leu Ser Ala Glu Asn Asp Phe Ser
        35                  40                  45

Ser Asp Ser Pro Glu Arg Lys Met Leu Pro Cys Tyr Ser Thr Ala Arg
50                  55                  60

Ile Pro Leu Pro Asn Leu Asn Glu Asp Leu Thr Cys Gly Asn Leu Leu
65                  70                  75                  80

Met Trp Glu Ala Val Thr Val Gln Thr Glu Val Ile Gly Ile Thr Ser
                85                  90                  95

Met Leu Asn Leu His Ala Gly Ser Gln Lys Val His Glu His Gly Gly
            100                 105                 110

Gly Lys Pro Ile Gln Gly Ser Asn Phe His Phe Ala Val Gly Gly
        115                 120                 125

Asp Pro Leu Glu Met Gln Gly Val Leu Met Asn Tyr Arg Thr Lys Tyr
130                 135                 140

Pro Glu Gly Thr Ile Thr Pro Lys Asn Pro Thr Ala Gln Ser Gln Val
145                 150                 155                 160

Met Asn Thr Asp His Lys Ala Tyr Leu Asp Lys Asn Asn Ala Tyr Pro
                165                 170                 175

Val Glu Cys Trp Ile Pro Asp Pro Ser Arg Asn Glu Asn Thr Arg Tyr
            180                 185                 190

Phe Gly Thr Phe Thr Gly Gly Glu Asn Val Pro Pro Val Leu His Val
        195                 200                 205

Thr Asn Thr Ala Thr Thr Val Leu Leu Asp Gln Gly Val Gly Pro
210                 215                 220

Leu Cys Lys Ala Asp Ser Leu Tyr Val Ser Ala Ala Asp Ile Cys Gly
225                 230                 235                 240

Leu Phe Thr Asn Ser Ser Gly Thr Gln Gln Trp Arg Gly Leu Ala Arg
                245                 250                 255

Tyr Phe Lys Ile Arg Leu Arg Lys Arg Ser Val Lys
            260                 265

<210> SEQ ID NO 503
<211> LENGTH: 268
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 503

Lys Gly Gly Val Glu Val Leu Glu Val Lys Thr Gly Val Asp Ala Ile
1               5                   10                  15

Thr Glu Val Glu Cys Phe Leu Asn Pro Glu Met Gly Asp Pro Asp Asp
            20                  25                  30

Asn Leu Arg Gly Tyr Ser Leu Lys Leu Thr Ala Glu Asn Ala Phe Asp
        35                  40                  45

Ser Asp Ser Pro Asp Lys Lys Met Leu Pro Cys Tyr Ser Thr Ala Arg
50                  55                  60

Ile Pro Leu Pro Asn Leu Asn Glu Asp Leu Thr Cys Gly Asn Leu Leu
65                  70                  75                  80

Met Trp Glu Ala Val Thr Val Lys Thr Glu Val Ile Gly Ile Thr Ser
                85                  90                  95

Met Leu Asn Leu His Ala Gly Ser Gln Lys Val His Glu Asn Gly Gly

```
                100                 105                 110
Gly Lys Pro Val Gln Gly Ser Asn Phe His Phe Phe Ala Val Gly Gly
            115                 120                 125

Asp Pro Leu Glu Met Gln Gly Val Leu Met Asn Tyr Arg Thr Lys Tyr
        130                 135                 140

Pro Gln Gly Thr Ile Thr Pro Lys Asn Pro Thr Ala Gln Ser Gln Val
145                 150                 155                 160

Met Asn Thr Asp His Lys Ala Tyr Leu Asp Lys Asn Asn Ala Tyr Pro
                165                 170                 175

Val Glu Cys Trp Ile Pro Asp Pro Ser Arg Asn Glu Asn Thr Arg Tyr
            180                 185                 190

Phe Gly Thr Tyr Thr Gly Gly Glu Asn Val Pro Pro Val Leu His Val
        195                 200                 205

Thr Asn Thr Ala Thr Thr Val Leu Leu Asp Glu Gln Gly Val Gly Pro
    210                 215                 220

Leu Cys Lys Ala Asp Ser Leu Tyr Val Ser Ala Ala Asp Ile Cys Gly
225                 230                 235                 240

Leu Phe Thr Asn Ser Ser Gly Thr Gln Gln Trp Arg Gly Leu Ala Arg
                245                 250                 255

Tyr Phe Lys Ile Arg Leu Arg Lys Arg Ser Val Lys
            260                 265
```

```
<210> SEQ ID NO 504
<211> LENGTH: 268
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 504

Lys Gly Gly Val Glu Val Leu Glu Val Lys Thr Gly Val Asp Ala Ile
1               5                   10                  15

Thr Glu Val Glu Cys Phe Leu Asn Pro Glu Met Gly Asp Pro Asp Asp
            20                  25                  30

His Leu Arg Gly Tyr Ser Gln His Leu Ser Ala Glu Asn Ala Phe Asp
        35                  40                  45

Ser Asp Ser Pro Asp Lys Lys Met Leu Pro Cys Tyr Ser Thr Ala Arg
    50                  55                  60

Ile Pro Leu Pro Asn Leu Asn Glu Asp Leu Thr Cys Gly Asn Leu Leu
65                  70                  75                  80

Met Trp Glu Ala Val Thr Val Lys Thr Glu Val Ile Gly Ile Thr Ser
                85                  90                  95

Met Leu Asn Leu His Ala Gly Ser Gln Lys Val His Glu Asn Gly Gly
            100                 105                 110

Gly Lys Pro Val Gln Gly Ser Asn Phe His Phe Phe Ala Val Gly Gly
        115                 120                 125

Asp Pro Leu Glu Met Gln Gly Val Leu Met Asn Tyr Arg Thr Lys Tyr
    130                 135                 140

Pro Gln Gly Thr Ile Thr Pro Lys Asn Pro Thr Ala Gln Ser Gln Val
145                 150                 155                 160

Met Asn Thr Asp His Lys Ala Tyr Leu Asp Lys Asn Asn Ala Tyr Pro
                165                 170                 175

Val Glu Cys Trp Ile Pro Asp Pro Ser Lys Asn Glu Asn Thr Arg Tyr
            180                 185                 190
```

```
Phe Gly Thr Tyr Thr Gly Gly Glu Asn Val Pro Pro Val Leu His Val
        195                 200                 205

Thr Asn Thr Ala Thr Thr Val Leu Leu Asp Glu Gln Gly Val Gly Pro
    210                 215                 220

Leu Cys Lys Ala Asp Ser Leu Tyr Val Ser Ala Ala Asp Ile Cys Gly
225                 230                 235                 240

Leu Phe Thr Asn Ser Ser Gly Thr Gln Gln Trp Arg Gly Leu Ala Arg
                245                 250                 255

Tyr Phe Lys Ile Arg Leu Arg Lys Arg Ser Val Lys
            260                 265

<210> SEQ ID NO 505
<211> LENGTH: 268
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 505

Lys Gly Gly Val Glu Val Leu Glu Val Lys Thr Gly Val Asp Ala Ile
1               5                   10                  15

Thr Glu Val Glu Cys Phe Leu Asn Pro Glu Met Gly Asp Pro Asp Asn
            20                  25                  30

Asp Leu Arg Gly Tyr Ser Leu Arg Leu Thr Ala Glu Thr Ala Phe Asp
        35                  40                  45

Ser Asp Ser Pro Asp Arg Lys Met Leu Pro Cys Tyr Ser Thr Ala Arg
50                  55                  60

Ile Pro Leu Pro Asn Leu Asn Glu Asp Leu Thr Cys Gly Asn Leu Leu
65                  70                  75                  80

Met Trp Glu Ala Val Thr Val Lys Thr Glu Val Ile Gly Ile Thr Ser
                85                  90                  95

Met Leu Asn Leu His Ala Gly Ser Gln Lys Val His Glu Asn Gly Gly
            100                 105                 110

Gly Lys Pro Ile Gln Gly Ser Asn Phe His Phe Phe Ala Val Gly Gly
        115                 120                 125

Asp Pro Leu Glu Met Gln Gly Val Leu Met Asn Tyr Arg Thr Lys Tyr
130                 135                 140

Pro Glu Gly Thr Val Thr Pro Lys Asn Pro Thr Ala Gln Ser Gln Val
145                 150                 155                 160

Met Asn Thr Asp His Lys Ala Tyr Leu Asp Lys Asn Asn Ala Tyr Pro
                165                 170                 175

Val Glu Cys Trp Ile Pro Asp Pro Ser Arg Asn Glu Asn Thr Arg Tyr
            180                 185                 190

Phe Gly Thr Tyr Thr Gly Gly Glu Asn Val Pro Pro Val Leu His Val
        195                 200                 205

Thr Asn Thr Ala Thr Thr Val Leu Leu Asp Glu Gln Gly Val Gly Pro
    210                 215                 220

Leu Cys Lys Ala Asp Ser Leu Tyr Val Ser Ala Ala Asp Ile Cys Gly
225                 230                 235                 240

Leu Phe Thr Asn Ser Ser Gly Thr Gln Gln Trp Arg Gly Leu Pro Arg
                245                 250                 255

Tyr Phe Lys Ile Arg Leu Arg Lys Arg Ser Val Lys
            260                 265
```

```
<210> SEQ ID NO 506
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 506

His His His His His His
1               5

<210> SEQ ID NO 507
<211> LENGTH: 10
<212> TYPE: PRT
<213> ORGANISM: Artificial Sequence
<220> FEATURE:
<221> NAME/KEY: MOD_RES
<222> LOCATION: (5)..(5)
<223> OTHER INFORMATION: Any amino acid
<220> FEATURE:
<221> NAME/KEY: source
<223> OTHER INFORMATION: /note="Description of Artificial Sequence:
      Synthetic polypeptide"

<400> SEQUENCE: 507

Gly Phe Thr Phe Xaa Asn Tyr Trp Met Thr
1               5                   10

<210> SEQ ID NO 508
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 508

Gly Phe Thr Phe Asn Asn Tyr Trp Met Thr
1               5                   10

<210> SEQ ID NO 509
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 509

Asn Ile Lys Lys Asp Gly Ser Glu Lys Tyr Tyr Val Asp Ser Val Arg
1               5                   10                  15

Gly

<210> SEQ ID NO 510
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 510

Val Arg Ser Gly Arg Tyr Phe Ala Leu Asp Asp
```

```
1               5                   10
```

<210> SEQ ID NO 511
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 511

```
Gly Gly Asp Asn Ile Gly Ser Arg Pro Val His
1               5                   10
```

<210> SEQ ID NO 512
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 512

```
Asp Asp Ser Asn Arg Pro Ser
1               5
```

<210> SEQ ID NO 513
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 513

```
Gln Val Trp Ser Ser Ser Thr Asp His Pro
1               5                   10
```

<210> SEQ ID NO 514
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 514

```
Gly Phe Thr Phe Ser Asn Tyr Trp Met Thr
1               5                   10
```

<210> SEQ ID NO 515
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 515

```
Asn Ile Lys Lys Asp Gly Ser Glu Lys Tyr Tyr Val Asp Ser Val Arg
1               5                   10                  15

Gly
```

-continued

```
<210> SEQ ID NO 516
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 516

Val Arg Ser Gly Arg Tyr Phe Ala Leu Asp Asp
1               5                   10

<210> SEQ ID NO 517
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 517

Gly Gly Asp Asn Ile Gly Ser Arg Pro Val His
1               5                   10

<210> SEQ ID NO 518
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 518

Asp Asp Ser Asn Arg Pro Ser
1               5

<210> SEQ ID NO 519
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 519

Gln Val Trp Ser Ser Ser Thr Asp His Pro
1               5                   10

<210> SEQ ID NO 520
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 520

Gly Phe Thr Phe Lys Asn Tyr Trp Met Thr
1               5                   10

<210> SEQ ID NO 521
<211> LENGTH: 17
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 521

Asn Ile Lys Lys Asp Gly Ser Glu Lys Tyr Tyr Val Asp Ser Val Arg
1               5                   10                  15

Gly

<210> SEQ ID NO 522
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 522

Val Arg Ser Gly Arg Tyr Phe Ala Leu Asp Asp
1               5                   10

<210> SEQ ID NO 523
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 523

Gly Gly Asp Asn Ile Gly Ser Arg Pro Val His
1               5                   10

<210> SEQ ID NO 524
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 524

Asp Asp Ser Asn Arg Pro Ser
1               5

<210> SEQ ID NO 525
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 525

Gln Val Trp Ser Ser Ser Thr Asp His Pro
1               5                   10

<210> SEQ ID NO 526
<211> LENGTH: 10
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 526

Gly Phe Thr Phe Gln Asn Tyr Trp Met Thr
1               5                   10

<210> SEQ ID NO 527
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 527

Asn Ile Lys Lys Asp Gly Ser Glu Lys Tyr Tyr Val Asp Ser Val Arg
1               5                   10                  15

Gly

<210> SEQ ID NO 528
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 528

Val Arg Ser Gly Arg Tyr Phe Ala Leu Asp Asp
1               5                   10

<210> SEQ ID NO 529
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 529

Gly Gly Asp Asn Ile Gly Ser Arg Pro Val His
1               5                   10

<210> SEQ ID NO 530
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 530

Asp Asp Ser Asn Arg Pro Ser
1               5

<210> SEQ ID NO 531
<211> LENGTH: 10
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 531

Gln Val Trp Ser Ser Thr Asp His Pro
1               5

<210> SEQ ID NO 532
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 532

Gly Phe Thr Phe Asn Asn Tyr Trp Met Thr
1               5                   10

<210> SEQ ID NO 533
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 533

Asn Ile Lys Lys Asp Gly Ser Glu Lys Tyr Tyr Val Asp Ser Val Arg
1               5                   10                  15

Gly

<210> SEQ ID NO 534
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 534

Val Arg Ser Gly Arg Tyr Phe Ala Leu Asp Asp
1               5                   10

<210> SEQ ID NO 535
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 535

Gly Gly Asp Asn Ile Gly Ser Arg Pro Val His
1               5                   10

<210> SEQ ID NO 536
<211> LENGTH: 7
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 536

Asp Asp Ser Asn Arg Pro Ser
1               5

<210> SEQ ID NO 537
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 537

Gln Val Trp Ser Ser Ser Thr Asp His Pro
1               5                   10

<210> SEQ ID NO 538
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 538

Gly Phe Thr Phe Asn Asn Tyr Trp Met Thr
1               5                   10

<210> SEQ ID NO 539
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 539

Asn Ile Lys Lys Asp Gly Ser Glu Lys Tyr Tyr Val Asp Ser Val Arg
1               5                   10                  15

Gly

<210> SEQ ID NO 540
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 540

Val Arg Ser Gly Arg Tyr Phe Ala Leu Asp Asp
1               5                   10

<210> SEQ ID NO 541
<211> LENGTH: 11
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 541

Gly Gly Asp Asn Ile Gly Ser Arg Pro Val His
1               5                   10

<210> SEQ ID NO 542
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 542

Asp Asp Ser Asn Arg Pro Ser
1               5

<210> SEQ ID NO 543
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 543

Gln Val Trp Ser Ser Ser Thr Asp His Pro
1               5                   10
```

What is claimed is:

1. A pharmaceutical composition comprising an antibody or antigen binding fragment thereof, wherein said antibody or antigen binding fragment thereof binds to BK virus VP 1 and comprises: a heavy chain variable region that comprises (a) a HCDR1 (CDR-Complementarity Determining Region) of SEQ ID NO: 6, (b) a HCDR2 of SEQ ID NO: 7, (c) a HCDR3 of SEQ ID NO: 8 and a light chain variable region that comprises: (d) a LCDR1 of SEQ ID NO:16, (e) a LCDR2 of SEQ ID NO: 17, and (f) a LCDR3 of SEQ ID NO: 18.

2. The pharmaceutical composition of claim 1, wherein the composition is prepared as a lyophilisate.

3. The pharmaceutical composition of claim 1 wherein the antibody or antigen binding fragment thereof is a monoclonal antibody, a chimeric antibody, a humanized antibody, a human engineered antibody, a human antibody, a single chain antibody (scFv) or an antibody fragment.

4. The pharmaceutical composition of claim 1, wherein said antibody or antigen binding fragment thereof comprises:
   a heavy chain variable region (vH) that comprises a sequence having at least 95% identity to SEQ ID NO: 12, and a light chain variable region (vL) that comprises a sequence having at least 95% identity to SEQ ID NO: 22.

5. The pharmaceutical composition of claim 4 wherein the vH comprises SEQ ID NO: 12 or a modification thereof selected from one or more of V5Q, G9P, T10G, N30S, N30K, and N30Q, and wherein the vL comprises SEQ ID NO: 22.

6. The pharmaceutical composition of claim 4 wherein the antibody or antigen binding fragment thereof is a monoclonal antibody, a chimeric antibody, a humanized antibody, a human engineered antibody, a human antibody, a single chain antibody (scFv) or an antibody fragment.

7. The pharmaceutical composition of claim 1 or claim 4 wherein the antibody or antigen binding fragment thereof has reduced glycosylation or no glycosylation or is hypofucosylated.

8. The pharmaceutical composition of claim 1 or claim 4 further comprising a pharmaceutically acceptable carrier.

9. The pharmaceutical composition of claim 8, wherein the pharmaceutically acceptable carrier contains histidine or a sugar.

10. The pharmaceutical composition of claim 9, wherein the sugar is sucrose.

11. The pharmaceutical composition of claim 1 or claim 4 comprising a plurality of the antibody or antigen binding fragment, wherein at least 0.05%, 0.1%, 0.5%, 1%, 2%, 3%, 5% or more or more of the antibodies in the composition have an α2,3-linked sialic acid residue.

12. The pharmaceutical composition of claim 1 or claim 4 comprising a plurality of the antibody or antigen binding fragment, wherein none of the antibodies comprise a bisecting GlcNAc.

13. A method of neutralizing a BK virus or JC virus infection comprising administering via injection or infusion to a patient in need an effective amount of the pharmaceutical composition of claim 1 or claim 4.

14. The method of claim 13, wherein the patient in need is diagnosed with BK viruria or BK viremia.

15. A method of treating or reducing the likelihood of a BK virus or JC virus associated disorder, comprising administering via injection or infusion to a patient in need an effective amount of the pharmaceutical composition of claim 1 or claim 4, and wherein the disorder is: nephropathy, BKVAN, hemorrhagic cystitis (HC), Progressive Multifocal Leukoencephalopathy (PML), granule cell neuronopathy (GCN), interstitial kidney disease, ureteral stenosis, vasculitis, colitis, retinitis, meningitis, and immune reconstitution inflammatory syndrome (IRIS).

16. The method of claim 15, wherein the pharmaceutical composition is administered in combination with another therapeutic agent.

17. The method of claim 16, wherein the therapeutic agent is an immunosuppressive agent.

18. The method of claim 17, wherein the immune suppressive agent is: a monophosphate dehydrogenase inhibitor, a purine synthesis inhibitor, a calcineurin inhibitor or an mTOR inhibitor.

19. The method of claim 18, wherein the immunosuppressive agent is mycophenolate mofetil (MMF), mycophenolate sodium, azathioprine, tacrolimus, sirolimus or cyclosporine.

20. The method of claim 16, wherein the therapeutic agent is an additional anti-VP1 antibody.

21. A pharmaceutical composition, comprising an antibody and a pharmaceutically acceptable carrier, wherein the antibody comprises a heavy chain variable region (vH) that comprises SEQ ID NO: 12, and a light chain variable region (vL) that comprises SEQ ID NO: 22, and wherein the pharmaceutically acceptable carrier contains histidine, sucrose, and a polysorbate.

* * * * *